United States Patent
Sahin et al.

(10) Patent No.: US 10,717,780 B2
(45) Date of Patent: Jul. 21, 2020

(54) AGENTS FOR TREATMENT OF CLAUDIN EXPRESSING CANCER DISEASES

(71) Applicants: Biontech AG, Mainz (DE); Ganymed Pharmaceuticals GmbH, Mainz (DE); TRON—Translationale Onkologie an der Universitätsmedizin der Johannes Gutenberg-Universität Mainz gemeinnützige GmbH, Mainz (DE)

(72) Inventors: Ugur Sahin, Mainz (DE); Ozlem Türeci, Mainz (DE); Christiane Stadler, Bensheim (DE); Julia Holland, Mainz (DE); Hayat Bähr-Mahmud, Wiesbaden (DE); Tim Beissert, Gross-Gerau (DE); Laura Plum, Mainz (DE); Fabrice Le Gall, Mainz (DE); Arne Jendretzki, Mainz-Kostheim (DE); Markus Fiedler, Halle an der Saale (DE)

(73) Assignees: BioNTech AG, Mainz (DE); Ganymed Pharmaceuticals GmbH, Mainz (DE); TRON—Translationale Onkologic an der Universitätsmedzin der Johannes Gutenberg-Universität Mainz gemcinnützige GmbH, Mainz (DE)

( * ) Notice: Subject to any disclaimer, the term of this patent is extended or adjusted under 35 U.S.C. 154(b) by 0 days.

(21) Appl. No.: 16/117,197

(22) Filed: Aug. 30, 2018

(65) Prior Publication Data
US 2019/0055311 A1 Feb. 21, 2019

Related U.S. Application Data

(62) Division of application No. 14/442,445, filed as application No. PCT/EP2013/003399 on Nov. 12, 2013, now Pat. No. 10,093,736.

(30) Foreign Application Priority Data

Nov. 13, 2012 (WO) .................. PCT/EP2013/004712
Jul. 30, 2013 (WO) .................. PCT/EP2013/002270

(51) Int. Cl.
*C07K 16/28* (2006.01)
*C07K 16/30* (2006.01)
*A61K 39/00* (2006.01)

(52) U.S. Cl.
CPC .......... *C07K 16/2809* (2013.01); *C07K 16/28* (2013.01); *C07K 16/30* (2013.01); *A61K 2039/505* (2013.01); *C07K 2317/31* (2013.01); *C07K 2317/622* (2013.01); *C07K 2317/73* (2013.01); *C07K 2317/74* (2013.01)

(58) Field of Classification Search
None
See application file for complete search history.

(56) References Cited

U.S. PATENT DOCUMENTS 7,635,472 B2 * 12/2009 Kufer ................. C07K 16/2803
424/130.1
9,487,584 B2 * 11/2016 Sahin .................... C07K 16/30

OTHER PUBLICATIONS

Martin et al (Journal of the National Cancer Institute, vol. 92, No. 14: pp. 1126-1135, Jul. 19, 2000) (Year: 2000).*
Apantaku et al. (Breast cancer diagnosis and screening, American Family Physician 2000) (Year: 2000).*
U.S. Appl. No. 14/442,445, filed May 13, 2015 (Sep. 22, 2016), Ugur Sahin (Biotech AG).
PCT, PCT/EP2013/003399 (WO 2014/075788), filed Nov. 12, 2013 (May 22, 2014), Ugur Sahin (Biotech AG).
Fortmüller, K. et al., Effective targeting of prostate cancer by lymphocytes redirected by a PSMA * CD3 bispecific single-chain diabody. Prostate. 2010; 71(6):588-96.
Klamp, T. et al., Highly Specific Auto-Antibodies against Claudin-18 Isoform 2 Induced by a Chimeric HBcAg Virus-Like Particle Vaccine Kill Tumor Cells and Inhibit the Growth of Lung Metastases. Cancer Res. 2011; 71(2):516-27.
Lal-Nag, M. et al., 11 Claudin-6: a novel receptor for CPE-mediated cytotoxicity in ovarian cancer. Oconogensis. 2012; 1(11): e33 (8 pages).
May, C. et al., Advances in bispecific biotherapeutics for the treatment of cancer. Biochem Pharmacol. 2012; 84(9):1105-12.
Penna et al., Antitumor x anti-CD3 bifunctional antibodies redirect T-cells activated in vivo with staphylococcal enterotoxin B to neutralize pulmonary metastases. Cancer Res. 1994; 54(10):2738-43.
Sahin, U. et al., Claudin-18 splice variant 2 is a pan-cancer target suitable for therapeutic antibody development. Clin Cancer Res. 2008; 14(23):7624-34.
International Search Report dated May 22, 2014 by the International Searching Authority for application PCT/EP2013/003399, filed on Nov. 13, 2013 and published as WO 2014/075788 on May 22, 2014 (Inventor—Sahin, et al.; Applicant—Biontech AG) (9 pages).
International Preliminary Report on Patentability dated May 19, 2015 by the International Searching Authority for application PCT/EP2013/003399, filed on Nov. 13, 2013 and published as WO 2014/075788 on May 22, 2014 (Inventor—Sahin, et al.; Applicant —Biontech AG) (5 pages).

* cited by examiner

*Primary Examiner* — Meera Natarajan
(74) *Attorney, Agent, or Firm* — Ballard Spahr LLP

(57) ABSTRACT

The present invention provides binding agents that contain n binding domain that is specific for CD3 allowing binding to T cells and a binding domain that is specific for a tumor-associated claudin molecule and methods of using these binding agents or nucleic acids encoding therefor for treating cancer.

12 Claims, 57 Drawing Sheets
Specification includes a Sequence Listing.

A

B

A

Bi-scFv CLDN6 x CD3 (6PHU5)

B

Bi-scFv CD3 x CLDN6 (6PHU3)

A bi-scFv CLDN18.2 x CD3

| Cap | hAgKozak | Sec | V$_H$ αCLDN18.2 | LL | V$_L$ αCLDN18.2 | SL | V$_H$ αCD3 | LL | V$_L$ αCD3 | His | 2hBgUTR | A120 | bi-scFv CD3 x CLDN18.2

| Cap | hAgKozak | Sec | V$_H$ αCD3 | LL | V$_L$ αCD3 | SL | V$_H$ αCLDN18.2 | LL | V$_L$ αCLDN18.2 | His | 2hBgUTR | A120 |

B

| Cap | 5'UTR | nsP1-4 | sgP | Sec | V$_H$ αCLDN18.2 | LL | V$_L$ αCLDN18.2 | SL | V$_H$ αCD3 | LL | V$_L$ αCD3 | His | 3'UTR | A120 |

FIG. 20A, FIG. 20B

A bi-scFv CLDN6 x CD3

| Cap | hAgKozak | Sec | V$_H$ αCLDN6 | LL | V$_L$ αCLDN6 | SL | V$_H$ αCD3 | LL | V$_L$ αCD3 | His | 2hBgUTR | A120 | bi-scFv CD3 x CLDN6

| Cap | hAgKozak | Sec | V$_H$ αCD3 | LL | V$_L$ αCD3 | SL | V$_H$ αCLDN6 | LL | V$_L$ αCLDN6 | His | 2hBgUTR | A120 |

B

| Cap | 5'UTR | nsP1-4 | SgP | Sec | V$_H$ αCD3 | LL | V$_L$ αCD3 | SL | V$_H$ αCLDN6 | LL | V$_L$ αCLDN6 | His | 3'UTR | A120 |

FIG. 31A, FIG. 31B

AGENTS FOR TREATMENT OF CLAUDIN EXPRESSING CANCER DISEASES

Claudins are integral membrane proteins located within the tight junctions of epithelia and endothelia. Claudins are predicted to have four transmembrane segments with two extracellular loops, and N- and C-termini located in the cytoplasm. The claudin (CLDN) family of transmembrane proteins plays a critical role in the maintenance of epithelial and endothelial tight junctions and might also play a role in the maintenance of the cytoskeleton and in cell signaling.

The claudin 18 (CLDN18) molecule is an integral transmembrane protein (tetraspanin) having four membrane spanning hydrophobic regions and two extracellular loops (loop1 embraced by hydrophobic region 1 and hydrophobic region 2; loop2 embraced by hydrophobic regions 3 and 4). CLDN18 exists in two different splice variants, which are described in mouse and in human (Niimi, Mol. Cell. Biol. 21:7380-90, 2001). The splice variants (Genbank accession number: splice variant 1 (CLDN18.1): NP_057453, NM_016369, and splice variant 2 (CLDN18.2): NM_001002026, NP_001002026) have a molecular weight of approximately 27.9/27.72 kD. The splice variants CLDN18.1 and CLDN18.2 differ in the N-terminal portion which comprises the first transmembrane (TM) region and loop1, whereas the primary protein sequence of the C-terminus is identical.

In normal tissues, there is no detectable expression of CLDN18.2 with exception of stomach where CLDN18.2 is expressed exclusively on short-lived differentiated gastric epithelial cells. CLDN18.2 is maintained in the course of malignant transformation and thus frequently displayed on the surface of human gastric cancer cells. Moreover, this pan-tumoral antigen is ectopically activated at significant levels in esophageal, pancreatic and lung adenocarcinomas. The CLDN18.2 protein is also localized in lymph node metastases of gastric cancer adenocarcinomas and in distant metastases especially into the ovary (so-called Krukenberg tumors).

CLDN6 is expressed in a series of different human cancer cells while expression in normal tissues is limited to placenta.

The differential expression of claudins such as CLDN18.2 and CLDN6 between cancer and normal cells, their membrane localization and their absence from the vast majority of toxicity relevant normal tissues makes these molecules attractive targets for cancer immunotherapy and the use of antibody-based therapeutics for targeting claudins in cancer therapy promises a high level of therapeutic specificity.

Approaches using the potential of T cells for the treatment of cancer include vaccination with tumor-derived proteins, RNA or peptide antigen, infusion of tumor-derived, ex-vivo expanded T cells (called adoptive transfer), T cell receptor gene transfer or direct engagement of T cells by bi- or trispecific antibodies. Likewise, many stimulants of T cell responses are clinically tested in combination or as monotherapy, such as ligands for Toll-like receptors, antibodies blocking CTLA-4 on T cells, immune stimulatory cytokines, or antibodies neutralizing molecules involved in immune escape of cancer cells such as TGF-beta or B7-H1. The intense development of T cell-based therapies is motivated by the observation that patients appear to live significantly longer if their tumors are infiltrated by T cells. Moreover, numerous mouse models have shown that engagement of T cells by various means can eradicate even large tumors and a number of T cell therapies have recently made significant progress in treating various cancer indications.

It has been an object of the invention to provide novel agents and methods for the therapy of cancer diseases.

The solution of the problem underlying the invention is based on the concept of generating a binding agent that contains a binding domain that is specific for a tumor-associated claudin molecule, i.e. cancer cells. The other binding domain is specific for CD3 allowing binding to T cells and allows to pull the T cells into the complex, thus making it possible to target the cytotoxic effect of the T cells to the cancer cells. Formation of this complex can induce signalling in cytotoxic T cells, either on its own or in combination with accessory cells, which leads to the release of cytotoxic mediators.

We report for the first time that binding agents targeting claudin and CD3 can induce potent T cell-mediated lysis and are effective in treating tumor diseases.

SUMMARY OF THE INVENTION

In one aspect the invention relates to a binding agent comprising at least two binding domains, wherein a first binding domain binds to claudin and a second binding domain binds to CD3. The binding agent of the invention may bind to a cytotoxic cell (by engaging the CD3 receptor) and a cancer cell expressing CLDN to be destroyed as a target.

In one embodiment the binding agent is a bispecific molecule such as a bispecific antibody, in particular a bispecific single chain antibody. In one embodiment said claudin is expressed in a cancer cell. In one embodiment said claudin is expressed on the surface of a cancer cell. In one embodiment said claudin is selected from the group consisting of claudin 18.2 and claudin 6. In one embodiment said first binding domain binds to an extracellular domain of said claudin. In one embodiment said first binding domain binds to native epitopes of CLDN present on the surface of living cells. In one embodiment said first binding domain binds to the first extracellular loop of CLDN. In one embodiment said second binding domain binds to the epsilon-chain of CD3. In one embodiment said CD3 is expressed on the surface of a T cell. In one embodiment binding of said binding agent to CD3 on T cells results in proliferation and/or activation of said T cells, wherein said activated T cells preferably release cytotoxic factors, e.g. performs and granzymes, and initiate cytolysis and apoptosis of cancer cells. In one embodiment said binding to claudin and/or said binding to CD3 is a specific binding.

In one embodiment the binding agent is in the format of a full-length antibody or an antibody fragment. In one embodiment the binding agent comprises four antibody variable domains with at least two binding domains, wherein at least one binding domain binds to claudin and at least one binding domain binds to CD3. In one embodiment the binding agent comprises a variable domain of a heavy chain of an immunoglobulin (VH) with a specificity for a claudin antigen (VH(CLDN)), a variable domain of a light chain of an immunoglobulin (VL) with a specificity for a claudin antigen (VL(CLDN)), a variable domain of a heavy chain of an immunoglobulin (VH) with a specificity for CD3 (VH (CD3)), and a variable domain of a light chain of an immunoglobulin (VL) with a specificity for CD3 (VL (CD3)).

In one embodiment the binding agent is in the format of a diabody that comprises a heavy chain variable domain connected to a light chain variable domain on the same polypeptide chain such that the two domains do not pair. In one embodiment the diabody comprises two polypeptide chains, wherein one polypeptide comprises VH(CLDN) and VL(CD3) and the other polypeptide chain comprises VH(CD3) and VL(CLDN).

In one embodiment the binding agent is in the format of a bispecific single chain antibody that consists of two scFv molecules connected via a linker peptide, wherein the heavy chain variable regions (VH) and the corresponding light chain variable regions (VL) are preferably arranged, from N-terminus to C-terminus, in the order VH(CLDN)-VL(CLDN)-VH(CD3)-VL(CD3). VH(CD3)-VL(CD3)-VH(CLDN)-VL(CLDN) or VH(CD3)-VL(CD3)-VL(CLDN)-VH(CLDN). In one embodiment said heavy chain variable regions (VH) and the corresponding light chain variable regions (VL) are connected via a long peptide linker, preferably, a peptide linker comprising the amino acid sequences (GGGGS)3 or VE(GGGGS)2GGVD. In one embodiment said two VH-VL or VL-VH scFv units are connected via a short peptide linker, preferable a peptide linker comprising the amino acid sequence SGGGGS or GGGGS.

In one embodiment said CLDN is CLDN18.2 and said VH(CLDN) comprises an amino acid sequence represented by SEQ ID NO: 8 or a fragment thereof or a variant of said amino acid sequence or fragment and the VL(CLDN) comprises an amino acid sequence represented by SEQ ID NO: 15 or a fragment thereof or a variant of said amino acid sequence or fragment.

In one embodiment said CLDN is CLDN18.2 and said VH(CLDN) comprises an amino acid sequence represented by SEQ ID NO: 6 or a fragment thereof or a variant of said amino acid sequence or fragment and the VL(CLDN) comprises an amino acid sequence represented by SEQ ID NO: 11 or a fragment thereof or a variant of said amino acid sequence or fragment.

In one embodiment said CLDN is CLDN6 and said VH(CLDN) comprises an amino acid sequence represented by SEQ ID NO: 22 or a fragment thereof or a variant of said amino acid sequence or fragment and the VL(CLDN) comprises an amino acid sequence represented by SEQ ID NO: 23 or a fragment thereof or a variant of said amino acid sequence or fragment.

In one embodiment said CLDN is CLDN6 and said VH(CLDN) comprises an amino acid sequence represented by SEQ ID NO: 22 or a fragment thereof or a variant of said amino acid sequence or fragment and the VL(CLDN) comprises an amino acid sequence represented by SEQ ID NO: 97, 98, 99 or 100, or a fragment thereof or a variant of said amino acid sequence or fragment.

In one embodiment said VH(CD3) comprises an amino acid sequence represented by SEQ ID NO: 36, 94 or 95, or a fragment thereof or a variant of said amino acid sequence or fragment and the VL(CD3) comprises an amino acid sequence represented by SEQ ID NO: 37 or 96 or a fragment thereof or a variant of said amino acid sequence or fragment.

In one embodiment said VH(CD3) comprises an amino acid sequence represented by SEQ ID NO: 36 or a fragment thereof or a variant of said amino acid sequence or fragment and the VL(CD3) comprises an amino acid sequence represented by SEQ ID NO: 37 or a fragment thereof or a variant of said amino acid sequence or fragment.

In one embodiment said VH(CD3) comprises an amino acid sequence represented by SEQ ID NO: 95, or a fragment thereof or a variant of said amino acid sequence or fragment and the VL(CD3) comprises an amino acid sequence represented by SEQ ID NO: 96 or a fragment thereof or a variant of said amino acid sequence or fragment.

In one aspect the binding agent of the invention is in the format of a bispecific single chain antibody that comprises two scFv molecules connected via a linker peptide, wherein the heavy chain variable regions (VH) and the corresponding light chain variable regions (VL) are arranged, from N-terminus to C-terminus, in the order VH(CLDN)-VL(CLDN)-VH(CD3)-VL(CD3). In one embodiment said VH(CD3) and VL(CD3) are connected via a peptide linker consisting of 15 to 20, preferably 15 or 20 amino acids, preferably glycine and/or serine, and preferably are connected via a peptide linker comprising the amino acid sequence (GGGGS)4. In one embodiment said VH(CLDN) and VL(CLDN) are connected via a peptide linker consisting of 15 to 20, preferably 15 or 20 amino acids, preferably glycine and/or serine, and preferably are connected via a peptide linker comprising the amino acid sequence (GGGGS)4. In one embodiment said two VH-VL scFv units are connected via a linker peptide comprising the amino acid sequence SKGGGGS. One or both of said two VH-VL scFv units may comprise one or more interface disulfide bridges.

In one aspect the binding agent of the invention is in the format of a bispecific single chain antibody that comprises two scFv molecules connected via a linker peptide, wherein the heavy chain variable regions (VH) and the corresponding light chain variable regions (VL) are arranged, from N-terminus to C-terminus, in the order VL(CLDN)-VH(CLDN)-VH(CD3)-VL(CD3). In one embodiment said VH(CD3) and VL(CD3) are connected via a peptide linker consisting of 15 to 20, preferably 15 or 20 amino acids, preferably glycine and/or serine, and preferably are connected via a peptide linker comprising the amino acid sequence (GGGGS)4. In one embodiment said VL(CLDN) and VH(CLDN) are connected via a peptide linker consisting of 20 to 25, preferably 20 or 25 amino acids, preferably glycine and/or serine, and preferably are connected via a peptide linker comprising the amino acid sequence (GGGGS)5. In one embodiment said VL-VH and VH-VL scFv units are connected via a linker peptide comprising the amino acid sequence SGGGGS. One or both of said two VL-VH or VH-VL scFv units may comprise one or more interface disulfide bridges.

In one aspect the binding agent of the invention is in the format of a bispecific single chain antibody that comprises two scFv molecules connected via a linker peptide, wherein the heavy chain variable regions (VH) and the corresponding light chain variable regions (VL) are arranged, from N-terminus to C-terminus, in the order VH(CLDN)-VL(CLDN)-VL(CD3)-VH(CD3). Preferably, said VL(CD3)-VH(CD3) scFv unit comprises one or more interface disulfide bridges. In one embodiment said VL(CD3) and VH(CD3) are connected via a peptide linker consisting of 20 to 25, preferably 20 or 25 amino acids, preferably glycine and/or serine, and preferably are connected via a peptide linker comprising the amino acid sequence (GGGGS)5. In one embodiment said VH(CLDN) and VL(CLDN) are connected via a peptide linker consisting of 15 to 20, preferably 15 or 20 amino acids, preferably glycine and/or serine, and preferably are connected via a peptide linker comprising the amino acid sequence (GGGGS)4. In one embodiment said VH-VL and VL-VH scFv units are connected via a linker peptide comprising the amino acid sequence SGGGGS. Said VH(CLDN)-VL(CLDN) scFv unit may comprise one or more interface disulfide bridges.

In one aspect the binding agent of the invention is in the format of a bispecific single chain antibody that comprises two scFv molecules connected via a linker peptide, wherein the heavy chain variable regions (VH) and the corresponding light chain variable regions (VL) are arranged, from N-terminus to C-terminus, in the order VL(CLDN)-VH (CLDN)-VL(CD3)-VH(CD3). Preferably, said VL(CD3)-VH(CD3) scFv unit comprises one or more interface disulfide bridges. In one embodiment said VL(CD3) and VH(CD3) are connected via a peptide linker consisting of 20 to 25, preferably 20 or 25 amino acids, preferably glycine and/or serine, and preferably are connected via a peptide linker comprising the amino acid sequence (GGGGS)5. In one embodiment said VL(CLDN) and VH(CLDN) are connected via a peptide linker consisting of 20 to 25, preferably 20 or 25 amino acids, preferably glycine and/or serine, and preferably are connected via a peptide linker comprising the amino acid sequence (GGGGS)5. In one embodiment said two VL-VH scFv units are connected via a linker peptide comprising the amino acid sequence SGGGGS. Said VL(CLDN)-VH(CLDN) scFv unit may comprise one or more interface disulfide bridges.

In one embodiment of any of the above aspects, said CLDN is CLDN18.2. Preferably said VH(CLDN) comprises an amino acid sequence represented by SEQ ID NO: 8 or a fragment thereof or a variant of said amino acid sequence or fragment and the VL(CLDN) comprises an amino acid sequence represented by SEQ ID NO: 15 or a fragment thereof or a variant of said amino acid sequence or fragment. Alternatively, said VH(CLDN) comprises an amino acid sequence represented by SEQ ID NO: 6 or a fragment thereof or a variant of said amino acid sequence or fragment and the VL(CLDN) comprises an amino acid sequence represented by SEQ ID NO: 11 or a fragment thereof or a variant of said amino acid sequence or fragment. In one embodiment said VH(CD3) comprises an amino acid sequence represented by SEQ ID NO: 95 or a fragment thereof or a variant of said amino acid sequence or fragment and the VL(CD3) comprises an amino acid sequence represented by SEQ ID NO: 96 or a fragment thereof or a variant of said amino acid sequence or fragment.

In one aspect the binding agent of the invention is in the format of a bispecific single chain antibody that comprises two scFv molecules connected via a linker peptide, wherein the heavy chain variable regions (VH) and the corresponding light chain variable regions (VL) are arranged, from N-terminus to C-terminus, in the order VH(CLDN)-VL(CLDN)-VH(CD3)-VL(CD3) or in the order VH(CD3)-VL(CD3)-VH(CLDN)-VL(CLDN). In one embodiment said VH(CLDN) and VL(CLDN) are connected via a peptide linker consisting of 15 to 20, preferably 15 or 20 amino acids, preferably glycine and/or serine, and preferably are connected via a peptide linker comprising the amino acid sequence (GGGGS)3. In one embodiment said VH(CD3) and VL(CD3) are connected via a peptide linker consisting of 15 to 20, preferably 15 or 20 amino acids, preferably glycine and/or serine, and preferably are connected via a peptide linker comprising the amino acid sequence GGGGS(GGS)3GGGS. In one embodiment said two VH-VL scFv units are connected via a linker peptide comprising the amino acid sequence SGGGGS.

In one embodiment of the above aspect, said CLDN is CLDN6. Preferably said VH(CLDN) comprises an amino acid sequence represented by SEQ ID NO: 22 or a fragment thereof or a variant of said amino acid sequence or fragment. Preferably said VL(CLDN) comprises an amino acid sequence represented by SEQ ID NO: 98, 99 or 100 or a fragment thereof or a variant of said amino acid sequence or fragment. Most preferably, said VL(CLDN) comprises an amino acid sequence represented by SEQ ID NO: 99 or a fragment thereof or a variant of said amino acid sequence or fragment. In one embodiment said VH(CD3) comprises an amino acid sequence represented by SEQ ID NO: 95, or a fragment thereof or a variant of said amino acid sequence or fragment and the VL(CD3) comprises an amino acid sequence represented by SEQ ID NO: 96 or a fragment thereof or a variant of said amino acid sequence or fragment.

In one embodiment said CLDN is CLDN18.2 and said binding agent of the invention comprises an amino acid sequence selected from the group consisting of SEQ ID NOs: 38, 39, 40 and 41 or a fragment or variant thereof.

In one embodiment said CLDN is CLDN18.2 and said binding agent of the invention comprises an amino acid sequence selected from the group consisting of SEQ ID NOs: 103, 66, 67, 68, 69, 70, 71, 72, 73, 74, 75, 76, 77, 78, 79, 80, 81, 82, 83, 84, 85, 86, 87, 88, 89, 90, 91, 92 and 93 or a fragment or variant thereof. In one embodiment, said CLDN is CLDN18.2 and said binding agent comprises an amino acid sequence selected from the group consisting of SEQ ID NOs: 103, 66, 67, 68, 69, 70, 71, 72, 73, 74, 75, 76, 77, 78, 79, 80, 81, 82, 83, 84, 85, 86, 87, 88, 89, 90, 91, 92 and 93 or a fragment or variant thereof, wherein said amino acid sequence lacks secretion signals such as N-terminal secretion signals, in particular the sequence according to SEQ ID NO: 51 and/or lacks His-tags such as C-terminal His-tags, in particular the sequence Gly-Gly-Ser-$(His)_6$ or $(His)_6$, if present.

In one embodiment said CLDN is CLDN6 and said binding agent of the invention comprises an amino acid sequence selected from the group consisting of SEQ ID NOs: 42, 43, 44 and 45 or a fragment or variant thereof.

In one embodiment said CLDN is CLDN6 and said binding agent of the invention comprises an amino acid sequence selected from the group consisting of SEQ ID NOs: 101, 102, 60, 61, 62, 63, 64 and 65 or a fragment or variant thereof. In one embodiment said CLDN is CLDN6 and said binding agent comprises an amino acid sequence selected from the group consisting of SEQ ID NOs: 101, 102, 60, 61, 62, 63, 64 and 65 or a fragment or variant thereof, wherein said amino acid sequence lacks secretion signals such as N-terminal secretion signals, in particular the sequence according to SEQ ID NO: 51 and/or lacks His-tags such as C-terminal His-tags, in particular the sequence Gly-Gly-Ser-$(His)_6$ or $(His)_6$, if present.

In one embodiment said cancer cells expressing CLDN18.2 are cancer cells of a cancer selected from the group consisting of gastric cancer, esophageal cancer, pancreatic cancer, lung cancer such as non small cell lung cancer (NSCLC), breast cancer, ovarian cancer, colon cancer, hepatic cancer, head-neck cancer, cancer of the gallbladder and the metastasis thereof, a Krukenberg tumor, peritoneal metastasis and/or lymph node metastasis.

In one embodiment said cancer cells expressing CLDN6 are cancer cells of a cancer selected from the group consisting of urinary bladder cancer, ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, uterine cancer, germ cell tumors such as a teratocarcinoma or an embryonal carcinoma, in particular germ cell tumors of the testis, and the metastatic forms thereof.

In one embodiment the binding agent has an N-terminal secretion signal and/or a C-terminal histidin epitope tag, preferable a six hisidin epitope tag.

In one aspect the invention relates to a recombinant nucleic acid which encodes a binding agent of the invention. In one embodiment the recombinant nucleic acid is in the form of a vector. In one embodiment the recombinant nucleic acid is RNA.

In one aspect the invention relates to a host cell comprising a recombinant nucleic acid of the invention.

In one aspect the invention relates to the binding agent of the invention, the recombinant nucleic acid of the invention or the host cell of the invention for use in therapy, in particular for use in treating or preventing cancer.

In one aspect the invention relates to a pharmaceutical composition comprising the binding agent of the invention, the recombinant nucleic acid of the invention or the host cell of the invention.

In one aspect the invention relates to a method of treating or preventing a cancer disease comprising administering to a patient the pharmaceutical composition of the invention.

In one embodiment cells of said cancer express a claudin to which said binding agent is capable of binding.

In one embodiment said claudin is CLDN18.2 and said cancer is selected from the group consisting of gastric cancer, esophageal cancer, pancreatic cancer, lung cancer such as non small cell lung cancer (NSCLC), breast cancer, ovarian cancer, colon cancer, hepatic cancer, head-neck cancer, cancer of the gallbladder and the metastasis thereof, a Krukenberg tumor, peritoneal metastasis and/or lymph node metastasis.

In one embodiment said claudin is CLDN6 and said cancer is selected from the group consisting of urinary bladder cancer, ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, uterine cancer, germ cell tumors such as a teratocarcinoma or an embryonal carcinoma, in particular germ cell tumors of the testis, and the metastatic forms thereof.

In one aspect, the invention provides a binding agent or nucleic acid coding therefor or a host cell as described herein for use in the methods of treatment described herein. In one embodiment, the invention provides a pharmaceutical composition as described herein for use in the methods of treatment described herein.

According to the invention, CLDN18.2 preferably has the amino acid sequence according to SEQ ID NO: 1 and CLDN6 preferably has the amino acid sequence according to SEQ ID NO: 2 or 3.

Other features and advantages of the instant invention will be apparent from the following detailed description and claims.

Design of the bi-scFvs in (A)N-terminal and (B)C-terminal position regarding the anti-TAA variable regions. Anti-CLDN18.2 $V_H$ and $V_L$ regions are generated from the sequence of a monoclonal CLDN18.2 antibody (mCLDN18.2ab). Anti-CD3 stands comprehensive for $V_H$ and $V_L$ regions generated from the sequences of the following monoclonal CD3 antibodies: UCHT1-HU (humanized mAB), UCHT1, CLB-T3, TR66, 145-2C11. Bi-scFv indicates bispecific single chain variable fragment; His, hexahistidyl-tag; HU, humanized; LL, long linker (15-18 amino acids); Sec, secretion signal; SL, short linker (5-6 amino acids); TAA, tumor associated antigen; V, variable region of the heavy (H) and light (L) chain of the antibody.

Figure 2:
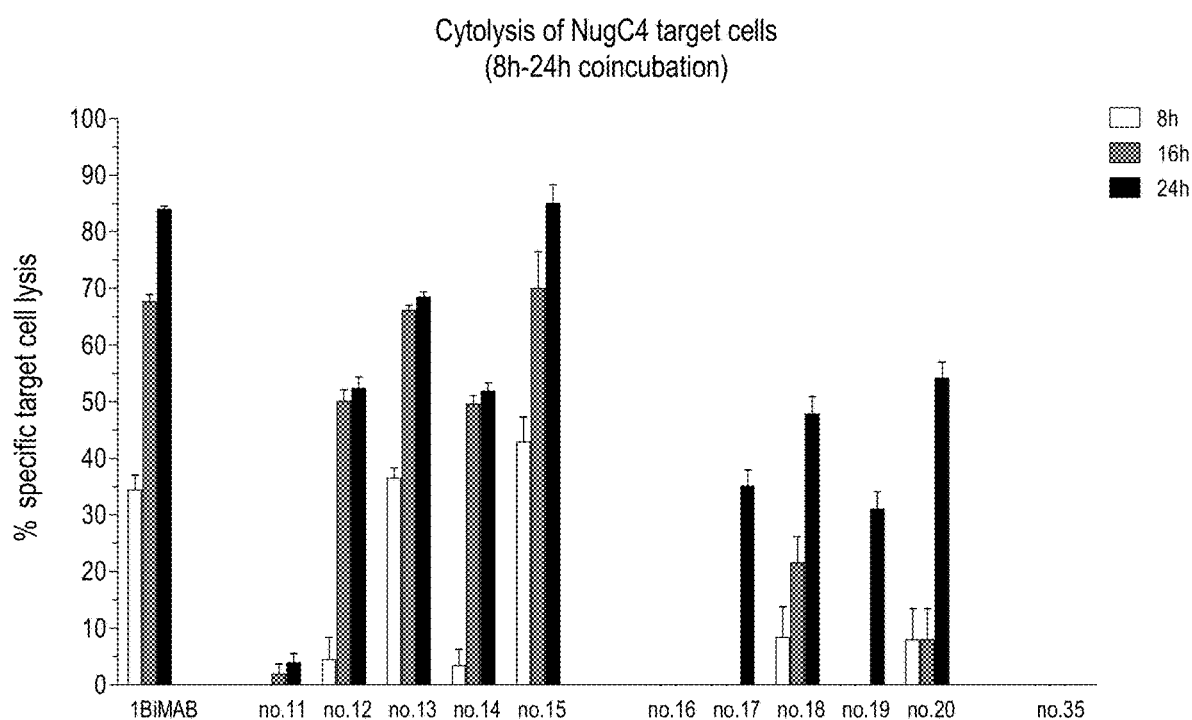

FIG. 2. Effect of domain orientation and anti-CD3-scFv selection on specific target cell lysis: 5'-mCLDN18.2ab $V_H$-$V_L$_TR66 $V_H$-$V_L$-3' bi-scFvs 1BiMAB and no. 15 are the most potent variants.

Several bi-scFv variants directed against CLDN18.2 and CD3 were transiently expressed in HEK293T cells and small-scale purified with Ni-NTA columns for the comparison of their potency in a cytotox assay. CLDN18.2 endogenously expressing NugC4 cells which stably express luciferase were taken as target cells. Human T cells and target cells were incubated in an E:T ratio of 5:1 with 5 ng/ml of each bi-scFv protein in a 96-well format. As negative controls no. 35 targeting a non-expressed TAA, no. 11, and no. 16—both targeting murine but not human T cells—were taken. Each test sample was plated sixfold, the control sample for $L_{min}$, was plated ninefold. Coincubation times before analysis were 8 h, 16 h, and 24 h. After addition of luciferin solution at the given time points, the luminescence was measured in an Infinite M200 TECAN reader. Specific target cell lysis was calculated by normalization to samples with control bi-scFv no. 35 ($L_{min}$). The most potent bi-scFv proteins—1BiMAB and no. 15—share the domain orientation and the anti-CD3 origin of mAB TR66 but differ in their codon optimization (HS and CHO, respectively) and the long linker sequences. CHO indicates Chinese Hamster Ovary; mAB, monoclonal antibody; HU, humanized; TAA, tumor associated antigen.

Figures 3A, 3B:
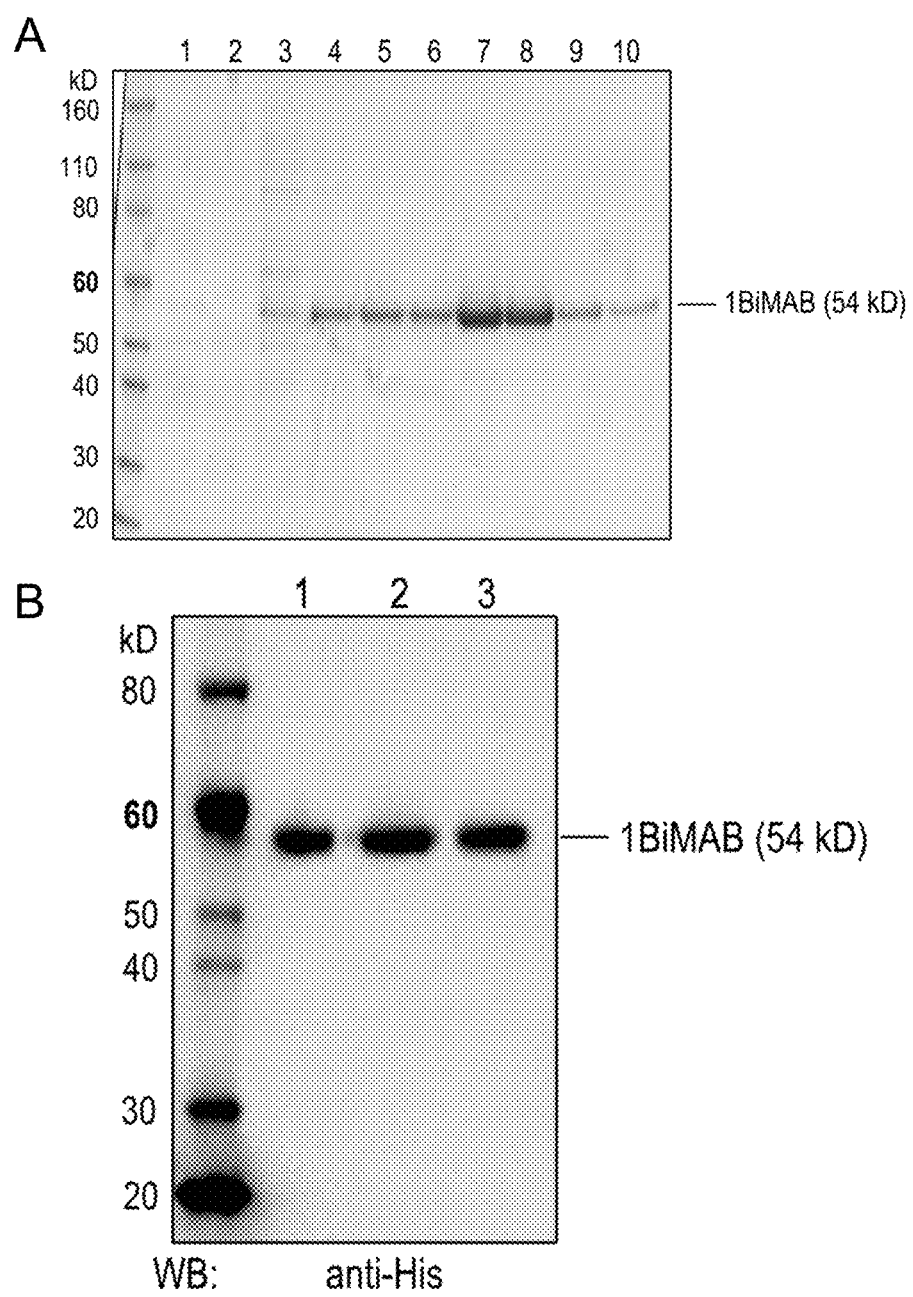

FIGS. 3A and 3B show a coomassie gel and western blot analysis of bi-scFv protein 1BiMAB.

Supernatant without FCS of monoclonal HEK293 cells stably expressing 1BiMAB was purified via Ni-NTA affinity chromatography (IMAC). Aliquots of different purification steps were loaded to 4-12% Bis-Tris gels. (A) Coomassie staining of cell supernatant, flow through and eight fractions of the eluate. Fractions of the first eluted peak were discarded, fractions of the second eluted peak were pooled for further studies, dialyzed against PBS and subsequently against 200 mM arginine buffer. (Lane 1: HEK293/1BiMAB SN; lane 2: IMAC flow through fraction; lanes 3-4: Fractions of elution peak 1 (discarded); lanes 5-10: Fractions of elution peak 2 (pooled)) (B) Western blot analysis of 0.5 μg of 1BiMAB from three independent purifications (lane 1, 2, 3). Detection was performed with primary monoclonal anti-His and secondary peroxidase conjugated anti-mouse antibody. IMAC indicates immobilized metal affinity chromatography; PBS, phosphate buffered saline; SN, supernatant; WB, western blot.

FIGS. 4A, 4B, 4C, and 4D show a Bi-scFv protein 1BiMAB binds efficiently and specifically to CLDN18.2-expressing target cells and human T cells.

(A) $2.5 \times 10^5$ CLDN18.2 endogenously expressing NugC4 cells were incubated with 50 μg/ml 1BiMAB or 10 μg/ml mCLDN18.2ab as positive control and the corresponding APC-conjugated secondary antibodies. Control stainings included secondary APC-conjugated antibodies alone (g-a-h, g-a-m), anti-His and g-a-m APC, or 1 BiMAB and g-a-m APC. Analysis was performed via flow cytometry. MFI of APC signal was calculated by FlowJo software. (B) $1 \times 10^5$ CLDN18.2 endogenously expressing NugC4 cells were stained with escalating 1BiMAB concentrations (20 pg/ml-20 μg/ml), anti-His and g-a-m APC. As negative control cells were incubated with anti-His and g-a-m APC. As positive control mCLDN18.2ab and g-a-h APC was used. MFI of APC signal was calculated by FlowJo software. (C) $1 \times 10^6$ human T cells were incubated with escalating 1BiMAB concentrations (2 ng/ml-2 μg/ml), anti-His and g-a-m APC. As negative control cells were incubated with anti-His and g-a-m APC or g-a-m APC alone. MFI of APC signal was calculated by FlowJo software. (D) $1 \times 10^5$ CLDN18.2 negative PA-1 cells were incubated with escalating 1 BiMAB concentrations (10 ng/ml-10 μg/ml), anti-His and g-a-m APC. As negative control, cells were stained with anti-His and g-a-m APC or g-a-h APC alone. 10 μg/ml mCLDN18.2ab and g-a-h APC were used to confirm CLDN18.2 negativity of cells.

G-a-h indicates goat-anti-human; g-a-m, goat-anti mouse; MFI, mean fluorescence intensity; TL, T lymphocyte.

Figure 5:
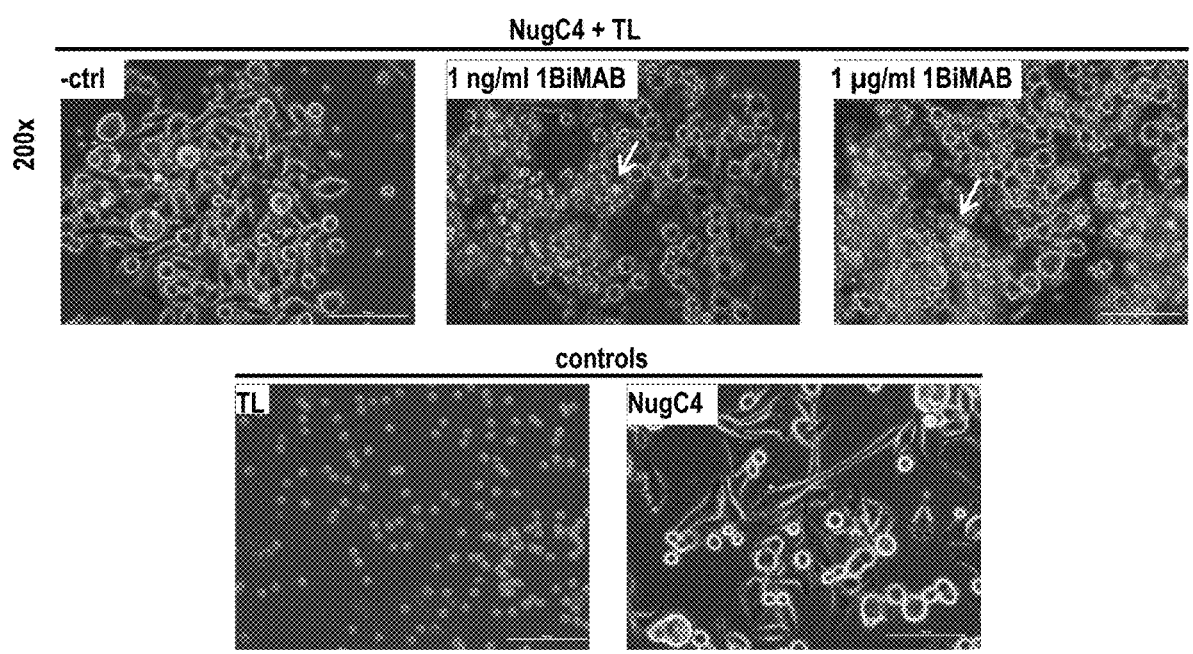

FIG. 5. Bi-scFv protein 1BiMAB leads to T cell clustering on CLDN18.2 positive target cells. CLDN18.2 endogenously expressing NugC4 cells were incubated for 24 h with 1 ng/ml and 1 μg/ml 1BiMAB and human T cells in an effector to target ratio of 5:1 in 6-well plates. T cells alone (TL), target cells alone (NugC4) and human T cells with target cells (–ctrl) were chosen as control samples. After 24 h samples were photographed with a Nikon Eclipse Ti microscope with 200× magnification. White arrowheads point to T cell clusters on target cells. TI, indicates T lymphocyte.

Figures 6A, 6B:
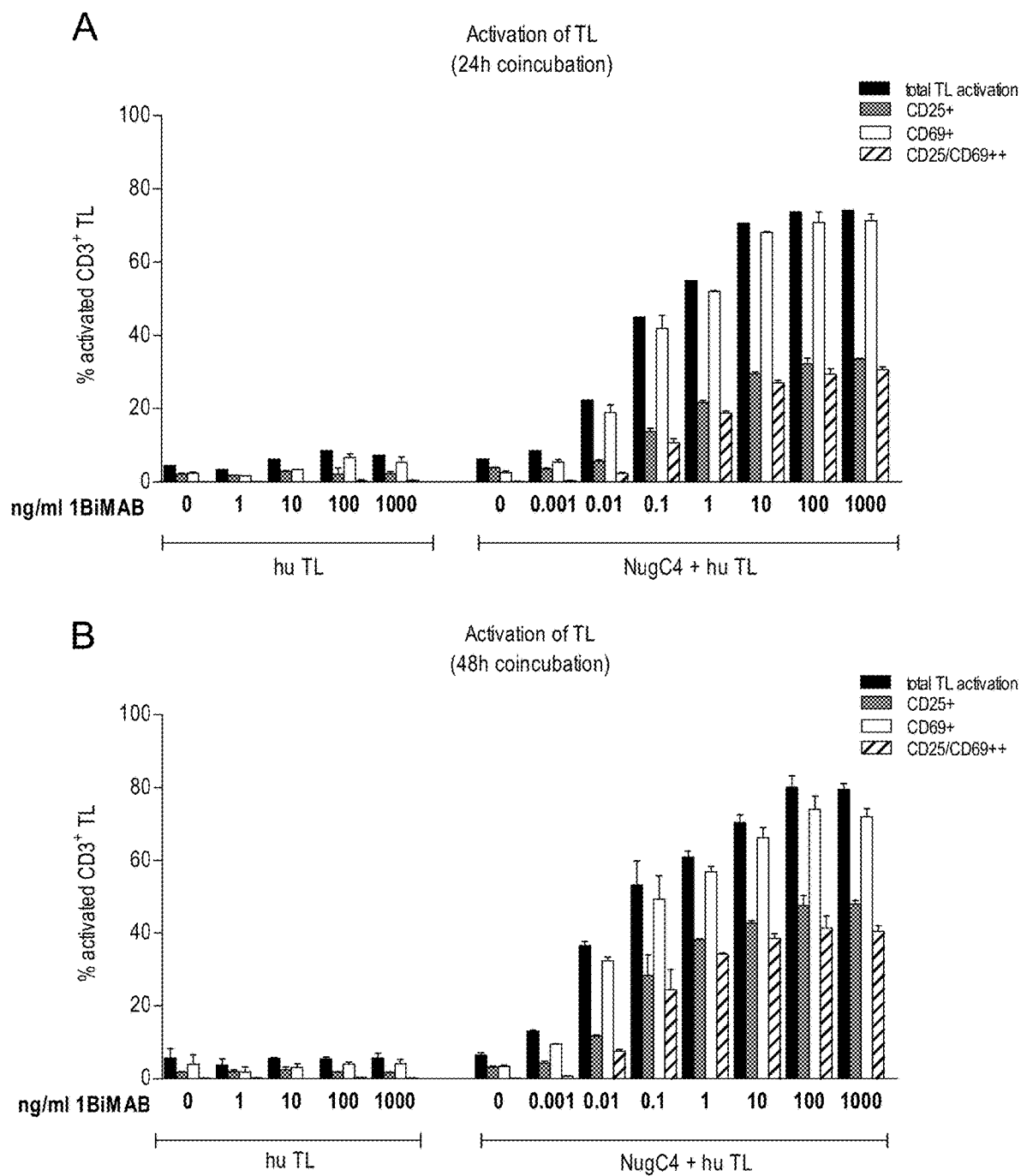

FIGS. 6A and 6B show 1BiMAB mediates T cell activation in a dose dependent manner.

CLDN18.2 endogenously expressing NugC4 cells were incubated for 24 h and 48 h with escalating concentrations of bi-scFv protein 1BiMAB (0.001-1000 ng/ml) and human T cells in an effector to target ratio of 5:1 in duplicates in a 24-well format. As control human T cells were incubated with 1-1000 ng/ml 1BiMAB without NugC4 target cells to verify the target dependent activation of T cells mediated by 1BiMAB. After 24 h (A) and 48 h (B) T cells were harvested and labeled with anti-CD3-FITC, anti-CD25-PE, and anti-CD69-APC and analyzed by flow cytometry. TL indicates T lymphocyte.

Figures 7A, 7B:
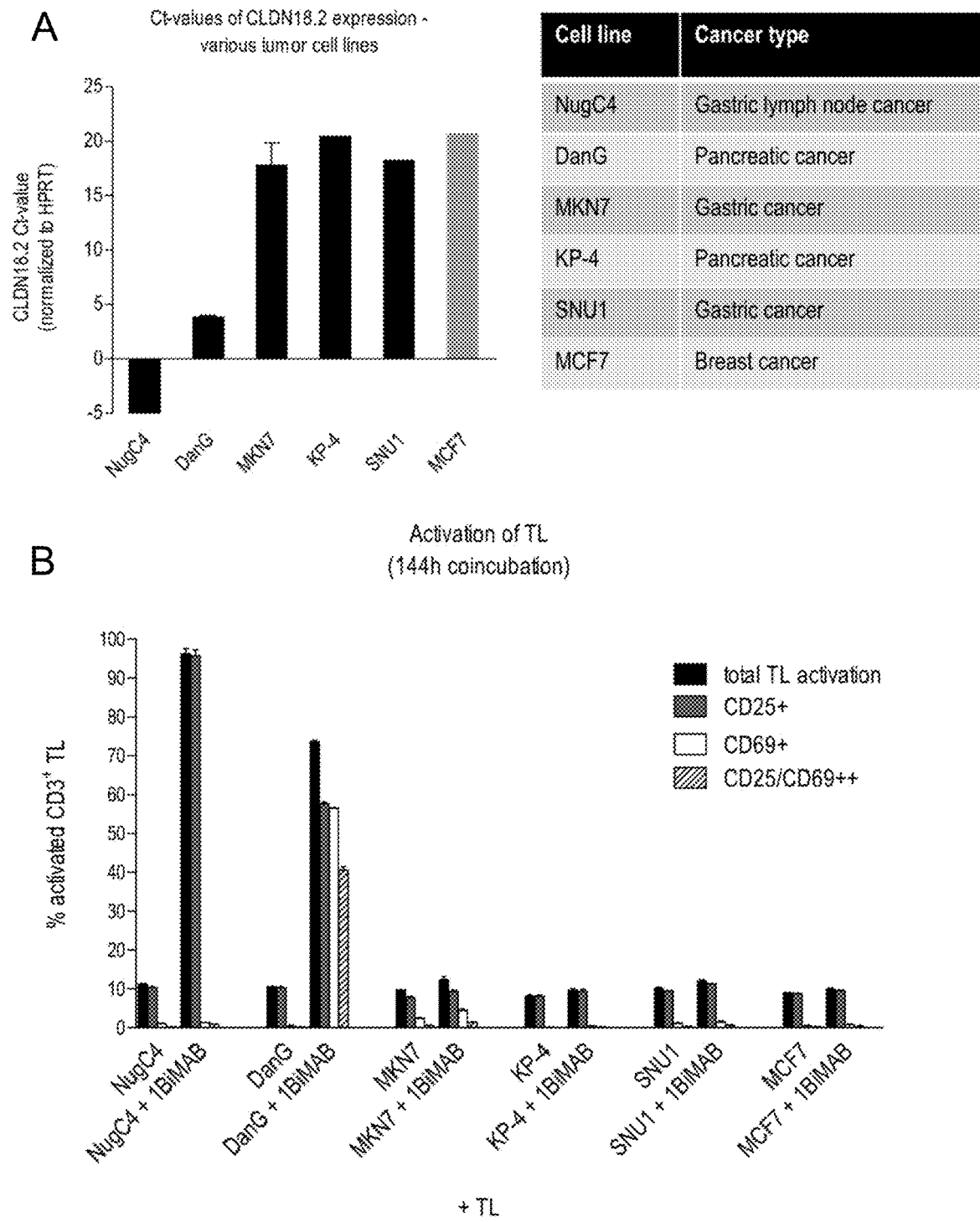

FIGS. 7A and 7B show 1BiMAB mediates strictly target dependent T cell activation even after long term incubation with CLDN18.2 high, low, and non-expressing cell lines.

(A) RT-PCR data generated from total RNA of six tumor cell lines are shown. Ct-values of CLDN18.2 expression normalized to housekeeping gene HPRT has been calculated from two independent experiments. Breast cancer cell line MCF7 (grey bar) was chosen as negative CLDN18.2-expressing control cell line. (B) Cancer cell lines from (A) were incubated for 144 h with 5 ng/ml bi-scFv protein 1BiMAB with or without human T cells in an effector to target ratio of 5:1 in duplicates in a 6-well format. T cells were labeled with anti-CD3-FITC, anti-CD25-PE and anti-CD69-APC to analyze total T cell population (CD3), early activation (CD69), and late activation (CD25) of T cells by flow cytometry. TL indicates T lymphocyte.

Figure 8A:
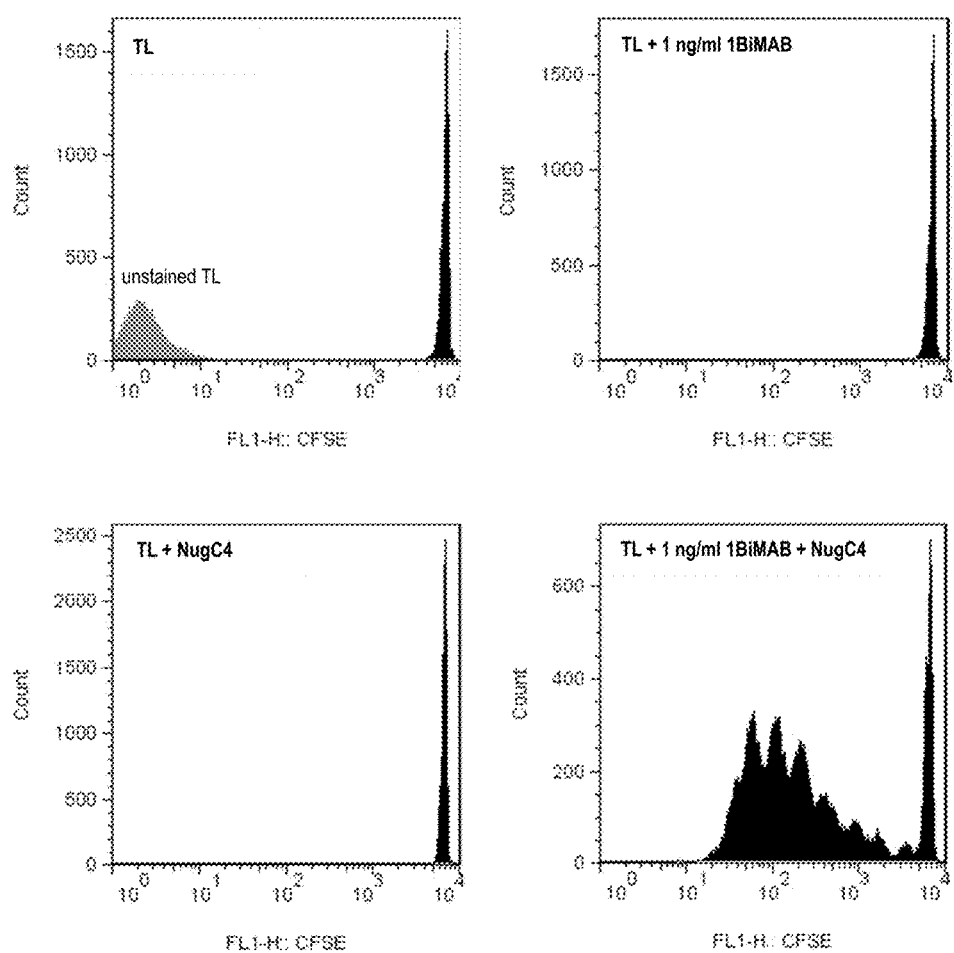
Figure 8B:
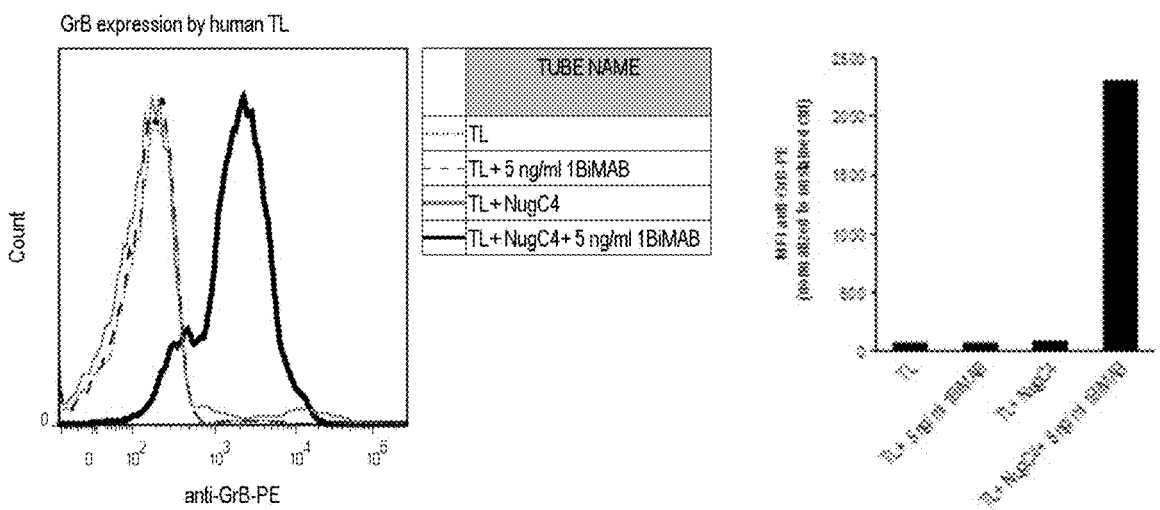

FIGS. 8A and 8B show 1BiMAB induces T cell proliferation and Granzyme B upregulation only in the presence of CLDN18.2 positive target cells.

(A) Human T cells were CFSE stained and cultivated alone (TL) or in the presence of 1 ng/ml 1BiMAB (TL–1 ng/ml 1BiMAB), NugC4 cells (TL+NugC4), or NugC4 cells and 1 ng/ml 1BiMAB (TL+1 ng/ml 1BiMAB+NugC4) for 120 h. A 5:1 effector to target ratio was selected. Decrease of CFSE signal indicating T cell proliferation was analyzed by flow cytometry. (B) Human T cells were incubated with or without NugC4 target cells and with or without 5 ng/ml bi-scFv 1BiMAB protein. Effector to target ratio was of 5:1 in a 6-well format. After 96 h of coincubation T cells were harvested and intracellularly stained with anti-GrB-PE and analyzed by flow cytometry. MFI of anti-GrB-PE signal was calculated by FlowJo software. The signal of unstained sample TL+. NugC4+5 ng/ml 1BiMAB was subtracted from all samples. CFSE indicates carboxyfluorescein succinimidyl ester; GrB, Granzyme B; MFI, mean fluorescence intensity; PE, phycoerythrin; TL, T lymphocytes.

Figure 9:
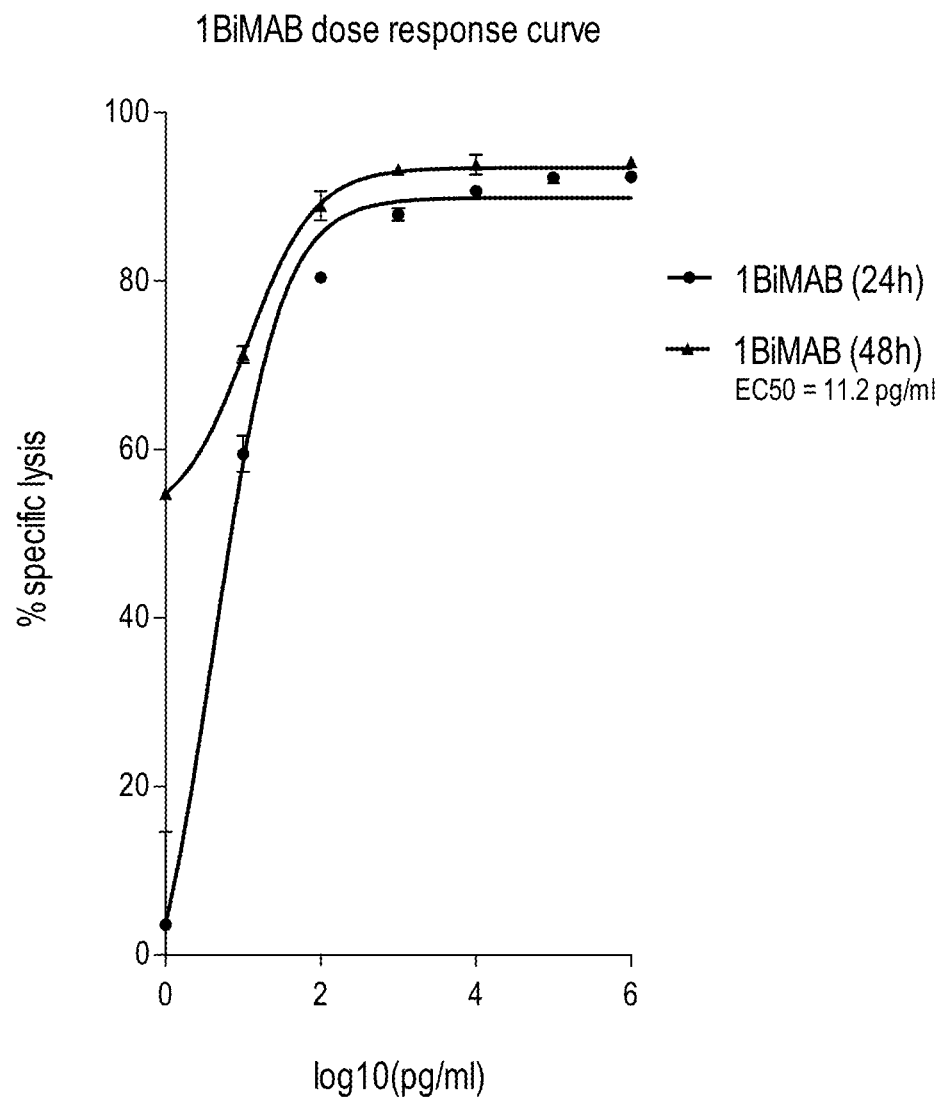

FIG. 9. EC50 of 1BiMAB for specific target cell lysis after 48 h is approximately 10 pg/ml.

CLDN18.2 endogenously expressing NugC4 cells which stably express luciferase were incubated for 24 h and 48 h with bi-scFv protein 1BiMAB in escalating concentrations (0.001-1000 ng/ml) with human T cells in an effector to target ratio of 5:1 in triplicates in a 96-well format. As minimum lysis ($L_{min}$) control effector and target cells were plated without bi-scFv 1BiMAB. Maximum lysis ($L_{max}$) for the normalization to spontaneous luminescence counts was achieved by addition of Triton X-100 to control wells containing effector and target cells in the absence of bi-scFv shortly prior to luciferin addition. After addition of luciferin solution the luminescence was measured in an Infinite M200 Tecan microplate reader after 24 h and 48 h. Specific target cell lysis was calculated by the formula: % specific lysis= $[1-(\text{luminescence}_{test\ sample}-L_{max})/(L_{min}-L_{max})]\times 100$. Values were plotted against log 10 of 1BiMAB concentration. EC50 indicates the half maximal effective concentration; L, lysis.

FIGS. 10A, 10B, 10C, and 10D show 1BiMAB shows therapeutic in vivo efficacy in an advanced SC tumor model.

NOD.Cg-Prkdscid IL2rgtmlWjl/SzJ (NSG) mice were injected SC with $1 \times 10^7$ HEK293 stably expressing CLDN18.2. Five days later $2 \times 10^7$ human PBMC effector cells were injected IP to groups G3 and G4, control groups (G1 and G2) received PBS only. Daily IP application of 5 μg bi-scFv protein 1 BiMAB per animal or vehicle as control started at the following day. Therapy was administered for 22 days, tumor volume was measured using a caliper and calculated by the formula $mm^3$=length mm×width mm× (width mm/2). (A) The tumor volume of single mice and the median per group is shown for treatment days 0 and 15 (upper row), and 3 and 13 days after the end of treatment (bottom row). (B) The mean tumor volume of the two treatment groups engrafted with human effector cells is shown. Dashes indicate sacrificed animals. (C) Kaplan-Meier survival curve presenting all groups from the day of tumor inoculation to day 41. Animals were sacrificed as soon as the tumor volume exceeded 500 mm$^3$. After day 41 all remaining animals were sacrificed to analyze the engraftment of human effector cells in the spleens of mice. (D) Splenocytes of all mice were isolated and stained with anti-CD45-APC and anti-CD3-FTC to detect human T cells by flow cytometry. Median engraftment is shown in a boxplot diagram. G indicates group; IP, intraperitoneal; PBMC, peripheral blood mononuclear cells; PBS, phosphate buffered saline; SC, subcutaneous.

Figure 11A:
Figure 11B:
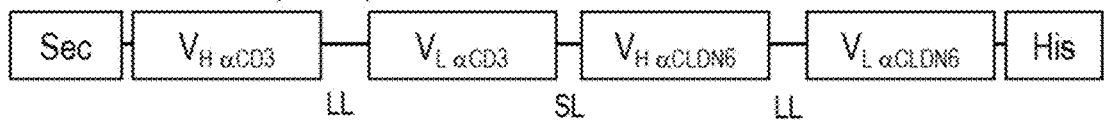

FIGS. 11A and 11B show a modular scheme illustrating the design of recombinant hi-scFv proteins targeting TAA CLDN6.

Design of the bi-scFvs in (A)N-terminal and (B)C-terminal position regarding the anti-TAA variable regions. Anti-CLDN6 $V_H$ and $V_L$ regions are generated from the sequence of a monoclonal CLDN6 antibody (mCLDN6ab). Anti-CD3 $V_H$ and $V_L$ regions are generated from the sequence of the monoclonal CD3 antibody TR66. Bi-scFv indicates bispecific single chain variable fragment; His, hexahistidyl-tag; LL, long linker (15-18 amino acids); Sec, secretion signal; SL, short linker (5 amino acids); TAA, tumor associated antigen; V, variable region of the heavy (H) and light (L) chain of the antibody.

Figure 12:
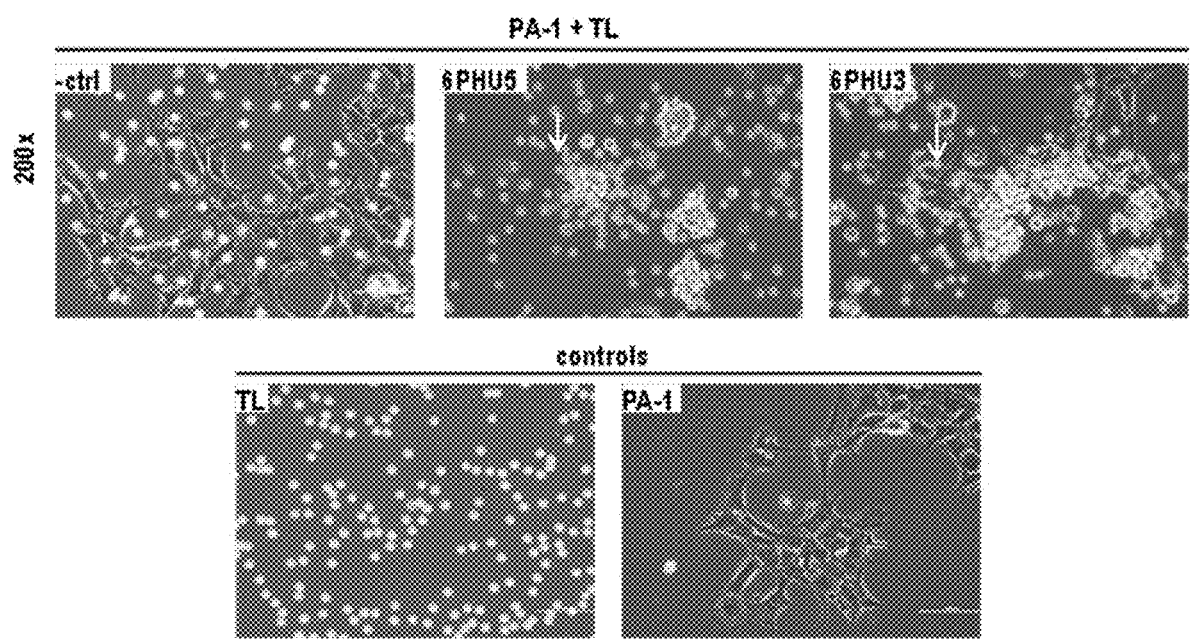

FIG. 12. Bi-scFv proteins 6PHU5 and 6PHU3 lead to T cell clustering on CLDN6 positive target cells.

CLDN6 endogenously expressing PA-1 cells were incubated for 24 h with 50 ng/ml 6PHU5 or 6PHU3 and human T cells in an effector to target ratio of 5:1 in 6-well plates. T cells alone (TL), target cells alone (PA-1) and human T cells with target cells (-ctrl) were chosen as control samples. After 24 h samples were photographed with a Nikon Eclipse Ti microscope with 200× magnification. White arrowheads point to T cell clusters on target cells. TL indicates T lymphocyte.

Figure 13:
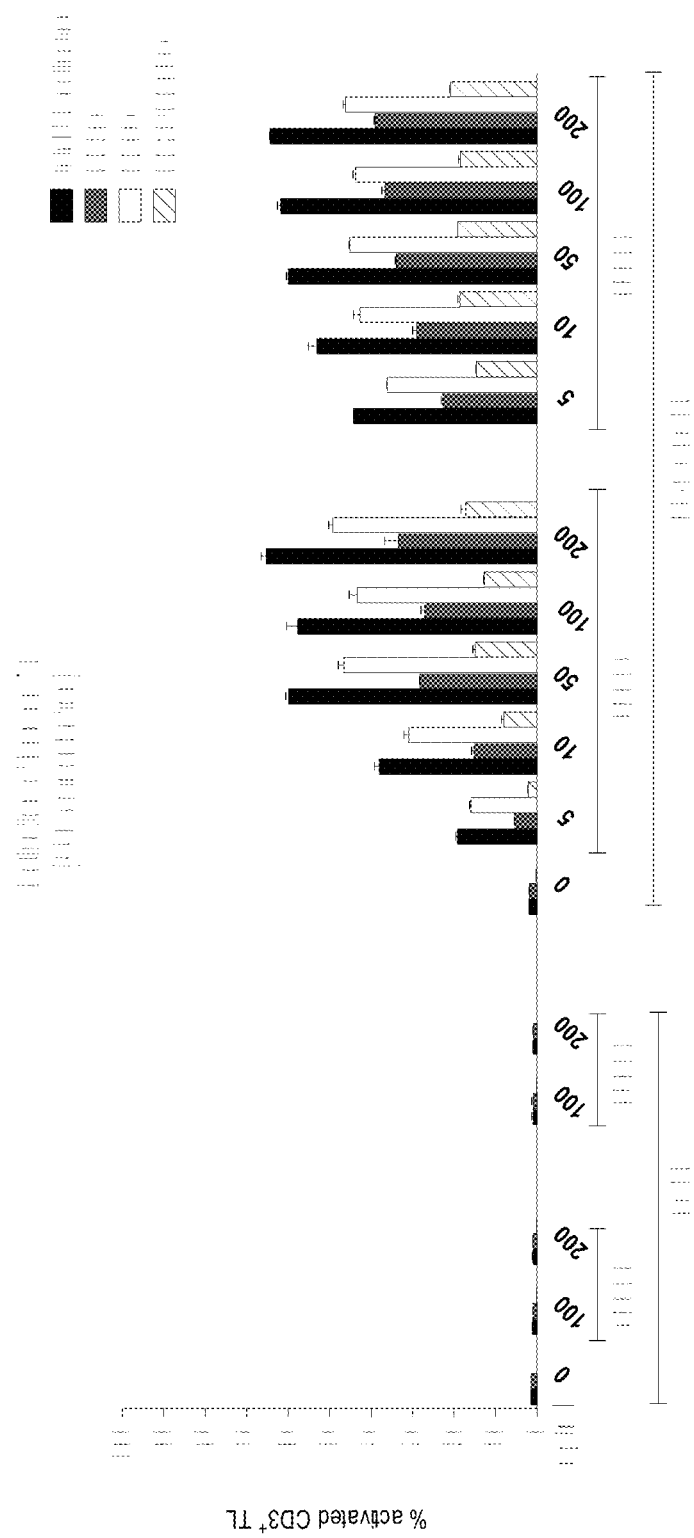

FIG. 13. Effect of domain orientation on efficacy: bi-scFv protein 6PHU3 is slightly more efficient in inducing T cell activation than 6PHU5.

CLDN6 endogenously expressing PA-1 cells were incubated for 44 h with escalating concentrations (5-200 ng/ml) of 6PHU5 or 6PHU3 and human T cells in an effector to target ratio of 5:1 in duplicates in a 6-well format. As control human T cells were incubated with 100 and 200 ng/ml 6PHU5 or 6PHU3 without target cells. After 44 h T cells were harvested and labeled with anti-CD3-FITC, anti-CD25-PE, and anti-CD69-APC. Dose-dependent T cell activation was analyzed by flow cytometry. Hu indicates human; TL, T lymphocyte.

Figure 14A:
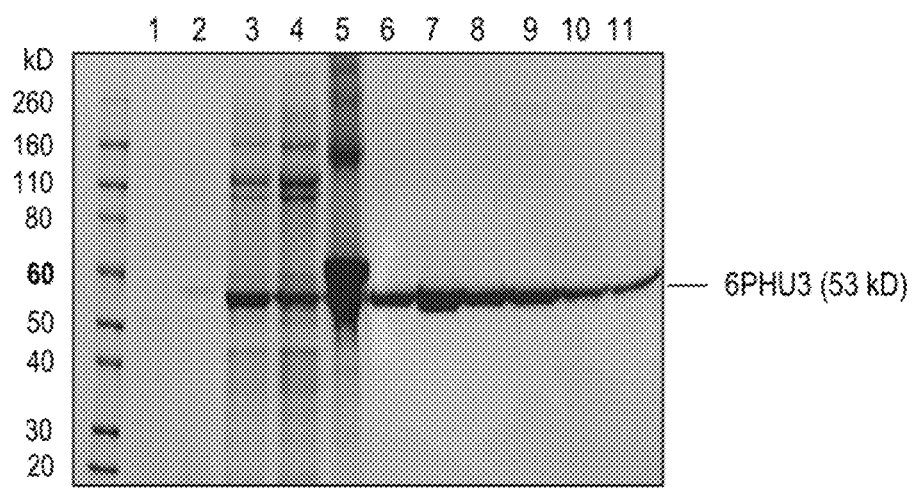
Figure 14B:
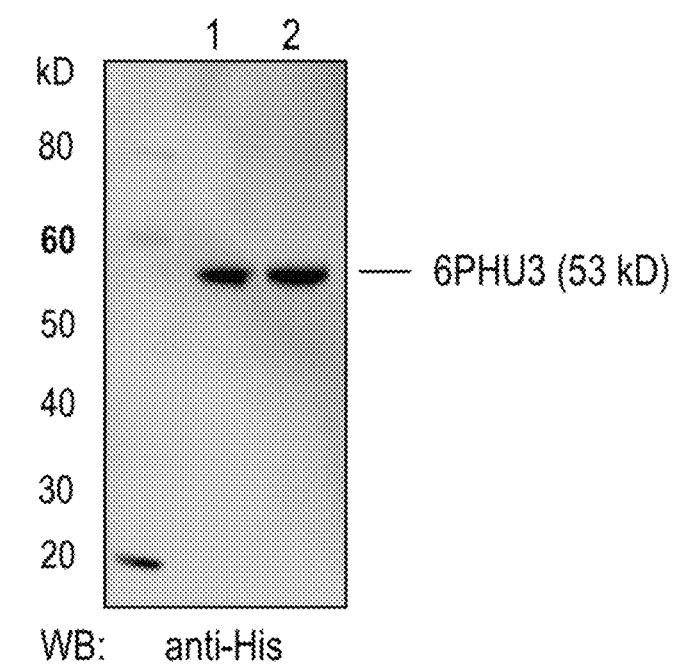

FIGS. 14A and 14B show a coomassie gel and western blot analysis of 6PHU3 protein.

Supernatant without FCS of polyclonal HEK293 cells stably expressing 6PHU3 was purified via Ni-NTA affinity chromatography (IMAC). Aliquots of different purification steps were loaded to 4-12% Bis-Tris gels. (A) Coomassie staining of cell supernatant, flow through and nine fractions of eluate. Fractions of the first eluted peak were discarded, fractions of the second and third eluted peaks were pooled for further studies, dialyzed against PBS and subsequently against 200 mM arginine buffer. (Lane 1: HEK293/6PHU3 SN; lane 2: IMAC flow through fraction: lanes 3-5: Fractions of elution peak 1 (discarded); lanes 6-11: Fractions of elution peaks 2 and 3 (pooled)) (B) Western blot analysis of 0.5 µg of 6PHU3 from two independent purifications. Detection was performed with primary monoclonal anti-His and secondary peroxidase conjugated anti-mouse antibody. IMAC indicates immobilized metal affinity chromatography; PBS; phosphate buffered saline; SN, supernatant; WB, western blot.

Figure 15A:
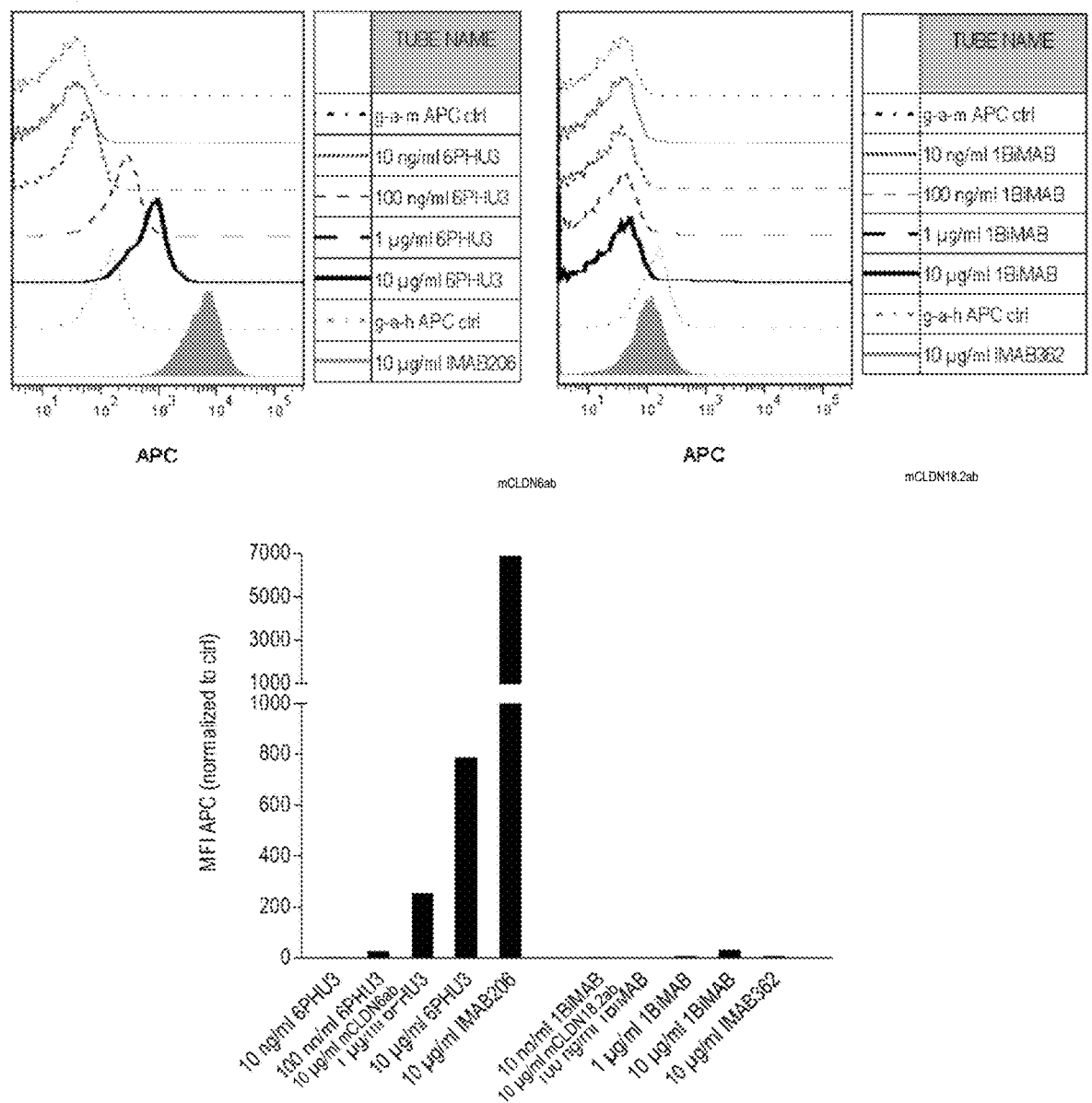
Figure 15A:
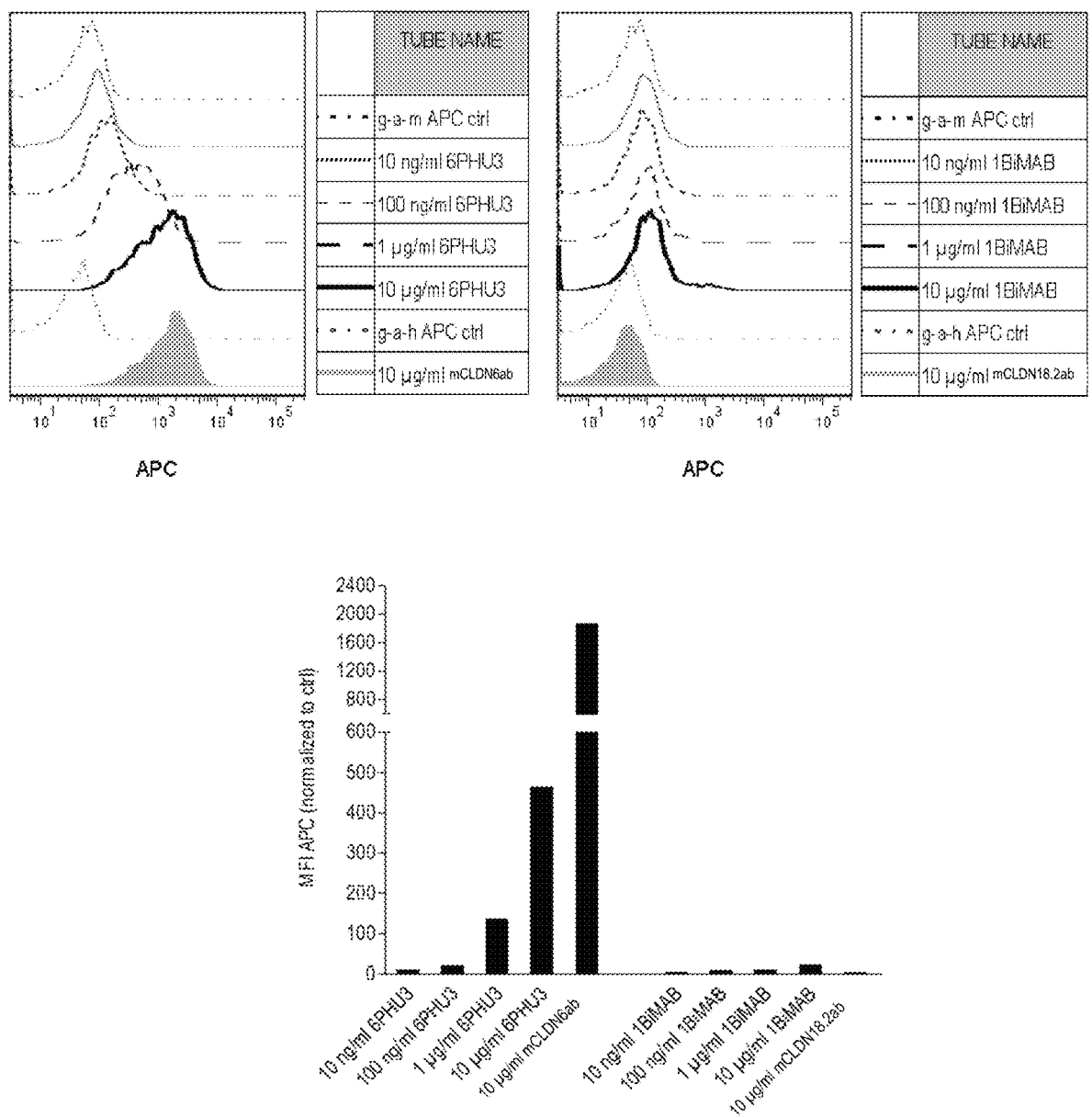
Figure 15B:
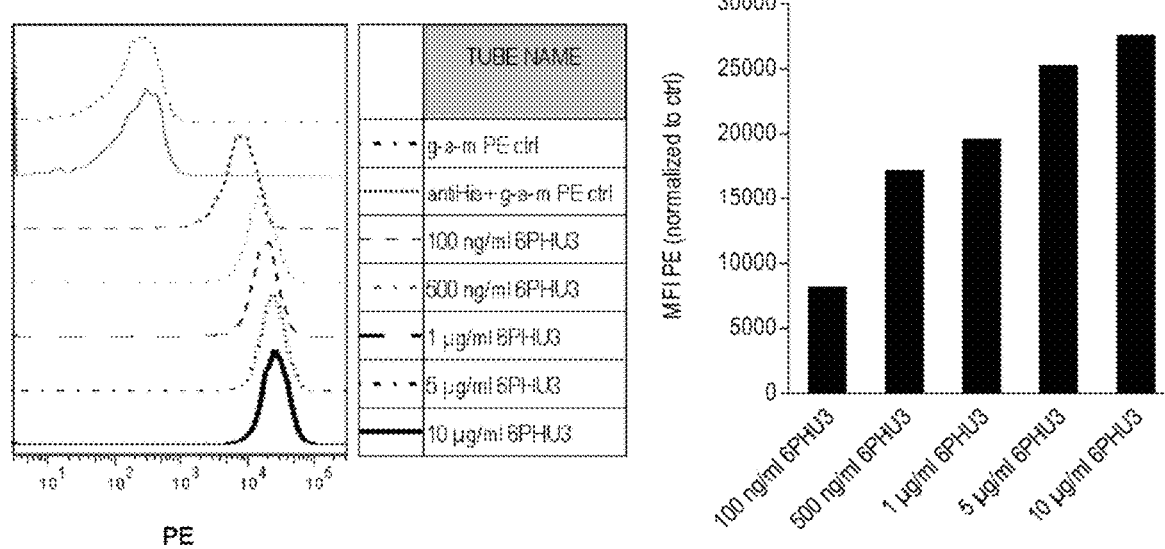
Figure 15C:
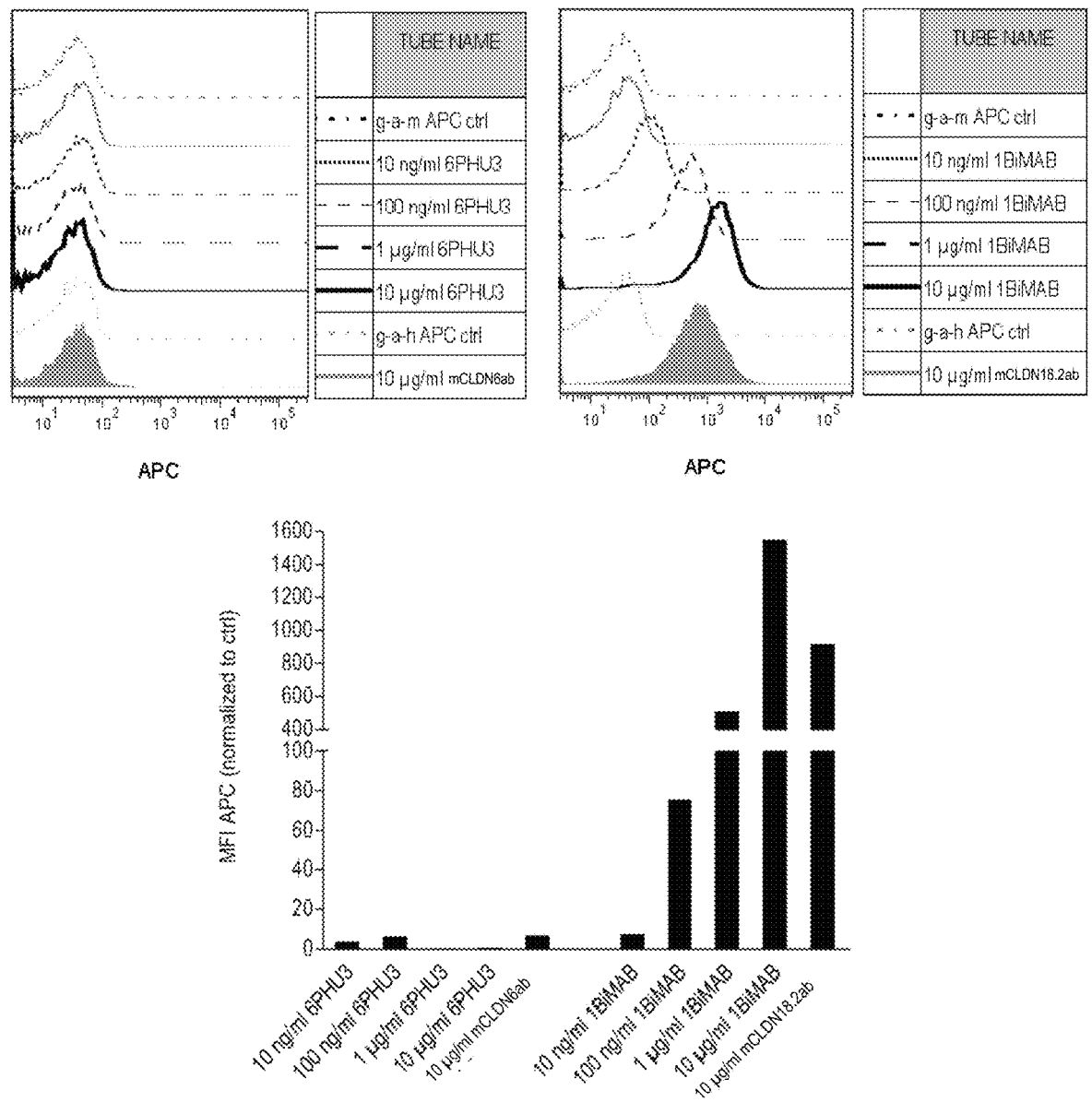

FIGS. 15A, 15B, and 15C show bi-scFv protein 6PHU3 binds efficiently and specifically to CLDN6-expressing target cells and human T cells.

(A) $1 \times 10^5$ CLDN6 endogenously expressing PA-1 and OV-90 cells were incubated with escalating concentrations of 6PHU3 or control bi-scFv 1BiMAB (10 ng/ml-10 µg/ml) and 10 µg/ml mCLDN6ab or control mAB mCLDN18.2ab with the corresponding APC-conjugated secondary antibodies. Control stainings were secondary APC-conjugated antibodies alone (g-a-h, g-a-m). Analysis was performed via flow cytometry. MFI of APC signal was calculated by FlowJo software. (B) $5 \times 10^5$ human T cells were incubated with escalating 6PHU3 concentrations (100 ng/ml-10 µg/ml), anti-His and g-a-m PE. As negative control cells were incubated with anti-His and g-a-m PE, or g-a-m PE alone. MFI of PE signal was calculated by FlowJo software. (C) $1 \times 10^5$ CLDN6 negative NugC4 cells were incubated with escalating 6PHU3 and 1BiMAB concentrations (10 ng/ml-10 µg/ml), anti-His and g-a-m APC. As negative control cells were incubated with g-a-m APC alone. 10 µg/ml mCLDN6ab and g-a-h APC were used to confirm CLDN6 negativity of cells. As positive control mCLDN18.2ab and g-a-h APC was used. MFI of APC signal was calculated by FlowJo software. APC indicates allophycocyanin; g-a-h, goat-anti-human; g-a-m, goat-anti-mouse; mAB, monoclonal antibody; MFI, mean fluorescence intensity; PE, phycoerythrin; TL, T lymphocyte.

Figures 16A, 16B:
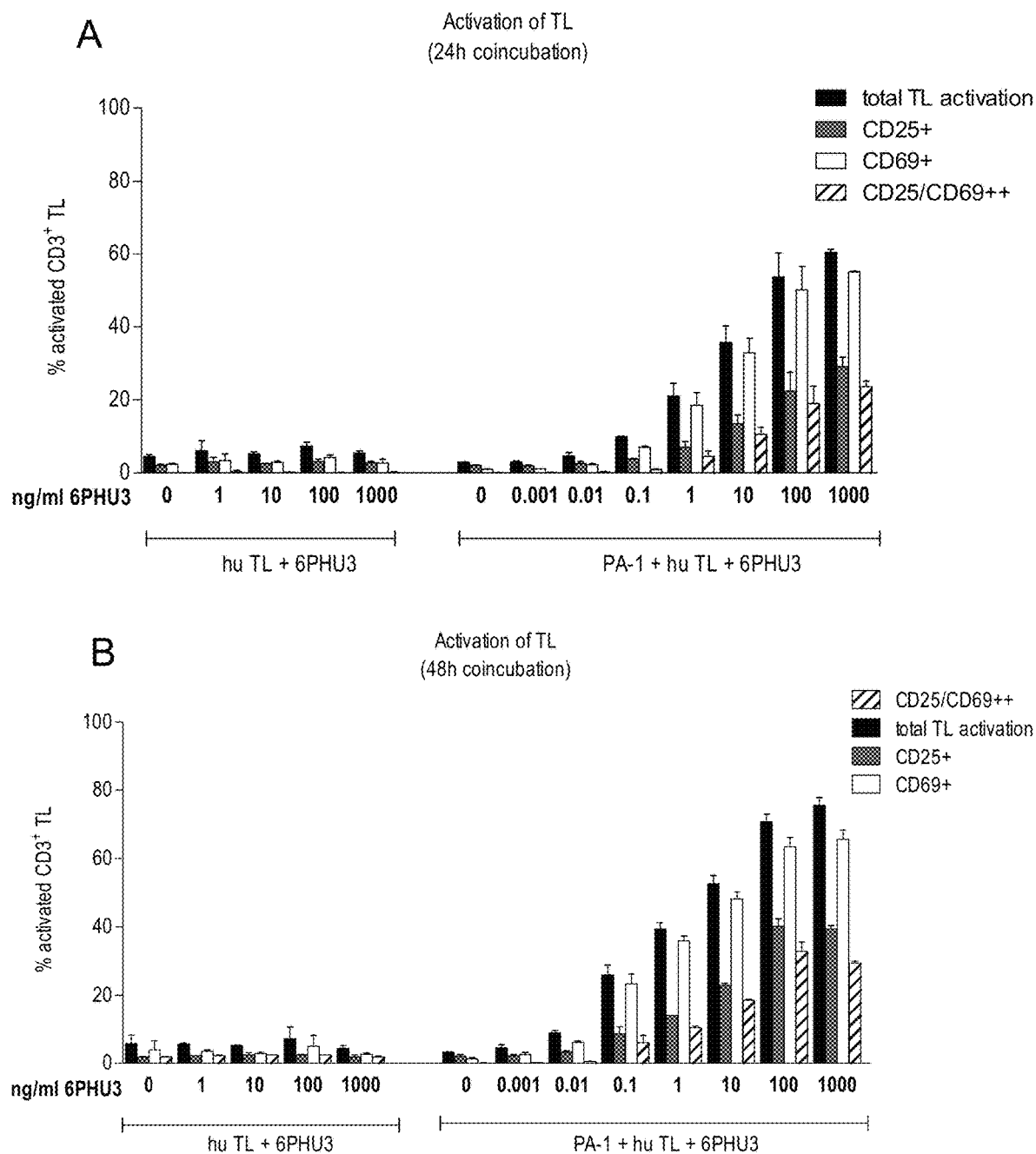

FIGS. 16A and 16B show 6PHU3 mediates T cell activation in a dose dependent manner.

CLDN6 endogenously expressing PA-1 cells were incubated for 24 h and 48 h with escalating concentrations of bi-scFv protein 6PHU3 (0.001-1000 ng/ml) and human T cells in an effector to target ratio of 5:1 in duplicates in a 24-well format. As control human T cells were incubated with 1-1000 ng/ml 6PHU3 without PA-1 target cells to verify the target dependent activation of T cells mediated by 6PHU3. After 24 h (A) and 48 h (B) T cells were harvested and labeled with anti-CD3-FITC, anti-CD25-PE, and anti-CD69-APC and analyzed by flow cytometry. TL indicates T lymphocyte.

Figure 17:
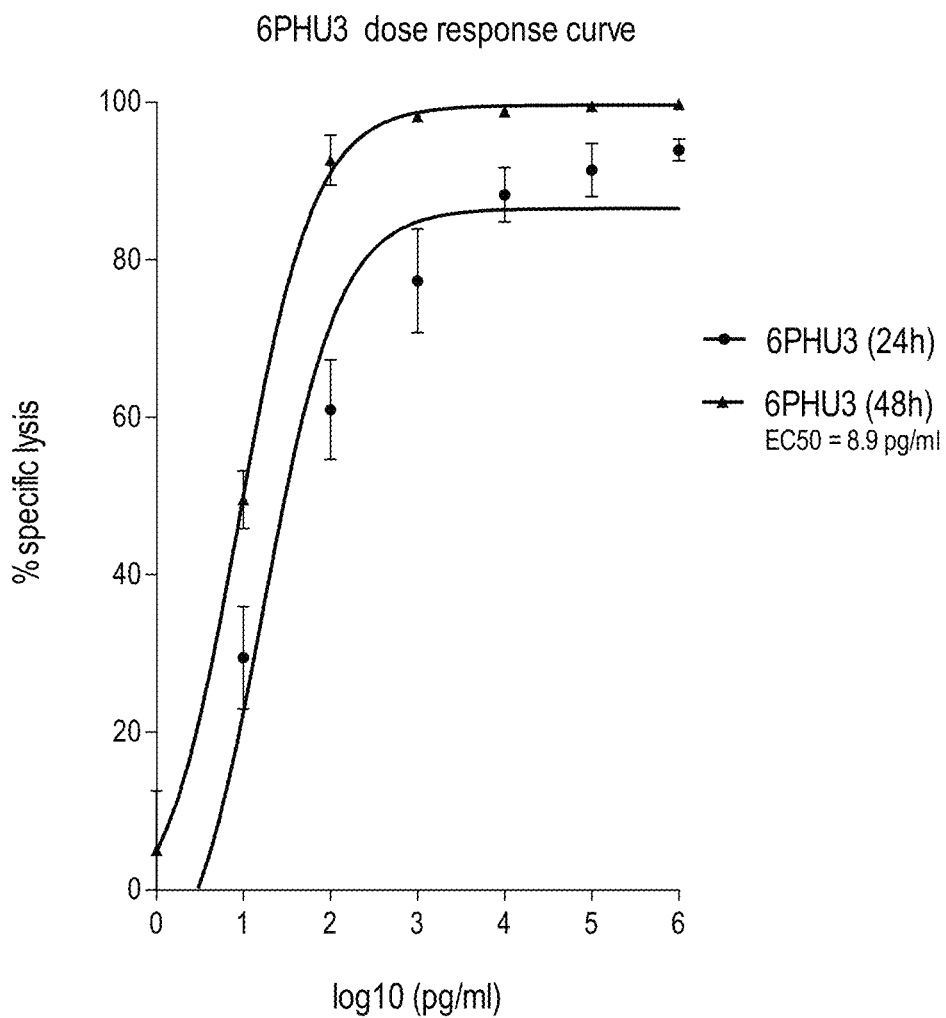

FIG. 17. EC50 of 6PHU3 for specific target cell lysis after 48 h is approximately 10 pg/ml.

CLDN6 endogenously expressing PA-1 cells which stably express luciferase were incubated for 24 h and 48 h with 6PHU3 protein in escalating concentrations (0.001-1000 ng/ml) with human T cells in an effector to target ratio of 5:1 in triplicates in a 96-well format. As minimum lysis control ($L_{min}$) effector and target cells were plated without bi-scFv 6PHU3. Maximum lysis ($L_{max}$) for the normalization to spontaneous luminescence counts was achieved by addition of Triton X-100 to control wells containing effector and target cells in the absence of bi-scFv shortly prior to luciferin addition. After addition of luciferin solution the luminescence was measured in an Infinite M200 Tecan microplate reader after 24 h and 48 h. Specific target cell lysis was calculated by the formula: % specific lysis=$[1-(\text{luminescence}_{test\ sample}-L_{max})/(L_{min}-L_{max})] \times 100$. Values were plotted against log 10 of 6PHU3 concentration. EC50 indicates the half maximal effective concentration; L, lysis.

FIGS. 18A, 18B, 18C, and 18D show 6PHU3 shows therapeutic in vivo efficacy in an advanced SC tumor model.

NOD.Cg-Prkd$^{scid}$ IL2rg$^{tm1Wjt}$/SzJ (NSG) mice were injected SC with 1×10⁷ PA-1 endogenously expressing CLDN6. 15 days later 2×10⁷ human PBMC were injected IP to groups G3 and G4, control groups (G1 and G2) received PBS only. Daily IP application of 5 µg 6PHU3 per animal or control bi-scFv 1BiMAB or vehicle alone as control started five days after PBMC injection. Therapy was administered for 25 days, tumor volume was measured using a caliper and calculated by the formula mm³=length mm×width mm× (width mm/2). (A) The tumor volume of single mice and the median per group is shown for treatment days 0 and 14 (upper row), and 21 and 25 (bottom row). (B) The mean tumor volume of all treatment groups is shown. Dashes indicate sacrificed animals. (C) A Kaplan-Meier survival curve of all groups from the day of tumor inoculation till day 45 is shown. Animals were sacrificed at a tumor volume >1500 mm³. After day 45 all remaining animals were sacrificed to analyze the engraftment of human effector cells in the spleens of mice. (D) Splenocytes of all mice were isolated and stained with anti-CD45-APC and anti-CD3-FITC to detect human T cells by flow cytometry. Median engraftment is shown in a boxplot diagram. IP indicates intraperitoneal; PBMC, peripheral blood mononuclear cells; PBS, phosphate buffered saline; SC, subcutaneous.

FIGS. 19A, 19B, 19C, 19D, and 19E show enhanced T cell infiltration into SC PA-1 tumors in response to 6PHU3 treatment.

NSG mice were injected SC with 1×10⁷ PA-1 endogenously expressing CLDN6. 15 days later 2×10⁷ human PBMC were injected IP to groups G3 and G4, control groups (G1 and G2) received PBS only. Daily IP application of 5 µg 6PHU3 per animal or control bi-scFv 1BiMAB or vehicle alone as control started five days after PBMC injection. Tumors were dissected at a size of 1500 mm3 or at the end of the experiment, and conserved in 4% buffered formaldehyde solution for paraffin embedding.

Paraffin embedded tumor tissues of SC PA-1 tumors were subjected to immunohistochemical stainings. Consecutive sections were stained either with polyclonal primary antibody anti-Claudin 6 or anti-human CD3. Primary antibodies were detected using secondary HRP-conjugated anti-rabbit antibodies. Upper rows of A-E show the CLDN6 staining, lower rows the CD3 staining. Images were taken with a Mirax scanner. (A) and (B) show the PBS control groups G1 and G2 that received no human effector cells and vehicle or bi-scFv 6PHU3, respectively, (C) shows control group G3 that received human effector cells and vehicle as treatment, (D) shows group G4 that received human effector cells and bi-scFv 6PHU3 as treatment, and (E) shows control group G5 that received human effector cells and control hi-scFv 1BiMAB. Positive signals appear as red staining. Black arrowheads point to examples of CD3 signals. IP indicates intraperitoneal; PBMC, peripheral blood mononuclear cells; PBS, phosphate buffered saline; SC, subcutaneous.

FIGS. 20A and 20B show a schematic illustration of IVT-RNA molecules encoding bi-scFv antibodies targeting TAA CLDN18.2.

Scheme of in vitro transcribed RNA sequences encoding anti-CLDN18.2 bi-scFv antibodies. (A) IVT-mRNA in 5'- and 3'-position regarding the anti-TAA variable regions. (B) IVT alphaviral replicon in 5'-position regarding the anti-TAA variable regions. Anti-CLDN18.2 V$_H$ and V$_L$ regions were generated from the sequence of a monoclonal CLDN18.2 antibody (mCLDN18.2ab). "Cap" is uniformly used for ARCA, beta-S-ARCA (D1) or beta-S-ARCA (D2). In (A) "anti-CD3" stands comprehensively for V$_H$ and V$_L$ regions generated from the sequences of the following monoclonal CD3 antibodies: UCHT1-HU (humanized mAB), UCHT1, CLB-T3, TR66, 145-2C11, in (B) "anti-CD3" describes only V$_H$ and V$_L$ from TR66. A indicates adenine; bi-scFv, bispecific single chain variable fragment; hAg, human alpha globin 5'-UTR; hBg, human beta globin 3'-UTR; His, hexahistidyl-tag; IVT, in vitro transcribed; LL, long linker (15-18 amino acids); nsP1-4, non-structural proteins 1-4; Sec, secretion signal; sgP, subgenomic promoter; SL, short linker (5-6 amino acids); TAA, tumor associated antigen; UTR, untranslated region; V, variable region of the heavy (H) and light (L) chain of the antibody.

Figure 21:
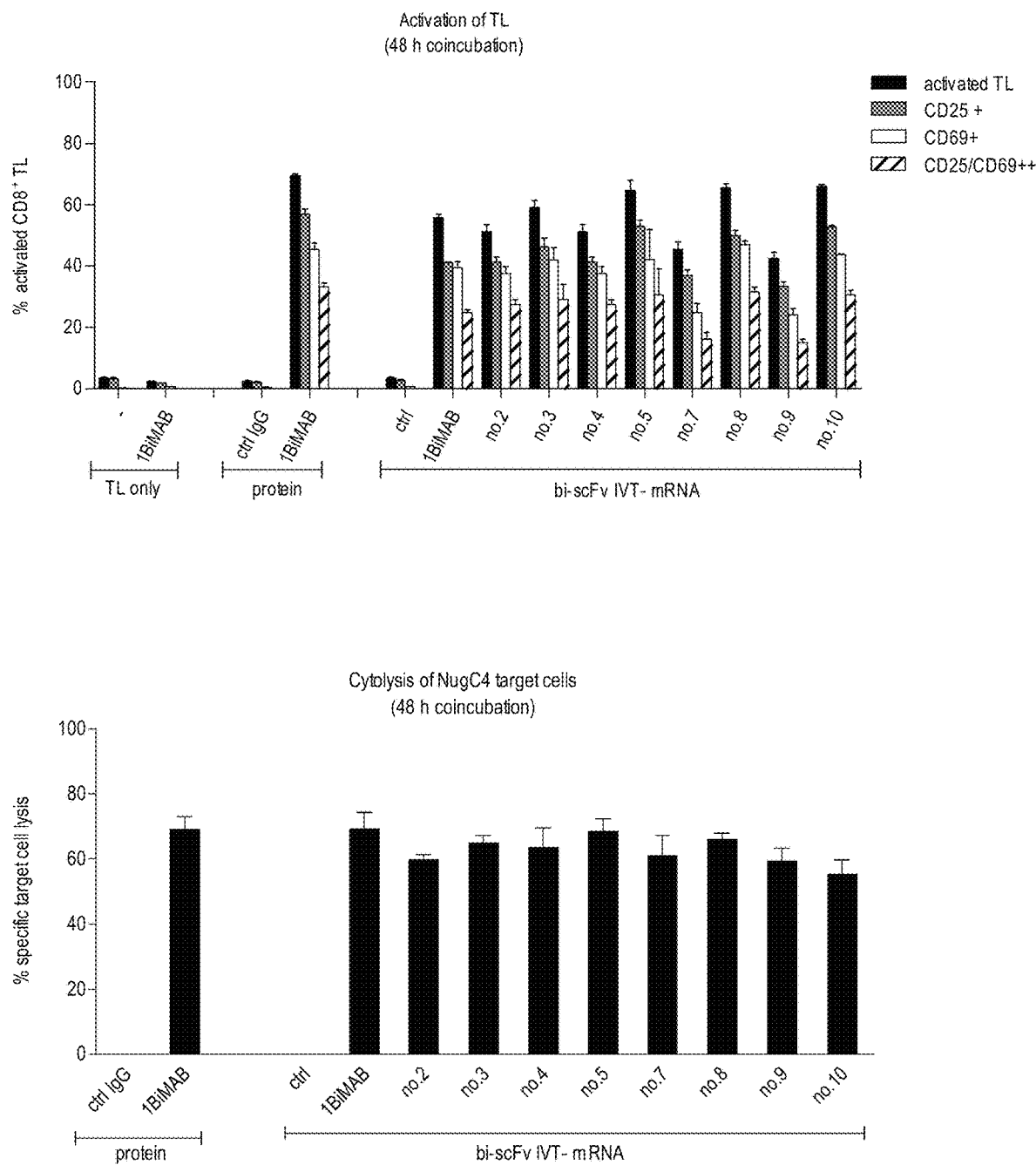

FIG. 21. Effect of domain orientation and anti-CD3-scFv selection on target dependent T cell activation and specific target cell lysis.

CLDN18.2 endogenously expressing NugC4 cells were transiently transfected with several bi-scFv variants directed against CLDN18.2 and CD3 for the comparison of their potency in a cytotox assay. Per variant, 5×10⁶ NugC4 cells were electroporated with 20 µg/ml IVT-mRNA. Transfected target cells were counted, 1×10⁶ cells seeded per 6-well plate and incubated with human cytotoxic T cells (CD8⁺ selected T cells) in an E:T ratio of 5:1. As negative controls a bi-scFv IVT-mRNA targeting a non-expressed TAA (ctrl), and the parental IgG mAB chCLDN18.2ab (ctrl IgG) targeting CLDN18.2 but not T cells were chosen. 1BiMAB protein served as positive control in a concentration of 5 ng/ml. As background dead cell reference, electroporated target cells were seeded without T cells and, as background activation reference, T cells were seeded without target cells. Each sample was seeded in duplicate. After 48 h T cells and target cells were harvested and labeled with anti-CD3-FITC, anti-CD25-PE, anti-CD69-APC and 7-AAD for live-dead staining and analyzed by flow cytometry. (A) TAA-dependent bi-scFv mediated T cell activation was observed with all anti-CLDN18.2 bi-scFv variants. (B) Specific target cell lysis was determined by subtraction of 7-AAD reference population from 7-AAD sample target cell population. The bi-scFv antibodies leading to a marginal higher target cell lysis—1 BiMAB and no. 5—share the domain orientation and the anti-CD3 origin of mAB TR66 but differ in their codon optimization (HS and CHO, respectively) and the long linker sequences. Bi-scFv indicates bispecific single chain variable fragment; ctrl, control; IgG, immunoglobuline G; IVT, in vitro transcribed; mRNA, messenger RNA; TL, T lymphocyte.

Figure 22:
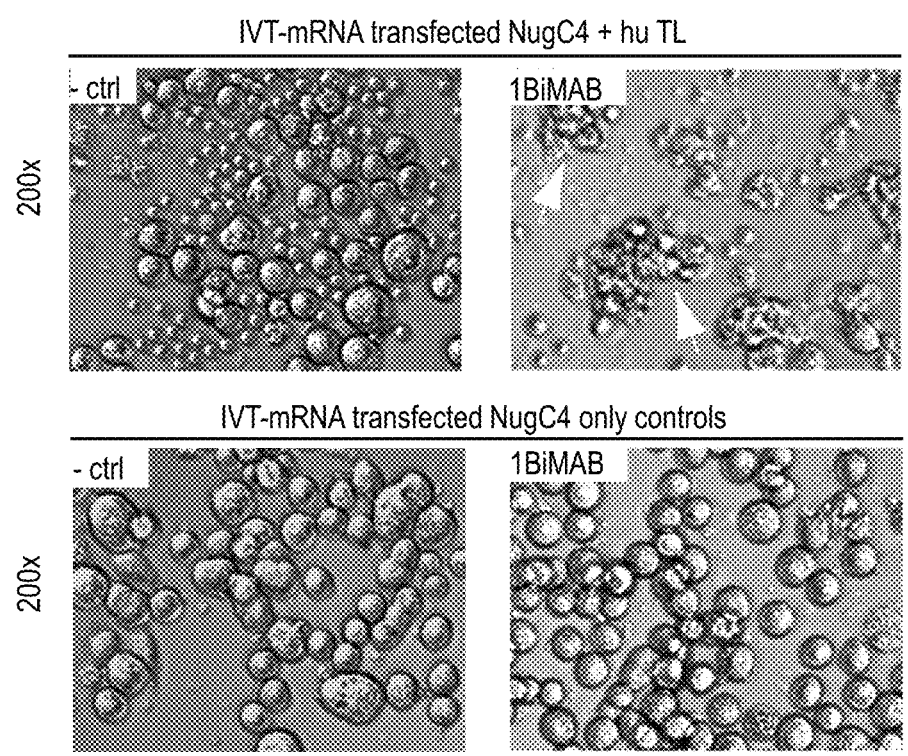

FIG. 22. Coincubation of target cells transfected with 1BiMAB IVT-mRNA and 13 human T cells leads to T cell clustering.

CLDN18.2 endogenously expressing NugC4 cells were transiently transfected by electroporation with 80 µg/ml 1BiMAB IVT-mRNA and coincubated with human cytotoxic T cells (CD8⁺ selected T cells) in an effector to target ratio of 5:1 in 96-well plates. As negative control sample NugC4 target cells transfected with a bi-scFv IVT-mRNA targeting a non-expressed TAA (−ctrl) coincubated with human cytotoxic T cells were used (upper row, left). The bottom row shows NugC4 cells transfected with control bi-scFv (left) or 1BiMAB IVT-mRNA (right) without human T cells. After 24 h of coincubation samples were photographed with a Nikon Eclipse Ti microscope in 200× magnification. White arrowheads point to T cell clusters on target cells. CTL indicates cytotoxic T lymphocyte; ctrl, control; hu, human.

Figures 23A, 23B:
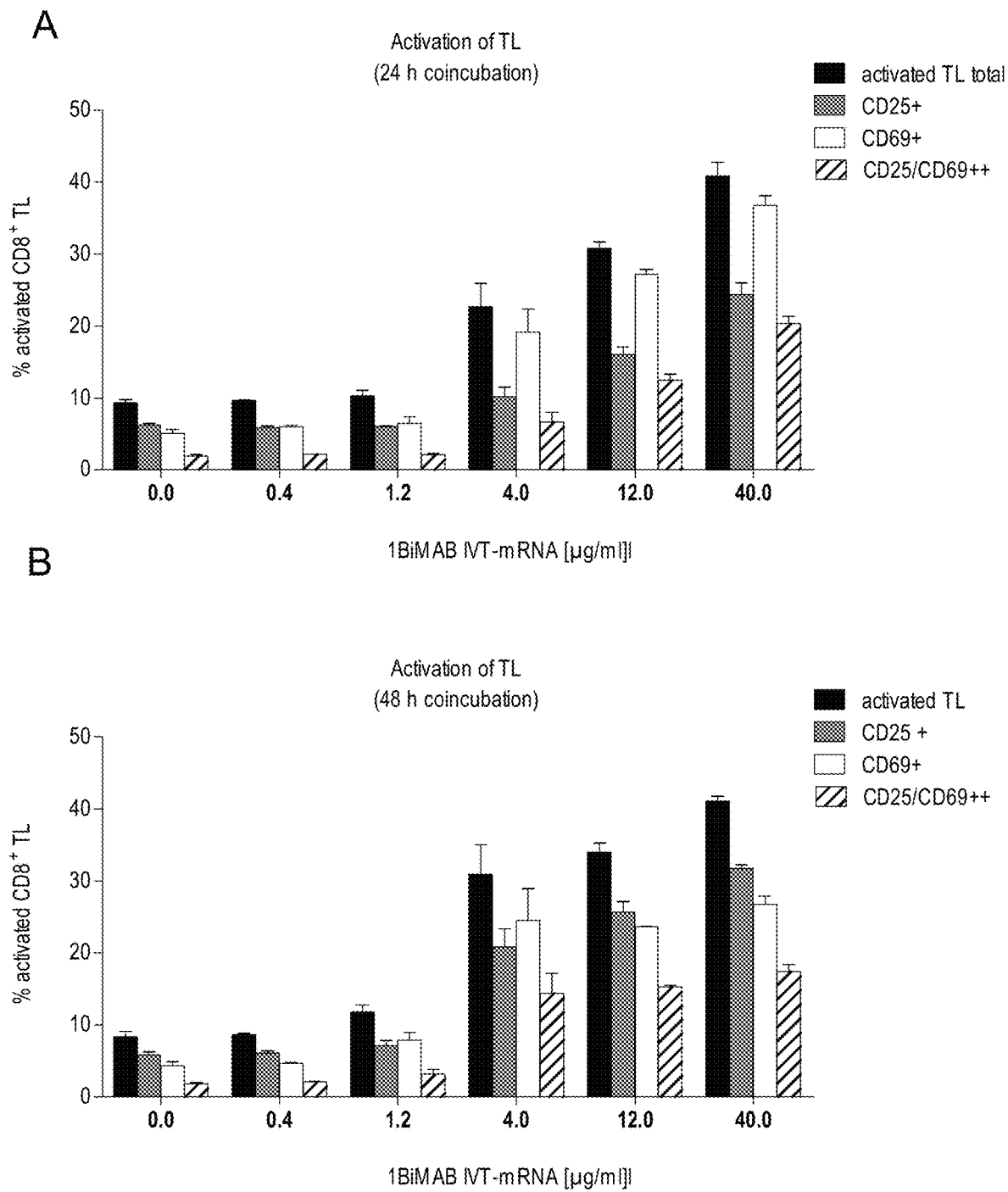

FIGS. 23A and 23B show 1BiMAB secreted by target cells after IVT-mRNA transfection mediates T cell activation in a concentration dependent manner.

CLDN18.2 endogenously expressing NugC4 cells were transiently transfected by electroporation with a total of 40 µg/ml IVT-mRNA containing 0.4-40 µg/ml 1BiMAB IVT-mRNA plus appropriate amounts of luciferase IVT-mRNA. Transfected target cells were coincubated with human cytotoxic T cells (CD8+ selected T cells) in an effector to target ratio of 5:1 in 6-well plates in duplicates. As T cell activation reference human T cells were coincubated with NugC4 target cells transfected with 40 µg/ml luciferase IVT-mRNA (0.0 µg/ml 1BiMAB IVT-mRNA). After 24 h (A) and 48 h (B) T cells were harvested and labeled with anti-CD3-FITC, anti-CD25-33 PE, and anti-CD69-APC and analyzed by flow cytometry. Graphs demonstrate percentage of positively stained cytotoxic human T cells as determined with FlowJo software. IVT indicates in vitro transcribed; mRNA, messenger RNA; TL, T lymphocyte.

Figure 24:
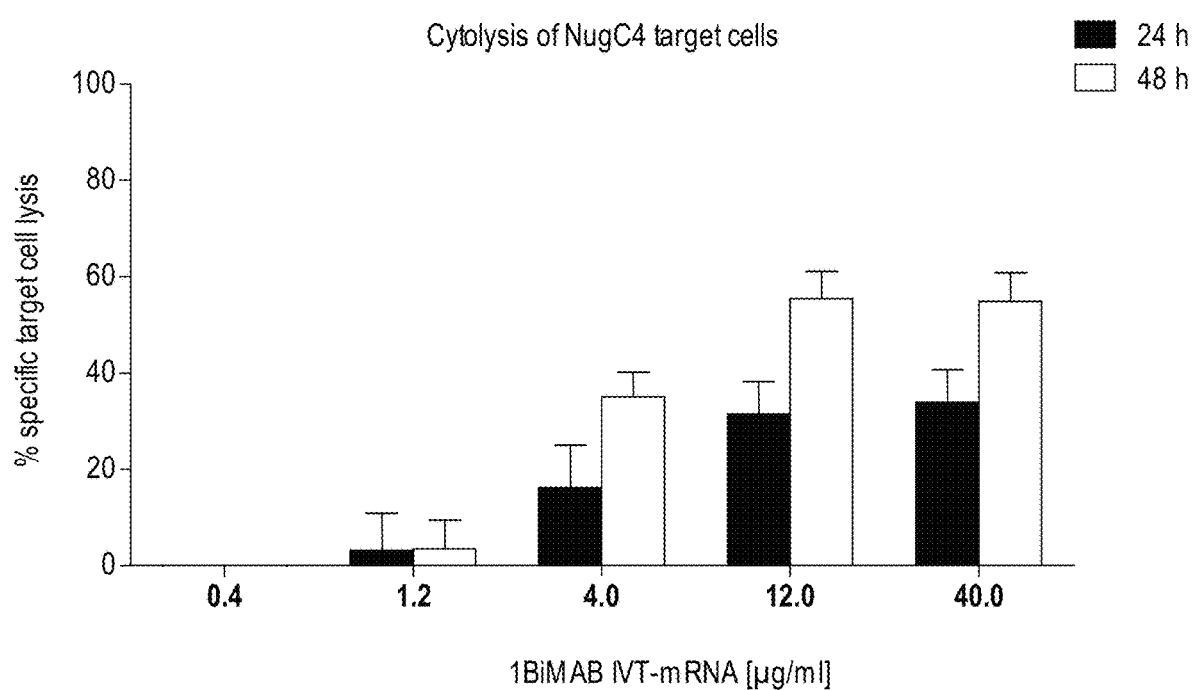

FIG. 24. 1BiMAB secreted by target cells after IVT-mRNA transfection leads to a concentration dependent target cell lysis.

CLDN18.2 endogenously expressing NugC4 cells were transiently transfected by electroporation with a total of 40 µg/ml IVT-mRNA containing 0.4-40 µg/ml 1BiMAB IVT-mRNA plus appropriate amounts of luciferase IVT-mRNA or with 40 µg/ml luciferase IVT-mRNA only as reference sample. Transfected target cells were seeded with human cytotoxic T cells (CD8 selected T cells) in an effector to target ratio of 5:1 or without effector cells to determine the percentage of background dead target cells by each individual electroporation. All samples were cultured in 6-well plates in duplicates. After 24 h (A) and 48 h (B) T cells were harvested, labeled with propidium iodide (PI) for life/dead staining and analyzed by flow cytometry. The percentage of dead (PI+) target cells was determined via FlowJo software. Values were further normalized to each individual background sample and to the reference sample. IVT indicates in vitro transcribed; mRNA, messenger RNA; TL, T lymphocyte.

Figure 25:
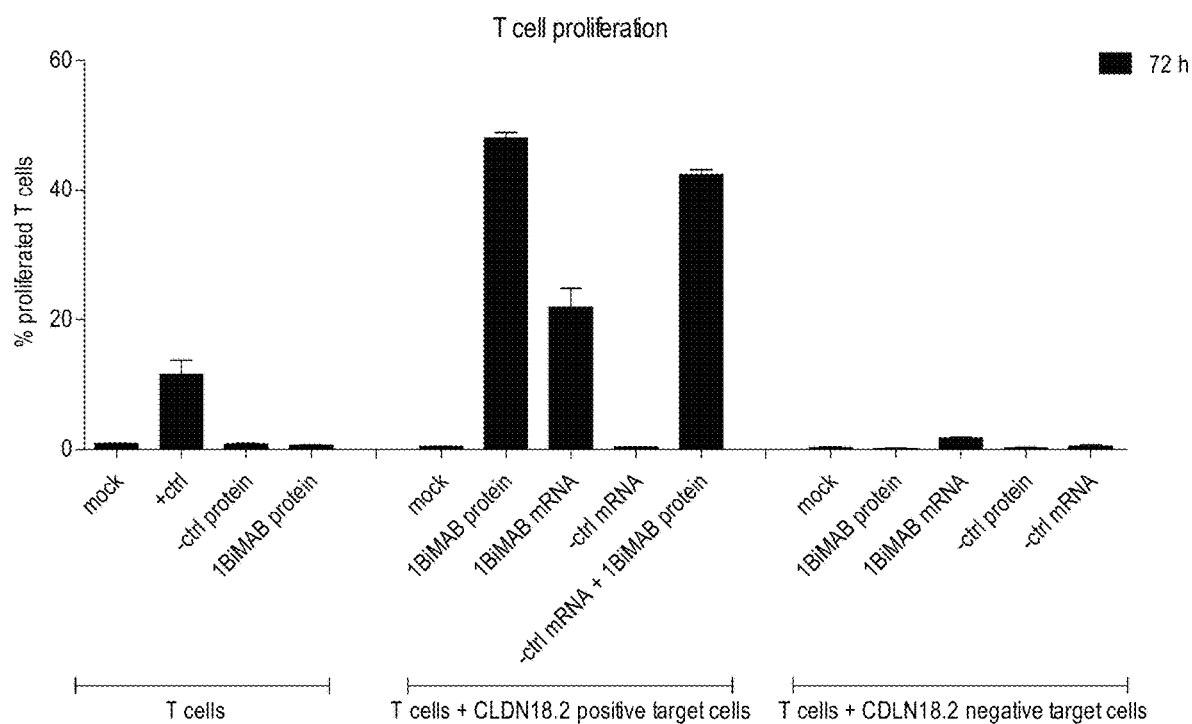

FIG. 25. T cell proliferation is specifically induced in response to 1BiMAB secretion by target cells in the presence of CLDN18.2

Human T cells were CFSE stained for the assay. T cells were cultivated without target cells (T cells) in combination with 5 µg/ml OKT3 and 2 µg/ml αCD28 as positive activation control (+ctrl), with 5 ng/ml non-targeting control bi-scFv (−ctrl protein) or with 5 ng/ml 1BiMAB protein (1BiMAB protein). T cells and NugC4 target cells overexpressing CLDN18.2 were incubated together (T cells+CLDN8.2 positive target cells) without anything (mock) or with 5 ng/ml 1BiMAB protein (1BiMAB protein). To test IVT-mRNA, NugC4 cells were transfected with 20 µg/ml 1BiMAB IVT-mRNA (1BiMAB mRNA) or a bi-scFv IVT-mRNA targeting a non-expressed TAA (−ctrl mRNA) and incubated with T cells. In addition, NugC4 cells transfected with a bi-scFv IVT-mRNA targeting a non-expressed TAA were combined with 5 ng/ml 1BiMAB protein (−ctrl mRNA-1BiMAB protein). As further specificity control, samples with the CLDN18.2-non expressing target cell line MDA-MB-231 together with T cells were included (T cells+CLDN18.2 negative target cells). MDA-MB-231 were either used untreated and incubated without anything (mock), with 5 ng/ml control bi-scFv protein (−ctrl protein) or 5 ng/ml 1BiMAB protein (1BiMAB protein) or MDA-MB-231 were transfected with 20 µg/ml 1BiMAB IVT-mRNA (1BiMAB mRNA) or a bi-scFv IVT-mRNA targeting a non-expressed TAA (−ctrl mRNA). The assay was performed in a 5:1 effector to target ratio in 96-wells, with each sample in triplicate and incubation times of 72 h. Decrease of CFSE signal indicating T cell proliferation was analyzed by flow cytometry, calculated by FlowJo software and plotted as % proliferating T cells. CFSE indicates carboxyfluorescein succinimidyl ester; IVT, in vitro transcribed; mRNA, messenger RNA.

Figures 26A, 26B:
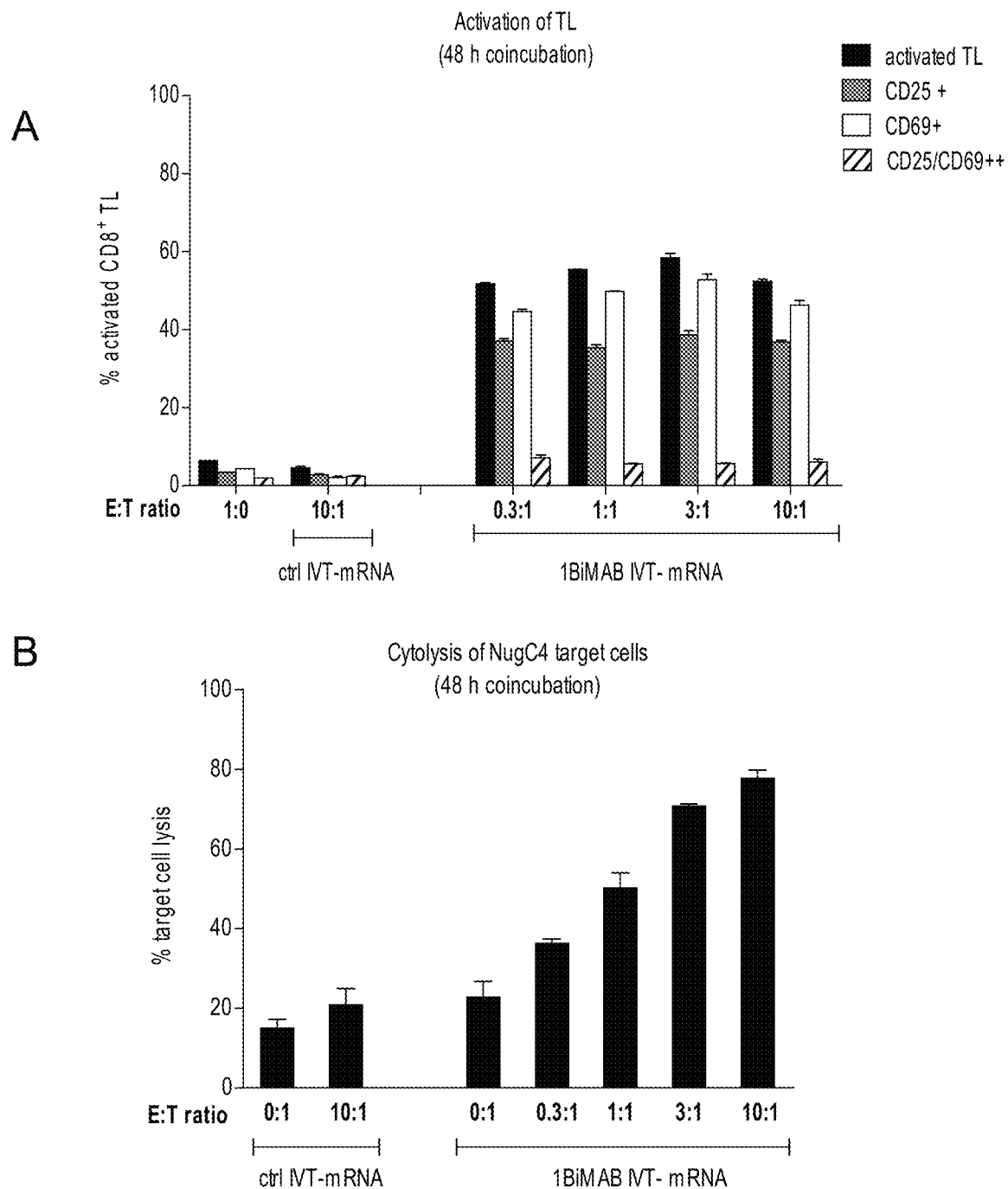

FIGS. 26A and 26B show T cell activation and T cell-mediated target cell lysis in response to 1BiMAB secretion starts with an effector to target ratio of 0.3:1.

CLDN18.2 endogenously expressing NugC4 cells were transiently transfected by electroporation with 40 µg/ml 1BiMAB IVT-mRNA. Transfected target cells were coincubated with human cytotoxic T cells (CD8+ selected T cells) in the indicated effector to target ratios from 0.3:1 to 10:1 in 6-well plates in duplicates. As references human T cells were cultured in the absence of target cells ((A) 1:0) and target cells transfected with control IVT-mRNA were cultured in the absence of effector cells ((B) 0:1). As negative control human T cells were coincubated with NugC4 target cells transfected with 40 µg/ml luciferase IVT-mRNA (ctrl IVT-mRNA) in an E:T ratio of 10:1 ((A) and (B) ctrl IVT-mRNA 10:1). After 48 h cells were harvested and labeled with anti-CD3-FITC, anti-CD25-PE, anti-CD69-APC and propidium iodide (PI) for life/dead staining and analyzed by flow cytometry. (A) shows the percentage of positively stained cytotoxic human T cells. (B) demonstrates the percentage of dead (PI+) target cells. All values were determined via FlowJo software. E:T indicates effector to target; IVT, in vitro transcribed; mRNA, messenger RNA; TL, T lymphocyte.

Figure 27A:
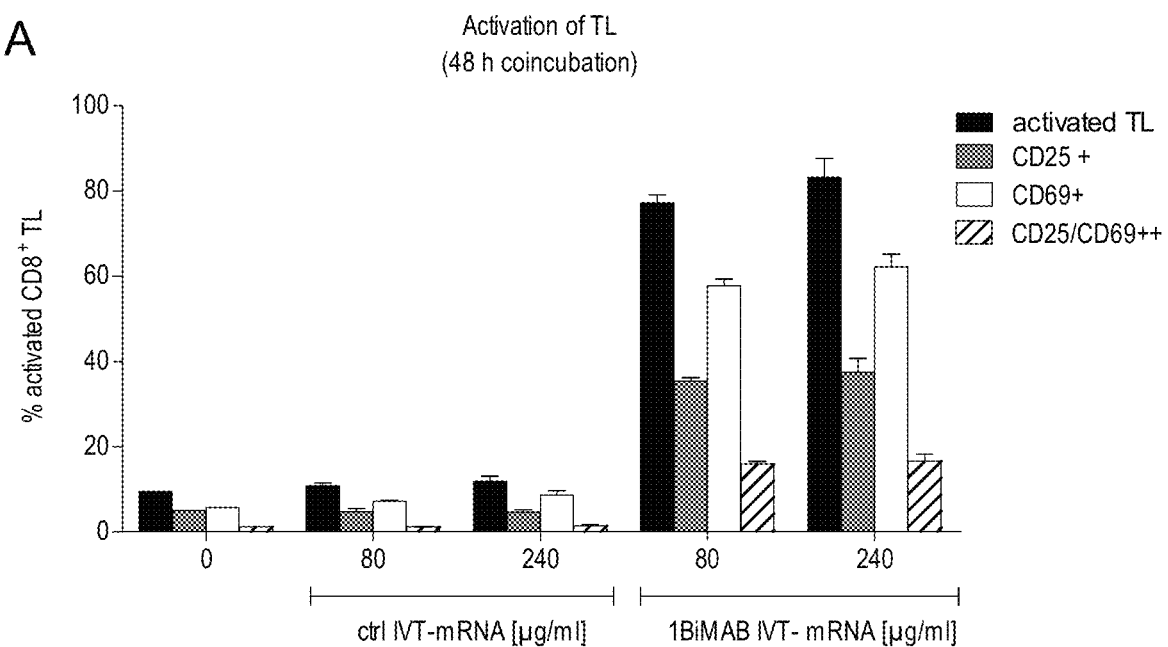
Figure 27B:
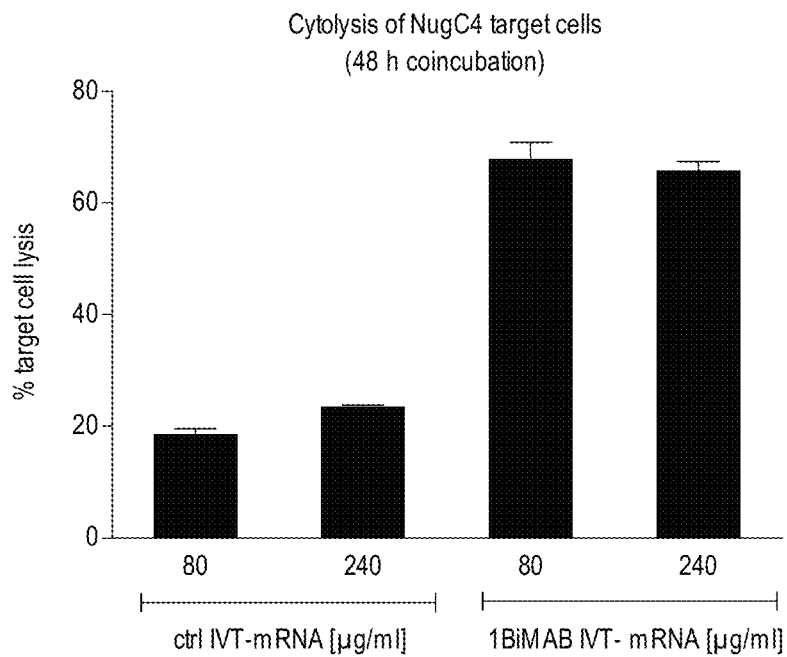

FIG. 27. Human cytotoxic T cells are able to serve as bi-scFv IVT-mRNA recipient and producer cells Human cytotoxic T cells were freshly isolated from PBMCs by CD8 positive selection and subsequently transiently transfected by electroporation with 80 or 240 µg/ml 1BiMAB IVT-mRNA. Transfected effector cells were coincubated with NugC4 target cells endogenously expressing CLDN18.2 in an effector to target ratio of 5:1 in 6-well plates in duplicates. As reference untreated human T cells were cultured with target cells. As negative control human T cells transfected with 80 or 240 µg/ml cGFP control IVT-mRNA were coincubated with NugC4 target cells. After 48 h cells were harvested and labeled with anti-CD3-FITC, anti-CD25-PE, anti-CD69-APC and propidium iodide (PI) for life/dead staining and analyzed by flow cytometry. (A) shows the percentage of positively stained cytotoxic human T cells. In (B) the percentage of dead (PI+) target cells normalized to the reference sample is plotted. All values were determined via FlowJo software. Ctrl indicates control; IVT; in vitro transcribed; mRNA, messenger RNA; TL, T lymphocyte.

Figure 28:
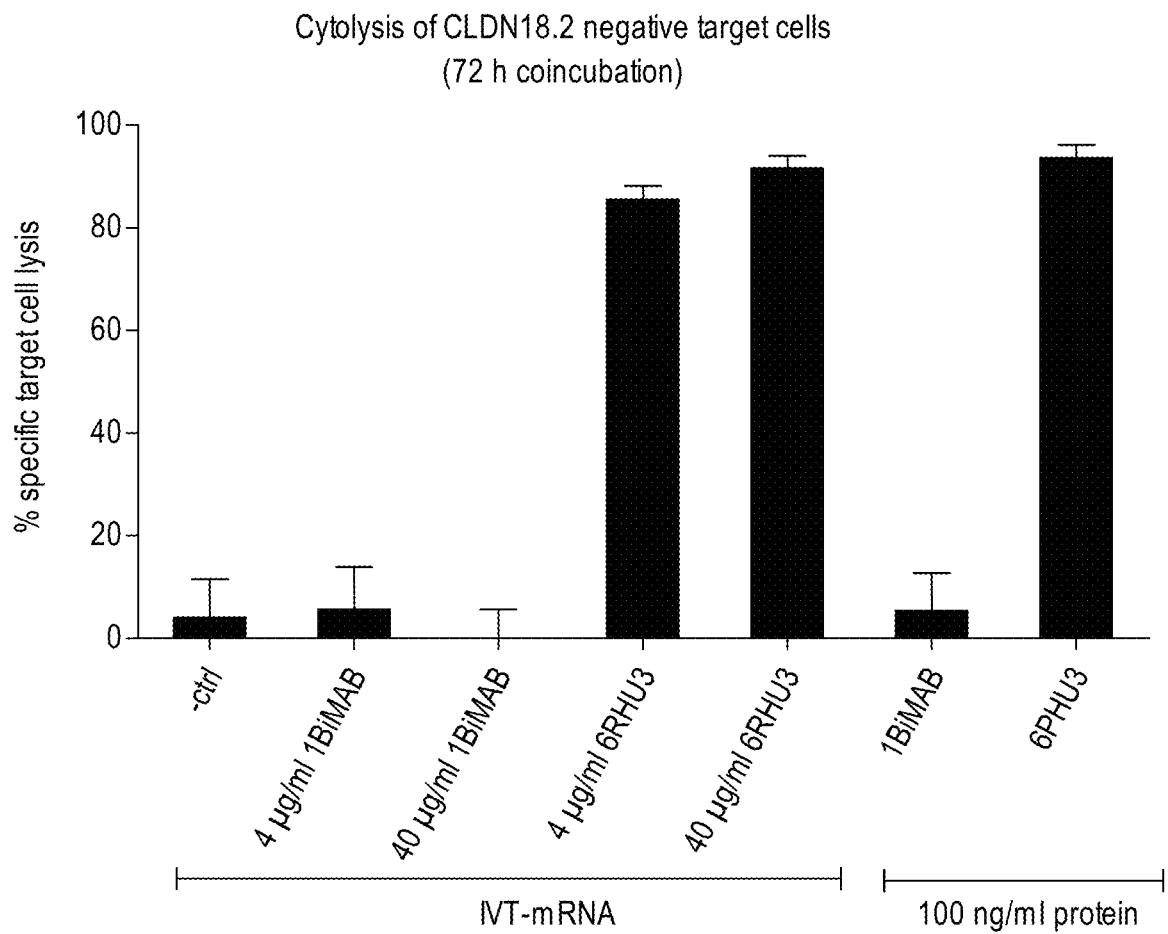

FIG. 28. CLDN18.2 negative target cells transfected with 1BiMAB IVT-mRNA are not lysed by T cells CLDN18.2 negative cell line PA-1 stably expressing luciferase served as target cell line. $5 \times 10^6$ PA-1/luc cells were transfected by electroporation with a total of 40 µg/ml IVT-mRNA. 4 and 40 µg/ml 1 BiMAB IVT-mRNA or 6RHU3 targeting endogenously expressed CLDN6 as positive control were transfected. As bi-scFv negative control, 40 µg/ml of bi-scFv IVT-mRNA targeting a non-expressed TAA (−ctrl) was transfected. This IVT-mRNA served also as fill-up RNA in the 4 µg/ml IVT-mRNA samples (IVT-mRNA 4 µg/ml 1BiMAB, IVT-mRNA 4 µg/ml 6RHU3). Protein control samples with 1BiMAB and 6PHU3 in combination with bi-scFv negative control transfected PA-1/luc cells and effector cells were included.

Transfected target cells were seeded with human cytotoxic T cells (Pan T cells) in an effector to target ratio of 5:1.

All samples were seeded in triplicates in a 96-well format and coincubated for 72 h. As minimum lysis control ($L_{min}$) each individual transfected target cell sample was seeded without effector cells. Maximum lysis ($L_{max}$) for the normalization to spontaneous luminescence counts was achieved by addition of Triton X-100 to control wells containing effector and non-treated target cells ($L_{max1}$) or non-treated target cells alone ($L_{max2}$) prior to luciferin addition. 30 min after addition of luciferin solution the luminescence was measured in an Infinite M200 Tecan microplate reader. Specific target cell lysis was calculated by the formula: % specific lysis=$[1-($luminescence$_{test\ sample}-L_{max1})/(L_{min\_test\ sample}-L_{max2})]\times 100$. Ctrl indicates control; IVT; in vitro transcribed; mRNA, messenger RNA.

Figures 29A, 29B:
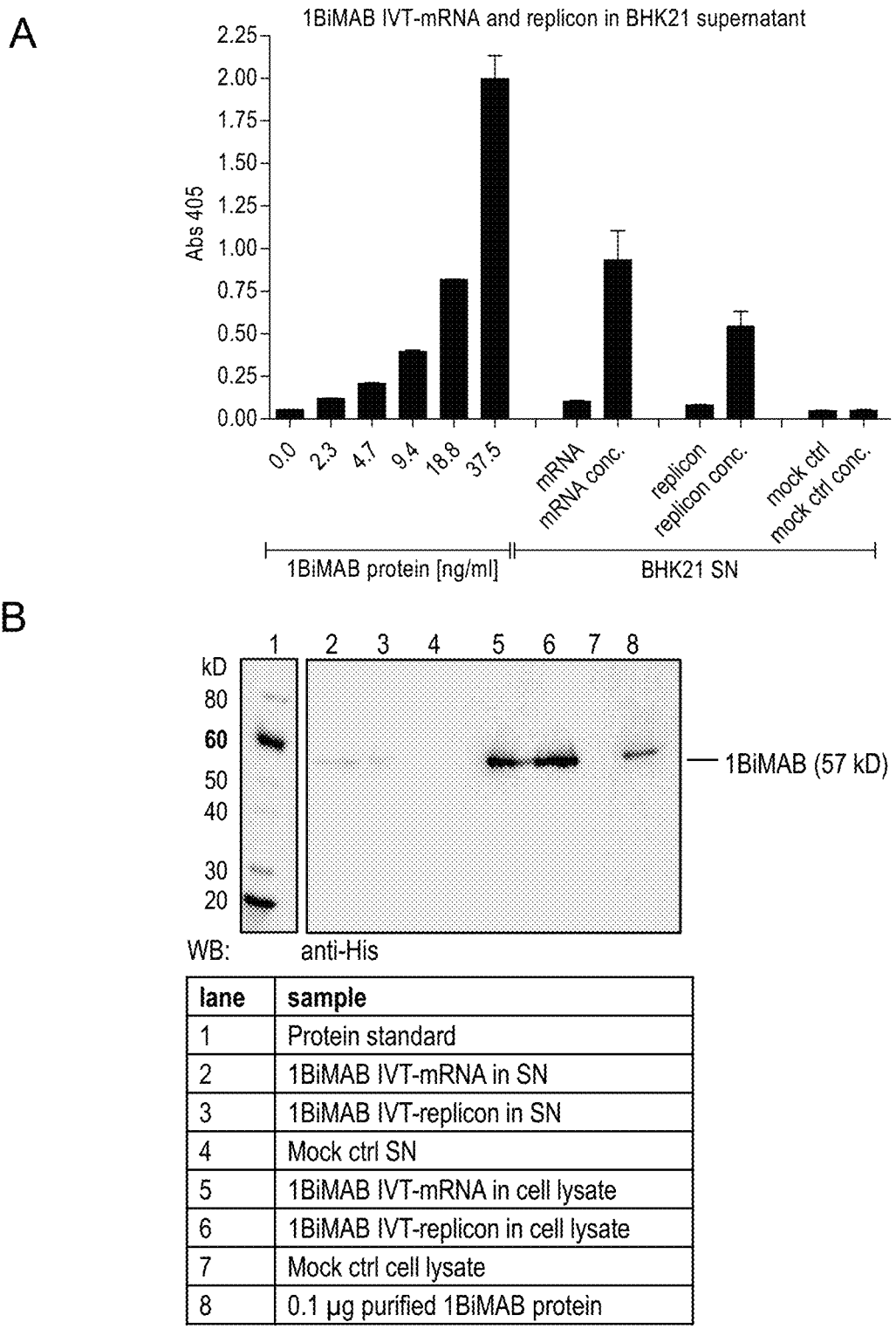
Figure 29C:
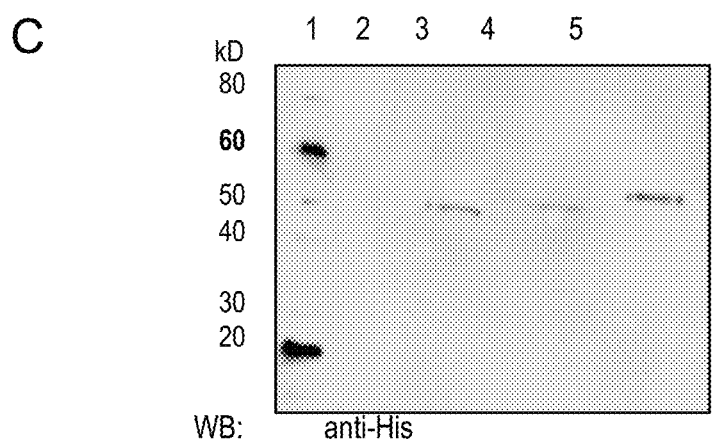

FIGS. 29A, 29B, and 29C show proof of 1BiMAB production by mammalian cells transfected with bi-scFv IVT-mRNA or -replicon RNA (A) $5\times 10^6$ BHK21 cells were transiently transfected by electroporation with 40 µg/ml of 1BiMAB IVT-mRNA or -replicon RNA. As mock control cells were electroporated without RNA. 18 h post transfection supernatant and cells were harvested. Cells were lysed and supernatants were subjected to ~50-fold concentration. Untreated and concentrated supernatants were analyzed by ELISA using Ni-NTA plates, anti-chCLDN18.2ab idiotypic mAB and a secondary AP-conjugated antibody. Purified 1BiMAB protein in a dilution row ranging from 2.3 to 37.5 ng/ml in steps of 2 was used as standard. (B) Concentrated supernatant, cell lysates of (A) and 0.1 µg purified 1BiMAB protein as positive control were separated via SDS-PAGE. Western Blot analysis was performed with primary monoclonal anti-His and secondary peroxidase conjugated anti-mouse antibody. (C) $5\times 10^6$ BHK21 cells were transiently transfected by electroporation with 40 µg/ml of 1BiMAB or no. 25 IVT-mRNA. As mock control cells were electroporated without RNA. 48 h post transfection supernatant was harvested and subjected to 40-fold concentration. SN and 0.1 µg purified 1BiMAB protein as positive control were separated via SDS-PAGE. Western Blot analysis was performed with primary monoclonal anti-His and secondary peroxidase conjugated anti-mouse antibody. Ctrl indicates control; mAB, monoclonal antibody; SN, supernatant; WB, Western blot.

Figure 30:
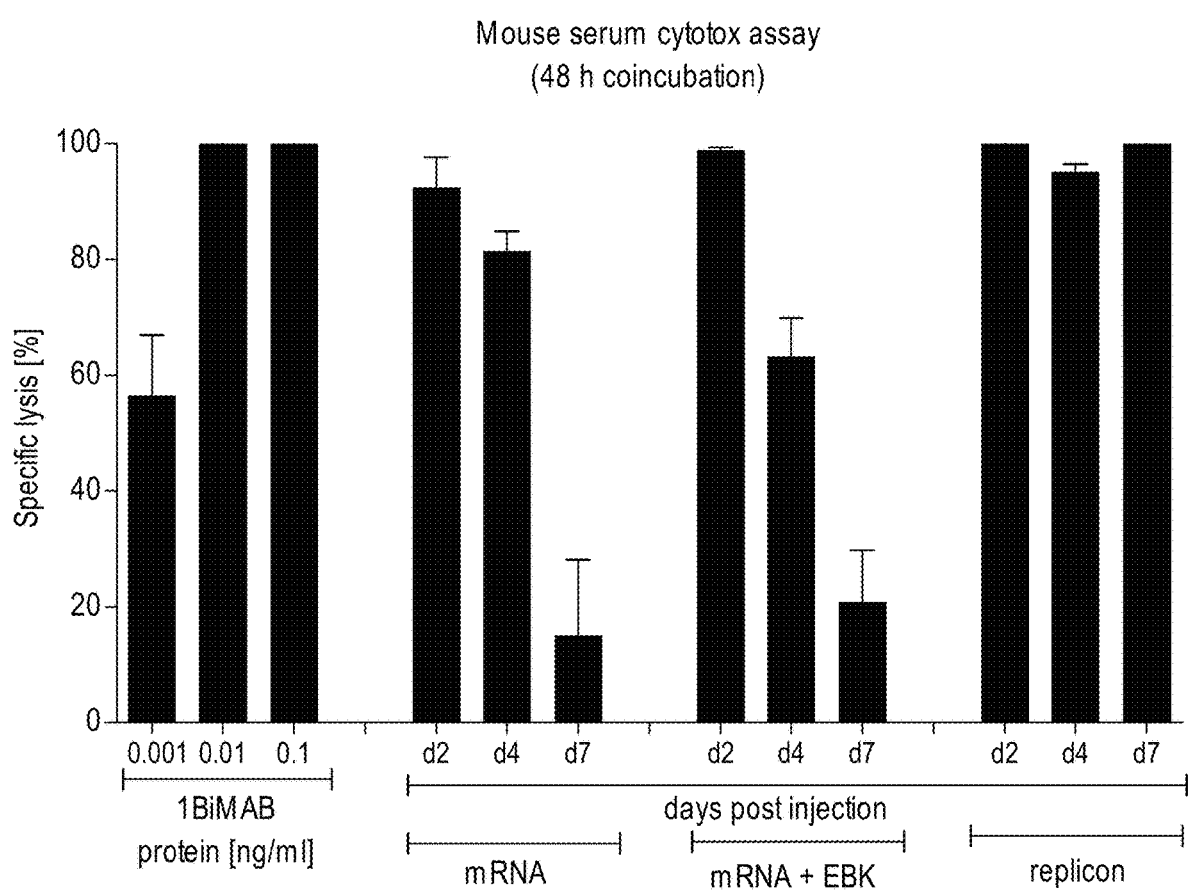

FIG. 30. Injection of 1BiMAB bi-scFv IVT-mRNA or -replicon RNA leads to in vivo production and detectable 1BiMAB bi-scFv molecules in mice 10 µg 1BiMAB IVT-mRNA with or without EBK IVT-mRNA or 10 µg 1BiMAB IVT-replicon was IM injected into NSG mice. Serum from blood, collected 2, 4 and 7 days post injection was applied in an in vitro cytox assay. CLDN18.2 and luciferase stably expressing NugC4-LVT-CLDN18.2/luc target cells were coincubated with human T cells in an E:T ratio of 30:1 with 20 µl sample serum for 48 h. Standard 1BiMAB protein control, $L_{min}$ and $L_{max}$ contained 20 µl NSG mock serum. EBK indicates vaccinia virus protein cocktail E3, B-18R, K3; 1M, intramuscular.

FIGS. 31A and 31B show a schematic illustration of IVT-RNA molecules encoding bi-scFv antibodies targeting TAA CLDN6.

Scheme of in vitro transcribed RNA sequences encoding anti-CLDN6 bi-scFv antibodies. (A) IVT mRNA in 5'- and 3'-position regarding the anti-TAA variable regions. (B) IVT alphaviral replicon in 3'-position regarding the anti-TAA variable regions. Anti-CLDN6 $V_H$ and $V_L$ regions are generated from the sequence of a monoclonal CLDN6 antibody (mCLDN6ab). "Cap" is uniformly used for ARCA, beta-S-ARCA (I)1 or beta-S-ARCA (D2). Anti-CD3 $V_H$ and $V_L$ regions are generated from the sequence of the monoclonal CD3 antibody TR66. A indicates adenine; bi-scFv, bispecific single chain variable fragment; hAg, human alpha globin 5'-UTR; hBg, human beta globin 3'-UTR; His, hexahistidyl-tag; IVT, in vitro transcribed; LL, long linker (15-18 amino acids); nsP1-4, non-structural proteins 1-4; Sec, secretion signal; sgP, subgenomic promoter; SL, short linker (5-6 amino acids); TAA, tumor associated antigen; UTR, untranslated region; V, variable region of the heavy (H) and light (L) chain of the antibody.

Figure 32:
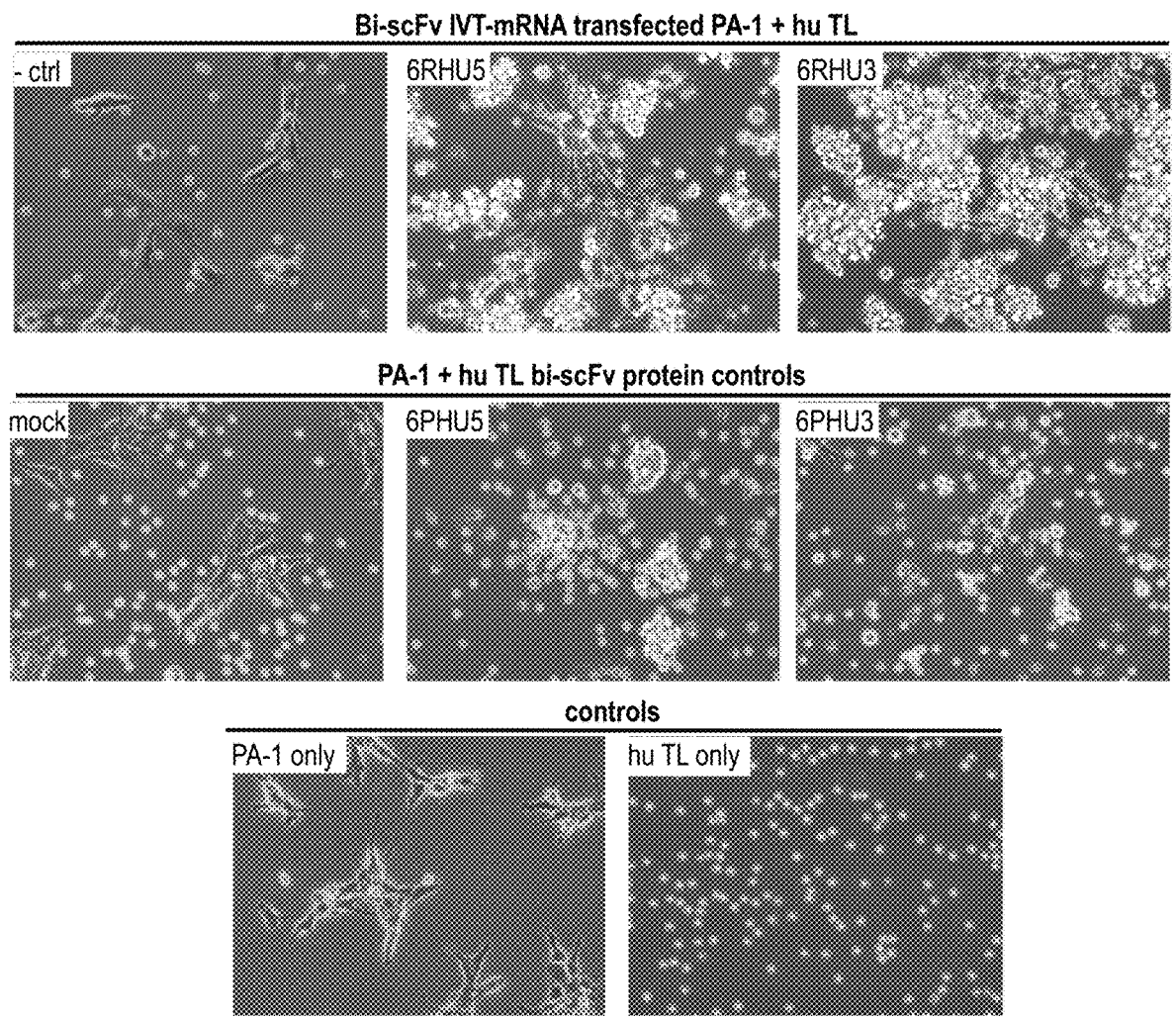

FIG. 32. Coincubation of target cells transfected with anti-CLDN6 bi-scFv IVT-mRNA and human T cells leads to T cell clustering.

CLDN6 endogenously expressing PA-1 cells were transiently transfected by electroporation with 20 µg/ml 6RHU5 or 6RHU3 IVT-mRNA and coincubated with human T cells (Pan T cells) in an effector to target ratio of 5:1 in 6-well plates. As negative control sample PA-1 target cells transfected with a bi-scFv IVT-mRNA targeting a non-expressed TAA (−ctrl) coincubated with human T cells were used (upper row, left photo). The middle row shows untreated PA-1 cells and human T cells without protein as negative control (mock, left photo) or with 50 µg/ml purified anti-CLDN6 bi-scFv proteins 6PHU5 (middle) or 6PHU3 (right) as positive controls. The bottom row shows untreated PA-1 cells (left) and human T cells alone (right). After 24 h of coincubation samples were photographed with a Nikon Eclipse Ti microscope in 200× magnification. White arrowheads point to T cell clusters on target cells. Bi-scFv indicates bispecific single chain variable fragment; ctrl, control; hu, human; IVT, in vitro transcribed; mRNA, messenger RNA; TL, T lymphocyte.

Figure 33A:
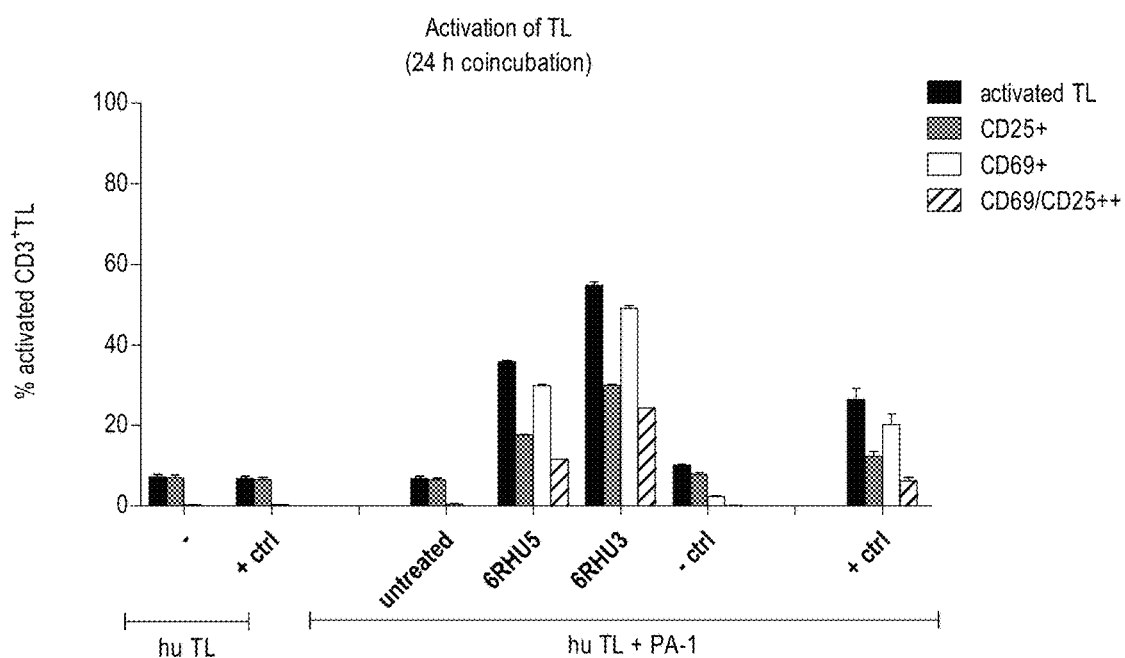
Figure 33B:
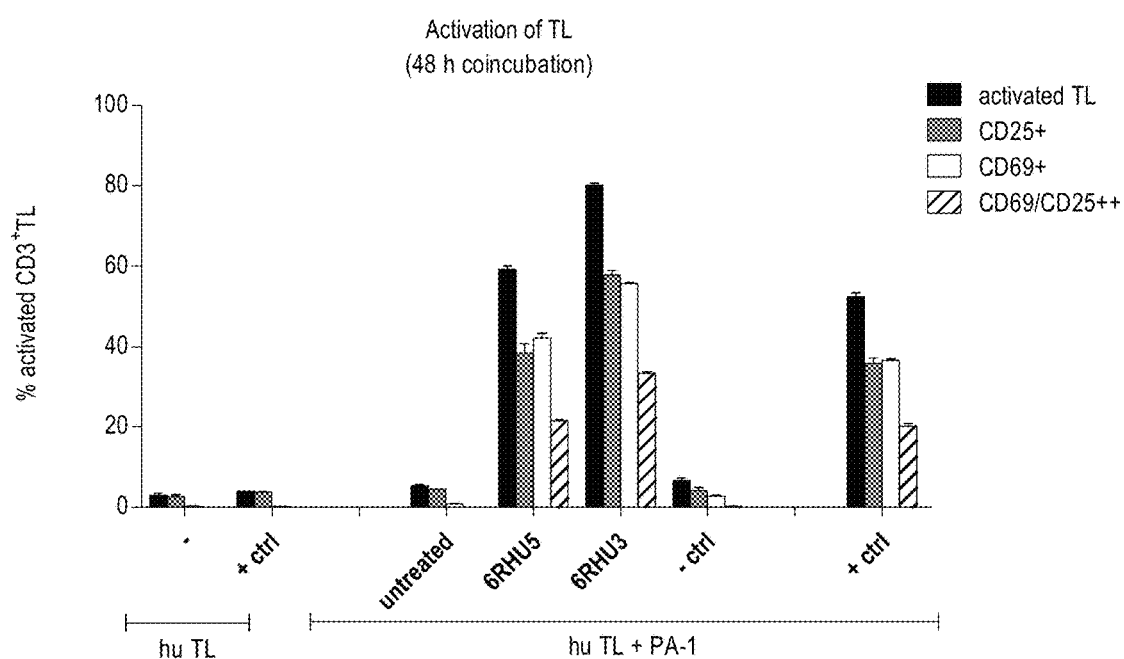

FIGS. 33A and 33B show the effects of domain orientation on efficacy: target cell transfection with anti-CLDN6 bi-scFv 6RHU3 leads to higher percentages of activated T cells than with 6RHU5.

CLDN6 endogenously expressing PA-1 cells were transiently transfected with the two bi-scFv variants 6RHU5 and 6RHU3 directed against CLDN6 and CD3 for the comparison of their potency in a T cell activation assay. Per variant $5\times 10^6$ PA-1 cells were electroporated with 20 µg/ml IVT-mRNA. Transfected target cells were re-counted, $1\times 10^6$ cells seeded per 6-well plate and incubated with human cytotoxic T cells (CD8$^+$ selected T cells) in an E:T ratio of 5:1. As negative controls untreated target cells (hu TL+PA-1 untreated) and target cells transfected with a bi-scFv IVT-mRNA targeting a non-expressed TAA (hu TL+PA-1−ctrl) were chosen. 6PHU5 protein served as positive control in a concentration of 50 ng/ml (hu TL+PA-1 protein ctrl). Further, T cells were seeded without target cells with or without 6PHU5 protein as background activation reference. Each sample was seeded in duplicate. Analysis was performed after 24 h and 48 h: T cells were harvested and labeled with anti-CD3-FITC, anti-CD25-PE, anti-CD69-APC and 7-AAD for live-dead staining and analyzed by flow cytometry. TAA-dependent bi-scFv mediated T cell activation was observed with both anti-CLDN6 bi-scFv variants after 24 h (A) and 48 h (B) of coincubation. Bi-scFv 6RHU3 transfection led to approximately 20% higher T cell activation in both time points. Bi-scFv indicates bispecific single chain variable fragment; ctrl, control; hu, human; IVT, in vitro transcribed; mRNA, messenger RNA; TL, T lymphocyte.

Figure 34:
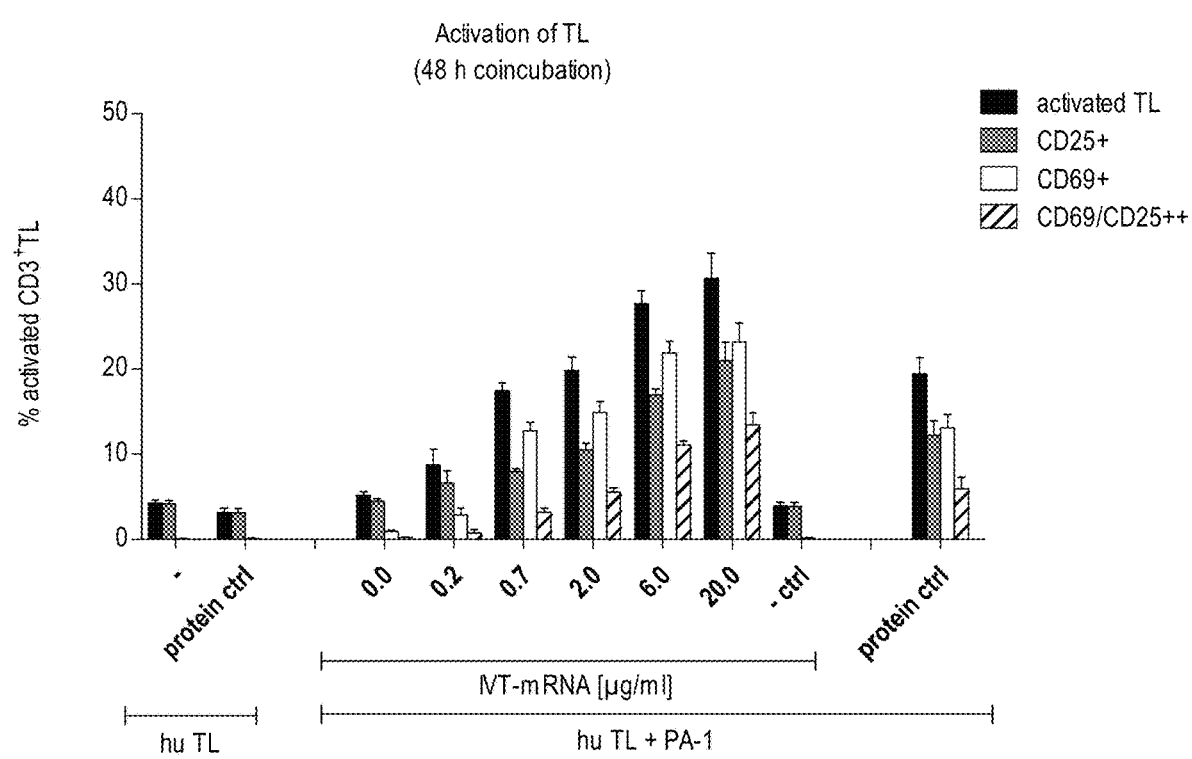

FIG. 34. 6RHU3 secretion mediates T cell activation in a concentration dependent manner.

CLDN6 endogenously expressing PA-1 cells were transiently transfected by electroporation with a total of 20 µg/ml IVT-mRNA containing 0.2-20 µg/ml 6RHU3 IVT-mRNA plus appropriate amounts of a bi-scFv IVT-mRNA targeting a non-expressed TAA. Transfection of 20 µg/ml bi-scFv IVT-mRNA targeting a non-expressed TAA (0.0 µg/ml 6RHU3 IVT-mRNA) served as specificity control. Transfected target cells were coincubated with human cytotoxic T cells (Pan T cells) in an effector to target ratio of 5:1 in 6-well plates in duplicates. As T cell activation reference human T cells were cultured alone without 6PHU5 protein (hu TL−) or with 6PHU5 protein (hu TL protein ctrl). As negative control T cells were coincubated with untreated PA-1 target cells (hu TL+PA-1−ctrl). 6PHU5 protein served as positive control in a concentration of 50 ng/ml (hu TL+PA-1 protein ctrl). After 48 h T cells were harvested and labeled with anti-CD3-FITC, anti-CD25-PE, and anti-CD69-APC and analyzed by flow cytometry. Graphs demonstrate percentages of positively stained human T cells as determined via FlowJo software. Bi-scFv indicates bispecific single chain variable fragment; ctrl, control; hu, human; IVT, in vitro transcribed; mRNA, messenger RNA; TL, T lymphocyte.

Figure 35:
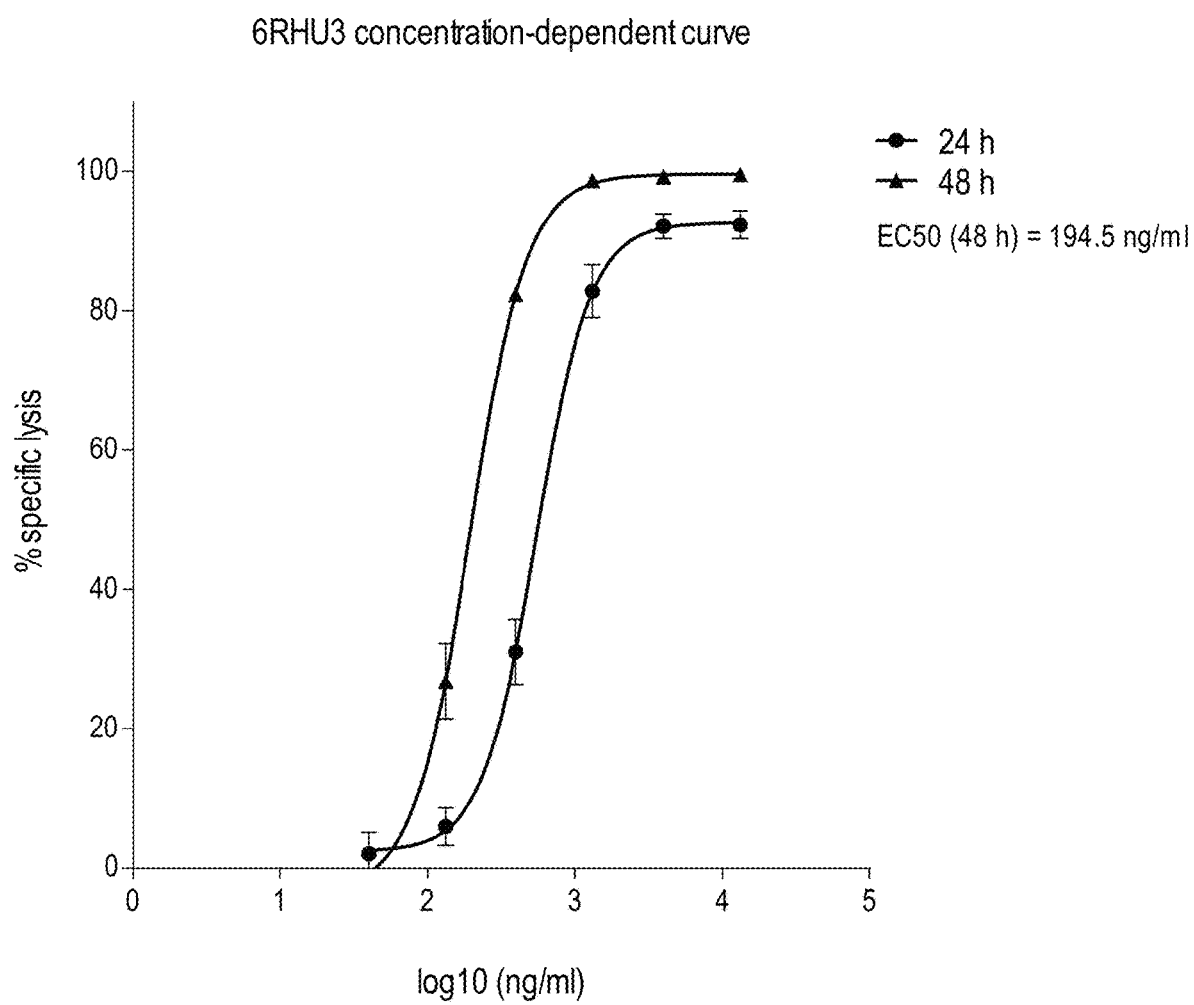

FIG. 35. EC50 of 6RHU3 for specific target cell lysis after 48 h is approximately 200 ng/ml.

CLDN6 endogenously expressing PA-1 cells which stably express luciferase were transiently transfected by electroporation with a total concentration of 13.3 µg/ml bi-scFv IVT-mRNA containing 0.004-13.3 µg/ml 6RHU3 and an appropriate amount of a bi-scFv IVT-mRNA targeting a non-expressed TAA. Transfected target cells were seeded with human T cells in an effector to target ratio of 5:1 in triplicates in a 96-well format. As minimum lysis control ($L_{min}$) each individual transfected target cell sample was seeded without effector cells. Maximum lysis ($L_{max}$) for the normalization to spontaneous luminescence counts was achieved by addition of Triton X-100 to control wells containing effector and non-treated target cells shortly prior to luciferin addition. 30 min after addition of luciferin solution the luminescence was measured in an Infinite M200 Tecan microplate reader after 24 h and 48 h. Specific target cell lysis was calculated by the formula: % specific lysis= [1−(luminescence$_{test\ sample}$−$L_{max}$)/($L_{min\_test\ sample}$−$L_{max}$)]×100. Values were plotted against log 10 of 6RHU3 concentration. EC50 indicates the half maximal effective concentration; L, lysis.

Figure 36:
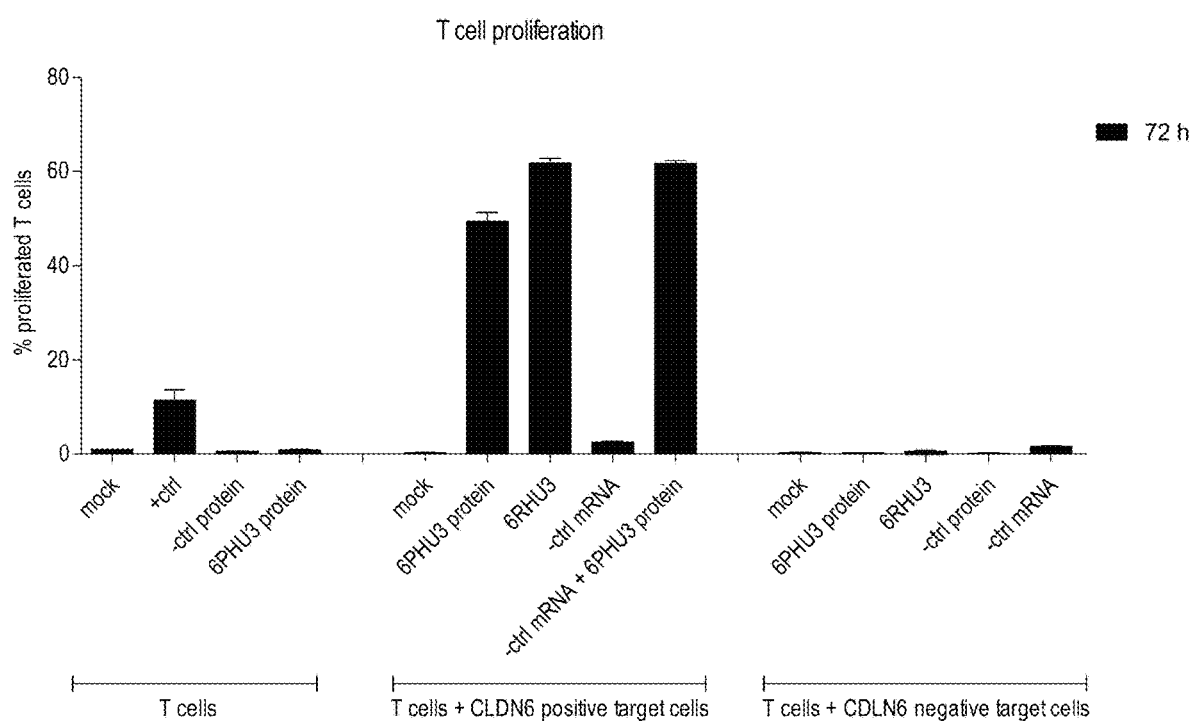

FIG. 36. T cell proliferation is specifically induced in response to 6RHU3 secretion by target cells in the presence of CLDN6.

Human T cells were CFSE stained for the assay. T cells were cultivated without target cells (T cells) in combination with 5 µg/ml OKT3 and 2 µg/ml αCD28 as positive activation control (−ctrl), with 5 ng/ml non-targeting control bi-scFv (−ctrl protein) or with 5 ng/ml 6PHU3 protein (6PHU3 protein). T cells and PA-1 target cells endogenously expressing CLDN6 were incubated together (T cells+CLDN6 positive target cells) without anything (mock) or with 5 ng/ml 6PHU3 protein (6PHU3 protein). To test IVT-mRNA, PA-1 cells were transfected with 20 µg/ml 6RHU3 IVT-mRNA (6RHU3 mRNA) or a bi-scFv IVT-mRNA targeting a non-expressed TAA (−ctrl mRNA) and incubated with T cells. In addition, PA-1 cells transfected with a bi-scFv IVT-mRNA targeting a non-expressed TAA were combined with 5 ng/ml 6PHU3 protein (−ctrl mRNA+ 6PHU3 protein). As further specificity control, samples with the CLDN6-non expressing target cell line MDA-MB-231 together with T cells were included (T cells+CLDN6 negative target cells). MDA-MB-231 were either used untreated and incubated without anything (mock), with 5 ng/ml control bi-scFv protein (−ctrl protein) or 5 ng/ml 6PHU3 protein (6PHU3 protein) or MDA-MB-231 were transfected with 20 µg/ml 6RHU3 IVT-mRNA (6RHU3 mRNA) or a bi-scFv IVT-mRNA targeting a non-expressed TAA (−ctrl mRNA). The assay was performed in a 5:1 effector to target ratio in 96-wells, with each sample in triplicate and incubation times of 72 h. Decrease of CFSE signal indicating T cell proliferation was analyzed by flow cytometry, calculated by FlowJo software and plotted as % proliferating T cells. CFSE indicates carboxyfluorescein succinimidyl ester; IVT, in vitro transcribed; mRNA, messenger RNA.

Figure 37A:
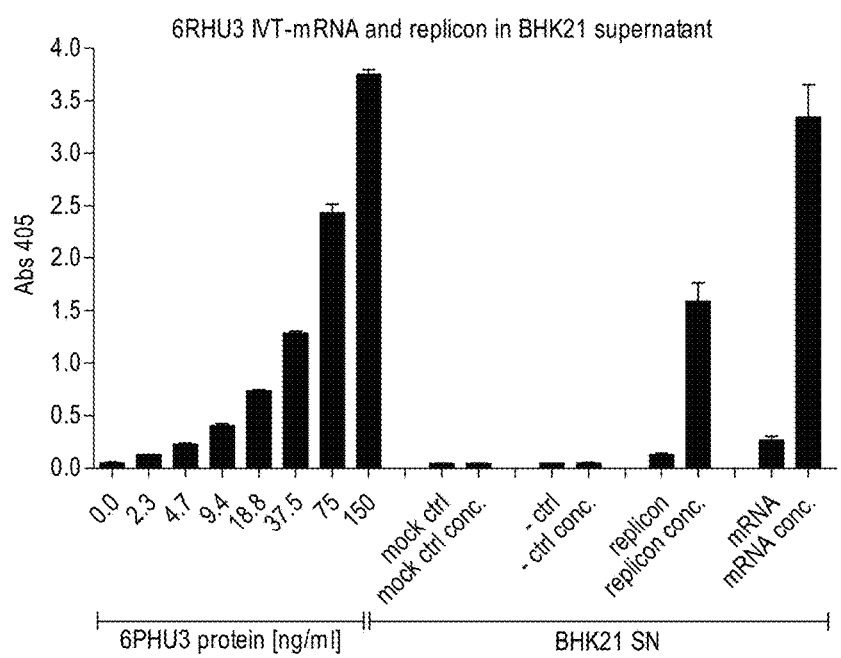
Figure 37B:
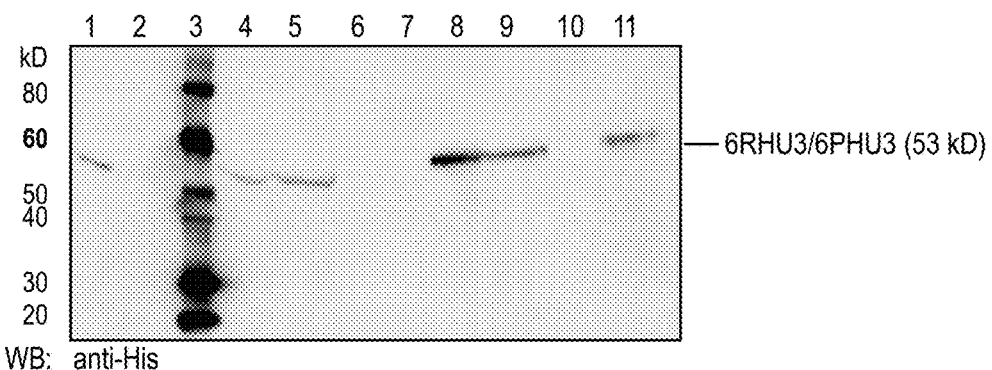
Figure 37C:
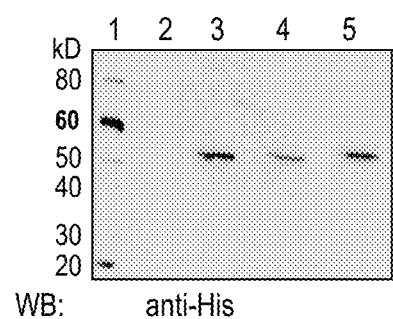

FIGS. 37A, 37B, and 37C show proof of 6RHU3 translation by mammalian cells transfected with bi-scFv IVT-mRNA or -replicon RNA (A) 5×10$^6$ BHK21 cells were transiently transfected by electroporation with 40 µg/ml of 6RHU3 IVT-mRNA or -replicon RNA. Transfection of 40 µg/ml no. 25 IVT-mRNA was included as extra sample. As mock ctrl cells were electroporated without RNA. 18 h post transfection supernatant and cells were harvested. Cells were lysed and supernatants were subjected to ~50-fold concentration. Untreated and concentrated supernatants were analyzed by ELISA using Ni-NTA plates, anti-mCLDN6ab idiotypic mAB and a secondary AP-conjugated antibody. Purified 6PHU3 protein in a dilution row ranging from 2.3 to 150 ng/ml in steps of 2 was used as standard. (B) Concentrated supernatant and cell lysates of (A) and 0.1 µg purified 6PHU3 protein as positive control were separated via SDS-PAGE. Western Blot analysis was performed with primary monoclonal anti-His and secondary peroxidase conjugated anti-mouse antibody. (C) 5×10$^6$ BHK21 cells were transiently transfected by electroporation with 40 µg/ml of 6RHU3 or no. 25 IVT-mRNA. As mock control cells were electroporated without RNA. 48 h post transfection supernatant was harvested and subjected to 40-fold concentration. SN and 0.1 µg purified 6PHU3 protein as positive control were separated via SDS-PAGE. Western Blot analysis was performed with primary monoclonal anti-His and secondary peroxidase conjugated anti-mouse antibody. Ctrl indicates control; mAB, monoclonal antibody; SN, supernatant; WB, Western blot.

Figure 38:
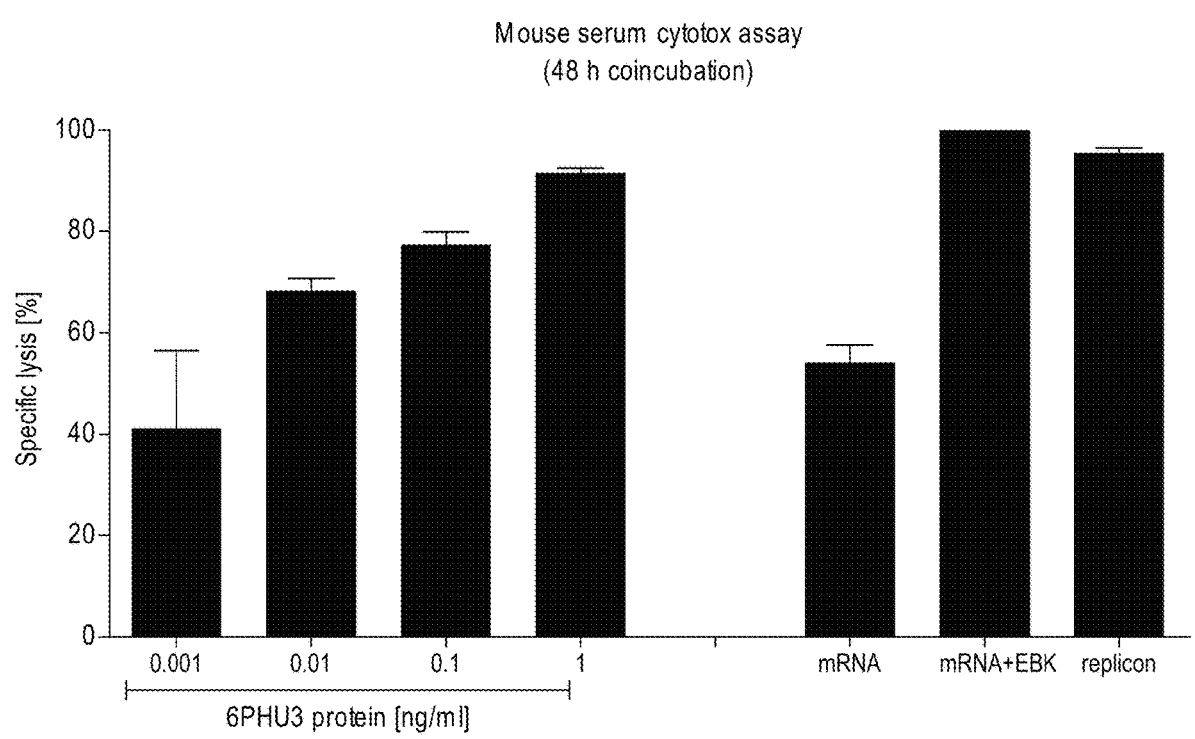
Figure 39A:
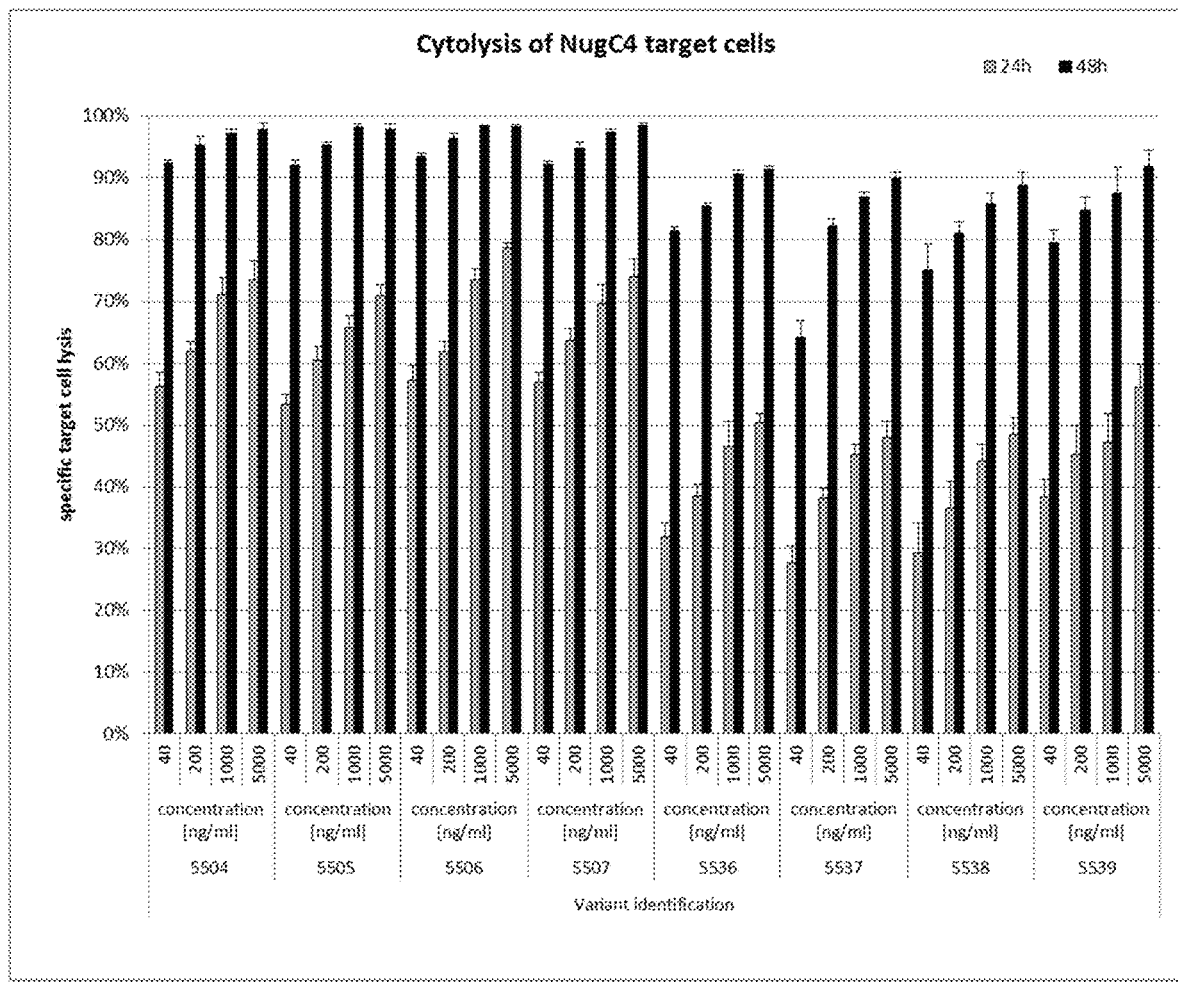
Figure 39B:
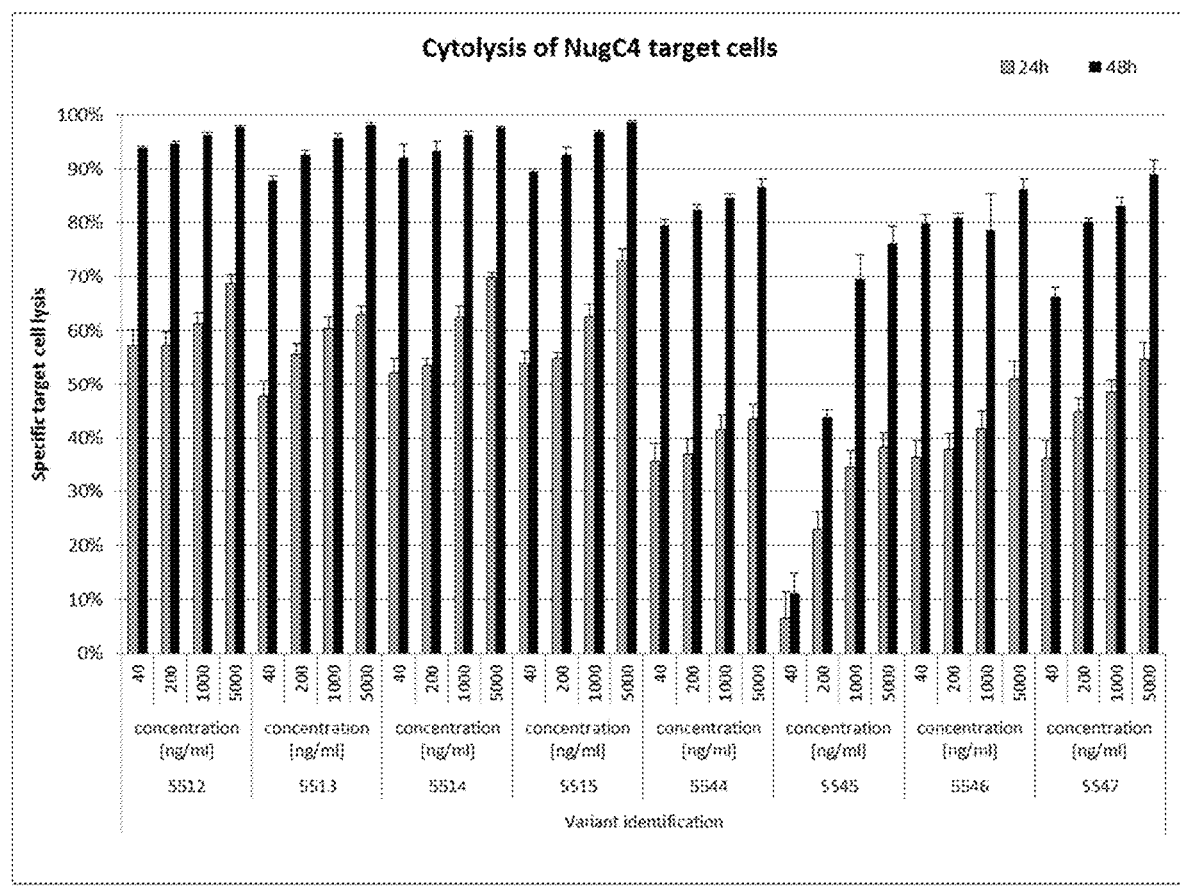
Figure 39C:
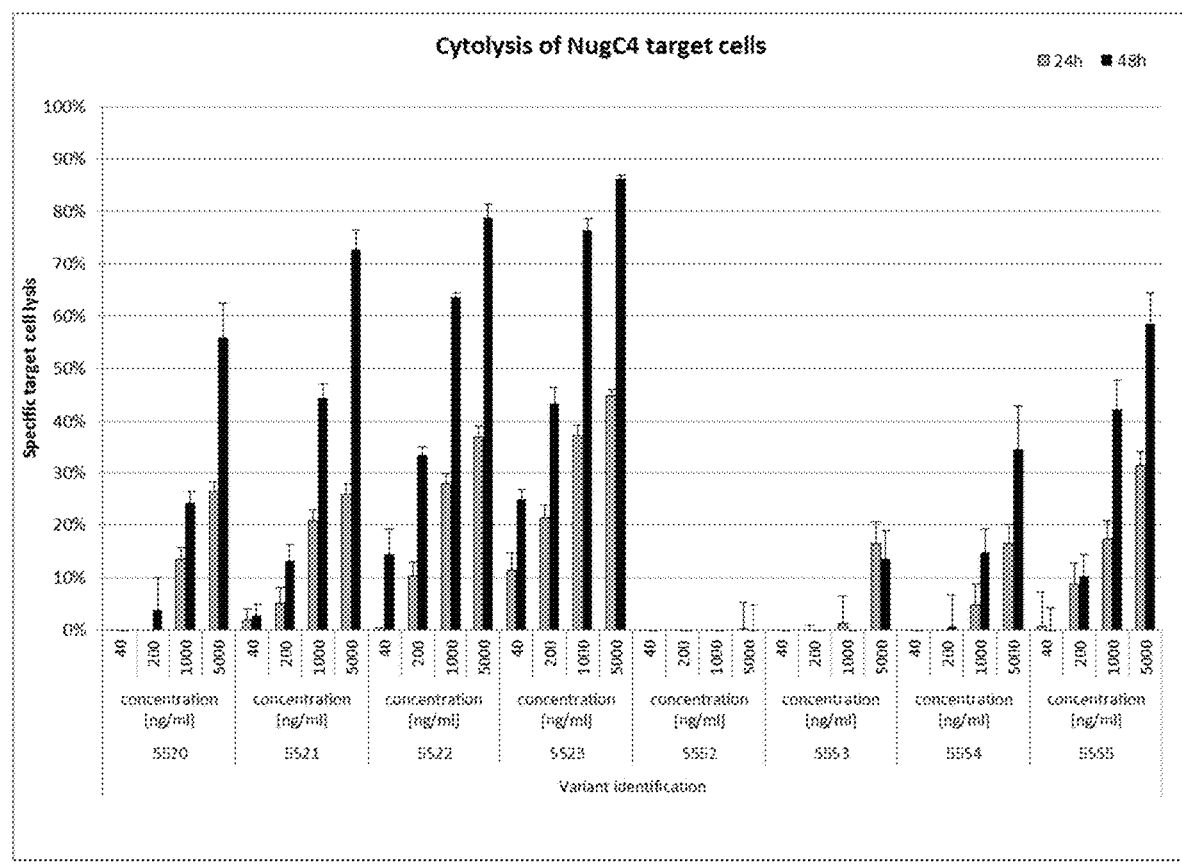
Figure 39D:
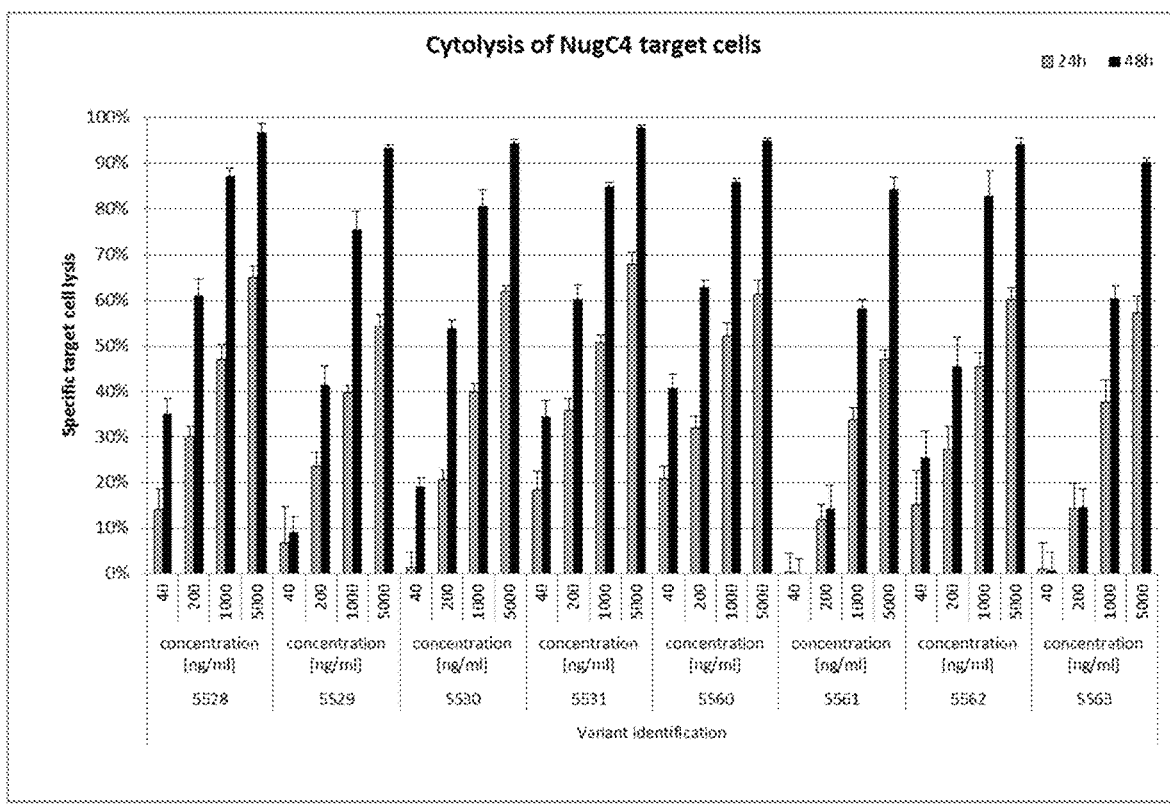

FIG. 38. Injection of 6RHU3 bi-scFv IVT-mRNA or -replicon RNA leads to in vivo translation and detectable bi-scFv molecules in mice 10 µg 6RHU3 IVT-mRNA with or without EBK IVT-mRNA or 10 µg 6RHU3 IVT-replicon was IM injected into NSG mice. Serum from blood, collected 7 days post injection was applied in an in vitro cytotox assay. CLDN6 endogenously and luciferase stably expressing PA-1/luc target cells were coincubated with human T cells in an E:T ratio of 30:1 with 20 µl sample serum for 48 h. Standard 6PHU3 protein control, $L_{min}$ and $L_{max}$ contained 20 µl NSG mock serum. EBK indicates vaccinia virus protein cocktail E3, B-18R, K3; IM, intramuscular.

FIGS. 39A, 39B, 39C, and 39D show the cytotoxic results of anti-CLDN18.2 bi-scFv proteins containing the scFv anti-(CD3 binding domain at the C-terminal part of the protein.

Bi-scFv variants directed against CLDN18.2 and CD3 were transiently expressed in CHO cells and purified with Protein-L resin for the comparison of their potency in a cytotoxic assay. CLDN18.2 endogenously expressing NugC4 cells which stably express luciferase were taken as target cells. Human T cells and target cells were incubated in an E:T ratio of 5:1 with 5000, 1000, 200 and 40 ng/ml of each of the bi-scFv proteins in a 96-well format. Each test sample was plated threefold, the control sample for $L_{min}$ was plated threefold. Coincubation times before analysis were 24 h and 48 h. After addition of luciferin solution at the given time points, the luminescence was measured in an Infinite M200 TECAN reader. Specific target cell lysis was calculated for each concentration and reported.
a. The variable domains of the anti-CD3 are in the VH-VL domain order and separated by the LL4 peptide linker.
b. The variable domains of the anti-CD3 are in the VH-VL order and separated by the LL4 peptide linker. The scFv anti-CD3 contains an interface disulfide bridge between the VH and VL domains.
c. The variable domains of the anti-CD3 are in the VL-VH order and separated by the LL5 peptide linker.
d. The variable domains of the anti-CD3 are in the VL-VH order and separated by the LL5 peptide linker. The scFv anti-CD3 contains an interface disulfide bridge between the VL and VH domains.

Figure 40A:
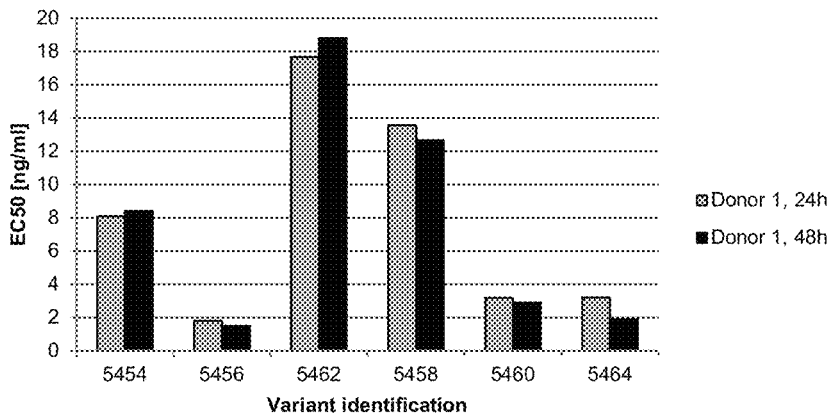
Figure 40B:
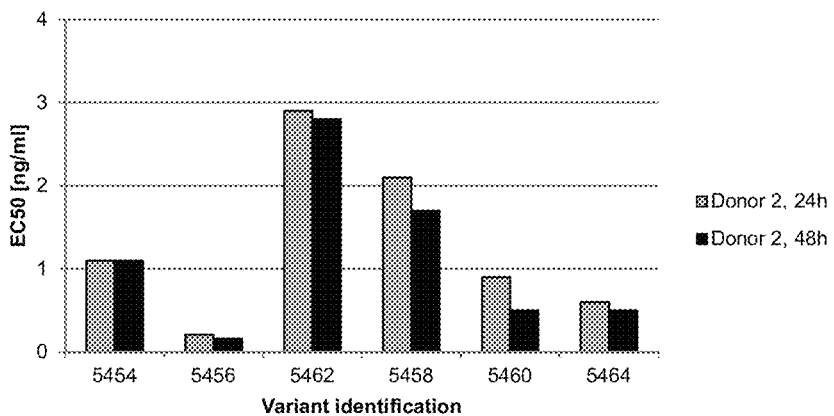
Figure 40C:
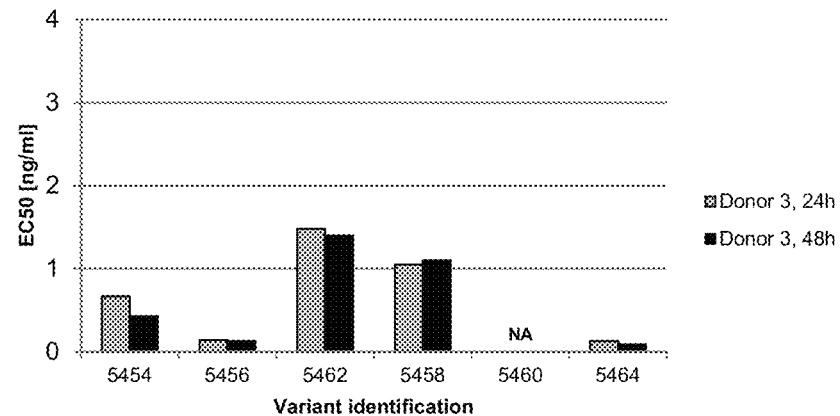

FIGS. 40A, 40B, and 40C show intra-assay comparison of EC50 values obtained in luciferase cytotoxic assay with anti-CLDN6 bi-scFv proteins.

Luciferase cytotoxic assays were performed with three different donors for T cell preparation. The calculated EC50 values, calculated with the 6 tested anti-CLDN6 bi-scFv proteins after 24 h and 48 h incubation, are reported for each independent assay (A, B and C). CLDN6 endogenously expressing PA-1 cells were incubated for 24 h and 48 h with escalating concentrations (0.025-50000 ng/ml for A and B, 0.0025-5000 ng/ml for C) of anti-CLDN6 bi-scFv proteins and human T cells in an effector to target ratio of 5:1 in triplicates in a 96-well format. As minimum lysis control ($L_{min}$) effector and target cells were plated without bi-scFv proteins. Maximum lysis ($L_{max}$) for the normalization to spontaneous luminescence counts was achieved by addition of Triton X-100 to control wells containing effector and target cells in the absence of bi-scFv shortly prior to luciferin addition. 30 min after addition of luciferin solution the luminescence was measured in an Infinite M200 Tecan microplate reader after 24 h and 48 h of target and effector cell incubation. Specific target cell lysis was calculated by the formula: % specific lysis=$[1-(luminescence_{test\ sample}-L_{max})/(L_{min}-L_{max})] \times 100$. EC50 indicates the half maximal effective concentration; L, lysis; NA, not applicable.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Claudins are a family of proteins that are the most important components of tight junctions, where they establish the paracellular barrier that controls the flow of molecules in the intercellular space between cells of an epithelium. Claudins are transmembrane proteins spanning the membrane 4 times with the N-terminal and the C-terminal end both located in the cytoplasm. The first extracellular loop, termed EC1 or ECL1, consists on average of 53 amino acids, and the second extracellular loop, termed EC2 or ECL2, consists of around 24 amino acids. Cell surface proteins of the claudin family, such as CLDN6 and CLDN18.2, are expressed in tumors of various origins, and are particularly suited as target structures in connection with antibody-mediated cancer immunotherapy due to their selective expression (no expression in a toxicity relevant normal tissue) and localization to the plasma membrane.

In the context of the present invention, the preferred claudins are CLDN6 and CLDN18.2. CLDN6 and CLDN18.2 have been identified as differentially expressed in tumor tissues, with the only normal tissues expressing CLDN18.2 being stomach and the only normal tissue expressing CLDN6 being placenta.

CLDN18.2 is selectively expressed in normal tissues in differentiated epithelial cells of the gastric mucosa. CLDN18.2 is expressed in cancers of various origins such as pancreatic carcinoma, esophageal carcinoma, gastric carcinoma, bronchial carcinoma, breast carcinoma, and ENT tumors. CLDN18.2 is a valuable target for the prevention and/or treatment of primary tumors, such as gastric cancer, esophageal cancer, pancreatic cancer, lung cancer such as non small cell lung cancer (NSCLC), ovarian cancer, colon cancer, hepatic cancer, head-neck cancer, and cancers of the gallbladder, and metastases thereof, in particular gastric cancer metastasis such as Krukenberg tumors, peritoneal metastasis, and lymph node metastasis.

CLDN6 has been found to be expressed, for example, in ovarian cancer, lung cancer, gastric cancer, breast cancer, hepatic cancer, pancreatic cancer, skin cancer, melanomas, head neck cancer, sarcomas, bile duct cancer, renal cell cancer, and urinary bladder cancer. CLDN6 is a particularly preferred target for the prevention and/or treatment of ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, uterine cancer, germ cell tumors such as a teratocarcinoma or an embryonal carcinoma, in particular germ cell tumors of the testis, and the metastatic forms thereof. In one embodiment, the cancer disease associated with CLDN6 expression is selected from the group consisting of ovarian cancer, lung cancer, metastatic ovarian cancer and metastatic lung cancer. Preferably, the ovarian cancer is a carcinoma or an adenocarcinoma. Preferably, the lung cancer is a carcinoma or an adenocarcinoma, and preferably is bronchiolar cancer such as a bronchiolar carcinoma or bronchiolar adenocarcinoma.

The term "CLDN" as used herein means claudin and includes CLDN18.2 and CLDN6. Preferably, a claudin is a human claudin.

The term "CLDN18" relates to claudin 18 and includes any variants, including claudin 18 splice variant 1 (claudin 18.1 (CLDN18.1)) and claudin 18 splice variant 2 (claudin 18.2 (CLDN18.2)).

The term "CLDN18.2" preferably relates to human CLDN18.2, and, in particular, to a protein comprising, preferably consisting of the amino acid sequence according to SEQ ID NO: 1 of the sequence listing or a variant of said amino acid sequence. The first extracellular loop of CLDN18.2 preferably comprises amino acids 27 to 81, more preferably amino acids 29 to 78 of the amino acid sequence shown in SEQ ID NO: 1. The second extracellular loop of CLDN18.2 preferably comprises amino acids 140 to 180 of the amino acid sequence shown in SEQ ID NO: 1. Said first and second extracellular loops preferably form the extracellular portion of CLDN18.2.

The term "CLDN6" preferably relates to human CLDN6, and, in particular, to a protein comprising, preferably consisting of the amino acid sequence of SEQ ID NO: 2 or SEQ ID NO: 3 of the sequence listing or a variant of said amino acid sequence. The first extracellular loop of CLDN6 preferably comprises amino acids 28 to 80, more preferably amino acids 28 to 76 of the amino acid sequence shown in SEQ ID NO: 2 or the amino acid sequence shown in SEQ ID NO: 3. The second extracellular loop of CLDN6 preferably comprises amino acids 138 to 160, preferably amino acids 141 to 159, more preferably amino acids 145 to 157 of the amino acid sequence shown in SEQ ID NO: 2 or the amino acid sequence shown in SEQ 11) NO: 3. Said first and second extracellular loops preferably form the extracellular portion of CLDN6.

The term "variant" according to the invention refers, in particular, to mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence. The term "variant" shall encompass any posttranslationally modified variants and conformation variants.

The second target molecule of the binding agents described herein is CD3 (cluster of differentiation 3). The CD3 complex denotes an antigen that is expressed on mature human T-cells, thymocytes and a subset of natural killer cells as part of the multimolecular T-cell receptor (TCR) complex. The T-cell co-receptor is a protein complex and is composed of four distinct chains. In mammals, the complex contains a CD3γ chain, a CD3δ chain, and two CD3ε chains. These chains associate with a molecule known as the T-cell receptor (TCR) and the ς-chain to generate an activation signal in T lymphocytes. The TCR, ζ-chain, and CD3 molecules together comprise the TCR complex.

The human CD3 epsilon is indicated in GenBank Accession No. NM_000733 and comprises SEQ ID NO: 4. The human CD3 gamma is indicated in GenBank Accession No. NM 000073. The human CD3 delta is indicated in GenBank Accession No. NM_000732. CD3 is responsible for the signal transduction of the TCR. As described by Lin and Weiss, Journal of Cell Science 114, 243-244 (2001), activation of the TCR complex by binding of MHC-presented specific antigen epitopes results in the phosphorylation of immunoreceptor tyrosine-based activation motifs (ITAMs) by Src family kinases, triggering recruitment of further kinases which results in T cell activation including $Ca^{2+}$ release. Clustering of CD3 on T cells, e.g. by immobilized anti-CD3-antibodies, leads to T cell activation similar to the engagement of the T cell receptor, but independent from its clone typical specificity.

As used herein, "CD3" includes human CD3 and denotes an antigen that is expressed on human T cells as part of the multimolecular T cell receptor complex.

With respect to CD3, the binding agent of the invention preferably recognizes the epsilon-chain of CD3, particular, it recognizes an epitope that corresponds to the first 27 N-terminal amino acids of CD3 epsilon or functional fragments of this 27 amino acid stretch.

According to the invention, the term "claudin positive cancer" or similar terms means a cancer involving cancer cells expressing a claudin, preferably on the surface of said cancer cells.

"Cell surface" is used in accordance with its normal meaning in the art, and thus includes the outside of the cell which is accessible to binding by proteins and other molecules A claudin is expressed on the surface of cells if it is located at the surface of said cells and is accessible to binding by claudin-specific antibodies added to the cells.

The term "extracellular portion" in the context of the present invention refers to a part of a molecule such as a protein that is facing the extracellular space of a cell and preferably is accessible from the outside of said cell, e.g., by antigen-binding molecules such as antibodies located outside the cell. Preferably, the term refers to one or more extracellular loops or domains or a fragment thereof.

The terms "part" or "fragment" are used interchangeably herein and refer to a continuous element. For example, a part of a structure such as an amino acid sequence or protein refers to a continuous element of said structure. A portion, a part or a fragment of a structure preferably comprises one or more functional properties of said structure. For example, a portion, a part or a fragment of an epitope or peptide is preferably immunologically equivalent to the epitope or peptide it is derived from. A part or fragment of a protein sequence preferably comprises a sequence of at least 6, in particular at least 8, at least 12, at least 15, at least 20, at least 30, at least 50, or at least 100 consecutive amino acids of the protein sequence.

According to the invention, CLDN18.2 is not substantially expressed in a cell if the level of expression is lower compared to expression in stomach cells or stomach tissue. Preferably, the level of expression is less than 10%, preferably less than 5%, 3%, 2%, 1%, 0.5%, 0.1% or 0.05% of the expression in stomach cells or stomach tissue or even lower. Preferably, CLDN18.2 is not substantially expressed in a cell if the level of expression exceeds the level of expression in non-cancerous tissue other than stomach by no more than 2-fold, preferably 1.5-fold, and preferably does not exceed the level of expression in said non-cancerous tissue. Preferably, CLDN18.2 is not substantially expressed in a cell if the level of expression is below the detection limit and/or if the level of expression is too low to allow binding by CLDN18.2-specific antibodies added to the cells.

According to the invention, CLDN18.2 is expressed in a cell if the level of expression exceeds the level of expression in non-cancerous tissue other than stomach preferably by more than 2-fold, preferably 10-fold, 100-fold, 1000-fold, or 10000-fold. Preferably, CLDN18.2 is expressed in a cell if the level of expression is above the detection limit and/or if the level of expression is high enough to allow binding by CLDN18.2-specific antibodies added to the cells. Preferably, CLDN18.2 expressed in a cell is expressed or exposed on the surface of said cell.

According to the invention, CLDN6 is not substantially expressed in a cell if the level of expression is lower compared to expression in placenta cells or placenta tissue. Preferably, the level of expression is less than 10%, preferably less than 5%, 3%, 2%, 1%, 0.5%, 0.1% or 0.05% of the expression in placenta cells or placenta tissue or even lower. Preferably, CLDN6 is not substantially expressed in a cell if the level of expression exceeds the level of expression in non-cancerous tissue other than placenta by no more than 2-fold, preferably 1.5-fold, and preferably does not exceed the level of expression in said non-cancerous tissue. Preferably, CLDN6 is not substantially expressed in a cell if the level of expression is below the detection limit and/or if the level of expression is too low to allow binding by CLDN6-specific antibodies added to the cells.

According to the invention, CLDN6 is expressed in a cell if the level of expression exceeds the level of expression in non-cancerous tissue other than placenta preferably by more than 2-fold, preferably 10-fold, 100-fold, 1000-fold, or 10000-fold. Preferably, CLDN6 is expressed in a cell if the level of expression is above the detection limit and/or if the level of expression is high enough to allow binding by CLDN6-specific antibodies added to the cells. Preferably, CLDN6 expressed in a cell is expressed or exposed on the surface of said cell.

According to the invention, the term "disease" refers to any pathological state, including cancer, in particular those forms of cancer described herein. Any reference herein to cancer or particular forms of cancer also includes cancer metastasis thereof. In a preferred embodiment, a disease to be treated according to the present application involves cells expressing claudin (CLDN) such as CLDN18.2 and/or CLDN6.

"Diseases associated with cells expressing CLDN" or similar expressions means according to the invention that CLDN is expressed in cells of a diseased tissue or organ. In one embodiment, expression of CLDN in cells of a diseased tissue or organ is increased compared to the state in a healthy tissue or organ. An increase refers to an increase by at least 10%, in particular at least 20%, at least 50%, at least 100%, at least 200%, at least 500%, at least 1000%, at least 10000% or even more. In one embodiment, expression is only found in a diseased tissue, while expression in a healthy tissue is repressed. According to the invention, diseases associated with cells expressing CLDN include cancer diseases. Furthermore, according to the invention, cancer diseases preferably are those wherein the cancer cells express CLDN.

As used herein, a "cancer disease" or "cancer" includes a disease characterized by aberrantly regulated cellular growth, proliferation, differentiation, adhesion, and/or migration. By "cancer cell" is meant an abnormal cell that grows by a rapid, uncontrolled cellular proliferation and continues to grow after the stimuli that initiated the new growth cease. Preferably, a "cancer disease" is characterized by cells expressing CLDN and a cancer cell expresses CLDN. A cell expressing CLDN preferably is a cancer cell, preferably of the cancers described herein.

The term "cancer" according to the invention comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above. The term cancer according to the invention also comprises cancer metastases.

According to the invention, a "carcinoma" is a malignant tumor derived from epithelial cells. This group represents the most common cancers, including the common forms of breast, prostate, lung and colon cancer.

"Adenocarcinoma" is a cancer that originates in glandular tissue. This tissue is also part of a larger tissue category known as epithelial tissue. Epithelial tissue includes skin, glands and a variety of other tissue that lines the cavities and organs of the body. Epithelium is derived embryologically from ectoderm, endoderm and mesoderm. To be classified as adenocarcinoma, the cells do not necessarily need to be part of a gland, as long as they have secretory properties. This form of carcinoma can occur in some higher mammals, including humans. Well differentiated adenocarcinomas tend to resemble the glandular tissue that they are derived from, while poorly differentiated may not. By staining the cells from a biopsy, a pathologist will determine whether the tumor is an adenocarcinoma or some other type of cancer. Adenocarcinomas can arise in many tissues of the body due to the ubiquitous nature of glands within the body. While each gland may not be secreting the same substance, as long as there is an exocrine function to the cell, it is considered glandular and its malignant form is therefore named adenocarcinoma. Malignant adenocarcinomas invade other tissues and often metastasize given enough time to do so. Ovarian adenocarcinoma is the most common type of ovarian carcinoma. It includes the serous and mucinous adenocarcinomas, the clear cell adenocarcinoma and the endometrioid adenocarcinoma.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system. In one embodiment, the term "metastasis" according to the invention relates to lymph node metastasis. One particular form of metastasis which is treatable using the therapy of the invention is metastasis originating from gastric cancer as primary site. In preferred embodiments such gastric cancer metastasis is Krukenberg tumors, peritoneal metastasis and/or lymph node metastasis.

Krukenberg tumor is an uncommon metastatic tumor of the ovary accounting for 1% to 2% of all ovarian tumors. Prognosis of Krukenberg tumor is still very poor and there is no established treatment for Krukenberg tumors. Krukenberg tumor is a metastatic signet ring cell adenocarcinoma of the ovary. Stomach is the primary site in most Krukenberg tumor cases (70%). Carcinomas of colon, appendix, and breast (mainly invasive lobular carcinoma) are the next most common primary sites. Rare cases of Krukenberg tumor originating from carcinomas of the gallbladder, biliary tract, pancreas, small intestine, ampulla of Vater, cervix, and urinary bladder/urachus have been reported.

By "treat" is meant to administer a compound or composition or a combination of compounds or compositions to a subject in order to prevent or eliminate a disease, including reducing the size of a tumor or the number of tumors in a subject; arrest or slow a disease in a subject; inhibit or slow the development of a new disease in a subject; decrease the frequency or severity of symptoms and/or recurrences in a subject who currently has or who previously has had a disease; and/or prolong, i.e. increase the lifespan of the subject.

In particular, the term "treatment of a disease" includes curing, shortening the duration, ameliorating, preventing, slowing down or inhibiting progression or worsening, or preventing or delaying the onset of a disease or the symptoms thereof.

In the context of the present invention, terms such as "protect", "prevent", "prophylactic", "preventive", or "protective" relate to the prevention or treatment or both of the occurrence and/or the propagation of a disease in a subject and, in particular, to minimizing the chance that a subject will develop a disease or to delaying the development of a disease. For example, a person at risk for cancer would be a candidate for therapy to prevent cancer.

By "being at risk" is meant a subject that is identified as having a higher than normal chance of developing a disease, in particular cancer, compared to the general population. In addition, a subject who has had, or who currently has, a disease, in particular cancer, is a subject who has an increased risk for developing a disease, as such a subject may continue to develop a disease. Subjects who currently have, or who have had, a cancer also have an increased risk for cancer metastases.

The term "patient" means according to the invention a subject for treatment, in particular a diseased subject, including human beings, nonhuman primates or another animals, in particular mammals such as cows, horses, pigs, sheeps, goats, dogs, cats or rodents such as mice and rats. In a particularly preferred embodiment, a patient is a human being.

"Target cell" shall mean any undesirable cell such as a cancer cell. In preferred embodiments, the target cell expresses CLDN.

The term "antigen" relates to an agent such as a protein or peptide comprising an epitope against which an immune response is directed and/or is to be directed. In a preferred embodiment, an antigen is a tumor-associated antigen, such as CLDN18.2 or CLDN6, i.e., a constituent of cancer cells which may be derived from the cytoplasm, the cell surface and the cell nucleus, in particular those antigens which are produced, preferably in large quantity, intracellular or as surface antigens on cancer cells.

In the context of the present invention, the term "tumor-associated antigen" preferably relates to proteins that are under normal conditions specifically expressed in a limited number of tissues and/or organs or in specific developmental stages and are expressed or aberrantly expressed in one or more tumor or cancer tissues. In the context of the present invention, the tumor-associated antigen is preferably associated with the cell surface of a cancer cell and is preferably not or only rarely expressed in normal tissues.

The term "epitope" refers to an antigenic determinant in a molecule, i.e., to the part in a molecule that is recognized by the immune system, for example, that is recognized by an antibody. For example, epitopes are the discrete, three-dimensional sites on an antigen, which are recognized by the immune system. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. An epitope of a protein preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 8, 9, 10, 11, 12, 13, 14, 15, 16, 17, 18, 19, 20, 21, 22, 23, 24, or 25 amino acids in length.

The term "antibody" refers to a glycoprotein comprising at least two heavy (H) chains and two light (L) chains inter-connected by disulfide bonds. The term "antibody" includes monoclonal antibodies, recombinant antibodies, human antibodies, humanized antibodies and chimeric antibodies. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "monoclonal antibody" as used herein refers to a preparation of antibody molecules of single molecular composition. A monoclonal antibody displays a single binding specificity and affinity. In one embodiment, the monoclonal antibodies are produced by a hybridoma which includes a B cell obtained from a non-human animal, e.g., mouse, fused to an immortalized cell.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "human antibody", as used herein, is intended to include antibodies having variable and constant regions derived from human germline immunoglobulin sequences. Human antibodies may include amino acid residues not encoded by human germline immunoglobulin sequences (e.g., mutations introduced by random or site-specific mutagenesis in vitro or by somatic mutation in vivo).

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen binding sites may be wild-type or modified by one or more amino acid substitutions, e.g. modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human, is less likely to elicit an immune response from a human subject when the antibodies are injected than would the constant region from a non human source. However the definition is not limited to this particular example.

Antibodies may be derived from different species, including but not limited to mouse, rat, rabbit, guinea pig and human.

Antibodies described herein include IgA such as IgA1 or IgA2, IgG1, IgG2, IgG3, IgG4, IgE, IgM, and IgD antibodies. In various embodiments, the antibody is an IgG1 antibody, more particularly an IgG1, kappa or IgG1, lambda isotype (i.e. IgG1, κ, λ), an IgG2a antibody (e.g. IgG2a, κ, λ), an IgG2b antibody (e.g. IgG2b, κ, λ), an IgG3 antibody (e.g. IgG3, κ, λ) or an IgG4 antibody (e.g. IgG4, κ, λ).

As used herein, a "heterologous antibody" is defined in relation to a transgenic organism producing such an antibody. This term refers to an antibody having an amino acid sequence or an encoding nucleic acid sequence corresponding to that found in an organism not consisting of the transgenic organism, and being generally derived from a species other than the transgenic organism.

As used herein, a "heterohybrid antibody" refers to an antibody having light and heavy chains of different organismal origins. For example, an antibody having a human heavy chain associated with a murine light chain is a heterohybrid antibody.

The antibodies described herein are preferably isolated. An "isolated antibody" as used herein, is intended to refer to an antibody which is substantially free of other antibodies having different antigenic specificities (e.g., an isolated antibody that specifically binds to CLDN18.2 is substantially free of antibodies that specifically bind antigens other than CLDN18.2). An isolated antibody that specifically binds to an epitope, isoform or variant of human CLDN18.2 may, however, have cross-reactivity to other related antigens, e.g., from other species (e.g., CLDN18.2 species homologs). Moreover, an isolated antibody may be substantially free of other cellular material and/or chemicals. In one embodiment of the invention, a combination of "isolated" monoclonal antibodies relates to antibodies having different specificities and being combined in a well defined composition or mixture.

The terms "antigen-binding portion" of an antibody (or simply "binding portion") or "antigen-binding fragment" of an antibody (or simply "binding fragment") or similar terms refer to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) Fab fragments, monovalent fragments consisting of the VL, VH, CL and CH domains; (ii) F(ab')$_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain: (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding fragment" of an antibody. A further example is binding-domain immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

The term "binding domain" characterizes in connection with the present invention a structure, e.g. of an antibody, which binds to/interacts with a given target structure/antigen/epitope. Thus, the binding domain according to the invention designates an "antigen-interaction-site".

All antibodies and derivatives of antibodies such as antibody fragments as described herein for the purposes of the invention are encompassed by the term "antibody". The term "antibody derivatives" refers to any modified form of an antibody, e.g., a conjugate of the antibody and another agent or antibody, or an antibody fragment. Furthermore, the antibodies and derivatives of antibodies as described herein are useful for producing binding agents of the invention such as antibody fragments.

Naturally occurring antibodies are generally monospecific, i.e. they bind to a single antigen. The present invention provides binding agents binding to a cytotoxic cell (by engaging the CD3 receptor) and a cancer cell (by engaging CLDN). The binding agents of the present invention are at least bispecific or multispecific such as trispecific, tetraspecific and so on.

The binding agent of the invention may be in the format of an antibody molecule or of an antibody-like molecule or of a protein scaffold with antibody-like properties or of a cyclic peptide with at least two binding specificities. Thus, the binding agent may comprise one or more antibodies as described herein or fragments thereof.

According to the invention, a bispecific molecule, in particular a bispecific protein, such as a bispecific antibody is a molecule that has two different binding specificities and thus may bind to two different types of antigen such as CLDN and CD3. Particularly, the term "bispecific antibody" as used herein refers to an antibody comprising two antigen-binding sites, a first binding site having affinity for a first antigen or epitope and a second binding site having binding affinity for a second antigen or epitope distinct from the first. In particular, a bispecific antibody is an artificial protein that is composed of fragments of two different antibodies (said fragments of two different antibodies forming two binding domains) and consequently binds to two different types of antigen. A bispecific antibody according to the invention is engineered to simultaneously bind to an immune cell, such as an immune effector cell, in particular a T cell such as a cytotoxic cell (by binding to CD3) and a target cell like a cancer cell (by binding to the tumor-associated antigen CLDN) to be destroyed.

The term "bispecific antibody" also includes diabodies. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90: 6444-6448; Poljak, R. J., et al. (1994) Structure 2: 1121-1123).

"Multispecific binding agents" are molecules which have more than two different binding specificities.

Particularly preferred according to the invention are bispecific antibodies including bispecific antibody fragments, in particular bispecific single chain antibodies including bispecific single chain antibody fragments. The term "bispecific single chain antibody" denotes a single polypeptide chain comprising two binding domains. In particular, the term "bispecific single chain antibody" or "single chain bispecific antibody" or related terms in accordance with the present invention preferably mean antibody constructs resulting from joining at least two antibody variable regions in a single polypeptide chain devoid of the constant and/or Fc portion(s) present in full immunoglobulins.

For example, a bispecific single chain antibody may be a construct with a total of two antibody variable regions, for example two VH regions, each capable of specifically binding to a separate antigen, and connected with one another through a short polypeptide spacer such that the two antibody variable regions with their interposed spacer exist as a single contiguous polypeptide chain. Another example of a bispecific single chain antibody may be a single polypeptide chain with three antibody variable regions. Here, two antibody variable regions, for example one VH and one VL, may make up an scFv, wherein the two antibody variable regions are connected to one another via a synthetic polypeptide linker, the latter often being genetically engineered so as to be minimally immunogenic while remaining maximally resistant to proteolysis. This scFv is capable of specifically binding to a particular antigen, and is connected to a further antibody variable region, for example a VH region, capable of binding to a different antigen than that bound by the scFv. Yet another example of a bispecific single chain antibody may be a single polypeptide chain with four antibody variable regions. Here, the first two antibody variable regions, for example a VH region and a VL region, may form one scFv capable of binding to one antigen, whereas the second VH region and VL region may form a second scFv capable of binding to another antigen. Within a single contiguous polypeptide chain, individual antibody variable regions of one specificity may advantageously be separated by a synthetic polypeptide linker, whereas the respective scFvs may advantageously be separated by a short polypeptide spacer as described above.

According to one embodiment of the invention, the first binding domain of the bispecific antibody comprises one antibody variable domain, preferably a VHH domain. According to one embodiment of the invention, the first binding domain of the bispecific antibody comprises two antibody variable domains, preferably a scFv, i.e. VH-VL or VL-VH. According to one embodiment of the invention, the second binding domain of the bispecific antibody comprises one antibody variable domain, preferably a VHH domain. According to one embodiment of the invention, the second binding domain of the bispecific antibody comprises two antibody variable domains, preferably a scFv, i.e. VH-VL or VL-VH. In its minimal form, the total number of antibody variable regions in the bispecific antibody according to the invention is thus only two. For example, such an antibody could comprise two VH or two VHH domains.

According to one embodiment of the invention, the first binding domain and the second binding domain of the bispecific antibody each comprise one antibody variable domain, preferably a VHH domain. According to one embodiment of the invention, the first binding domain and the second binding domain of the bispecific antibody each comprise two antibody variable domains, preferably a scFv, i.e. VH-VL or VL-VH. In this embodiment, the binding agent of the invention preferably comprises (i) a heavy chain variable domain (VH) of a CLDN antibody, (ii) a light chain variable domain (VL) of a CLDN antibody, (iii) a heavy chain variable domain (VH) of a CD3 antibody and (iv) a light chain variable domain (VL) of a CD3 antibody.

Bispecific full-length antibodies may be obtained by covalently linking two monoclonal antibodies or by conventional hybrid-hybridoma techniques. Covalent linking of two monoclonal antibodies is described in Anderson, Blood 80 (1992), 2826-34. In the context of this invention, one of the antibodies is specific for CLDN and the other one for CD3.

In one embodiment, the bispecific binding agent is in the format of an antibody-like molecule with a heavy chain containing two consecutive N-terminal variable domains with different specificities and a light chain with two consecutive variable domains with different specificities resulting in four binding domains with two different specificities (Wu et al., Nat. Biotechnology, 2007, 25(11)), wherein one specificity is CD3 and the other specificity is CLDN.

In a preferred embodiment, the bispecific binding agent of the invention is in the format of an antibody fragment.

In one embodiment, the bispecific molecules according to the invention comprises two Fab regions, one being directed against CLDN and the other being directed against CD3. In one embodiment, the molecule of the invention is an antigen binding fragment (Fab)2 complex. The Fab2 complex is composed of two Fab fragments, one Fab fragment comprising a Fv domain, i.e. VH and VL domains, specific for a CD3 antigen, and the other Fab fragment comprising a Fv domain specific for CLDN. Each of the Fab fragments may be composed of two single chains, a VL-CL module and a VH-CH module. Alternatively, each of the individual Fab fragments may be arranged in a single chain, preferably, VL-CL-CH-VH, and the individual variable and constant domains may be connected with a peptide linker. In general, the individual single chains and Fab fragments may be connected via disulfide bonds, adhesive domains, chemically linked and/or peptide linker. The bispecific molecule may also comprise more than two Fab fragments, in particular, the molecule may be a Fab3, Fab4, or a multimeric Fab complex with specificity for 2, 3, 4, or more different antigens. The invention also includes chemically linked Fabs.

In one embodiment, the binding agent according to the invention includes various types of bivalent and trivalent single-chain variable fragments (scFvs), fusion proteins mimicking the variable domains of two antibodies. A single-chain variable fragment (scFv) is a fusion protein of the variable regions of the heavy (VH) and light chains (VL) of immunoglobulins, connected with a short linker peptide of ten to about 25 amino acids. The linker is usually rich in glycine for flexibility, as well as serine or threonine for solubility, and can either connect the N-terminus of the VH with the C-terminus of the VL, or vice versa. Divalent (or bivalent) single-chain variable fragments (di-scFvs, bi-scFvs) can be engineered by linking two scFvs. This can be done by producing a single peptide chain with two VH and two VL regions, yielding tandem scFvs. The invention also includes multispecific molecules comprising more than two scFvs binding domains. This makes it possible that the molecule comprises either multiple antigen specificities and is a trispecific, tetraspecific, or multispecific molecule, or the molecule is a bispecific molecule comprising more than one scFv binding domain with specificity for the same antigen. In particular, the molecule of the invention may be a multispecific single chain Fv.

Another possibility is the creation of scFvs with linker peptides that are too short for the two variable regions to fold together (about five amino acids), forcing scFvs to dimerize. This type is known as diabodies. Still shorter linkers (one or two amino acids) lead to the formation of trimers, so-called triabodies or tribodies. Tetrabodies have also been produced. They exhibit an even higher affinity to their targets than diabodies.

A particularly preferred example of a bispecific antibody fragment is a diabody (Kipriyanov, Int. J. Cancer 77 (1998), 763-772), which is a small bivalent and bispecific antibody fragment. Diabodies comprise a heavy chain variable domain (VH) connected to a light chain variable domain (VL) on the same polypeptide chain (VH-VL) connected by a peptide linker that is too short to allow pairing between the two domains on the same chain. This forces pairing with the complementary domains of another chain and promotes the assembly of a dimeric molecule with two functional antigen binding sites. To construct bispecific diabodies of the invention, the V-domains of an anti-CD3 antibody and an anti-CLDN antibody may be fused to create the two chains VH(CD3)-VL(CLDN), VH(CLDN)-VL(CD3). Each chain by itself is not able to bind to the respective antigen, but recreates the functional antigen binding sites of an anti-CD3 antibody and an anti-CLDN antibody on pairing with the other chain. To this end, a peptide linker that is too short to allow pairing between the two domains on the same chain is used. The two scFv molecules, with a linker between heavy chain variable domain and light chain variable domain that is too short for intramolecular dimerization, are co-expressed and self assemble to form bi-specific molecules with the two binding sites at opposite ends.

In one embodiment, the multispecific molecule according to the invention comprises variable (VH, VL) and constant domains (C) of immunoglobulins. In one embodiment the bispecific molecule is a minibody, preferably, a minibody comprising two single VH-VL-C chains that are connected with each other via the constant domains (C) of each chain. According to this aspect, the corresponding variable heavy chain regions (VH), corresponding variable light chain regions (VL) and constant domains (C) are arranged, from N-terminus to C-terminus, in the order VH(CLDN)-VL(CLDN)-(C) and VH(CD3)-VL(CD3)-C, wherein C is preferably a CH3 domain. Pairing of the constant domains results in formation of the minibody.

According to another particularly preferred aspect, the bispecific binding agent of the invention is in the format of a bispecific single chain antibody construct, whereby said construct comprises or consists of at least two binding domains, whereby one of said domains binds to CLDN and a second domain binds to CD3. Such molecules, also termed "bispecific T cell engagers" (BiTEs; the term BiTE only refers to bi-specific molecules of which one arm is specific for CD3) consist of two scFv molecules connected via a linker peptide.

As used herein, a "bispecific single chain antibody" denotes a single polypeptide chain comprising two binding domains. Each binding domain comprises one variable region from an antibody heavy chain ("VH region"), wherein the VH region of the first binding domain specifically binds to the CLDN, and the VH region of the second binding domain specifically binds to CD3. The two binding domains are optionally linked to one another by a short polypeptide spacer. A non-limiting example for a polypeptide spacer is Gly-Gly-Gly-Gly-Ser (G-G-G-G-S) and repeats thereof. Each binding domain may additionally comprise one variable region from an antibody light chain ("VH region"), the VH region and VL region within each of the first and second binding domains being linked to one another via a polypeptide linker long enough to allow the VH region and VL region of the first binding domain and the VH region and VL region of the second binding domain to pair with one another.

According to this aspect, the corresponding variable heavy chain regions (VH) and the corresponding variable light chain regions (VL) are arranged, from N-terminus to C-terminus, in the order VH(CLDN)-VL(CLDN)-VH(CD3)-VL(CD3), VH(CD3)-VL(CD3)-VH(CLDN)-VL(CLDN) or VH(CD3)-VL(CD3)-VL(CLDN)-VH(CLDN). It is, however, also envisaged that the bispecific single chain antibodies of the invention comprise other domain arrangements, such as VL(CLDN)-VH(CLDN)-VH(CD3)-VL(CD3), VL(CLDN)-VH(CLDN)-VL(CD3)-VH(CD3), VH(CLDN)-VL(CLDN)-VL(CD3)-VH(CD3), VL(CD3)-VH(CD3)-VH(CLDN)-VL(CLDN), VL(CD3)-VH(CD3)-VL(CLDN)-VH(CLDN).

A long linker generally connects the corresponding variable heavy chain regions (VH) and the corresponding variable light chain regions (VL) to create a scFv binding domain while a short linker generally connects two scFv binding domains. The linker is generally designed to provide flexibility and protease resistance, and preferably, the linker comprises glycine and/or serine amino acid residues. Short peptide linkers may consist of 12 or less such as 11, 10, 9, 8, 7, 6, 5, 4, 3 or 2 amino acids, and preferably, 5 or 6 amino acids. Short peptide linkers preferably comprise the amino acid sequences SGGGGS or GGGGS. Long peptide linkers may consist of 12 or more, such as 15 to 25 or 15 to 20 or 15 to 18 amino acids. Long peptide linkers preferably comprise the amino acid sequences (GGGGS)3 or VE(GGSGGS)2GGVD. Further long peptide linkers may comprise the amino acid sequences (GGGGS)4, (GGGGS)5 or GGGGS(GGS)3GGGS.

Binding agents according to the invention may also comprises an amino acid sequence for facilitating secretion of the molecule, such as a N-terminal secretion signal, and/or one or more epitope tags facilitating binding, purification or detection of the molecule.

Preferably, the secretion signal is a signal sequence (e.g. selected from any one of SEQ ID NOs: 51, 52, 53, 54, 55) that allows a sufficient passage through the secretory pathway and/or secretion of the binding agent into the extracellular environment. Preferably, the secretion signal sequence is cleavable and is removed from the mature binding agent. The secretion signal sequence preferably is chosen with respect to the cell or organism wherein the binding agent is produced in.

The amino acid sequence of an epitope tag may be introduced to any position within the amino acid sequence of the binding agent, and may take the shape of a loop within the encoded protein structure, or it may be N-terminally or C-terminally fused to the binding agent. Preferably, the epitope tag is C-terminally fused to the binding agent. The epitope tag may contain a cleavage site that allows a removal of the tag from the binding agent. Said epitope tag can be any kind of epitope tag that is functional under native and/or denaturing conditions, preferable a histidin tag, most preferable a tag comprising six histidins.

The bispecific binding agent of the invention may contain, in addition to said first and second binding domain, a further binding domain which serves e.g. to enhance selectivity for tumor cells. This can be achieved e.g. by providing binding domains that bind to other antigens expressed on tumor cells.

In the context of the present invention, the binding agents generated are preferably capable of eliciting immune effector functions as described herein. Preferably, said immune effector functions are directed against cells carrying the tumor-associated antigen CLDN on their surface.

The term "immune effector functions" in the context of the present invention includes any functions mediated by components of the immune system that result e.g. in the inhibition of tumor growth and/or inhibition of tumor development, including inhibition of tumor dissemination and metastasis. Preferably, immune effector functions result in killing of tumor cells. Such functions comprise complement dependent cytotoxicity (CDC), antibody-dependent cell-mediated cytotoxicity (ADCC), antibody-dependent cell-mediated phagocytosis (ADCP), induction of apoptosis in the cells carrying the tumor-associated antigen, cytolysis of the cells carrying the tumor-associated antigen, and/or inhibition of proliferation of the cells carrying the tumor-associated antigen. Binding agents may also exert an effect simply by binding to tumor-associated antigens on the surface of a cancer cell. For example, antibodies may block the function of the tumor-associated antigen or induce apoptosis just by binding to the tumor-associated antigen on the surface of a cancer cell.

The binding agents described herein may be conjugated to a therapeutic moiety or agent, such as a cytotoxin, a drug (e.g., an immunosuppressant) or a radioisotope. A cytotoxin or cytotoxic agent includes any agent that is detrimental to and, in particular, kills cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Suitable therapeutic agents for forming conjugates include, but are not limited to, antimetabolites (e.g., methotrexate, 6-mercaptopurine, 6-thioguanine, cytarabine, fludarabin, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC), and anti-mitotic agents (e.g., vincristine and vinblastine). In a preferred embodiment, the therapeutic agent is a cytotoxic agent or a radiotoxic agent. In another embodiment, the therapeutic agent is an immunosuppressant. In yet another embodiment, the therapeutic agent is GM-CSF. In a preferred embodiment, the therapeutic agent is doxorubicin, cisplatin, bleomycin, sulfate, carmustine, chlorambucil, cyclophosphamide or ricin A.

Binding agents also can be conjugated to a radioisotope, e.g., iodine-131, yttrium-90 or indium-111, to generate cytotoxic radiopharmaceuticals.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62: 119-58 (1982).

The term "binding" according to the invention preferably relates to a specific binding.

According to the present invention, an agent such as an antibody is capable of binding to a predetermined target if it has a significant affinity for said predetermined target and binds to said predetermined target in standard assays. "Affinity" or "binding affinity" is often measured by equilibrium dissociation constant ($K_D$). Preferably, the term "significant affinity" refers to the binding to a predetermined target with a dissociation constant ($K_D$) of $10^{-5}$ M or lower, $10^{-6}$ M or lower, $10^{-7}$ M or lower, $10^{-8}$ M or lower, $10^{-9}$ M or lower, $10^{-10}$ M or lower, $10^{-11}$ M or lower, or $10^{-12}$ M or lower.

An agent is not (substantially) capable of binding to a target if it has no significant affinity for said target and does not bind significantly, in particular does not bind detectably, to said target in standard assays. Preferably, the agent does not detectably bind to said target if present in a concentration of up to 2, preferably 10, more preferably 20, in particular 50 or 100 µg/ml or higher. Preferably, an agent has no significant affinity for a target if it binds to said target with a $K_D$ that is at least 10-fold, 100-fold, $10^3$-fold, $10^4$-fold, $10^5$-fold, or $10^6$-fold higher than the Kr for binding to the predetermined target to which the agent is capable of binding. For example, if the $K_D$ for binding of an agent to the target to which the agent is capable of binding is $10^{-7}$ M, the $K_D$ for binding to a target for which the agent has no significant affinity would be at least $10^{-6}$ M, $10^{-5}$ M, $10^{-4}$ M, $10^{-3}$ M, $10^{-2}$ M, or $10^{-1}$ M.

An agent such as an antibody is specific for a predetermined target if it is capable of binding to said predetermined target while it is not capable of binding to other targets, i.e. has no significant affinity for other targets and does not significantly bind to other targets in standard assays. According to the invention, an agent is specific for CLDN if it is capable of binding to CLDN but is not (substantially) capable of binding to other targets. Preferably, an agent is specific for CLDN if the affinity for and the binding to such other targets does not significantly exceed the affinity for or binding to CLDN-unrelated proteins such as bovine serum albumin (BSA), casein, human serum albumin (HSA) or non-claudin transmembrane proteins such as MHC molecules or transferrin receptor or any other specified polypeptide. Preferably, an agent is specific for a predetermined target if it binds to said target with a $K_D$ that is at least 10-fold, 100-fold, $10^3$-fold, $10^4$-fold, $10^5$-fold, or $10^6$-fold lower than the $K_D$ for binding to a target for which it is not specific. For example, if the $K_D$ for binding of an agent to the target for which it is specific is $10^{-7}$ M, the $K_D$ for binding to a target for which it is not specific would be at least $10^{-6}$ M, $10^{-7}$ M, $10^{-4}$ M, $10^{-3}$ M, $10^{-2}$ M, or $10^{-1}$ M.

Binding of an agent to a target can be determined experimentally using any suitable method; see, for example, Berzofsky et al., "Antibody-Antigen Interactions" In Fundamental Immunology, Paul, W. E., Ed., Raven Press New York, N Y (1984), Kuby, Janis Immunology, W. H. Freeman and Company New York, N Y (1992), and methods described herein. Affinities may be readily determined using conventional techniques, such as by equilibrium dialysis; by using the BIAcore 2000 instrument, using general procedures outlined by the manufacturer; by radioimmunoassay using radiolabeled target antigen; or by another method known to the skilled artisan. The affinity data may be analyzed, for example, by the method of Scatchard et al., Ann N.Y. Acad. ScL, 51:660 (1949). The measured affinity of a particular antibody-antigen interaction can vary if measured under different conditions, e.g., salt concentration, pH. Thus, measurements of affinity and other antigen-binding parameters, e.g., $K_D$, $IC_{50}$, are preferably made with standardized solutions of antibody and antigen, and a standardized buffer.

As used herein, "isotype" refers to the antibody class (e.g., IgM or IgG1) that is encoded by heavy chain constant region genes.

As used herein, "isotype switching" refers to the phenomenon by which the class, or isotype, of an antibody changes from one Ig class to one of the other Ig classes.

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally occurring.

The term "rearranged" as used herein refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin (antibody) gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

In one embodiment, a binding agent of the invention has the ability of binding to CLDN18.2, i.e. the ability of binding to an epitope present in CLDN18.2, preferably an epitope located within the extracellular domains of CLDN18.2, in particular the first extracellular loop, preferably amino acid positions 29 to 78 of CLDN18.2. In particular embodiments, an agent having the ability of binding to CLDN18.2 binds to an epitope on CLDN18.2 which is not present on CLDN18.1.

An agent having the ability of binding to CLDN18.2 preferably binds to CLDN18.2 but not to CLDN18.1. Preferably, an agent having the ability of binding to CLDN18.2 is specific for CLDN18.2. Preferably, an agent having the ability of binding to CLDN18.2 binds to CLDN18.2 expressed on the cell surface. In particular preferred embodiments, an agent having the ability of binding to CLDN18.2 binds to native epitopes of CLDN18.2 present on the surface of living cells.

In a preferred embodiment, an agent having the ability of binding to CLDN18.2 comprises a heavy chain variable region (VH) comprising an amino acid sequence selected from the group consisting of SEQ ID NOs: 5, 6, 7, 8, 9, 10, and a fragment thereof.

In a preferred embodiment, an agent having the ability of binding to CLDN18.2 comprises a light chain variable region (VL) comprising an amino acid sequence selected from the group consisting of SEQ ID NOs: 11, 12, 13, 14, 15, 16, 17, 18, 19, and a fragment thereof.

In certain preferred embodiments, an agent having the ability of binding to CLDN18.2 comprises a combination of heavy chain variable region (VH) and light chain variable region (VL) selected from the following possibilities (i) to (ix):

(i) the VH comprises an amino acid sequence represented by SEQ ID NO: 5 or a fragment thereof and the VL comprises an amino acid sequence represented by SEQ ID NO: 12 or a fragment thereof,
(ii) the VH comprises an amino acid sequence represented by SEQ ID NO: 6 or a fragment thereof and the VL comprises an amino acid sequence represented by SEQ ID NO: 11 or a fragment thereof,
(iii) the VH comprises an amino acid sequence represented by SEQ ID NO: 7 or a fragment thereof and the VL comprises an amino acid sequence represented by SEQ ID NO: 13 or a fragment thereof,
(iv) the VH comprises an amino acid sequence represented by SEQ ID NO: 9 or a fragment thereof and the VL comprises an amino acid sequence represented by SEQ ID NO: 16 or a fragment thereof,
(v) the VH comprises an amino acid sequence represented by SEQ ID NO: 8 or a fragment thereof and the VL comprises an amino acid sequence represented by SEQ ID NO: 15 or a fragment thereof,
(vi) the VH comprises an amino acid sequence represented by SEQ ID NO: 10 or a fragment thereof and the VL comprises an amino acid sequence represented by SEQ ID NO: 14 or a fragment thereof,
(vii) the VH comprises an amino acid sequence represented by SEQ ID NO: 10 or a fragment thereof and the VL comprises an amino acid sequence represented by SEQ ID NO: 17 or a fragment thereof,
(viii) the VH comprises an amino acid sequence represented by SEQ ID NO: 10 or a fragment thereof and the VL comprises an amino acid sequence represented by SEQ ID NO: 18 or a fragment thereof,
(ix) the VH comprises an amino acid sequence represented by SEQ ID NO: 10 or a fragment thereof and the VL comprises an amino acid sequence represented by SEQ ID NO: 19 or a fragment thereof.

In a particularly preferred embodiment, an agent having the ability of binding to CLDN18.2 comprises the following combination of heavy chain variable region (VH) and light chain variable region (VL):
the VH comprises an amino acid sequence represented by SEQ ID NO: 8 or a fragment thereof and the VL comprises an amino acid sequence represented by SEQ ID NO: 15 or a fragment thereof.

In a further particularly preferred embodiment, an agent having the ability of binding to CLDN18.2 comprises the following combination of heavy chain variable region (VH) and light chain variable region (VL):
the VH comprises an amino acid sequence represented by SEQ ID NO: 6 or a fragment thereof and the VL comprises an amino acid sequence represented by SEQ ID NO: 11 or a fragment thereof.

The term "fragment" refers, in particular, to one or more of the complementarity-determining regions (CDRs), preferably at least the CDR3 variable region, of the heavy chain variable region (VH) and/or of the light chain variable region (VL). In one embodiment said one or more of the complementarity-determining regions (CDRs) are selected from a set of complementarity-determining regions CDR1, CDR2 and CDR3. In a particularly preferred embodiment, the term "fragment" refers to the complementarity-determining regions CDR1, CDR2 and CDR3 of the heavy chain variable region (VH) and/or of the light chain variable region (VL).

In one embodiment a binding agent comprising one or more CDRs, a set of CDRs or a combination of sets of CDRs as described herein comprises said CDRs together with their intervening framework regions. Preferably, the portion will also include at least about 50% of either or both of the first and fourth framework regions, the 50% being the C-terminal 50% of the first framework region and the N-terminal 50% of the fourth framework region. Construction of binding agents made by recombinant DNA techniques may result in the introduction of residues N- or C-terminal to the variable regions encoded by linkers introduced to facilitate cloning or other manipulation steps, including the introduction of linkers to join variable regions of the invention to further protein sequences including immunoglobulin heavy chains, other variable domains (for example in the production of diabodies) or protein labels.

In one embodiment a binding agent comprising one or more CDRs, a set of CDRs or a combination of sets of CDRs as described herein comprises said CDRs in a human antibody framework.

In one embodiment, a binding agent of the invention has the ability of binding to CLDN6, i.e. the ability of binding to an epitope present in CLDN6, preferably an epitope located within the extracellular domains of CLDN6, in particular the first extracellular loop, preferably amino acid positions 28 to 76 of CLDN6 or the second extracellular loop, preferably amino acid positions 141 to 159 of CLDN6. In particular embodiments, an agent having the ability of binding to CLDN6 binds to an epitope on CLDN6 which is not present on CLDN9. Preferably, an agent having the ability of binding to CLDN6 binds to an epitope on CLDN6 which is not present on CLDN4 and/or CLDN3. Most preferably, an agent having the ability of binding to CLDN6 binds to an epitope on CLDN6 which is not present on a CLDN protein other than CLDN6.

An agent having the ability of binding to CLDN6 preferably hinds to CLDN6 but not to CLDN9 and preferably does not bind to CLDN4 and/or CLDN3. Preferably, an agent having the ability of binding to CLDN6 is specific for CLDN6. Preferably, an agent having the ability of binding to CLDN6 binds to CLDN6 expressed on the cell surface. In particular preferred embodiments, an agent having the ability of binding to CLDN6 binds to native epitopes of CLDN6 present on the surface of living cells.

In a preferred embodiment, an agent having the ability of binding to CLDN6 comprises a heavy chain variable region (VH) comprising an amino acid sequence selected from the group consisting of SEQ ID NOs: 20, 22, 24, 26, and a fragment thereof.

In a preferred embodiment, an agent having the ability of binding to CLDN6 comprises a light chain variable region (VL) comprising an amino acid sequence selected from the group consisting of SEQ ID NOs: 21, 23, 25, 27, 28, 29, 97, 98, 99, 100, and a fragment thereof.

In certain preferred embodiments, an agent having the ability of binding to CLDN6 comprises a combination of heavy chain variable region (VH) and light chain variable region (VL) selected from the following possibilities (i) to (xi):
(i) the VH comprises an amino acid sequence represented by SEQ ID NO: 20 or a fragment 33 thereof and the VL comprises an amino acid sequence represented by SEQ ID NO: 21 or a fragment thereof,
(ii) the VH comprises an amino acid sequence represented by SEQ ID NO: 22 or a fragment thereof and the VL comprises an amino acid sequence represented by SEQ ID NO: 23 or a fragment thereof,
(iii) the VH comprises an amino acid sequence represented by SEQ ID NO: 24 or a fragment thereof and the VL comprises an amino acid sequence represented by SEQ ID NO: 25 or a fragment thereof,
(iv) the VH comprises an amino acid sequence represented by SEQ ID NO: 26 or a fragment thereof and the VL comprises an amino acid sequence represented by SEQ ID NO: 27 or a fragment thereof,
(v) the VH comprises an amino acid sequence represented by SEQ ID NO: 22 or a fragment thereof and the VL comprises an amino acid sequence represented by SEQ ID NO: 21 or a fragment thereof,
(vi) the VH comprises an amino acid sequence represented by SEQ ID NO: 22 or a fragment thereof and the VL comprises an amino acid sequence represented by SEQ ID NO: 28 or a fragment thereof,
(vii) the VH comprises an amino acid sequence represented by SEQ ID NO: 22 or a fragment thereof and the VL, comprises an amino acid sequence represented by SEQ ID NO: 29 or a fragment thereof,
(viii) the VH comprises an amino acid sequence represented by SEQ ID NO: 22 or a fragment thereof and the VL comprises an amino acid sequence represented by SEQ ID NO: 97 or a fragment thereof,
(ix) the VH comprises an amino acid sequence represented by SEQ ID NO: 22 or a fragment thereof and the VL comprises an amino acid sequence represented by SEQ ID NO: 98 or a fragment thereof,
(x) the VH comprises an amino acid sequence represented by SEQ ID NO: 22 or a fragment thereof and the VL comprises an amino acid sequence represented by SEQ ID NO: 99 or a fragment thereof,
(xi) the VH comprises an amino acid sequence represented by SEQ ID NO: 22 or a fragment thereof and the VL comprises an amino acid sequence represented by SEQ ID NO: 100 or a fragment thereof.

In a particularly preferred embodiment, an agent having the ability of binding to CLDN6 comprises the following combination of heavy chain variable region (VH) and light chain variable region (VL):
the VH comprises an amino acid sequence represented by SEQ ID NO: 22 or a fragment thereof and the VL comprises an amino acid sequence represented by SEQ ID NO: 23 or a fragment thereof.

In a further particularly preferred embodiment, an agent having the ability of binding to CLDN6 comprises the following combination of heavy chain variable region (VH) and light chain variable region (VL):
the VH comprises an amino acid sequence represented by SEQ ID NO: 22 or a fragment thereof and the VL comprises an amino acid sequence represented by SEQ ID NO: 97 or a fragment thereof.

In a further particularly preferred embodiment, an agent having the ability of binding to CLDN6 comprises the following combination of heavy chain variable region (VH) and light chain variable region (VL):
the VH comprises an amino acid sequence represented by SEQ ID NO: 22 or a fragment thereof and the VL comprises an amino acid sequence represented by SEQ ID NO: 98 or a fragment thereof.

In a further particularly preferred embodiment, an agent having the ability of binding to CLDN6 comprises the following combination of heavy chain variable region (VH) and light chain variable region (VL):
the VH comprises an amino acid sequence represented by SEQ ID NO: 22 or a fragment thereof and the VL comprises an amino acid sequence represented by SEQ ID NO: 99 or a fragment thereof.

In a further particularly preferred embodiment, an agent having the ability of binding to CLDN6 comprises the following combination of heavy chain variable region (VH) and light chain variable region (VL):
the VH comprises an amino acid sequence represented by SEQ ID NO: 22 or a fragment thereof and the VL comprises an amino acid sequence represented by SEQ ID NO: 100 or a fragment thereof.

The term "fragment" refers, in particular, to one or more of the complementarity-determining regions (CDRs), preferably at least the CDR3 variable region, of the heavy chain variable region (VH) and/or of the light chain variable region (VL). In one embodiment said one or more of the complementarity-determining regions (CDRs) are selected from a set of complementarity-determining regions CDR1, CDR2 and CDR3. In a particularly preferred embodiment, the term "fragment" refers to the complementarity-determining regions CDR1, CDR2 and CDR3 of the heavy chain variable region (VH) and/or of the light chain variable region (VL).

In one embodiment a binding agent comprising one or more CDRs, a set of CDRs or a combination of sets of CDRs as described herein comprises said CDRs together with their intervening framework regions. Preferably, the portion will also include at least about 50% of either or both of the first and fourth framework regions, the 50% being the C-terminal 50% of the first framework region and the N-terminal 50% of the fourth framework region. Construction of binding agents made by recombinant DNA techniques may result in the introduction of residues N- or C-terminal to the variable regions encoded by linkers introduced to facilitate cloning or other manipulation steps, including the introduction of linkers to join variable regions of the invention to further protein sequences including immunoglobulin heavy chains, other variable domains (for example in the production of diabodies) or protein labels.

In one embodiment a binding agent comprising one or more CDRs, a set of CDRs or a combination of sets of CDRs as described herein comprises said CDRs in a human antibody framework.

Anti-CD3 antibodies which are useful for providing binding agents according to the invention include but are not limited to UCHT1-HS (humanized mAB), UCHT1-MM (murine mAB), CLB-T3, TR66, 145-2C11.

UCHT1 is a monoclonal IgG1 anti-CD3 monoclonal antibody which detects CD3 in human and primate sample types. CLB-T3 is a mouse monoclonal anti-CD3 antibody which is directed against the CD3 antigen and reacts with 80-90% human peripheral T lymphocytes and medullary thymocytes. TR66 is a mouse IgG1 monoclonal anti-CD3 antibody which recognizes the epsilon-chain of human CD3. 145-2C11 is an armenian hamster monoclonal anti-mouse CD3 antibody.

Preferably, the VH and VL regions of the CD3-binding domain are derived from antibodies/antibody molecules and antibody-like molecules which are capable of specifically recognizing the human CD3 in the context of other TCR subunits as present on activated primary human T cells expressing the TCR in its native configuration. The VH and VL regions derived from an antibody specific for the CD3-epsilon chain are most preferred and said (parental) antibodies should be capable of specifically binding epitopes reflecting the native or near-native structure or a conformational epitope of human CD3 presented in the context of the TCR complex. In a preferred embodiment of the invention, the VH and VL regions of the CD3-binding domain are derived from a CD3 specific antibody selected from the group consisting of UCHT1-HS, UCHT1-MM, CLB-T3 and TR66, preferably TR66.

In a preferred embodiment, an agent having the ability of binding to CD3 comprises a heavy chain variable region (VH) comprising an amino acid sequence selected from the group consisting of SEQ ID NOs: 30, 32, 34, 36, 94, 95, and a fragment thereof.

In a preferred embodiment, an agent having the ability of binding to CD3 comprises a light chain variable region (VL) comprising an amino acid sequence selected from the group consisting of SEQ ID NOs: 31, 33, 35, 37, 96, and a fragment thereof.

In certain preferred embodiments, an agent having the ability of binding to CD3 comprises a combination of heavy chain variable region (VH) and light chain variable region (VL) selected from the following possibilities (i) to (ix):
(i) the VH comprises an amino acid sequence represented by SEQ ID NO: 30 or a fragment thereof and the VL comprises an amino acid sequence represented by SEQ ID NO: 31 or a fragment thereof,
(ii) the VH comprises an amino acid sequence represented by SEQ ID NO: 32 or a fragment thereof and the VL comprises an amino acid sequence represented by SEQ ID NO: 33 or a fragment thereof,
(iii) the VH comprises an amino acid sequence represented by SEQ ID NO: 34 or a fragment thereof and the VL comprises an amino acid sequence represented by SEQ ID NO: 34 or a fragment thereof,
(iv) the VH comprises an amino acid sequence represented by SEQ ID NO: 36 or a fragment thereof and the VL comprises an amino acid sequence represented by SEQ ID NO: 37 or a fragment thereof,
(v) the VH comprises an amino acid sequence represented by SEQ ID NO: 94 or a fragment thereof and the VL comprises an amino acid sequence represented by SEQ ID NO: 37 or a fragment thereof,
(vi) the VH comprises an amino acid sequence represented by SEQ ID NO: 95 or a fragment thereof and the VL comprises an amino acid sequence represented by SEQ TD NO: 37 or a fragment thereof,
(vii) the VH comprises an amino acid sequence represented by SEQ ID NO: 36 or a fragment thereof and the VL comprises an amino acid sequence represented by SEQ ID NO: 96 or a fragment thereof,
(viii) the VH comprises an amino acid sequence represented by SEQ ID NO: 94 or a fragment thereof and the VL comprises an amino acid sequence represented by SEQ ID NO: 96 or a fragment thereof,
(ix) the VH comprises an amino acid sequence represented by SEQ ID NO: 95 or a fragment thereof and the VL comprises an amino acid sequence represented by SEQ ID NO: 96 or a fragment thereof.

In a particularly preferred embodiment, an agent having the ability of binding to CD3 comprises the following combination of heavy chain variable region (VH) and light chain variable region (VL):
the VH comprises an amino acid sequence represented by SEQ ID NO: 36 or a fragment thereof and the VL comprises an amino acid sequence represented by SEQ ID NO: 37 or a fragment thereof.

In a further particularly preferred embodiment, an agent having the ability of binding to CD3 comprises the following combination of heavy chain variable region (VH) and light chain variable region (VL):
the VH comprises an amino acid sequence represented by SEQ ID NO: 94 or a fragment thereof and the VL comprises an amino acid sequence represented by SEQ ID NO: 37 or a fragment thereof.

In a further particularly preferred embodiment, an agent having the ability of binding to CD3 comprises the following combination of heavy chain variable region (VH) and light chain variable region (VL):
the VH comprises an amino acid sequence represented by SEQ ID NO: 95 or a fragment thereof and the VL comprises an amino acid sequence represented by SEQ ID NO: 96 or a fragment thereof.

The term "fragment" refers, in particular, to one or more of the complementarity-determining regions (CDRs), preferably at least the CDR3 variable region, of the heavy chain variable region (VH) and/or of the light chain variable region (VL). In one embodiment said one or more of the complementarity-determining regions (CDRs) are selected from a set of complementarity-determining regions CDR1, CDR2 and CDR3. In a particularly preferred embodiment, the term "fragment" refers to the complementarity-determining regions CDR1, CDR2 and CDR3 of the heavy chain variable region (VH) and/or of the light chain variable region (VL).

In one embodiment a binding agent comprising one or more CDRs, a set of CDRs or a combination of sets of CDRs as described herein comprises said CDRs together with their intervening framework regions. Preferably, the portion will also include at least about 50% of either or both of the first and fourth framework regions, the 50% being the C-terminal 50% of the first framework region and the N-terminal 50% of the fourth framework region. Construction of binding agents made by recombinant DNA techniques may result in the introduction of residues N- or C-terminal to the variable regions encoded by linkers introduced to facilitate cloning or other manipulation steps, including the introduction of linkers to join variable regions of the invention to further protein sequences including immunoglobulin heavy chains, other variable domains (for example in the production of diabodies) or protein labels.

In one embodiment a binding agent comprising one or more CDRs, a set of CDRs or a combination of sets of CDRs as described herein comprises said CDRs in a human antibody framework.

According to the invention, a preferred binding agent targeting CLDN18.2 comprises an amino acid sequence selected from the group consisting of SEQ ID NOs: 38, 39, 40 and 41 or a variant thereof.

According to the invention, a further preferred binding agent targeting CLDN18.2 comprises an amino acid sequence selected from the group consisting of SEQ ID NOs: 103, 66, 67, 68, 69, 70, 71, 72, 73, 74, 75, 76, 77, 78, 79, 80, 81, 82, 83, 84, 85, 86, 87, 88, 89, 90, 91, 92 and 93 or a fragment or variant thereof. In one embodiment, said amino acid sequence lacks secretion signals such as N-terminal secretion signals, in particular the sequence according to SEQ ID NO: 51 and/or lacks His-tags such as C-terminal His-tags, in particular the sequence Gly-Gly-Ser-(His)$_6$ or (His)$_6$,if present.

According to the invention, a preferred binding agent targeting CLDN6 comprises an amino acid sequence selected from the group consisting of SEQ ID NOs: 42, 43, 44 and 45 or a variant thereof.

According to the invention, a further preferred binding agent targeting CLDN6 comprises an amino acid sequence selected from the group consisting of SEQ ID NOs: 101, 102, 60, 61, 62, 63, 64 and 65 or a fragment or variant thereof. In one embodiment said amino acid sequence lacks secretion signals such as N-terminal secretion signals, in particular the sequence according to SEQ ID NO: 51 and/or lacks His-tags such as C-terminal His-tags, in particular the sequence Gly-Gly-Ser-(His)$_6$ or (His)$_6$, if present.

It is to be understood that the binding agents described herein may be delivered to a patient by administering a nucleic acid such as RNA encoding the agent and/or by administering a host cell comprising a nucleic acid such as RNA encoding the agent. Thus, a nucleic acid encoding a binding agent when administered to a patient may be present in naked form or in a suitable delivery vehicle such as in the form of liposomes or viral particles, or within a host cell. The nucleic acid provided can produce the agent over extended time periods in a sustained manner mitigating the instability at least partially observed for therapeutic antibodies, in particular bispecific antibodies. Nucleic acids to be delivered to a patient can be produced by recombinant means. If a nucleic acid is administered to a patient without being present within a host cell, it is preferably taken up by cells of the patient for expression of the binding agent encoded by the nucleic acid. If a nucleic acid is administered to a patient while being present within a host cell, it is preferably expressed by the host cell within the patient so as to produce the binding agent encoded by the nucleic acid.

The term "recombinant" in the context of the present invention means "made through genetic engineering". Preferably, a "recombinant object" such as a recombinant nucleic acid in the context of the present invention is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

The term "nucleic acid", as used herein, is intended to include DNA and RNA such as genomic DNA, cDNA, mRNA, recombinantly produced and chemically synthesized molecules. A nucleic acid may be single-stranded or double-stranded. RNA includes in vitro transcribed RNA (IVT RNA) or synthetic RNA.

Nucleic acids may be comprised in a vector. The term "vector" as used herein includes any vectors known to the skilled person including plasmid vectors, cosmid vectors, phage vectors such as lambda phage, viral vectors such as adenoviral or baculoviral vectors, or artificial chromosome vectors such as bacterial artificial chromosomes (RAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

In the context of the present invention, the term "RNA" relates to a molecule which comprises ribonucleotide residues and preferably being entirely or substantially composed of ribonucleotide residues. "Ribonucleotide" relates to a nucleotide with a hydroxyl group at the 2'-position of a β-D-ribofuranosyl group. The term includes double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

According to the present invention, the term "RNA" includes and preferably relates to "mRNA" which means "messenger RNA" and relates to a "transcript" which may be produced using DNA as template and encodes a peptide or protein. mRNA typically comprises a 5' non translated region (5'-UTR), a protein or peptide coding region and a 3' non translated region (3'-UTR). mRNA has a limited half-time in cells and in vitro. Preferably, mRNA is produced by in vitro transcription using a DNA template. In one embodiment of the invention, the RNA is obtained by in vitro transcription or chemical synthesis. The in vitro transcription methodology is known to the skilled person. For example, there is a variety of in vitro transcription kits commercially available.

In one embodiment of the present invention, RNA is self-replicating RNA, such as single stranded self-replicating RNA. In one embodiment, the self-replicating RNA is single stranded RNA of positive sense. In one embodiment, the self-replicating RNA is viral RNA or RNA derived from viral RNA. In one embodiment, the self-replicating RNA is alphaviral genomic RNA or is derived from alphaviral genomic RNA. In one embodiment, the self-replicating RNA is a viral gene expression vector. In one embodiment, the virus is Semliki forest virus. In one embodiment, the self-replicating RNA contains one or more transgenes at least one of said transgenes encoding the binding agent described herein. In one embodiment, if the RNA is viral RNA or derived from viral RNA, the transgenes may partially or completely replace viral sequences such as viral sequences encoding structural proteins. In one embodiment, the self-replicating RNA is in vitro transcribed RNA.

The genome of alphaviruses is single stranded RNA of positive sense (ssRNA(+)) that encodes two open reading frames (ORF) for large polyproteins. The ORF at the 5'-end of the genome encodes the non-structural proteins nSP1 to nSP4 (nsP1-4), which are translated and processed to an RNA-dependent RNA-polymerase (replicase); the ORF at the 3'-end encodes the structural proteins—capsid and glycoproteins. Both ORFs are separated by the so called subgenomic promoter (SGP), which governs the transcription of the structural ORF. When exploited as gene vectors, the structural proteins behind the SGP are commonly replaced by transgenes. In order to package such vectors into viral particles, the structural proteins are commonly expressed in trans from helper constructs. Alphaviruses replicate in the cytoplasm of infected cells exclusively at the RNA level. After infection, the ssRNA(+) genome acts as mRNA for the translation of the nsP1234 poly-protein precursor which is at early stages of the viral life cycle autoprotcolytically processed to the fragments nsP123 and nsP4. Fragments nsP123 and nsP4 form the (−)strand replicase complex that transcribes (−)stranded RNA from the genomic RNA template. At later stages, the nsP1234 polyprotein is completely cleaved to the single proteins which assemble to the (+)strand replicase complex that synthesizes new (−)stranded genomes, as well as subgenomic transcripts that code the structural proteins or transgenes. Subgenomic RNA as well as new genomic RNA is capped and poly-adenylated and thus recognized as mRNA after target cells infection. Only new genomic RNA contains a packaging signal which ensures exclusive packaging of genomic RNA into budding virions. The attractiveness of alphaviral replicons for vectorology is based on the positive orientation of the capped and poly-adenylated RNA genome. Translatable replicon RNA can easily be synthesized in vitro, whereby capping may be achieved with cap-analoga added to the in vitro transcription reaction and poly-A tails may be encoded as poly-T tracks on the plasmid templates. In vitro transcribed (IVT) replicons are transfected by conventional transfection techniques and even low amounts of starting IVT RNA are multiplied rapidly. Within a few hours after transfer, transgenes which are placed downstream of the SGP are transcribed to very high copy numbers of about 40.000 to 200.000 copies of subgenomic RNA per cell, thus it is not surprising that recombinant proteins are strongly expressed. Dependent on the specific aim, IVT replicons may be transfected directly into target cells, or packaged into alphaviral particles with helper vectors that provide structural genes in trans. Transfer into the skin or muscles leads to high and sustained local expression, paralleled by a strong induction of humoral and cellular immune response In order to increase expression and/or stability of the RNA used according to the present invention, it may be modified, preferably without altering the sequence of the expressed peptide or protein.

The term "modification" in the context of RNA as used according to the present invention includes any modification of RNA which is not naturally present in said RNA.

In one embodiment of the invention, the RNA used according to the invention does not have uncapped 5'-triphosphates. Removal of such uncapped 5'-triphosphates can be achieved by treating RNA with a phosphatase.

The RNA according to the invention may have modified naturally occurring or synthetic ribonucleotides in order to increase its stability and/or decrease cytotoxicity. For example, in one embodiment, in the RNA used according to the invention 5-methylcytidine is substituted partially or completely, preferably completely, for cytidine. Alternatively or additionally, in one embodiment, in the RNA used according to the invention pseudouridine is substituted partially or completely, preferably completely, for uridine.

In one embodiment, the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap (m7G). In the context of the present invention, the term "5'-cap" includes a 5'-cap analog that resembles the RNA cap structure and is modified to possess the ability to stabilize RNA if attached thereto, preferably in vivo and/or in a cell.

Providing an RNA with a 5'-cap or 5'-cap analog may be achieved by in vitro transcription of a DNA template in the presence of said 5'-cap or 5'-cap analog, wherein said 5'-cap is co-transcriptionally incorporated into the generated RNA strand, or the RNA may be generated, for example, by in vitro transcription, and the 5'-cap may be attached to the RNA post-transcriptionally using capping enzymes, for example, capping enzymes of vaccinia virus.

The RNA may comprise further modifications. For example, a further modification of the RNA used in the present invention may be an extension or truncation of the naturally occurring poly(A) tail or an alteration of the 5'- or 3'-untranslated regions (UTR) such as introduction of a UTR which is not related to the coding region of said RNA, for example, the insertion of one or more, preferably two copies of a 3'-UTR derived from a globin gene, such as alpha2-globin, alpha1-globin, beta-globin, preferably beta-globin, more preferably human beta-globin.

Therefore, in order to increase stability and/or expression of the RNA used according to the present invention, it may be modified so as to be present in conjunction with a poly-A sequence, preferably having a length of 10 to 500, more preferably 30 to 300, even more preferably 65 to 200 and especially 100 to 150 adenosine residues. In an especially preferred embodiment the poly-A sequence has a length of approximately 120 adenosine residues. In addition, incorporation of two or more 3'-non translated regions (UTR) into the 3'-non translated region of an RNA molecule can result in an enhancement in translation efficiency. In one particular embodiment the 3'-UTR is derived from the human β-globin gene.

Preferably, RNA if delivered to, i.e. transfected into, a cell, in particular a cell present in vivo, expresses the protein, peptide or antigen it encodes.

The term "transfection" relates to the introduction of nucleic acids, in particular RNA, into a cell. For purposes of the present invention, the term "transfection" also includes the introduction of a nucleic acid into a cell or the uptake of a nucleic acid by such cell, wherein the cell may be present in a subject, e.g., a patient. Thus, according to the present invention, a cell for transfection of a nucleic acid described herein can be present in vitro or in vivo, e.g. the cell can form part of an organ, a tissue and/or an organism of a patient. According to the invention, transfection can be transient or stable. For some applications of transfection, it is sufficient if the transfected genetic material is only transiently expressed. Since the nucleic acid introduced in the transfection process is usually not integrated into the nuclear genome, the foreign nucleic acid will be diluted through mitosis or degraded. Cells allowing episomal amplification of nucleic acids greatly reduce the rate of dilution. If it is desired that the transfected nucleic acid actually remains in the genome of the cell and its daughter cells, a stable transfection must occur. RNA can be transfected into cells to transiently express its coded protein.

The term "stability" of RNA relates to the "half-life" of RNA. "Half-life" relates to the period of time which is needed to eliminate half of the activity, amount, or number of molecules. In the context of the present invention, the half-life of an RNA is indicative for the stability of said RNA. The half-life of RNA may influence the "duration of expression" of the RNA. It can be expected that RNA having a long half-life will be expressed for an extended time period.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "In vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector".

The term "translation" according to the invention relates to the process in the ribosomes of a cell by which a strand of messenger RNA directs the assembly of a sequence of amino acids to make a peptide or protein.

The term "expression" is used according to the invention in its most general meaning and comprises the production of RNA and/or peptides or proteins, e.g. by transcription and/or translation. With respect to RNA, the term "expression" or "translation" relates in particular to the production of peptides or proteins. It also comprises partial expression of nucleic acids. Moreover, expression can be transient or stable. According to the invention, the term expression also includes an "aberrant expression" or "abnormal expression".

"Aberrant expression" or "abnormal expression" means according to the invention that expression is altered, preferably increased, compared to a reference, e.g. a state in a subject not having a disease associated with aberrant or abnormal expression of a certain protein, e.g., a tumor antigen. An increase in expression refers to an increase by at least 10%, in particular at least 20%, at least 50% or at least 100%, or more. In one embodiment, expression is only found in a diseased tissue, while expression in a healthy tissue is repressed.

The term "specifically expressed" means that a protein is essentially only expressed in a specific tissue or organ. For example, a tumor antigen specifically expressed in gastric mucosa means that said protein is primarily expressed in gastric mucosa and is not expressed in other tissues or is not expressed to a significant extent in other tissue or organ types. Thus, a protein that is exclusively expressed in cells of the gastric mucosa and to a significantly lesser extent in any other tissue, such as testis, is specifically expressed in cells of the gastric mucosa. In some embodiments, a tumor antigen may also be specifically expressed under normal conditions in more than one tissue type or organ, such as in 2 or 3 tissue types or organs, but preferably in not more than 3 different tissue or organ types. In this case, the tumor antigen is then specifically expressed in these organs. For example, if a tumor antigen is expressed under normal conditions preferably to an approximately equal extent in lung and stomach, said tumor antigen is specifically expressed in lung and stomach.

According to the invention, the term "RNA encoding" means that RNA, if present in the appropriate environment, preferably within a cell, can be expressed to produce a protein or peptide it encodes.

Some aspects of the invention rely on the adoptive transfer of host cells which are transfected in vitro with a nucleic acid such as RNA encoding a binding agent described herein and transferred to recipients such as patients, preferably after ex vivo expansion from low precursor frequencies to clinically relevant cell numbers. The host cells used for treatment according to the invention may be autologous, allogeneic, or syngeneic to a treated recipient.

The term "autologous" is used to describe anything that is derived from the same subject. For example, "autologous transplant" refers to a transplant of tissue or organs derived from the same subject. Such procedures are advantageous because they overcome the immunological barrier which otherwise results in rejection.

The term "allogeneic" is used to describe anything that is derived from different individuals of the same species. Two or more individuals are said to be allogeneic to one another when the genes at one or more loci are not identical.

The term "syngeneic" is used to describe anything that is derived from individuals or tissues having identical genotypes, i.e., identical twins or animals of the same inbred strain, or their tissues.

The term "heterologous" is used to describe something consisting of multiple different elements. As an example, the transfer of one individual's bone marrow into a different individual constitutes a heterologous transplant. A heterologous gene is a gene derived from a source other than the subject.

The term "peptide" according to the invention comprises oligo- and polypeptides and refers to substances comprising two or more, preferably 3 or more, preferably 4 or more, preferably 6 or more, preferably 8 or more, preferably 9 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" refers to large peptides, preferably to peptides with more than 100 amino acid residues, but in general the terms "peptides" and "proteins" are synonyms and are used interchangeably herein.

The teaching given herein with respect to specific amino acid sequences, e.g. those shown in the sequence listing, is to be construed so as to also relate to variants of said specific sequences resulting in sequences which are functionally equivalent to said specific sequences, e.g. amino acid sequences exhibiting properties identical or similar to those of the specific amino acid sequences. One important property is to retain binding to a target or to sustain effector functions. Preferably, a sequence which is a variant with respect to a specific sequence, when it replaces the specific sequence in an antibody retains binding of said antibody to CLDN and/or CD3 and preferably functions of said antibody as described herein, e.g. CDC mediated lysis or ADCC mediated lysis.

For example, the sequences shown in the sequence listing can be modified so as to remove one or more, preferably all free cysteine residues, in particular by replacing the cysteine residues by amino acids other than cysteine, preferably serine, alanine, threonine, glycine, tyrosine, leucine or methionine, most preferably alanine or serine. For example, the cysteine at position 103 of the sequence shown in SEQ ID NO: 36 of the sequence listing or the corresponding cysteine in a sequence comprising said sequence may be modified in this way. Further cysteines which can be modified this way are the cysteines at position 178 of SEQ ID NO: 42, at position 197 of SEQ ID NO: 43, at position 427 of SEQ ID NO: 44 or at position 446 of SEQ ID NO: 45.

It will be appreciated by those skilled in the art that in particular the sequences of the CDR, hypervariable and variable regions can be modified without losing the ability to bind CLDN and/or CD3. For example, CDR regions will be either identical or highly homologous to the regions of antibodies specified herein. By "highly homologous" it is contemplated that from 1 to 5, preferably from 1 to 4, such as 1 to 3 or 1 or 2 substitutions may be made in the CDRs. In addition, the hypervariable and variable regions may be modified so that they show substantial homology with the regions of antibodies specifically disclosed herein.

For the purposes of the present invention, "variants" of an amino acid sequence comprise amino acid insertion variants, amino acid addition variants, amino acid deletion variants and/or amino acid substitution variants. Amino acid deletion variants that comprise the deletion at the N-terminal and/or C-terminal end of the protein are also called N-terminal and/or C-terminal truncation variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the protein.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence will be at least about 60%, 65%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

The binding agents of the invention can be produced either intracellullarly (e.g. in the cytosol, in the periplasma or in inclusion bodies) and then isolated from the host cells and optionally further purified; or they can be produced extracellularly (e.g. in the medium in which the host cells are cultured) and then isolated from the culture medium and optionally further purified. Methods and reagents used for the recombinant production of polypeptides, such as specific suitable expression vectors, transformation or transfection methods, selection markers, methods of induction of protein expression, culture conditions, and the like, are known in the art. Similarly, protein isolation and purification techniques are well known to the skilled person.

The term "cell" or "host cell" preferably relates to an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably said term relates according to the invention to any cell which can be transfected with an exogenous nucleic acid. Preferably, the cell when transfected with an exogenous nucleic acid and transferred to a recipient can express the nucleic acid in the recipient. The term "cell" includes bacterial cells; other useful cells are yeast cells, fungal cells or mammalian cells. Suitable bacterial cells include cells from gram-negative bacterial strains such as strains of Escherichia coli, Proteus, and Pseudomonas, and gram-positive bacterial strains such as strains of Bacillus, Streptomyces, Staphylococcus, and Lactococcus. Suitable fungal cell include cells from species of Trichoderma, Neurospora, and Aspergillus. Suitable yeast cells include cells from species of Saccharomyces (Tor example Saccharomyces cerevisiae), Schizosaccharomyces (for example Schizosaccharomyces pombe), Pichia (for example Pichia pastoris and Pichia methanolied), and Hansenula. Suitable mammalian cells include for example CHO cells, BHK cells, HeLa cells, COS cells, 293 HEK and the like. However, amphibian cells, insect cells, plant cells, and any other cells used in the art for the expression of heterologous proteins can be used as well. Mammalian cells are particularly preferred for adoptive transfer, such as cells from humans, mice, hamsters, pigs, goats, and primates. The cells may be derived from a large number of tissue types and include primary cells and cell lines such as cells of the immune system, in particular antigen-presenting cells such as dendritic cells and T cells, stem cells such as hematopoietic stem cells and mesenchymal stem cells and other cell types. An antigen-presenting cell is a cell that displays antigen in the context of major histocompatibility complex on its surface. T cells may recognize this complex using their T cell receptor (TCR).

"Reduce", "decrease" or "inhibit" as used herein means an overall decrease or the ability to cause an overall decrease, preferably of 5% or greater, 10% or greater, 20% or greater, more preferably of 50% or greater, and most preferably of 75% or greater, in the level, e.g. in the level of expression or in the level of proliferation of cells.

Terms such as "increase" or "enhance" preferably relate to an increase or enhancement by about at least 10%, preferably at least 20%, preferably at least 30%, more preferably at least 40%, more preferably at least 50%, even more preferably at least 80%, and most preferably at least 100%, at least 200%, at least 500%, at least 1000%, at least 10000% or even more.

Antibody-dependent Cell-mediated Cytotoxicity

ADCC describes the cell-killing ability of effector cells as described herein, in particular lymphocytes, which preferably requires the target cell being marked by an antibody.

ADCC preferably occurs when antibodies bind to antigens on tumor cells and the antibody Fc domains engage Fc receptors (FcR) on the surface of immune effector cells. Several families of Fc receptors have been identified, and specific cell populations characteristically express defined Fc receptors. ADCC can be viewed as a mechanism to directly induce a variable degree of immediate tumor destruction that leads to antigen presentation and the induction of tumor-directed T-cell responses. Preferably, in vivo induction of ADCC will lead to tumor-directed T-cell responses and host-derived antibody responses.

Complement-dependent Cytotoxicity

CDC is another cell-killing method that can be directed by antibodies. IgM is the most effective isotype for complement activation. IgG1 and IgG3 are also both very effective at directing CDC via the classical complement-activation pathway. Preferably, in this cascade, the formation of antigen-antibody complexes results in the uncloaking of multiple Clq binding sites in close proximity on the $C_H2$ domains of participating antibody molecules such as IgG molecules (Clq is one of three subcomponents of complement C1). Preferably these uncloaked Clq binding sites convert the previously low-affinity Clq-IgG interaction to one of high avidity, which triggers a cascade of events involving a series of other complement proteins and leads to the proteolytic release of the effector-cell chemotactic/activating agents C3a and C5a. Preferably, the complement cascade ends in the formation of a membrane attack complex, which creates pores in the cell membrane that facilitate free passage of water and solutes into and out of the cell.

Antibodies described herein for e.g. providing VL and VH regions can be produced by a variety of techniques, including conventional monoclonal antibody methodology, e.g., the standard somatic cell hybridization technique of Kohler and Milstein, Nature 256: 495 (1975). Although somatic cell hybridization procedures are preferred, in principle, other techniques for producing monoclonal antibodies can be employed, e.g., viral or oncogenic transformation of B-lymphocytes or phage display techniques using libraries of antibody genes.

The preferred animal system for preparing hybridomas that secrete monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

Other preferred animal systems for preparing hybridomas that secrete monoclonal antibodies are the rat and the rabbit system (e.g. described in Spieker-Polet et al., Proc. Natl. Acad. Sci. U.S.A. 92:9348 (1995), see also Rossi et al., Am. J. Clin. Pathol. 124: 295 (2005)).

In yet another preferred embodiment, human monoclonal antibodies can be generated using transgenic or transchromosomal mice carrying parts of the human immune system rather than the mouse system. These transgenic and transchromosomic mice include mice known as HuMAb mice and KM mice, respectively, and are collectively referred to herein as "transgenic mice." The production of human antibodies in such transgenic mice can be performed as described in detail for CD20 in WO2004 035607

Yet another strategy for generating monoclonal antibodies is to directly isolate genes encoding antibodies from lymphocytes producing antibodies of defined specificity e.g. see Babcock et al., 1996; A novel strategy for generating monoclonal antibodies from single, isolated lymphocytes producing antibodies of defined specificities. For details of recombinant antibody engineering see also Welschof and Kraus, Recombinant antibodes for cancer therapy ISBN-0-89603-918-8 and Benny K. C. Lo Antibody Engineering ISBN 1-58829-092-1.

To generate antibodies, mice can be immunized with carrier-conjugated peptides derived from the antigen sequence, i.e. the sequence against which the antibodies are to be directed, an enriched preparation of recombinantly expressed antigen or fragments thereof and/or cells expressing the antigen, as described. Alternatively, mice can be immunized with DNA encoding the antigen or fragments thereof. In the event that immunizations using a purified or enriched preparation of the antigen do not result in antibodies, mice can also be immunized with cells expressing the antigen, e.g., a cell line, to promote immune responses.

The immune response can be monitored over the course of the immunization protocol with plasma and serum samples being obtained by tail vein or retroorbital bleeds. Mice with sufficient titers of immunoglobulin can be used for fusions. Mice can be boosted intraperitonealy or intravenously with antigen expressing cells 3 days before sacrifice and removal of the spleen to increase the rate of specific antibody secreting hybridomas.

To generate hybridomas producing monoclonal antibodies, splenocytes and lymph node cells from immunized mice can be isolated and fused to an appropriate immortalized cell line, such as a mouse myeloma cell line. The resulting hybridomas can then be screened for the production of antigen-specific antibodies. Individual wells can then be screened by ELISA for antibody secreting hybridomas. By Immunofluorescence and FACS analysis using antigen expressing cells, antibodies with specificity for the antigen can be identified. The antibody secreting hybridomas can be replated, screened again, and if still positive for monoclonal antibodies can be subcloned by limiting dilution. The stable subclones can then be cultured in vitro to generate antibody in tissue culture medium for characterization.

Antibodies also can be produced in a host cell transfectoma using, for example, a combination of recombinant DNA techniques and gene transfection methods as are well known in the art (Morrison, S. (1985) Science 229: 1202).

For example, in one embodiment, the gene(s) of interest, e.g., antibody genes, can be ligated into an expression vector such as a eukaryotic expression plasmid such as used by the GS gene expression system disclosed in WO 87/04462, WO 89/01036 and EP 338 841 or other expression systems well known in the art. The purified plasmid with the cloned antibody genes can be introduced in eukaryotic host cells such as CHO cells, NS/0 cells, HEK293T cells or HEK293 cells or alternatively other eukaryotic cells like plant derived cells, fungal or yeast cells. The method used to introduce these genes can be methods described in the art such as electroporation, lipofectine, lipofectamine or others. After introduction of these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells.

Alternatively, the cloned antibody genes can be expressed in other expression systems, including prokaryotic cells, such as microorganisms, e.g. E. coli. Furthermore, the antibodies can be produced in transgenic non-human animals, such as in milk from sheep and rabbits or in eggs from hens, or in transgenic plants; see e.g. Verma, R., et al. (1998) J. Immunol. Meth. 216: 165-181; Pollock, et al. (1999) J. Immunol. Meth. 231: 147-157; and Fischer, R., et al. (1999) Biol. Chem. 380: 825-839.

Chimerization

Nonlabeled murine antibodies are highly immunogenic in man when repetitively applied leading to reduction of the therapeutic effect. The main immunogenicity is mediated by the heavy chain constant regions. The immunogenicity of murine antibodies in man can be reduced or completely avoided if respective antibodies are chimerized or humanized. Chimeric antibodies are antibodies, the different portions of which are derived from different animal species, such as those having a variable region derived from a murine antibody and a human immunoglobulin constant region. Chimerisation of antibodies is achieved by joining of the variable regions of the murine antibody heavy and light chain with the constant region of human heavy and light chain (e.g. as described by Kraus et al., in Methods in Molecular Biology series, Recombinant antibodies for cancer therapy ISBN-0-89603-918-8). In a preferred embodiment chimeric antibodies are generated by joining human kappa-light chain constant region to murine light chain variable region. In an also preferred embodiment chimeric antibodies can be generated by joining human lambda-light chain constant region to murine light chain variable region. The preferred heavy chain constant regions for generation of chimeric antibodies are IgG1, IgG3 and IgG4. Other preferred heavy chain constant regions for generation of chimeric antibodies are IgG2, IgA, IgD and IgM.

Humanization

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332: 323-327; Jones, P. et al. (1986) Nature 321: 522-525; and Queen, C. et al. (1989) Proc. Natl. Acad. Sci. U.S.A. 86: 10029-10033). Such framework sequences can be obtained from public DNA databases that include germline antibody gene sequences. These germline sequences will differ from mature antibody gene sequences because they will not include completely assembled variable genes, which are formed by V (D) J joining during B cell maturation. Germline gene sequences will also differ from the sequences of a high affinity secondary repertoire antibody at individual evenly across the variable region.

The ability of antibodies and other binding agents to bind an antigen can be determined using standard binding assays (e.g., ELISA, Western Blot, Immunofluorescence and flow cytometric analysis).

To purify antibodies, selected producer cell lines can be grown in two-liter spinner-flasks for recombinant antibody purification. Alternatively, antibodies can be produced in dialysis based bioreactors. Supernatants can be filtered and, if necessary, concentrated before affinity chromatography with protein L-sepharose. Eluted IgG can be checked by gel electrophoresis and high performance liquid chromatography to ensure purity. The buffer solution can be exchanged into PBS, and the concentration can be determined by OD280 using the respective extinction coefficient. The recombinant antibodies can be aliquoted and stored at −80° C.

In order to demonstrate binding of monoclonal antibodies to living cells expressing antigen, flow cytometry can be used. Cell lines expressing naturally or after transfection antigen and negative controls lacking antigen expression (grown under standard growth conditions) can be mixed with various concentrations of monoclonal antibodies in hybridoma supernatants or in PBS containing 1% FBS, and can be incubated at 4° C. for 30 min. After washing, the APC- or Alexa647-labeled anti IgG antibody can bind to antigen-bound monoclonal antibody under the same conditions as the primary antibody staining. The samples can be analyzed by flow cytometry with a FACS instrument using light and side scatter properties to gate on single, living cells. In order to distinguish antigen-specific monoclonal antibodies from non-specific binders in a single measurement, the method of co-transfection can be employed. Cells transiently transfected with plasmids encoding antigen and a fluorescent marker can be stained as described above. Transfected cells can be detected in a different fluorescence channel than antibody-stained cells. As the majority of transfected cells express both transgenes, antigen-specific monoclonal antibodies bind preferentially to fluorescence marker expressing cells, whereas non-specific antibodies bind in a comparable ratio to non-transfected cells. An alternative assay using fluorescence microscopy may be used in addition to or instead of the flow cytometry assay. Cells can be stained exactly as described above and examined by fluorescence microscopy.

In order to demonstrate binding of monoclonal antibodies to living cells expressing antigen, immunofluorescence microscopy analysis can be used. For example, cell lines expressing either spontaneously or after transfection antigen and negative controls lacking antigen expression are grown in chamber slides under standard growth conditions in DMEM/F12 medium, supplemented with 10% fetal calf serum (FCS), 2 mM L-glutamine, 100 IU/ml penicillin and 100 µg/ml streptomycin. Cells can then be fixed with methanol or paraformaldehyde or left untreated. Cells can then be reacted with monoclonal antibodies against the antigen for 30 min. at 25° C. After washing, cells can be reacted with an Alexa555-labelled anti-mouse IgG secondary antibody (Molecular Probes) under the same conditions. Cells can then be examined by fluorescence microscopy.

Cell extracts from cells expressing antigen and appropriate negative controls can be prepared and subjected to sodium dodecyl sulfate (SDS) polyacrylamide gel electrophoresis. After electrophoresis, the separated antigens will be transferred to nitrocellulose membranes, blocked, and probed with the monoclonal antibodies to be tested. IgG binding can be detected using anti-mouse IgG peroxidase and developed with ECL substrate.

Antibodies can be further tested for reactivity with antigen by Immunohistochemistry in a manner well known to the skilled person, e.g. using paraformaldehyde or acetone fixed cryosections or paraffin embedded tissue sections fixed with paraformaldehyde from non-cancer tissue or cancer tissue samples obtained from patients during routine surgical procedures or from mice carrying xenografted tumors inoculated with cell lines expressing spontaneously or after transfection antigen. For immunostaining, antibodies reactive to antigen can be incubated followed by horseradish-peroxidase conjugated goat anti-mouse or goat anti-rabbit antibodies (DAKO) according to the vendors instructions.

Preclinical Studies

Binding agents described herein also can be tested in an in vivo model (e.g. in immune deficient mice carrying xenografted tumors inoculated with cell lines expressing CLDN to determine their efficacy in controlling growth of CLDN-expressing tumor cells.

In vivo studies after xenografting CLDN-expressing tumor cells into immunocompromised mice or other animals can be performed using binding agents described herein. Binding agents can be administered to tumor free mice followed by injection of tumor cells to measure the effects of the binding agents to prevent formation of tumors or tumor-related symptoms. Binding agents can be administered to tumor-bearing mice to determine the therapeutic efficacy of respective binding agents to reduce tumor growth, metastasis or tumor related symptoms. Application of binding agents can be combined with application of other substances as cystostatic drugs, growth factor inhibitors, cell cycle blockers, angiogenesis inhibitors or antibodies to determine synergistic efficacy and potential toxicity of combinations. To analyze toxic side effects mediated by binding agents animals can be inoculated with binding agents or control reagents and thoroughly investigated for symptoms possibly related to CLDN-binding agent therapy.

Mapping of epitopes recognized by binding agents can be performed as described in detail in "Epitope Mapping Protocols (Methods in Molecular Biology) by Glenn E. Morris ISBN-089603-375-9 and in "Epitope Mapping: A Practical Approach" Practical Approach Series, 248 by Olwyn M. R. Westwood, Frank C. Hay.

The compounds and agents described herein may be administered in the form of any suitable pharmaceutical composition.

The pharmaceutical compositions of the invention are preferably sterile and contain an effective amount of the binding agents described herein and optionally of further agents as discussed herein to generate the desired reaction or the desired effect.

Pharmaceutical compositions are usually provided in a uniform dosage form and may be prepared in a manner known per se. A pharmaceutical composition may e.g. be in the form of a solution or suspension.

A pharmaceutical composition may comprise salts, buffer substances, preservatives, carriers, diluents and/or excipients all of which are preferably pharmaceutically acceptable. The term "pharmaceutically acceptable" refers to the non-toxicity of a material which does not interact with the action of the active component of the pharmaceutical composition.

Salts which are not pharmaceutically acceptable may be used for preparing pharmaceutically acceptable salts and are included in the invention. Pharmaceutically acceptable salts of this kind comprise in a non limiting way those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts.

Suitable buffer substances for use in a pharmaceutical composition include acetic acid in a salt, citric acid in a salt, boric acid in a salt and phosphoric acid in a salt.

Suitable preservatives for use in a pharmaceutical composition include benzalkonium chloride, chlorobutanol, paraben and thimerosal.

An injectable formulation may comprise a pharmaceutically acceptable excipient such as Ringer Lactate.

The term "carrier" refers to an organic or inorganic component, of a natural or synthetic nature, in which the active component is combined in order to facilitate, enhance or enable application. According to the invention, the term "carrier" also includes one or more compatible solid or liquid fillers, diluents or encapsulating substances, which are suitable for administration to a patient.

Possible carrier substances for parenteral administration are e.g. sterile water, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxypropylene copolymers.

The term "excipient" when used herein is intended to indicate all substances which may be present in a pharmaceutical composition and which are not active ingredients such as, e.g., carriers, binders, lubricants, thickeners, surface active agents, preservatives, emulsifiers, buffers, flavoring agents, or colorants.

The agents and compositions described herein may be administered via any conventional route, such as by parenteral administration including by injection or infusion. Administration is preferably parenterally, e.g. intravenously, intraarterially, subcutaneously, intradermally or intramuscularly.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The agents and compositions described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an agent or composition described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a patient is insufficient with an initial dose, higher doses (or effectively higher doses achieved by a different, more localized route of administration) may be used.

The agents and compositions described herein can be administered to patients, e.g., in vivo, to treat or prevent a variety of disorders such as those described herein. Preferred patients include human patients having disorders that can be corrected or ameliorated by administering the agents and compositions described herein. This includes disorders involving cells characterized by an altered expression pattern of CLDN such as CLDN18.2 and/or CLDN6.

For example, in one embodiment, agents described herein can be used to treat a patient with a cancer disease, e.g., a cancer disease such as described herein characterized by the presence of cancer cells expressing CLDN.

The pharmaceutical compositions and methods of treatment described according to the invention may also be used for immunization or vaccination to prevent a disease described herein.

The pharmaceutical composition of the invention may be administered together with supplementing immunity-enhancing substances such as one or more adjuvants and may comprise one or more immunity-enhancing substances to further increase its effectiveness, preferably to achieve a synergistic effect of immunostimulation. The term "adjuvant" relates to compounds which prolongs or enhances or accelerates an immune response. Various mechanisms are possible in this respect, depending on the various types of adjuvants. For example, compounds which allow the maturation of the DC, e.g. lipopolysaccharides or CD40 ligand, form a first class of suitable adjuvants. Generally, any agent which influences the immune system of the type of a "danger signal" (LPS, GP96, dsLNA etc.) or cytokines, such as GM-CSF, can be used as an adjuvant which enables an immune response to be intensified and/or influenced in a controlled manner. CpG oligodeoxynucleotides can optionally also be used in this context, although their side effects which occur under certain circumstances, as explained above, are to be considered. Particularly preferred adjuvants are cytokines, such as monokines, lymphokines, interleukins or chemokines, e.g. IL-1, IL-2, Il-3, IL-4, IL-5, IL-6, IL-7, IL-8, IL-9, TL-10, IL-12, INFα, INF-γ, GM-CSF, LT-α, or growth factors, e.g. hGH. Further known adjuvants are aluminium hydroxide, Freund's adjuvant or oil such as Montanide®, most preferred Montanide® ISA51. Lipopeptides, such as Pam3Cys, are also suitable for use as adjuvants in the pharmaceutical composition of the present invention.

The agents and compositions provided herein may be used alone or in combination with conventional therapeutic regimens such as surgery, irradiation, chemotherapy and/or bone marrow transplantation (autologous, syngeneic, allogeneic or unrelated).

Treatment of cancer represents a field where combination strategies are especially desirable since frequently the combined action of two, three, four or even more cancer drugs/therapies generates synergistic effects which are considerably stronger than the impact of a monotherapeutic approach. Thus, in another embodiment of the present invention, a cancer treatment which utilizes immune- or vaccination-based mechanisms such as the methods and pharmaceutical compositions of the present invention may be effectively combined with various other drugs and/or methods targeting similar or other specific mechanisms. Among those are e.g. combinations with conventional tumor therapies, multi-epitope strategies, additional immunotherapy, and treatment approaches targeting angiogenesis or apoptosis (for review see e.g. Andersen et al. 2008: Cancer treatment: the combination of vaccination with other therapies. Cancer Immunology Immunotherapy, 57(11): 1735-1743.) Sequential administration of different agents may inhibit cancer cell growth at different check points, while other agents may e.g. inhibit neo-angiogenesis, survival of malignant cells or metastases, potentially converting cancer IC into a chronic disease. The following list provides some non-limiting examples of anti-cancer drugs and therapies which can be used in combination with the present invention:

1. Chemotherapy

Chemotherapy is the standard of care for multiple types of cancer. The most common chemotherapy agents act by killing cells that divide rapidly, one of the main properties of cancer cells. Thus, a combination with conventional chemotherapeutic drugs such as e.g. alkylating agents, antimetabolites, anthracyclines, plant alkaloids, topoisomerase inhibitors, and other antitumour agents which either affect cell division or DNA synthesis may significantly improve the therapeutic effects of the present invention by clearing suppressor cells, reboot of the immune system, by rendering tumor cells more susceptible to immune mediated killing, or by additional activation of cells of the immune system. A synergistic anti-cancer action of chemotherapeutic and vaccination-based immunotherapeutic drugs has been demonstrated in multiple studies (see e.g. Quoix et al. 2011: Therapeutic vaccination with TG4010 and first-line chemotherapy in advanced non-small-cell lung cancer: a controlled phase 2B trial. Lancet Oncol. 12(12): 1125-33.; sec also Liseth et al. 2010: Combination of intensive chemotherapy and anticancer vaccines in the treatment of human malignancies: the hematological experience. J Biomed Biotechnol. 2010: 6920979; see also Hirooka et al 2009: A combination therapy of gemcitabine with immunotherapy for patients with inoperable locally advanced pancreatic cancer. Pancreas 38(3): c69-74). There are hundreds of chemotherapeutic drugs available which are basically suitable for combination therapies. Some (non-limiting) examples of chemotherapeutic drugs which can be combined with the present invention are carboplatin (Paraplatin), cisplatin (Platinol, Platinol-AQ), cyclophosphamide (Cytoxan, Neosar), docetaxel (Taxotere), doxorubicin (Adriamycin), erlotinib (Tarceva), etoposide (VePesid), fluorouracil (5-FU), gemcitabine (Gemzar), imatinib mesylate (Gleevec), irinotecan (Camptosar), methotrexate (Folex, Mexate, Amethopterin), paclitaxel (Taxol, Abraxane), sorafinib (Nexavar), sunitinib (Sutent), topotecan (Hycamtin), vincristine (Oncovin, Vincasar PFS), and vinblastine (Velban).

2. Surgery

Cancer surgery—an operation to remove the tumor—remains the foundation of cancer treatment. Surgery can be combined with other cancer treatments in order to delete any remaining tumor cells. Combining surgical methods with subsequent immunotherapeutic treatment is a promising approach which has been demonstrated countless times.

3. Radiation

Radiation therapy remains an important component of cancer treatment with approximately 50% of all cancer patients receiving radiation therapy during their course of illness. The main goal of radiation therapy is to deprive cancer cells of their multiplication (cell division) potential. The types of radiation used to treat cancer are photons radiation (x-rays and gamma rays) and particle radiations (electron, proton and neutron beams.) There are two ways to deliver the radiation to the location of the cancer. External beam radiation is delivered from outside the body by aiming high-energy rays (photons, protons or particle radiation) to the location of the tumor. Internal radiation or brachytherapy is delivered from inside the body by radioactive sources, sealed in catheters or seeds directly into the tumor site. Radiation therapy techniques which are applicable in combination with the present invention are e.g. fractionation (radiation therapy delivered in a fractionated regime, e.g. daily fractions of 1.5 to 3 Gy given over several weeks), 3D conformal radiotherapy (3DCRT; delivering radiation to the gross tumor volume), intensity modulated radiation therapy (IMRT; computer-controlled intensity modulation of multiple radiation beams), image guided radiotherapy (IGRT; a technique comprising pre-radiotherapy imaging which allows for correction), and stereotactic body radiation therapy (SRBT, delivers very high individual doses of radiation over only a few treatment fractions). For a radiation therapy review see Baskar et al. 2012: Cancer and radiation therapy: current advances and future directions. Int. J Med Sci. 9(3): 193-199.

4. Antibodies

Antibodies (preferably monoclonal antibodies) achieve their therapeutic effect against cancer cells through various mechanisms. They can have direct effects in producing apoptosis or programmed cell death. They can block components of signal transduction pathways such as e.g. growth factor receptors, effectively arresting proliferation of tumor cells. In cells that express monoclonal antibodies, they can bring about anti-idiotype antibody formation. Indirect effects include recruiting cells that have cytotoxicity, such as monocytes and macrophages. This type of antibody-mediated cell kill is called antibody-dependent cell mediated cytotoxicity (ADCC). Antibodies also bind complement, leading to direct cell toxicity, known as complement dependent cytotoxicity (CDC). Combining surgical methods with immunotherapeutic drugs or methods is an successful approach, as e.g. demonstrated in Gadri et al. 2009: Synergistic effect of dendritic cell vaccination and anti-CD20 antibody treatment in the therapy of murine lymphoma. J Immunother. 32(4): 333-40. The following list provides some non-limiting examples of anti-cancer antibodies and potential antibody targets (in brackets) which can be used in combination with the present invention: Abagovomab (CA-125), Abciximab (CD41), Adecatumumab (EpCAM), Afutuzumab (CD20), Alacizumab pegol (VEGFR2), Altumomab pentetate (CEA), Amatuximab (MORAb-009), Anatumomab mafenatox (TAG-72), Apolizumab (HLA-DR), Arcitumomab (CEA), Bavituximab (phosphatidylserine), Bectumomab (CD22), Belimumab (BAFF), Bevacizumab (VEGF-A), Bivatuzumab mertansine (CD44 v6), Blinatumomab (CD19), Brentuximab vedotin (CD30 TNFRSF8), Cantuzumab mertansin (mucin CanAg), Cantuumab ravtansine (MUC1), Capromab pendetide (prostatic carcinoma cells), Carlumab (CNTO888), Catumaxomab (EpCAM, CD3), Cetuximab (EGFR), Citatuzumab bogatox (EpCAM), Cixutumumab (IGF-1 receptor), Claudiximab (Claudin), Clivatuzumab tetraxetan (MUC), Conatumumab (FRAIL-R2), Dacetuzumab (CD40), Dalotuzumab (insulin-like growth factor I receptor), Denosumab (RANKL), Detumomab (B-lymphoma cell), Drozitumab (DR5), Ecromeximab (GD3 gangliosidc), Edrecolomab (EpCAM), Elotuzumab (SLAMF7), Enavatuzumab (PDL192), Ensituximab (NPC-lC), Epratuzumab (CD22), Ertumaxomab (HER2/neu, CD3), Etaracizumab (integrin αvβ3), Farletuzumab (folate receptor 1), FBTA05 (CD20), Ficlatuzumab (SCH 900105), Figitumumab (TGF-1 receptor), Flanvotumab (glycoprotein 75), Fresolimumab (TGF-3), Galiximab (CD80), Ganitumab (IGF-I), Gcemtuzumab ozogamicin (CD33), Gevokizumab (IL-1β), Girentuximab (carbonic anhydrase 9 (CA-IX)), Glembatumumab vedotin (GPNMB), Ibritumomab tiuxetan (CD20), Icrucumab (VEGFR-1), Igovoma (CA-125). Indatuximab ravtansine (SDC1), Intctumumab (CD51), Inotuzumab ozogamicin (CD22), Ipilimumab (CD152), Iratumumab (CD30), Labetuzumab (CEA), Lexatumumab (TRAIL-R2), Libivirumab (hepatitis B surface antigen), Lintuzumab (CD33), Lorvotuzumab mertansine (CD56), Lucatumumab (CD40), Lumiliximab (CD23), Mapatumumab (TRAIL-R1), Matuzumab (EGFR), Mepolizumab (IL-5), Milatuzumab (CD74), Mitumomab (GD3 ganglioside), Mogamulizumab (CCR4), Moxctumomab pasudotox (CD22), Nacolomab tafenatox (C242 antigen), Naptumomab estafenatox (5T4), Narnmatumab (RON), Necitumumab (EGFR), Nimotuzumab (EGFR), Nivolumab (IgG4), Ofatumumab (CD20), Olaratumab (PDGF-R α), Onartuzumab (human scatter factor receptor kinase), Oportuzumab monatox (EpCAM), Oregovomab (CA-125), Oxelumab (OX-40), Panitumumab (EGFR), Patritumab (HER3), Pemtumoma (MUC1), Pertuzumab (HER2/neu), Pintumomab (adenocarcinoma antigen), Pritumumab (vimentin), Racotumomab (N-glycolyl-neuraminic acid), Radretumab (fibronectin extra domain-B), Rafivirumab (rabies virus glycoprotein), Ramucirumab (VEGFR2), Rilotumumab (HGF), Rituximab (CD20), Robatumumab (IGF-1 receptor), Samalizumab (CD200), Sibrotuzumab (FAP), Siltuximab (IL-6). Tabalumab (BAFF), Tacatuzumab tetraxetan (alpha-fetoprotein), Taplitumomab paptox (CD19), Tenatumomab (tenascin C), Teprotumumab (CD221), Ticilimumab (CTLA-4), Tigatuzumab (TRAIL-R2), TNX-650 (IL-13), Tositumomab (CD20), Trastuzumab (HER2/ncu), TRBS07 (GD2), Tremelimumab (CTLA-4), Tucotuzumab celmoleukin (EpCAM), Ublituximab (MS4A1), Urelumab (4-1BB), Volociximab (integrin α5β1), Votumumab (tumor antigen CTAA16.88), Zalutumumab (EGFR), Zanolimumab (CD4).

5. Cytokines, Chemokines, Costimulatory Molecules, Fusion Proteins

Combined usage of the antigen-coding pharmaceutical compositions of the present invention with cytokines, chemokines, costimulatory molecules and/or fusion proteins thereof to evoke beneficial immune modulation or tumor inhibition effects is another embodiment of the present invention. In order to increase the infiltration of immune cells into the tumor and facilitate the movement of antigen-presenting cells to tumor-draining lymph nodes, various chemokines with C, CC, CXC and CX3C structures might be used. Some of the most promising chemokines are e.g CCR7 and its ligands CCL19 and CCL21, furthermore CCL2, CCL3, CCL5, and CCL16. Other examples are CXCR4, CXCR7 and CXCL12. Furthermore, costimulatory or regulatory molecules such as e.g. B7 ligands (17.1 and 17.2) are useful. Also useful are other cytokines such as e.g. interleukins especially (e.g. IL-1 to IL17), interferons (e.g. IFNalpha1 to IFNalpha8, IFNalpha10, IFNalpha13, IFNalpha14, IFNalpha16, IFNalpha17, IFNalpha21. IFNbeta1, IFNW, IFNE1 and IFNK), hematopoietic factors, TGFs (e.g. TGF-α, TGF-β, and other members of the TGF family), finally members of the tumor necrosis factor family of receptors and their ligands as well as other stimulatory molecules, comprising but not limited to 4-1BB, 4-1BB-L, CD137, CD137L, CTLA-4GITR, GITRL, Fas, Fas-L, TNFR1, TRAIL-R1, TRAIL-R2, p75NGF-R, DR6, LT.beta.R, RANK, EDAR1, XEDAR, Fn114, Troy/Trade, TAJ, TNFRII, HVEM, CD27, CD30, CD40, 4-1BB, OX40, GITR, GITRL, TACI, BAFF-R, BCMA, RELT, and CD95 (Fas/APO-1), glucocorticoid-induced TNFR-related protein, TNF receptor-related apoptosis-mediating protein (TRAMP) and death receptor-6 (DR6). Especially CD40/CD40L and OX40/OX40L are important targets for combined immunotherapy because of their direct impact on T cell survival and proliferation. For a review see Lechner et al. 2011: Chemokines, costimulatory molecules and fusion proteins for the immunotherapy of solid tumors. Immunotherapy 3 (11), 1317-1340.

6. Bacterial Treatments

Researchers have been using anaerobic bacteria, such as *Clostridium novyi*, to consume the interior of oxygen-poor tumours. These should then die when they come in contact with the tumour's oxygenated sides, meaning they would be harmless to the rest of the body. Another strategy is to use anaerobic bacteria that have been transformed with an enzyme that can convert a non-toxic prodrug into a toxic drug. With the proliferation of the bacteria in the necrotic and hypoxic areas of the tumour, the enzyme is expressed solely in the tumour. Thus, a systemically applied prodrug is metabolised to the toxic drug only in the tumour. This has been demonstrated to be effective with the nonpathogenic anaerobe *Clostridium sporogenes*.

7. Kinase Inhibitors

Another large group of potential targets for complementary cancer therapy comprises kinase inhibitors, because the growth and survival of cancer cells is closely interlocked with the deregulation of kinase activity. To restore normal kinase activity and therefor reduce tumor growth a broad range of inhibitors is in used. The group of targeted kinases comprises receptor tyrosine kinases e.g. BCR-ABL, B-Raf, EGFR, HER-2/ErbB2, IGF-IR, PDGFR-α, PDGFR-β, c-Kit, Flt-4, Flt3, FGFR1, FGFR3, FGFR4, CSF1R, c-Met, RON, c-Ret, ALK, cytoplasmic tyrosine kinases e.g. c-SRC, c-YES, Abl, JAK-2, serine/threonine kinases e.g. ATM, Aurora A & B, CDKs, mTOR, PKCi, PLKs, b-Raf, S6K, STK11/LKB1 and lipid kinases e.g. PI3K, SKL Small molecule kinase inhibitors are e.g. PHA-739358, Nilotinib, Dasatinib, and P1)166326, NSC 743411, Lapatinib (GW-572016), Canertinib (CI-1033), Semaxinib (SU5416), Vatalanib (PTK787/7K222584), Sutent (SU 1248), Sorafenib (BAY 43-9006) and Leflunomide (SU101). For more information see e.g. Zhang et al. 2009: Targeting cancer with small molecule kinase inhibitors. Nature Reviews Cancer 9, 28-39.

8. Toll-like Receptors

The members of the Toll-like receptor (TLRs) family are an important link between innate and adaptive immunity and the effect of many adjuvants rely on the activation of TLRs. A large number of established vaccines against cancer incorporate ligands for TLRs for boosting vaccine responses. Besides TLR2, TLR3, TLR4 especially TLR7 and TLR8 have been examined for cancer therapy in passive immunotherapy approaches. The closely related TLR7 and TLR8 contribute to antitumor responses by affecting immune cells, tumor cells, and the tumor microenvironment and may be activated by nucleoside analogue structures. All TLR's have been used as stand-alone immunotherapeutics or cancer vaccine adjuvants and may be synergistically combined with the formulations and methods of the present invention. For more information see van Duin et al. 2005: Triggering TLR signaling in vaccination. Trends in Immunology, 27(1):49-55.

9. Angiogenesis Inhibitors

In addition to therapies which target immune modulatory receptors affected by tumor-mediated escape mechanisms and immune suppression there are therapies which target the tumor environment. Angiogenesis inhibitors prevent the extensive growth of blood vessels (angiogenesis) that tumors require to survive. The angiogenesis promoted by tumor cells to meet their increasing nutrient and oxygen demands for example can be blocked by targeting different molecules. Non-limiting examples of angiogenesis-mediating molecules or angiogenesis inhibitors which may be combined with the present invention are soluble VEGF (VEGF isoforms VEGF121 and VEGF165, receptors VEGFR1, VEGFR2 and co-receptors Neuropilin-1 and Neuropilin-2) 1 and NRP-1, angiopoietin 2, TSP-1 and TSP-2, angiostatin and related molecules, endostatin, vasostatin, calreticulin, platelet factor-4, TIMP and CDAI, Meth-1 and Meth-2, IFN-α, β and γ, CXCL10, IL-4, -12 and -18, prothrombin (kringle domain-2), antithrombin III fragment, prolactin, VEG1, SPARC, osteopontin, maspin, canstatin, proliferin-related protein, restin and drugs like e.g. bevacizumab, itraconazole, carboxyamidotriazole, TNP-470, CM101, IFN-α, platelet factor-4, suramin, SU5416, thrombospondin, VEGFR antagonists, angiostatic steroids+heparin, cartilage-derived angiogenesis Inhibitory factor, matrix metalloproteinase inhibitors, 2-methoxyestradiol, tecogalan, tetrathiomolybdate, thalidomide, thrombospondin, prolactinα V133 inhibitors, linomide, tasquinimod, For review see Schoenfeld and Dranoff 2011: Anti-angiogenesis immunotherapy. Hum Vaccin. (9):976-81.

10. Small Molecule Targeted Therapy Drugs

Small molecule targeted therapy drugs are generally inhibitors of enzymatic domains on mutated, overexpressed, or otherwise critical proteins within the cancer cell. Prominent and non-limiting examples are the tyrosine kinase inhibitors imatinib (Gleevec/Glivec) and gefitinib (Iressa). The use of small molecules e.g. sunitinib malate and/or sorafenib tosylate targeting some kinases in combination with vaccines for cancer therapy is also described in previous patent application US2009004213.

11. Virus-based Vaccines

There are a number of virus-based cancer vaccines available or under development which can be used in a combined therapeutic approach together with the formulations of the present invention. One advantage of the use of such viral vectors is their intrinsic ability to initiate immune responses, with inflammatory reactions occurring as a result of the viral infection creating the danger signal necessary for immune activation. An ideal viral vector should be safe and should not introduce an anti-vector immune response to allow for boosting antitumour specific responses. Recombinant viruses such as vaccinia viruses, herpes simplex viruses, adenoviruses, adeno-associated viruses, retroviruses and avipox viruses have been used in animal tumour models and based on their encouraging results, human clinical trials have been initiated. Especially important virus-based vaccines are virus-like particles (VLPs), small particles that contain certain proteins from the outer coat of a virus. Virus-like particles do not contain any genetic material from the virus and cannot cause an infection but they can be constructed to present tumor antigens on their coat. VLPs can be derived from various viruses such as e.g. the hepatitis B virus or other virus families including Parvoviridae (e.g. adeno-associated virus), Retroviridae (e.g. HIV), and Flaviviridae (e.g. Hepatitis C virus). For a general review see Sorensen and Thompsen 2007: Virus-based immunotherapy of cancer: what do we know and where are we going? APMIS 115(11):1177-93; virus-like particles against cancer are reviewed in Buonaguro et al. 2011: Developments in virus-like particle-based vaccines for infectious diseases and cancer. Expert Rev Vaccines 10(11):1569-83; and in Guillen et al. 2010: Virus-like particles as vaccine antigens and adjuvants: application to chronic disease, cancer immunotherapy and infectious disease preventive strategies. Procedia in Vaccinology 2 (2), 128-133.

12. Multi-epitope Strategies

The use of multi epitopes shows promising results for vaccination. Fast sequencing technologies combined with intelligent algorithms systems allow the exploitation of the tumor mutanome and may provide multi epitopes for individualized vaccines which can be combined with the present invention. For more information see 2007: Vaccination of metastatic colorectal cancer patients with matured dendritic cells loaded with multiple major histocompatibility complex class I peptides. J Immunother 30: 762-772; furthermore Castle et al. 2012: Exploiting the mutanome for tumor vaccination. Cancer Res 72 (5): 1081-91.

13. Adoptive T Cell Transfer

For example, a combination of a tumor antigen vaccination and T cell transfer is described in: Rapoport et al. 2011: Combination immunotherapy using adoptive T-cell transfer and tumor antigen vaccination on the basis of hTHRT and survivin after ASCT for myeloma. Blood 117(3):788-97.

14. Peptide-based Target Therapies

Peptides can bind to cell surface receptors or affected extracellular matrix surrounding the tumor. Radionuclides which are attached to these peptides (e.g. RGDs) eventually kill the cancer cell if the nuclide decays in the vicinity of the cell. Especially oligo- or multimers of these binding motifs are of great interest, since this can lead to enhanced tumor specificity and avidity. For non-limiting examples see Yamada 2011: Peptide-based cancer vaccine therapy for prostate cancer, bladder cancer, and malignant glioma. Nihon Rinsho 69(9): 1657-61.

15. Other Therapies

There are numerous other cancer therapies which can be combined with the formulations and methods of the present invention in order to create synergistic effects. Non-limiting examples are treatments targeting apoptosis, hyperthermia, hormonal therapy, telomerase therapy, insulin potentiation therapy, gene therapy and photodynamic therapy.

The present invention is further illustrated by the following examples which are not be construed as limiting the scope of the invention.

EXAMPLES

Example 1

Generation and Testing of Bispecific Binding Agents Targeting CLDN18.2 and CD3 a. Sequence Origin, Design of Bi-scFv Constructs, and Cloning into Expression Vectors Bispecific tandem single chain antibody constructs (bi-scFv) containing binding domains specific for the human T cell receptor component CD3 and human tumor associated antigens (TAA) were prepared. The corresponding variable heavy chain regions ($V_H$) and the corresponding variable light chain regions ($V_L$) for each construct were specifically arranged from N- to C-terminus in consecutive order:

N-$V_H^{\alpha CLDN18.2}$-$V_L^{\alpha CLDN18.2}$-$V_H^{\alpha CD3}$-$V_L^{\alpha CD3}$-C (1BiMAB, 18PHU5, no. 11-15)

N-$V_H^{\alpha CD3}$-$V_L^{\alpha CD3}$-$V_H^{\alpha CLDN18.2}$-$V_L^{\alpha CLDN18.2}$-C (18PHU3, no. 16-20)

Table 1 summarizes all bi-scFv constructs specific for the TAA CLDN18.2 and PLAC1 that were generated in the course of the invention. The bi-scFv constructs were generated by gene synthesis by GeneArt AG (GeneArt/Life Technologies GmbH, Regensburg, Germany) using the $V_H$ and $V_L$ sequences of the corresponding antibodies. Codon optimizations such as *Homo sapiens* (HS), *Mus musculus* (MM), or Chinese Hamster Ovary (CHO) were implemented by GeneArt's GeneOptimizer® software, and are listed in Table 1. Information on specificity, sequence origin from monoclonal antibodies (mAB), codon usage, additional sequence features and references of all applied domains are summarized in Table 2. Variable domain sequence origin of the respective CD3 antibodies are listed in Table 2. Due to the high homology of human and mouse TAAs, the same anti-TAA $V_H$ and $V_L$ sequences could be used for the generation of bi-scFv constructs for mouse assays, but in combination with the $V_H$, $V_L$ sequences of the mouse specific anti-CD3 antibody clone 145-2C11.

Figure 1A:
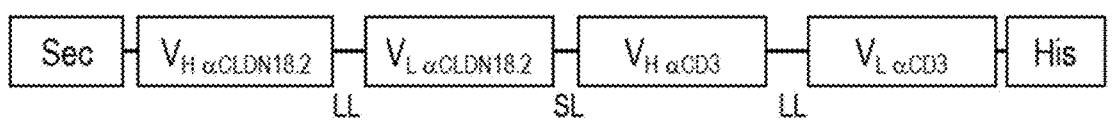
FIGS. 1A and 1B show a modular scheme illustrating the design of recombinant bi-scFv proteins targeting TAA CLDN18.2.
Figure 1B:
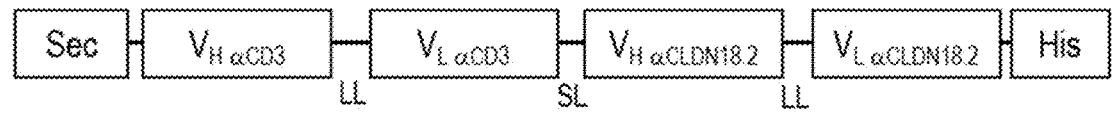

DNA cloning and expression vector construction was carried out according to standard procedures (Green/Sambrook, Molecular Cloning, 2012) well known by the skilled person. Briefly, the leadoff bi-scFv DNA sequences were provided with a 5' HindIII and a 3' XhoI restriction site (HindIII and XbaI in case of bi-scFv 1BiMAB) for cloning into expression plasmids. A secretion signal sequence was introduced at the 5' end upstream of the bi-scFv sequence for protein secretion from cellular cytoplasm into the culture medium. A sequence coding for a 15 to 18 amino acid flexible glycine-serine peptide linker was inserted to join the $V_H$ and $V_L$ domains for the composition of the single chain variable antibody fragments (scFv) of which one binds to CD3 and the other to the TAA. To form a bispecific single chain antibody, the two scFv domain sequences were connected by a sequence coding for a short peptide linker (GGGGS). Together with this linker sequence a BamHI restriction site was introduced for scFv domain exchanges for the cloning of upcoming bi-scFV constructs. In-depth, 5'scFv-domains could be exchanged by HindIII and BamHI restriction and 3'scFv-domains by BamHI and XhoI restriction. For construct schemata see also FIG. 1.

All used bi-scFv antibody constructs were cloned into the standard mammalian expression vector pcDNA™3.1/myc-His (+) (Invitrogen/Life Technologies GmbH, Darmstadt, Germany). The C-terminal 6×His-tag served for metal affinity purification of the protein and for detection analysis. All constructs were verified by sequencing via MWG's single read sequence service (Eurofins MWG Operon. Ebersberg, Germany).

TABLE 1

Summary of TAA and CD3 specific bispecific single chain antibody constructs

| Internal name | TAA | Specificity | 5'-$V_H$-$V_L$ | 3'-$V_H$-$V_L$ | Codon usage |
|---|---|---|---|---|---|
| 1BiMAB | CLDN18.2 | human | mCLDN18.2ab | TR66 | HS |
| no. 11 | CLDN18.2 | murine | mCLDN18.2ab | 145-2C11 | CHO |
| no. 12 | CLDN18.2 | human | mCLDN18.2ab | UCHT1-HU | CHO |
| no. 13 | CLDN18.2 | human | mCLDN18.2ab | UCHT1 | CHO |
| no. 14 | CLDN18.2 | human | mCLDN18.2ab | CLB-T3 | CHO |
| no. 15 | CLDN18.2 | human | mCLDN18.2ab | TR66 | CHO |
| no. 16 | CLDN18.2 | murine | 145-2C11 | mCLDN18.2ab | CHO |
| no. 17 | CLDN18.2 | human | UCHT1-HU | mCLDN18.2ab | CHO |
| no. 18 | CLDN18.2 | human | UCHT1 | mCLDN18.2ab | CHO |
| no. 19 | CLDN18.2 | human | CLB-T3 | mCLDN18.2ab | CHO |
| no. 20 | CLDN18.2 | human | TR66 | mCLDN18.2ab | CHO |
| 18PHU5 | CLDN18.2 | human | mCLDN18.2ab | TR66 | HS |
| 18PHU3 | CLDN18.2 | human | TR66 | mCLDN18.2ab | HS |
| 18PMU5 | OLDN18.2 | murine | mCLDN18.2ab | 145-2C11 | MM |
| 18PMU3 | CLDN18.2 | murine | 145-2C11 | mCLDN18.2ab | MM |
| control bi-scFv | | | | | |
| no. 35 | PLAC1 | human | 78H11 | TR66 | CHO |

CHO, Chinese Hamster Ovary;
HS, *Homo sapiens*;
HU, humanized;
MM, *Mus*

TABLE 2

Summary of bi-scFv construct information

| | CD3 binding moiety | | TAA binding moiety | | Species | | | |
|---|---|---|---|---|---|---|---|---|
| Internal name | mAB origin | Species reactivity | TAA | mAB origin | reactivity | 5'-$V_H$-$V_L$ | 3'-$V_H$-$V_L$ | Short linker |
| 1BiMAB | TR66 | human | CLDN18.2 | mCLDN18.2ab | human, murine | mCLDN18.2ab | TR66 | GGGGS |
| no.11 | 145-2C11 | murine | CLDN18.2 | mCLDN18.2ab | human, murine | mCLDN18.2ab | 145-2C11 | SGGGGS |
| no.12 | UCHT1-HU | human | CLDN18.2 | mCLDN1B.2ab | human, murine | mCLDN18.2ab | UCHT1-HU | SGGGGS |
| no.13 | UCHT1 | human | CLDN18.2 | mCLDN18.2ab | human, murine | mCLDN18.2ab | UCHT1 | SGGGGS |
| no.14 | CLB-T3 | human | CLDN18.2 | mCLDN18.2ab | human, murine | mCLDN18.2ab | CLB-T3 | SGGGGS |
| no.15 | TR66 | human | CLDN18.2 | mCLDN18.2ab | human, murine | mCLDN18.2ab | TR66 | SGGGGS |
| no.16 | 145-2C11 | murine | CLDN18.2 | mCLDN18.2ab | human, murine | 145-2C11 | mCLDN18.2ab | SGGGGS |

TABLE 2-continued

Summary of bi-scFv construct information

| | | | | | | | | |
|---|---|---|---|---|---|---|---|---|
| no.17 | UCHT1-HU | human | CLDN18.2 | mCLDN18.2ab | human, murine | UCHT1-HU | mCLDN18.2ab | SGGGGS |
| no.18 | UCHT1 | human | CLDN18.2 | mCLDN18.2ab | human, murine | UCHT1 | mCLDN18.2ab | SGGGGS |
| no.19 | CLB-T3 | human | CLDN18.2 | mCLDN18.2ab | human, murine | CLB-T3 | mCLDN18.2ab | SGGGGS |
| no.20 | TR66 | human | CLDN18.2 | mCLDN18.2ab | human, murine | TR66 | mCLDN18.2ab | SGGGGS |
| 18PHU5 | TR66 | human | CLDN18.2 | mCLDN18.2ab | human, murine | mCLDN18.2ab | TR66 | SGGGGS |
| 18PHU3 | TR66 | human | CLDN18.2 | mCLDN18.2ab | human, murine | TR66 | mCLDN18.2ab | SGGGGS |
| 18PMU5 | 145-2C11 | murine | CLDN18.2 | mCLDN18.2ab | human, murine | mCLDN18.2ab | 145-2C11 | SGGGGS |
| 18PMU3 | 145-2C11 | murine | CLDN18.2 | mCLDN18.2ab | human, murine | 145-2C11 | mCLDN18.2ab | SGGGGS |
| no.35 | TR66 | human | PLAC1 | 78H11 | human, murine | 78H11 | TR66 | SGGGGS |

| Internal name | 5'-long linker | 3'-long linker | Secretion signal | Codon usage | Anti-CD3 mAB reference |
|---|---|---|---|---|---|
| 1BiMAB | (GGGGS)$_3$ | VE(GGSGGS)$_2$ GGVD | MGWSCIILFLVATATGVHS | HS | Lanzavecchia & Scheidegger, Eur J Immunol 1987 |
| no.11 | (GGGGS)$_3$ | (GGGGS)$_3$ | MGWSCIILFLVATATGVHS | CHO | Leo et al., Proc Natl Acad Sci, 1987 |
| no.12 | (GGGGS)$_3$ | (GGGGS)$_3$ | MGWSCIILFLVATATGVHS | CHO | Shalaby et al., J Exp Med 1992 |
| no.13 | (GGGGS)$_3$ | (GGGGS)$_3$ | MGWSCIILFLVATATGVHS | CHO | Beverley et al., Eur J Immunol 1981 |
| no.14 | (GGGGS)$_3$ | (GGGGS)$_3$ | MGWSCIILFLVATATGVHS | CHO | Van Lier et al., Immunology 1989 |
| no.15 | (GGGGS)$_3$ | (GGGGS)$_3$ | MGWSCIILFLVATATGVHS | CHO | Lanzavecchia & Scheidegger, Eur J Immunol 1987 |
| no.16 | (GGGGS)$_3$ | (GGGGS)$_3$ | MNSGLQLVFFVLTLKGIQG | CHO | Leo et al., Proc Nat Acad Sci, 1987 |
| no.17 | (GGGGS)$_3$ | (GGGGS)$_3$ | MGWSCIILFLVATATGVHS | CHO | Shalaby et al., J Exp Med 1992 |
| no.18 | (GGGGS)$_3$ | (GGGGS)$_3$ | MNSGLQLVFFVLTLKGIQG | CHO | Beverley at al., Eur J Immunol 1981 |
| no.19 | (GGGGS)$_3$ | (GGGGS)$_3$ | MNFGLSLIFLALILKGVQC | CHO | Van Lier et al., Immunology 1989 |
| no.20 | (GGGGS)$_3$ | (GGGGS)$_3$ | MEWSWIFLFLLSVTTGVHS | CHO | Lanzavecchia & Scheidegger, Eur J Immunol 1987 |
| 18PHU5 | (GGGGS)$_3$ | VE(GGSGGS)$_2$ GGVD | MGWSCIILFLVATATGVHS | HS | Lanzavecchia & Scheidegger, Eur J Immunol 1987 |
| 18PHU3 | VE(GGSGGS)$_2$ GGVD | (GGGGS)$_3$ | MGWSCIILFLVATATGVHS | HS | Lanzavecchia & Scheidegger, Eur J Immunol 1987 |
| 18PMU5 | (GGGGS)$_3$ | VE(GGSGGS)$_2$ GGVD | MGWSCIILFLVATATGVHS | MM | Leo et al., Proc Natl Acad Sci, 1987 |
| 18PMU3 | VE(GGSGGS)$_2$ GGVD | (GGGGS)$_3$ | MNSGLQLVFFVLTLKGIQG | MM | Leo et al., Proc Natl Acad Sci, 1987 |

TABLE 2-continued

Summary of bi-scFv construct information

| no.35 | (GGGGS)$_3$ | (GGGGS)$_3$ | MGWLWNLLFLMAAAQSAQA | CHO | Lanzavecchia & Scheidegger, Eur J Immunol 1987 |

CHO indicates Chinese Hamster Ovary; HS, *Homo sapiens*; mAB, monoclonal antibody; MM, *Mus musculus*; TAA, tumor associated antigen.

b. Generation of Stable Producer Cell Lines

To generate stable producer cell clones of CLDN18.2 specific bi-scFv proteins the human embryonic kidney cell line HEK293 (ATCC CRL-1573) and the Chinese Hamster Ovary cell line CHO-K1 (ATCC CCL-61) were used.

HEK293 Transfection $1 \times 10^7$ HEK293 cells were plated two days prior to transfection on 14.5 cm tissue culture dishes in 20 ml complete DMEM medium (DMEM/F-12 GlutaMax supplemented with 10% heat inactivated FBS and 0.5% penicillin-streptomycin; all reagents from Gibco/Life Technologies GmbH, Darmstadt, Germany). Before transfection, cells were washed with DPBS supplemented with 2 mM EDTA, then 20 ml of plain DMEM medium without FBS or antibiotics were added. 20 µg of linearized DNA of the constructs described under Example 1.a were diluted in 0.5 ml plain DMEM/F-12 medium. 75 µl of 1 mg/ml linear PEI solution (Polyethylenimine; Polysciences Europe GmbH, Eppelheim, Germany) were added to the diluted DNA and rigorously vortexed. After 15 min incubation at RT, the DNA/PEI complexes were added dropwise to the cells, cell culture dishes were gently rotated and then incubated at 37° C., 5% $CO_2$. 24 h after transfection the medium was changed. Selection of transfected cells started 48 h after transfection with G418 sulfate (Gibco/Life Technologies GmbH, Darmstadt, Germany) in a final concentration of 0.8 mg/ml. G418 was added permanently to the culture medium for cell culturing.

CHO-K1 Transfection $1 \times 10^6$ CHO-K1 cells were plated one day prior to transfection on 6-well tissue culture plates in 2 ml complete DMEM medium (DMEM/F-12 GlutaMax supplemented with 10% heat inactivated FBS, without antibiotics; all reagents from Gibco/Life Technologies GmbH, Darmstadt, Germany). Before transfection, cells were washed with DPBS supplemented with 2 mM EDTA, then 1.5 ml of plain DMEM medium without FCS or antibiotics were added. 4 µg of linearized DNA of the constructs described under Example 1.a were diluted in 0.25 ml plain DMEM/F-12 medium and mixed gently. In a second reaction tube, 2.5 µl Lipofectamine 2000 (Invitrogen/Life Technologies GmbH, Darmstadt, Germany) were diluted in 0.25 ml plain DMEM/F12 medium, mixed gently and incubated for 5 min at RT. DNA mix and Lipofectamine mix were combined in a 1:1 ratio, mixed gently and incubated for 20 min at RT. The DNA/Lipofectamine 2000 complexes were added dropwise to the cells, cell culture dishes were gently rotated and then incubated at 37° C., 5% $CO_2$. 6 h after transfection the medium was changed to complete DMEM/F-12 medium. Cells were splitted the following day in a 1:10 ratio. Selection of transfected cells started 48 h after transfection with G418 sulfate (Gibco/Life Technologies GmbH, Darmstadt, Germany) in a final concentration of 0.5 mg/ml. G418 was added permanently to the culture medium for cell culturing.

c. Selection of HEK293 as Producer Cells

Expression of bi-scFv proteins by stably transfected HEK293 and CHO-K1 cell lines described under Example 1.b was characterized by immunofluorescence staining to detect bi-scFv expression according to standard procedures (Current Protocols in Immunology, 2012). Briefly, $2 \times 10^5$ cells were grown on glass slides for 24 h and then permealized with 2% PFA, DPBS supplemented with 5% BSA and 0.2% Saponin was used as blocking buffer. After washing with DPBS and blocking with blocking buffer, cells were incubated with primary antibody Anti-HIS Epitope-Tag (Dianova GmbH, Hamburg, Germany) diluted 1:500 in blocking buffer for 30 min at RT. After washing with blocking buffer, secondary Cy3-conjugated goat-anti-mouse IgG (H-L) antibody (Jackson ImmunoResearch Europe, Suffolk, England) diluted 1:500 in blocking buffer was added and incubated for 3h at RT. After washing with blocking buffer and 1120, cells were embedded in DAKO-mounting medium (Dako, Carpinteria, Calif., USA) supplemented with Hoechst 33342 dye (Pierce/Thermo Fisher Scientific, Rockford, Ill., USA). Slides were investigated and photographed with a Nikon-Eclipse Ti fluorescence microscope for the presence of bi-scFv positive cells (data not shown). HEK293 cells showed an overall better expression of bi-scFv proteins than CHO-K1 cells and were therefore chosen as producer cell line.

d. Production and Detection of Bi-scFv Protein 1BiMAB with HEK293 Clone #28

Bi-scFv 1BiMAB was chosen as first bi-scFv protein to be produced, purified and used for the establishment of various assays. For this purpose, clonal cell lines of HEK293 bulk cells stably expressing 1BiMAB (see Example 1.b) were produced by single cell sorting using a FACSAria cell sorter (BI) Biosciences, Heidelberg, Germany). After expansion of nearly 40 clonal lines, the best producer clone was selected by immunofluorescence as described under Example 1.c. Selected producer clone #28 was expanded and cultured in a 10-layer Cell Factory (Nunc, Roskilde, Denmark) in DMEM/F-12 GlutaMax supplemented with 10% FBS, 0.5% penicillin-streptomycin and 0.8 mg/ml G418 (all reagents from Gibco/Life Technologies GmbH, Darmstadt, Germany) according to the manufacturer's guidelines. At confluent stage, cells were washed with DPBS and medium was changed to DMEM/F-12 medium with antibiotics but without FBS. Cell supernatant containing bi-scFv protein 1BiMAB was harvested every 3-5 days for up to 4 weeks. Supernatant was filtered with 500 ml Steritop Filter Units (Merck Millipore, Billerica, Mass., USA) and stored at 4° C. until FPLC-purification.

Before FPLC-purification, presence of bi-scFv in the cell culture supernatant was tested by polyacrylamid gel electrophoresis followed by coomassie staining and western blot analysis performed by standard (Current Protocols in Protein Science, 2012). The supernatant was concentrated 5×-10× by Centricon Centrifugal Filter Devices −10K MWCO (Merck Millipore, Billerica, Mass., USA) according to the manufacturer's protocol. Concentrated and non-concentrated supernatants were separated on NuPAGE Novex 4-12% Bis-Tris Gels (Invitrogen/Life Technologies GmbH, Darmstadt, Germany). Subsequently, the gels were stained with Coomassie Brilliant Blue solution according to standard procedures to detect bi-scFv protein 1BiMAB between 50 and 60 kD and other proteins contained in the cell culture supernatant. Western blot analysis was performed to specifically detect bi-scFc protein 1BiMAB via its 6×His-tag. Briefly, after blotting proteins on PVDF membrane and blocking with PBST/3% milk powder, the membrane was incubated for 1 h at 4° C. with primary antibody Anti-HIS Epitope-Tag (Dianova GmbH, Hamburg, Germany) diluted 1:500 in blocking buffer. After washing with blocking buffer, membranes were incubated with Fc-specific secondary peroxidase-conjugated goat-anti-mouse IgG antibody (Sigma Aldrich, Germany) diluted 1:10000 in blocking buffer for 1 h at 4° C. After washing with blocking buffer, the signals were visualized by SuperSignal West Femto Chemiluminescent Substrate (Pierce/Thermo Fisher Scientific, Rockford, Ill., USA) and recorded by an ImageQuant LAS 4000 Imager (GE Healthcare Life Sciences, Munich, Germany). Signals of bi-scFv were detected between 50 and 60 kD as compared to the internal molecular weight standard (see FIGS. 3A and B).

e. Purification and Quantification of Bi-scFv Protein 1BiMAB

Cell culture supernatant of HEK293 clone #28 containing bi-scFv protein 1BiMAB (described under Example 1.d) was subjected to immobilized metal affinity chromatography (IMAC) using standard procedures (Current Protocols in Protein Science, 2012). Briefly, filtered cell culture supernatant was loaded onto a His Trap FF 5 ml column connected to an ÄKTA Purifier 10 FPLC system (both GE Healthcare Life Sciences, Munich, Germany). PBS washing buffer contained 10 mM imidazol, PBS elution buffer contained 500 mM NaCl, 50 mM $NaH_2PO_4$ and 250 mM imidazol, pH of both buffers was adjusted to 7.4. Elution was performed by a stepwise gradient. Eluted bi-scFv protein 1BiMAB was immediately dialyzed against 1×PBS using a Slide-A-Lyzer G2 Dialysis Cassette 10K MWCO (Pierce/Thermo Fisher Scientific, Rockford, Ill., USA). After dialysis against 1×PBS, bi-scFv was dialyzed against an $H_2O$ based 200 mM arginine buffer (L-Arginin-monohydrochloride; Roth, Karlsruhe, Germany).

Bi-scFv concentration was determined by measurement at 280 nm with a NanoDrop 2000c under consideration of the extinction coefficient and the molecular weight of bi-scFv protein 1 BiMAB determined via the ProtParam tool (http://web.expasy.org/protparam/). Purified protein was aliquoted and stored at −80° C. for long time storage or kept at 4° C. for immediate use.

Quality and purity of bi-scFv protein 1BiMAB was tested by Coomassie staining and western blot analysis as described under Example 1.d (see also FIGS. 3A and B). A BSA standard dilution was included in the Coomassie procedure to roughly confirm the concentration measured by NanoDrop (data not shown).

f. Establishment of an ELISA Assay

For the quantification of 1BiMAB in cell culture supernatant of HEK293 cells, a specific ELISA assay had to be established. For this purpose, supernatant from Example 1.d and purified bi-scFv protein 1BiMAB described under Example 1.c was used. BSA pre-blocked Ni-NTA plates (Thermo Fisher Scientific, Rockford, Ill., USA) were used to immobilize bi-scFv protein 1BiMAB via its 6×His-tag. All washing steps were conducted three times with 200 µl 1×PBS/0.05% Tween (washing buffer) per well and all steps were executed at room temperature. As standard, purified 1BiMAB protein was used, diluted in 1×PBS within the range of 10-500 ng/ml. Supernatants were diluted 1:10 in 1×PBS. 100 µl of diluted protein or supernatant were transferred to each well and incubated for one hour while shaking. After washing, an anti-idiotypic antibody against the $V_H$-$V_L$ domains of mCLDN18.2ab was diluted to a final concentration of 0.5 µg/ml in 1×PBS/3% BSA. 100 µl of the anti-mCLDN18.2ab solution were added per well and incubated for one hour while shaking. After washing, an AP-conjugated anti-mouse-Fc antibody (Jackson ImmunoResearch Europe, Suffolk, England) was diluted to a final concentration of 300 ng/ml in 1×PBS/3% BSA. 100 µl of this secondary antibody solution were added per well and incubated for an additional hour while shaking. As negative controls, secondary antibody only, 1BiMAB plus secondary antibody, and anti-mCLDN18.2ab plus secondary antibody were used. In addition, HEK293 cell supernatant without bi-scFv protein was included in the assay. Finally, 50 µl AP substrate solution (1.5 mg pNPP per ml substrate buffer, AppliChem GmbH, Darmstadt, Germany) were added per well after washing. After 5, 15, and 30 min incubation in the dark absorption at 405 nm with an excitation wavelength of 492 nm was measured with an Infinite M200 Tecan microplate-reader (Tecan, Männedorf, Switzerland). Concentration of bi-scFv protein from supernatant was determined by calculation against the standard row (data not shown).

g. Transient Transfection of CLDN18.2-specific Bi-scFv Proteins for Comparison Studies To transiently generate preferably high amounts of CLDN18.2 specific bi-scFv proteins the human embryonic kidney cell line HEK293T (ATCC CRL-11268) was used for transfection. $1×10^7$ HEK293T cells were plated two days prior to transfection on 14.5 cm tissue culture dishes in 20 ml complete DMEM medium (DMEM/F-12 GlutaMax supplemented with 10% heat inactivated FBS and 0.5% penicillin-streptomycin; all reagents from Gibco/Life Technologies GmbH, Darmstadt, Germany). Before transfection, cells were washed with DPBS supplemented with 2 mM EDTA, then 20 ml of plain DMEM medium without FBS or antibiotics were added. 20 µg of the circular DNA constructs 1BiMAB, no. 11-20, and no. 35 (described under Example 1.b) were diluted in 0.5 ml plain DMEM/F-12 medium. 75 µl of 1 mg ml linear PEI solution (Polyethylenimine; Polysciences Europe GmbH, Eppelheim, Germany) were added to the diluted DNA and rigorously vortexed. After 15 min incubation at RT, the DNA/PEI complexes were added dropwise to the cells, cell culture dishes were gently rotated and then incubated at 37° C., 5% $CO_2$ for 24 h. After a medium change with plain DMEM/F-12 cells were incubated for another 48 h at 33° C., 5% $CO_2$. Cell supernatant was harvested after incubation and sterile filtered with 0.2 µm Minisart syringe filters (Sigma-Aldrich, Germany). Subsequently, bi-scFv proteins were small-scale purified from cell culture supernatants by Ni-NTA spin columns according to the manufacturer's protocol (Qiagen, Hilden, Germany). Bi-scFv protein concentrations were estimated by an ELISA as described under Example 1.f and verified by western blot analysis as described under Example 1.e (data not shown). Purified proteins were stored at 4° C. for immediate use.

Example 2

Establishment of Functional Assays to Monitor Specific T Cell Activation and Target Cell Lysis by Redirected T Cells Mediated by Bi-scFv Proteins FPLC-purified bi-scFv protein 1BiMAB was used to establish in vitro assays to monitor the capability of bi-scFv proteins to specifically redirect human effector cells to TAA-positive target cells. The aim was to visualize the effects and to quantify the activation of human T cells and the specific target cell lysis.

a. Microscopic Analysis of T Cells Redirected to Target Cells by Bi-scFv Protein For the visualization of bi-scFv protein functionality, an assay to show the redirection of effector cells to CLDN18.2-expressing target cells by bi-scFv proteins via microscope had to be established. For this purpose, the gastric carcinoma cell line NugC4 that endogenously expresses relatively high levels of human CLDN18.2 (Sahin U. et al., Clin Cancer Res. 2008 Dec. 1; 14(23):7624-34) was used as target cell line.

Human effector cells were freshly isolated from human blood from healthy donors according to standard procedures (Current Protocols in Immunology, 2012): briefly, blood was diluted with DPBS, layered on Ficoll-Paque Plus (GE Healthcare Life Sciences, Munich, Germany) and centrifuged. Peripheral blood mononuclear cells (PBMCs) were collected from the interphase, washed with cold DPBS supplemented with 2 mM EDTA and counted. Human T cells were subsequently separated by magnetic-activated cell separation (MACS) from PBMCs by Pan T Cell Isolation Kit II (Miltenyi Biotec, Teterow, Germany) according to the manufacturer's guidelines.

$1 \times 10^5$ NugC4 cells were seeded per well into tissue culture 6-well plates. Human cells were prepared as described above and added in an effector to target (E:T) ratio of 5:1. RPMI 1640 medium supplemented with 5% heat inactivated human AB serum, 0.5% penicillin-streptomycin, 1×NEAA and 1 mM sodium pyruvate (Gibco/Life Technologies GmbH, Darmstadt, Germany) was used for all cells and the final volume per well was adjusted to 2 ml per well. Control samples comprised target or T cells alone with and without bi-scFv protein. Tissue culture plates were subsequently incubated at 37° C., 5% $CO_2$. The assay was continuously observed with a Wilovert S inverted microscope (Hund, Wetzlar, Germany) from 6h to 48 h of coincubation. Significant effects in terms of T cell clustering on target cells, formation of an immunologic synapse and target cell killing in the presence of bi-scFv protein 1BiMAB were seen at 24 h. After 48 h viable target cells could hardly be found. Pictures were taken at 24 h with a Nikon Eclipse TS100 inverted microscope (Nikon, Japan). See also FIG. 5.

This assay was further on included as visibility control in all cytotox assays in various well formats.

b. Target-dependent T Cell Activation by Bi-scFv Protein 1BiMAB

For the detection of a specific activation of human T cells by bi-scFv proteins a flow cytometric assay was established. For the detection of T cell activation, the early activation marker CD69 and the late activation marker CD25 were selected for staining by fluorescence-conjugated antibodies. For the detection of human T cells in the mixture of target and T cells, CD3 on T cells was stained.

The assay set-up from above was chosen (Example 2.a). Briefly, NugC4 target cells were seeded with human T cells in an E:T ratio of 5:1 in 2 ml complete medium and bi-scFv protein 1BiMAB was added in a concentration within the range of 0.001-1000 ng/ml. Control samples contained target or T cells alone with and without bi-scFv protein 1BiMAB. After 24 h and/or 48 h—depending on the result of the visibility control—all cells were harvested by gentle scraping with Cell Scrapers (Sarstedt A G & Co, Nürmbrecht, Germany) and transferred to 5 ml round bottom tubes (BI) Falcon, Heidelberg, Germany). Cells were centrifuged and washed with DPBS. For cell staining Mouse Anti-Human CD3-FITC, Mouse Anti-Human CD69-APC, and Mouse Anti-Human CD25-PE (all antibodies 1D Biosciences, Heidelberg, Germany) were used. Cell pellets were resuspended in 50 µl FACS-buffer (DPBS supplemented with 5% FBS) containing the fluorescence-conjugated antibodies. After incubation for 20 min at 4° C. in the dark, samples were washed with 4 ml DPBS and cell pellets were resuspended in 200 µl FACS buffer containing propidium iodide (PI) or 7-AAD (both Sigma Aldrich, Germany) in a final dilution of 1:1000 for the detection of dead cells. Samples were kept on ice and dark throughout the measurement. Establishment of the assay was performed with a FACSCalibur, later measurements were performed with a FACSCanto II flow cytometer (both BD Biosciences, Heidelberg, Germany). Analysis was evaluated by FlowJo software (Tree Star, San Carlos, Calif., USA).

As shown in FIGS. 6A and B, no 1BiMAB mediated T cell activation is detectable in the absence of target cells underlining the strict target dependency of bi-scFv functionality. A significant T cell activation in the presence of target cells occurred with only 0.01 ng/ml 1BiMAB after 24 h. Maximum efficiency was reached using 100 ng/ml 1BiMAB.

Besides the study of T cell activation, this assay also allows the qualitative analysis of bi-scFv mediated effects on target cell killing by gating on the target cell population and estimating the percentage of PI- or 7-AAD-positive target cells (no data shown). All analyses were performed with FlowJo software (Tree Star, San Carlos, Calif., USA).

c. Luciferase Cytotox Assay

To determine subtle differences in the target cell killing potential of bi-scFv proteins directed against CLDN18.2 and CD3, a highly sensitive assay had to be developed. The aim was, to establish an assay with which the target cell killing could be quantitatively monitored in a high throughput fashion. To achieve this, a luciferase cytotox assay was chosen. Herewith the measurement of luciferase-expression by viable target cells allows to indirectly determine the target cell lysis mediated by cytotoxic effector cells in the presence of antibody.

First, NugC4 cells (described above) were transduced with a lentiviral vector carrying firefly luciferase, an EGFP reporter gene and an antibiotic selection marker. After antibiotic selection of transduced cells, EGFP high expressing cells were sorted by a FACSAria cell sorter (BD Biosciences, Heidelberg, Germany), analyzed for high luciferase expression and subsequently expanded for further studies.

Human effector cells were prepared as described under Example 2.a. Establishment of the assay was performed within the range of 1-100 ng/ml of the bi-scFv protein 1BiMAB, whereby a concentration of 5 ng/ml was found to result in highly efficient and reproducible effects and was further used as standard concentration. NugC4 cells stably expressing luciferase (described above) were used as target cells. $1 \times 10^4$ target cells were seeded per well into white flat bottom 96-well plates. Human T cells (prepared as described under Example 2.a) were added in an E:T ratio of 5:1. The medium described above (Example 2.a) was used and the final volume per well was adjusted to 100 µl. Test samples and control samples were plated at least in triplicates. Cell culture microplates were incubated for 24 h and 48 h at 37° C., 5% $CO_2$. For analysis, 50 µl of a water solution containing 1 mg/ml luciferin (BD Monolight, BD Biosciences, Heidelberg, Germany) and 50 mM HEPES were added per well and plates subsequently incubated for 30 min in the dark at 37° C. Luminescence arising from oxidation of luciferin by luciferase expressing viable cells was measured in a microplate-reader (Infinite M200, Tecan, Männedorf, Switzerland). Percentage of specific target cell lysis was calculated by the following formula: % specific lysis=$[1-(\text{luminescence}_{test\ sample}-L_{max})/(L_{min}-L_{max})]\times 100$, whereas "L" indicates lysis. $L_{min}$ refers to the minimum lysis in the absence of bi-scFv and $L_{max}$ to the maximum lysis (equal to spontaneous luminescence counts) in the absence of bi-scFv achieved by addition of Triton X-100 (2% final concentration).

Potential direct effects of bi-scFv proteins on target cells independent of effector cells were determined by plating target cells without human T cells including all controls such as $L_{min}$ and $L_{max}$.

This assay was used for further studies to investigate the specific T cell mediated lysis of target cells. Modifications were implemented e.g. by varying bi-scFv concentrations, bi-scFv proteins, E:T ratios, or effector cells (CD8−, CD4+ T cells, PBMCs).

Example 3

Selection of a CLDN18.2-specific Bi-scFv Lead Candidate

Luciferase Cytotox Assay with Various CLDN18.2-specific Bi-scFv Proteins for the Selection of the Most Potent Bi-scFv Variant All 10 CHO-codon optimized constructs (no. 11-20) specific for the TAA CLDN18.2 were tested in comparison to the human codon optimized bi-scFv protein 1 BiMAB in a luciferase cytotox assay with NugC4 target cells that endogenously express CLDN18.2 and ectopically express luciferase (see also Example 2.c). Characteristics of used bi-scFv proteins are specified in Table 2. Bi-scFv no. 35 specific for TAA PLAC1 was used as isotype control because PLAC1 is not expressed by NugC4 cells. Binding activity to CD3 on human T cells had been proven in a FACS binding assay (data not shown). All bi-scFv proteins were generated as described under Example 1.g and used for a cytotox assay set up as described under Example 2.c.

All bi-scFv proteins were used in a final concentration of 5 ng/ml. For the determination of $L_{min}$, control bi-scFv protein no. 35 was seeded with target and T cells ninefold, test samples were plated sixfold. Per time point one plate was prepared for analysis.

The specific lysis at each analyzed time point (8 h, 16 h, 24 h) was plotted against the used bi-scFv proteins. Bi-scFv proteins 1BiMAB (SEQ ID NO: 39) and no. 15 (SEQ ID NO: 41)—which are constructed in the same orientation and contain the same anti-CD3 sequence (TR66) and differ only in their codon usage on nucleic acid level and in the linker sequences—proved to be the most potent antibodies in mediating target cell lysis (see FIG. 2). Because 1BiMAB and no. 15 are equal in their efficiency, the so far better investigated bi-scFv protein 1 BiMAB was selected for all following assays. Constructs 18PHU3 and 18PHU5 (see Table 1 and 2) were compared at a later time point to 1BiMAB. Efficiency of 18PHU5 was equivalent to 1BiMAB, 18PHU3 was less potent (data not shown).

Example 4

Binding Capacity of Bi-scFv Protein 1BiMAB

Establishment of a FACS-based Binding Assay

To assess the binding capacity of the CLDN18.2 and the CD3-targeting moieties of bi-scFv proteins a flow cytometric assay was established. CLDN18.2 endogenously expressing NugC4 cells were used to investigate the anti-CLDN18.2 site and human T cells were used to investigate the anti-CD3 site.

For the investigation of the anti-CLDN18.2 binding capacity, NugC4 cells were trypsinized, washed with complete RPMI 1640 medium and subsequently with DPBS. All washing steps were conducted by centrifugation at 1200 rpm for 6 min at 4° C. $2.5\times 10$ NugC4 cells were transferred to 5 ml round bottom tubes and incubated with 50 g/ml FPLC-purified 1BiMAB protein in FACS-buffer for 30 min at 4° C. Cells were washed with 2 ml FACS-buffer and subsequently incubated with 3.3 µg/ml of monoclonal antibody Anti-HIS Epitope-Tag (Dianova GmbH, Hamburg, Germany) for 30 min at 4° C. After washing with 2 ml FACS-buffer, the cell pellet was incubated with an APC-conjugated goat-anti-mouse secondary antibody (Jackson ImmunoResearch Europe, Suffolk, England) in a 1:200 dilution in FACS-buffer for 20 min at 4° C. in the dark. Cells were washed twice with 2 ml FACS-buffer and finally resuspended in 150 µl FACS-buffer supplemented with 1 µg/ml PI (Sigma Aldrich, Germany) to counterstain dead cells. Another staining with the same procedure was included using 50 µg/ml 1BiMAB and APC-conjugated goat-anti-mouse secondary antibody (1:200) but without Anti-HIS Epitope-Tag antibody. Negative control samples included secondary goat-anti-mouse APC antibody alone, monoclonal antibody Anti-HIS Epitope-Tag plus secondary goat-anti-mouse APC antibody. As positive control 10 µg/ml monoclonal CLDN18.2-specific antibody mCLDN18.2ab stained with secondary goat-anti-human APC antibody (Jackson ImmunoResearch Europe, Suffolk, England) and its secondary antibody only control were implemented.

Figure 4A:
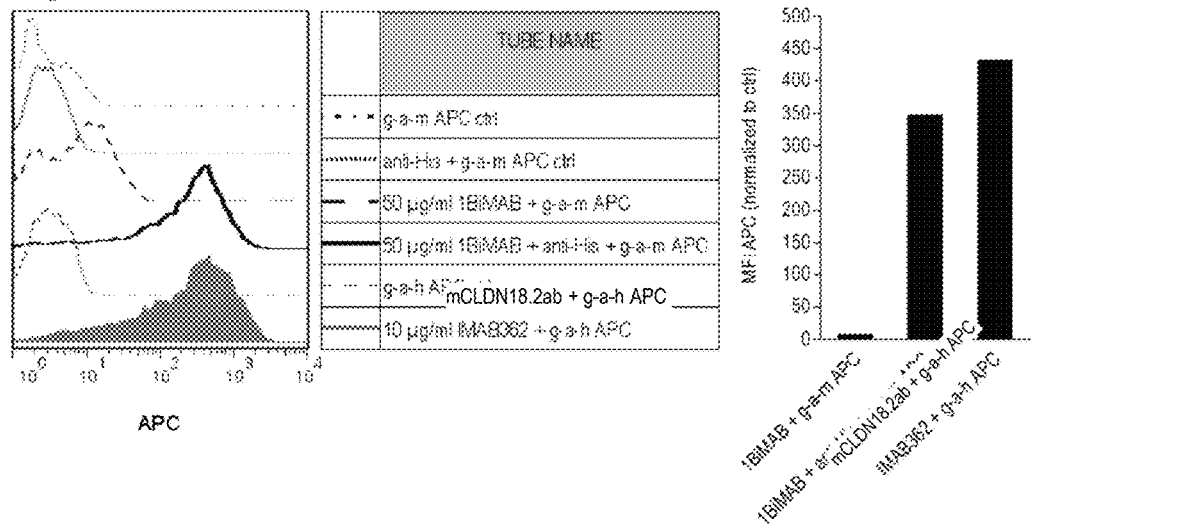
Figure 4B:
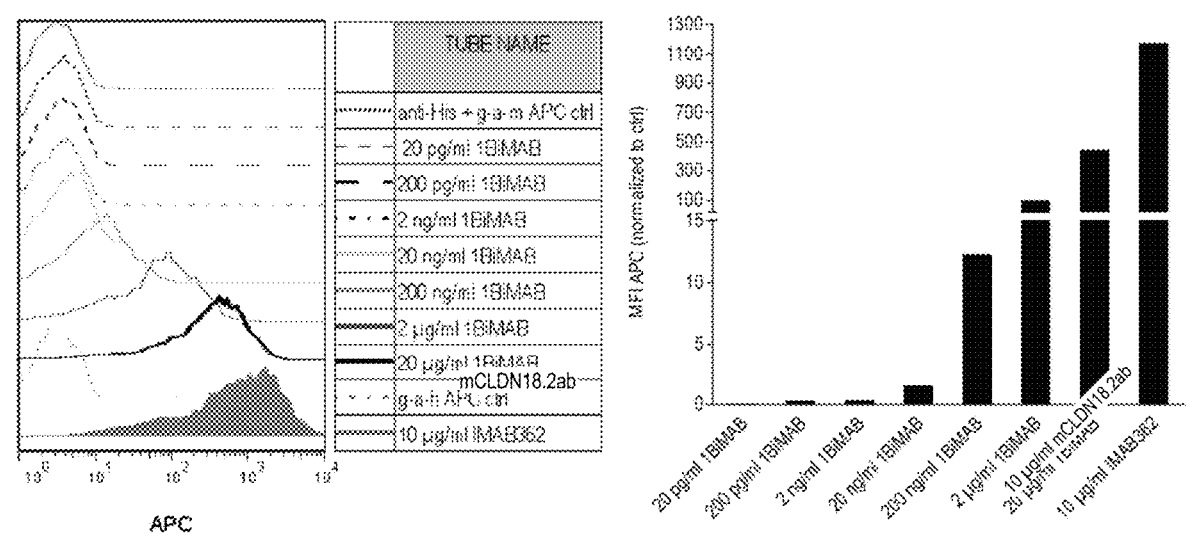
Figure 4C:
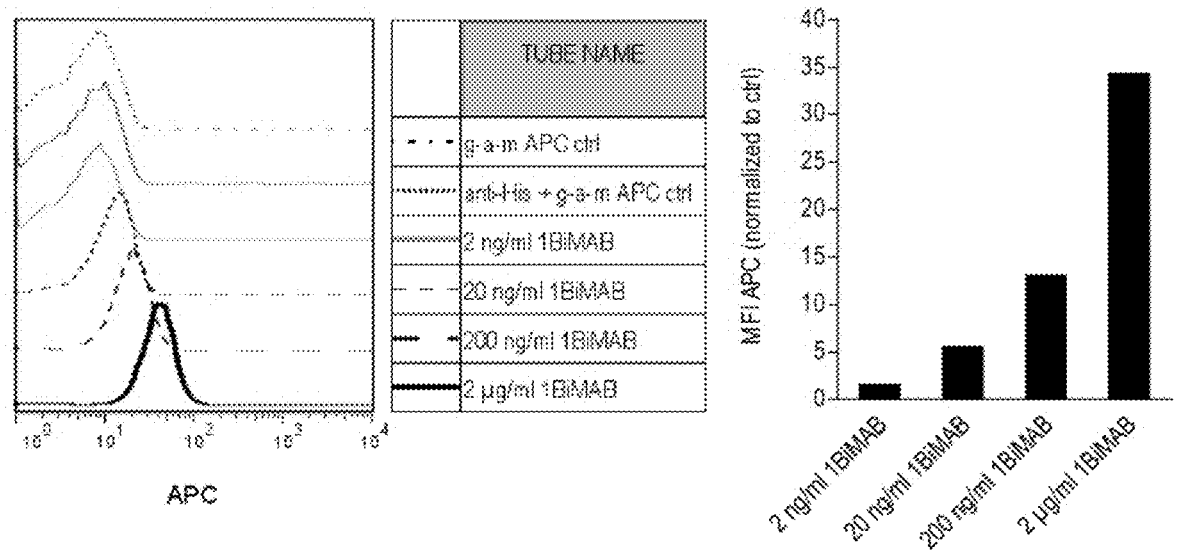
Figure 4D:
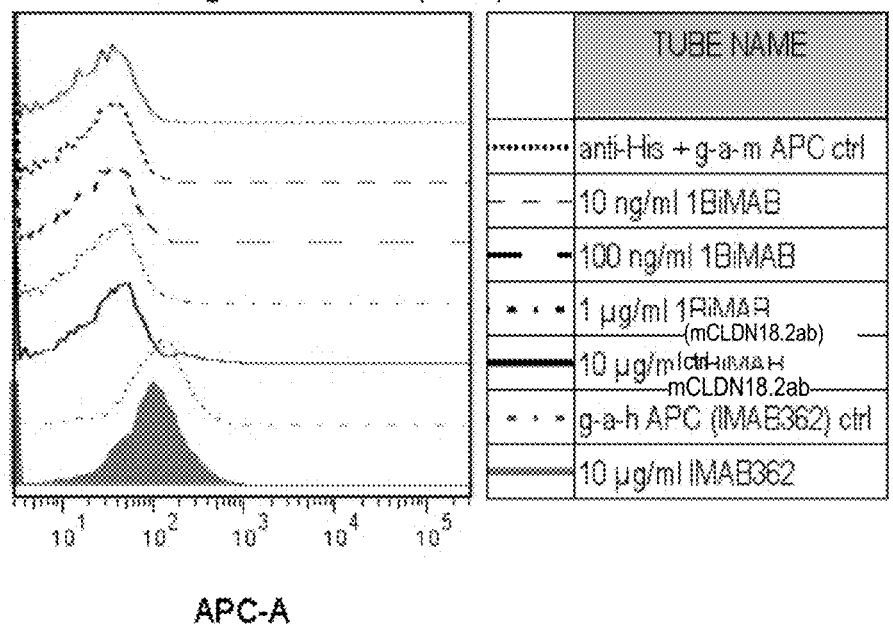

Samples were measured with a FACSCalibur flow cytometer (BD Biosciences, Heidelberg, Germany) and analyzed by FlowJo Software (Tree Star, San Carlos, Calif., USA). Strong signals were detected by sequential staining with 1BiMAB, Anti-HIS Epitope-Tag and goat-anti-mouse APC. Signal intensity was comparable to positive control mCLDN18.2ab with goat-anti-human APC. A low direct binding of goat-anti-mouse APC to 1BiMAB was observed in the sample stained with 1BiMAB and goat-anti-mouse APC without Anti-HIS Epitope-Tag (see FIG. 4A). For all further FACS-binding assays to investigate the binding capacity of bi-scFv proteins the sequential staining protocol with bi-scFv, Anti-HIS Epitope-Tag and goat-anti-mouse APC was used (see FIGS. 4B, C, and D). To rule out an unspecific binding of 1BiMAB, target cells that do not express CLDN18.2 as verified by RT-PCR (data not shown) were subjected to the FACS-based binding assay. No unspecific binding of 1BiMAB was detected as shown in FIG. 4D.

For investigation of the binding capacity of the anti-CD3 arm of bi-scFv protein 1BiMAB, human T cells were used. $1\times 10^6$ T cells prepared as described in Example 2.a were transferred to 5 ml round bottom tubes and incubated with FPLC-purified 1BiMAB protein within a range of 0.002-2 µg/ml in FACS-buffer for 30 min at 4° C. Further staining procedure was as described above. Control samples included secondary goat-anti-mouse APC antibody alone and monoclonal antibody Anti-HIS Epitope-Tag plus secondary goatanti-mouse APC antibody. Measurement and analysis were performed as described above. A significant signal was obtained with 2 µg/ml 1BiMAB (see FIG. 4C).

Example 5

Investigation of Highly Specific, Target Dependent T Cell Activation by Bi-scFv 1BiMAB Cancer cell lines that endogenously express high or low levels of CLDN18.2 and cancer cell lines that do not express CLDN18.2 were chosen to prove the strict target dependency of bi-scFv protein 1 BiMAB in an in vitro cytotox assay. The chosen cell lines were of the two predominant carcinoma types that express CLDN18.2: gastric (NugC4, MKN7, SNU-1) and pancreatic (DanG, KP-4) carcinoma. Breast carcinoma cell line MCF7 was used as negative control.

a. CLDN18.2 RT-PCR of Cancer Cell Lines

Total RNA was extracted from the carcinoma cell lines mentioned above by RNEasy Mini Kit procedure according to the manufacturer's protocol (Quiagen, Hilden, Germany). 5 µg of RNA were used for cDNA synthesis with SuperScript II Reverse Transcriptase (Life Technologies GmbH, Darmstadt, Germany).

RT-PCR analyses was run on an ABI Prism 7300 Real Time PCR System (Applied Biosystems/Life Technologies GmbH, Darmstadt, Germany) using Sybr Green dye and the following primers:

```
CLDN18.2:
for       TGGCTCTGTGTCGACACTGTG;

rev       GTGTACATGTTAGCTGTGGAC

HPRT:
for       TGACACTGGCAAAACAATGCA;

rev       GGTCCTTTTCACCAGCAAGCT
```

Delta Ct was calculated by subtraction of the Ct-value of the housekeeping gene HPRT from the Ct-value of CLDN18.2 (for results see FIG. 7A).

b. Exclusive T Cell Activation in the Presence of CLDN18.2

A cytotoxic assay was set up as described under Example 2.a. The carcinoma cell lines examined for CLDN18.2 transcripts under Example 5.a via quantitative RT-PCR were used as target cells. The concentration of bi-scFv protein 1BiMAB in this assay was set to 5 ng/ml. Target cells were seeded with human T cells and 1BiMAB in duplicates to analyze T cell activation. To monitor any potential alloreactivity of T cells against target cells independently of bi-scF protein 1BiMAB, target and T cells were seeded without 1BiMAB in duplicates. Cells were continuously sighted through a microscope to observe T cell clustering and target cell binding. In the case of the high CLDN18.2-expressing cell line NugC4, significant effects occurred after 24 h; after 48 h viable target cells were hardly visible. In the case of the low CLDN18.2-expressing cell line DanG, first effects were seen after 96 h and significant effects after 120 h. With the CLDN18.2 negative cell lines no effects indicating any T cell activation could be seen even after 144 h. T cells of all samples were analyzed after 144 h of coincubation with target cells via flow cytometry as described under Example 2.a for the early T cell activation marker CD69 and the late activation marker CD25, counterstained with CD3 for the T cell population and PI for dead cells. Intriguingly, up to 100% of the T cells coincubated with NugC4 and 1BiMAB were CD25 positive but CD69 negative indicating a long-term activation of T cells when CD69 downregulation already occurred. Roughly 75% of T cells coincubated with DanG and 1BiMAB were activated, of which about 40% simultaneously expressed CD25 and CD69 indicating a T cell activation that is still ongoing. T cells coincubated with the CLDN18.2 negative cell lines did not show any sign of T cell activation induction: neither CD69 nor CD25 expression was significantly elevated compared to the levels of samples without 1 BiMAB (see also FIG. 7B).

Example 6

Investigation of Bi-scFv Protein 1BiMAB Induced T Cell Function a. Induction of T Cell Proliferation T cell proliferation is an indicator of T cell activation. To show T cell proliferation in response to bi-scFv protein 1BiMAB in the presence of CLDN18.2 positive target cells, a flow cytometric assay was used. Briefly, $1 \times 10^6$ human T cells isolated as described under Example 2.a were stained in the dark at 37° C. for 10 min with 0.5 µM carboxyfluorescein diacetate succinimidyl ester (CellTrace CFSE, Invitrogen/Life Technologies GmbH, Germany) dissolved in DPBS. Staining was stopped by addition of 5 volumes of cold complete RPMI 1640 medium. Cells were kept on ice for 5 min and washed 3 times with complete RPMI medium (5% heat inactivated human AB serum, 0.5% penicillin-streptomycin, Ix NEAA and 1 mM sodium pyruvate) and were subsequently resuspended to $1 \times 10^5$ cells per ml. A cytotox assay as described under Example 2.b was set up with CLDN18.2 endogenously expressing NugC4 cells and human T cells as effector cells. 50 U IL-2 per ml medium were added to the cells. Samples included T cells alone, T cells with 1 ng/ml 1BiMAB, T cells and NugC4 cells, and T cells with 1 ng/ml 1BiMAB and NugC4 cells. After 120 h of coincubation, the T cells were harvested, collected in 5 ml round bottom tubes, washed and stained with a 1:1000 7-AAD DPBS solution to counterstain dead cells for 15 min at 4° C. After washing with DPBS, cells were resuspended in FACS-buffer and analyzed with a FACSCanto II (BD Biosciences, Heidelberg, Germany).

Proliferation of T cells was detected by decreasing CFSE-signal only in the presence of target cells and bi-scFv protein 1BiMAB (see also FIG. 8A).

b. Induction of Serine Protease Granzyme B

To demonstrate the upregulation of proteolytic molecules after T cell activation mediated by bi-scFv protein 1BiMAB in the presence of CLDN18.2 positive target cells, the detection of serine protease Granzyme B via flow cytometric analysis was elected. A cytotox assay as described under Example 2.b was set up with CLDN18.2 endogenously expressing NugC4 cells and human T cells as effector cells. Samples included T cells alone, T cells with 5 ng/ml 1BiMAB, T cells and NugC4 cells, and T cells with 5 ng/ml 1BiMAB and NugC4 cells. After 96 h of coincubation, the T cells were harvested, collected in 5 ml round bottom tubes, washed and stained with a 1:1000 7-AAD DPBS solution to counterstain dead cells for 15 min at 4° C. After washing with DPBS, cells were fixed with 100 µl Cytoperm/Cytofix solution for 20 min at RT. Cells were washed with 1× Perm/Wash and subsequently stained with PE-conjugated Mouse Anti-Human Granzyme B antibody for 20 min at RT. After washing, cells were resuspended in FACS-buffer and analyzed with a FACSCanto II (all reagents and FACS machine BD Biosciences, Heidelberg, Germany).

Granzyme B upregulation in T cells was detected only in the presence of target cells and bi-scFv protein 1BiMAB (see also FIG. 8B).

Example 7

Determination of EC50 of Bi-scFv Protein 1 BiMAB in an In Vitro Cytotox Assay

Luciferase Cytotox Assay

For the determination of the half maximal effective dose of bi-scFv protein 1BiMAB, a titration row of 1BiMAB was tested in an in vitro luciferase cytotox assay, mainly as described under Example 2.c.

Stably luciferase-expressing NugC4 cells described under Example 2.c were incubated with human T cells and bi-scFv protein 1BiMAB concentrations within the range of 1 pg/ml to 1 µg/ml (in steps of 10) or without 1BiMAB to determine the $L_{min}$ values. Luminescence of viable cells was measured with an Infinite M200 Tecan plate reader 24 h and 48 h after assay set up. Specific target cell lysis was calculated by the formula exemplified under Example 2.c.

Maximum lysis was reached after 48 h with 1-10 ng/ml 1BiMAB. The determined EC50 after 48 h in this assay is approximately 10 pg/ml (see also FIG. 9). Outcome of this assay strongly depends on the potency of the human T cells which varies according to the immune status of the donor as also reported by others (e.g. Lutterbuese, R et al., Proc. Natl. Acad. Sci. USA. 2010 Jul. 13; 107(28):12605-10). In addition to that, the used target cell line NugC4 shows varying expression of CLDN18.2 also influencing the outcome. Thus, an EC50 value variation of bi-scFv protein 1BiMAB in a range within 10-300 pg/ml has been observed during the course of this invention.

Example 8

Efficacy in a Mouse Xenograft Model

Figure 10A:
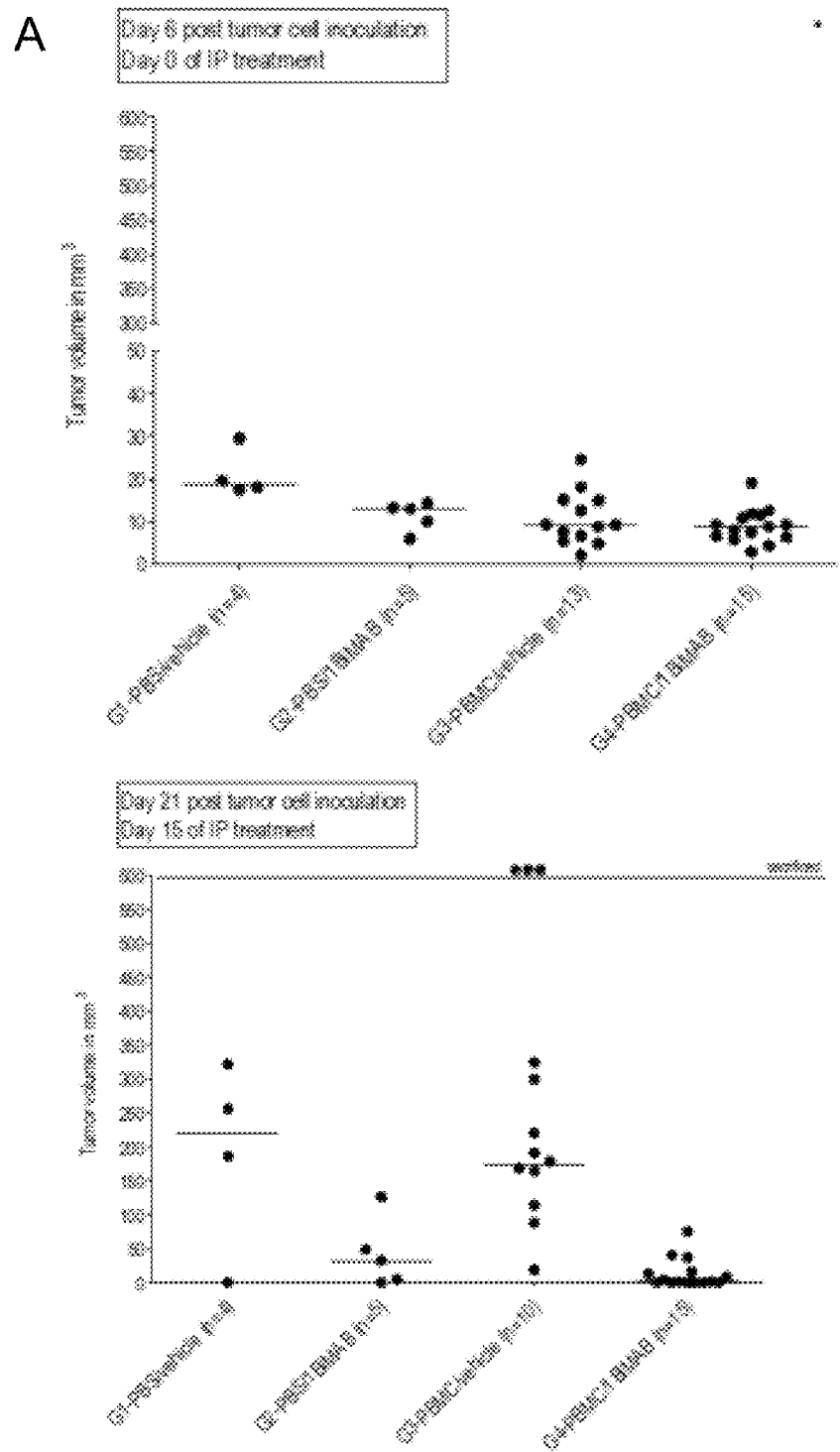
Figure 10A:
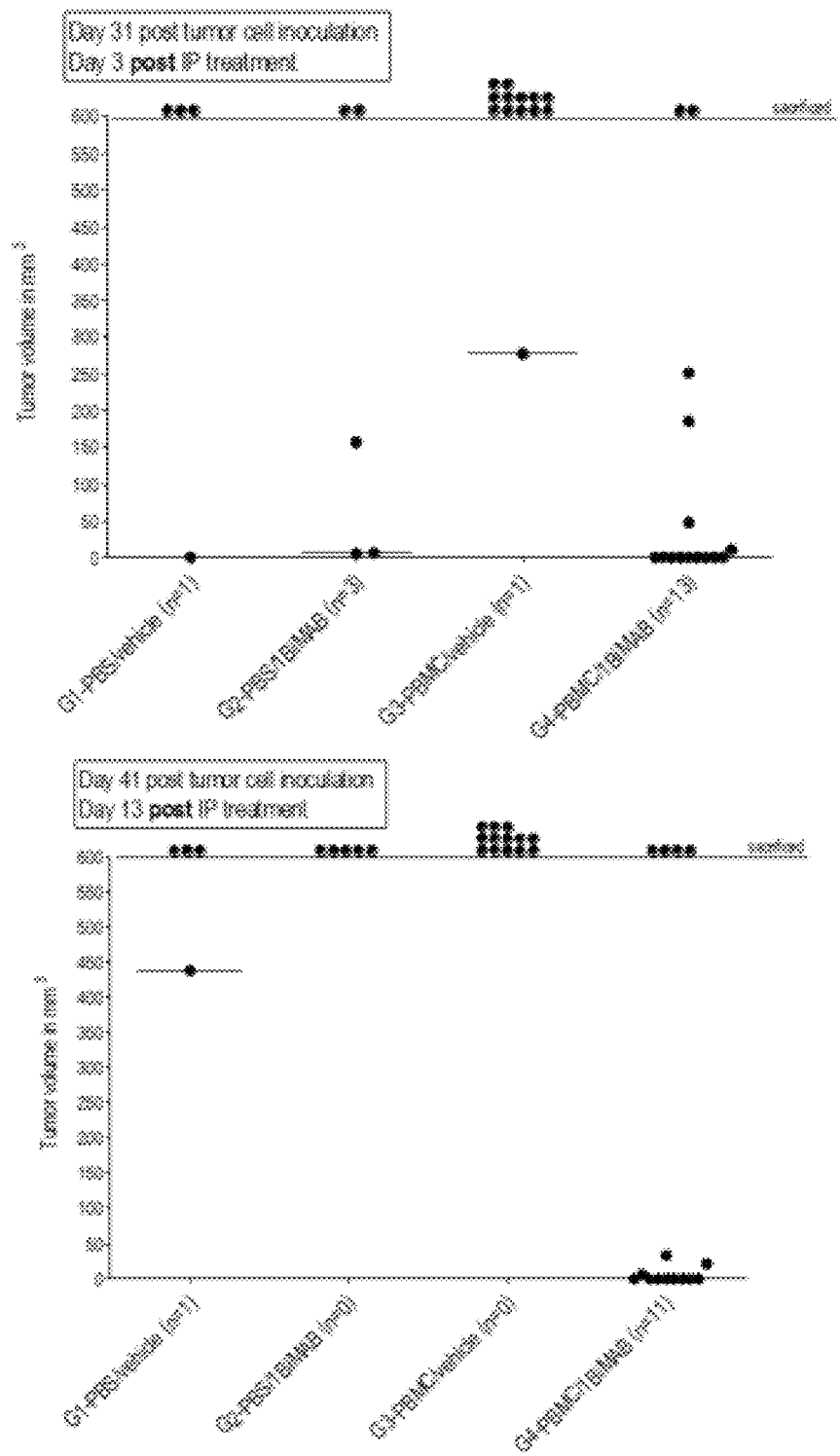
Figure 10B:
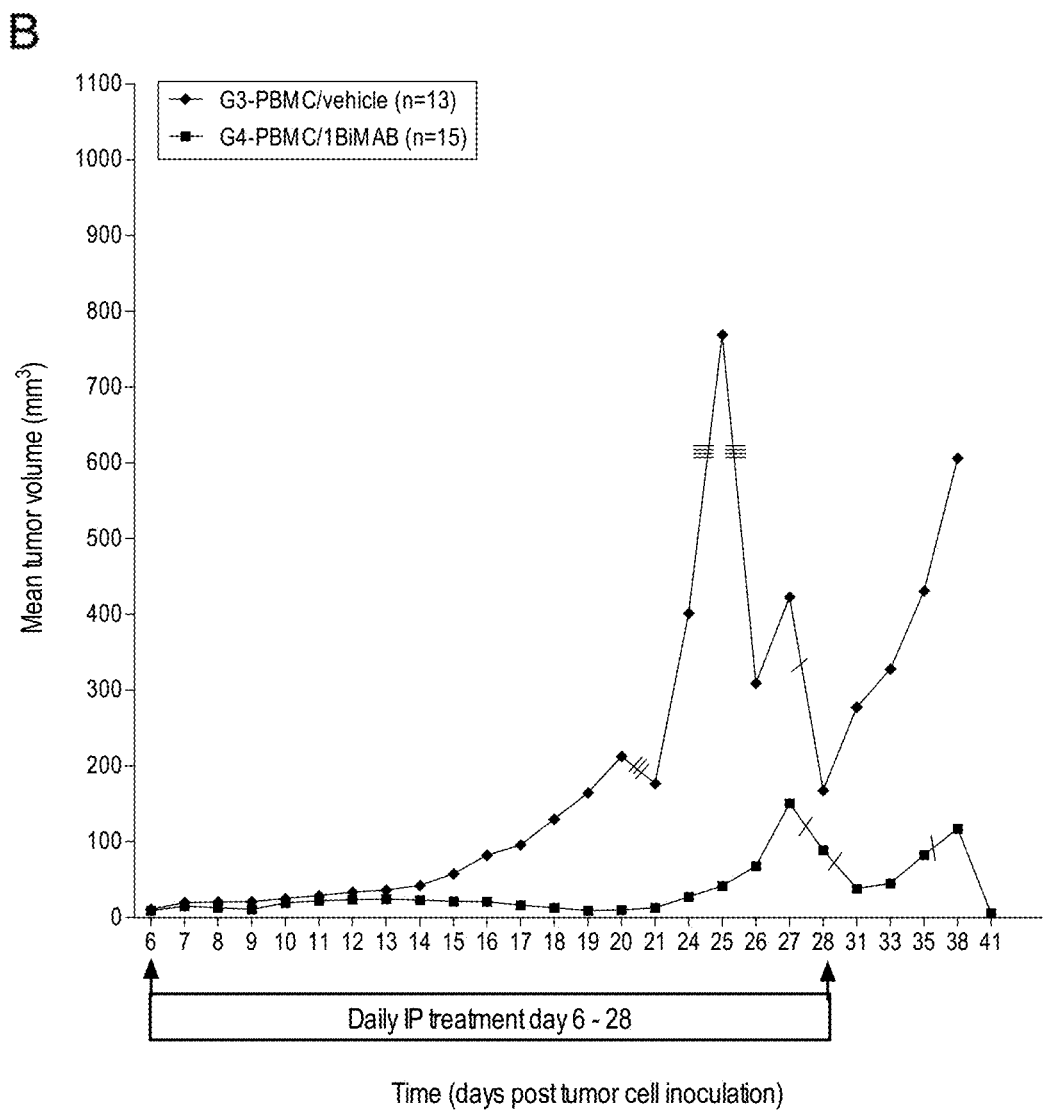
Figure 10C:
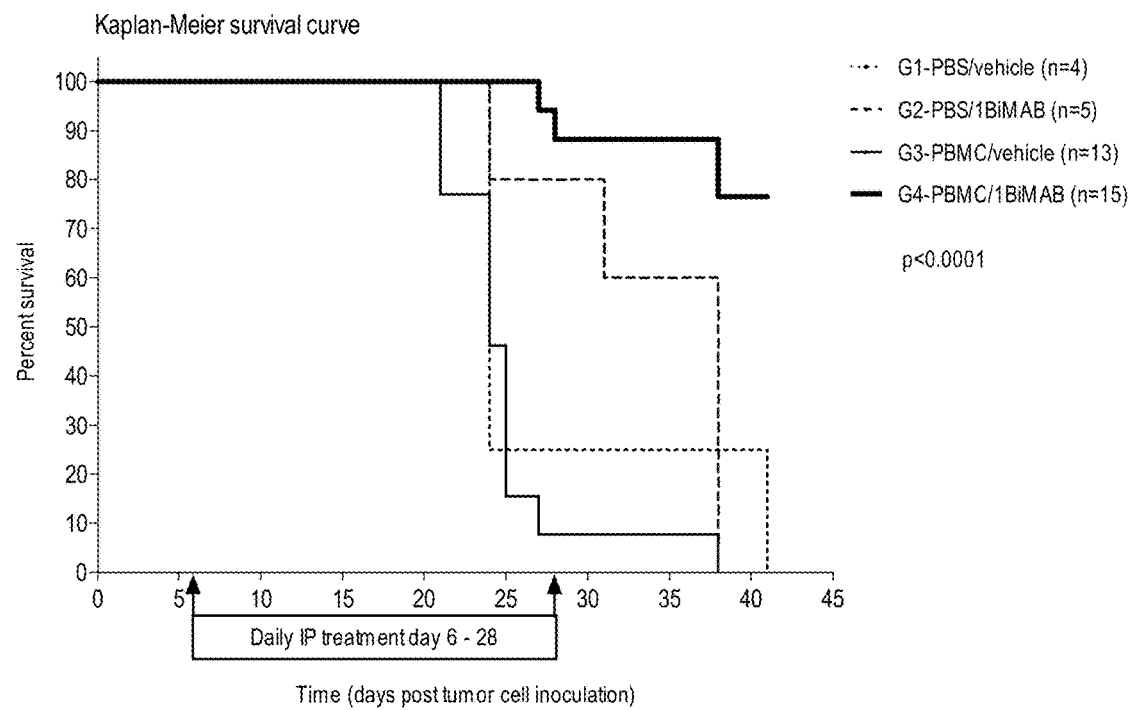

To investigate the therapeutic potential of bi-scFv protein 1BiMAB in vivo, the mouse strain NOD.Cg-Prkd$^{scid}$ IL2rg$^{tm1wj1}$/SzJ or short NSG (Jackson laboratory, Bar Harbour, Me., USA) was chosen. For the described study the engraftment of human effector cells and human T lymphocytes in mice is indispensable to study the effects of T cell engaging bi-scFv in vivo. Because of the complete lack of B-, T- and NK cells the mouse strain NSG is suitable for this kind of xenograft studies. A mouse model with mainly engrafted human T cells after PBMC injection was established as part of the invention.

a. Late Onset Treatment of Advanced Highly CLDN18.2 Expressing Tumors in Mice with Bi-scFv Protein 1BiMAB In the exemplified study, 40 female NSG mice at the age of 8 weeks were subcutaneously inoculated with $1 \times 10^7$ HEK293 cells stably expressing high levels of human CLDN18.2 (HEK293-CLDN18.2). 5 days after tumor cell inoculation mice were stratified according to their tumor volume into treatment groups, mice without tumor growth were excluded. At the same day peripheral blood mononuclear cells (PBMCs) were isolated from human blood of healthy donors by Ficoll density gradient technique as described under Example 2.a and used as effector cells in vivo. $2 \times 10^7$ PBMCs diluted in 300 µl DPBS were injected intraperitoneally at the day of isolation to the experimental treatment groups designated with "PBMC". With "PBS" designated treatment groups received 300 µl plain DPBS intraperitoneally instead and served as control without human effector cells. With the "PBS" control groups the investigation of a potential effect on tumor growth by 1BiMAB itself or any potential side effects which are caused by 1BiMAB or vehicle and not by human effector cells against mouse tissue (i.e. graft-versus-host reaction exerted by human effector cells against murine tissue) could be examined. Group "PBS/vehicle" comprised 4 mice (n=4), "PBS/1BiMAB" 5 mice (n=5), "PBMC/vehicle" 13 mice (n=13) and "PBMC/1BiMAB" 15 mice (n=15). The therapy was started 1 day after DPBS or PBMC application: groups "PBS/1BiMAB" and "PBMC/1BiMAB" received intraperitoneally 5 µg purified bi-scFv protein 1BiMAB diluted in 200 µl of DPBS per animal. Groups "PBS/vehicle" and "PBMC/vehicle" received intraperitoneally 200 µl of vehicle buffer (200 mM L-Arginin-monohydrochloride dissolved in H$_2$O, sterile filtered) diluted in DPBS. Treatment groups are summarized in Table 3. Therapy was conducted on a daily basis for 22 days. Twice per week tumor dimensions were measured with a digital calibrated caliper and the tumor volume calculated according to the formula mm$^3$=length×width×(width/2). FIGS. 10A and B exemplify the inhibition of tumor growth and the elimination of tumor burden in half of the mice of the "PBMC/1BiMAB" group only by the antibody in the presence of human effector cells. Mice were sacrificed by cervical dislocation when the tumor volume exceeded 500 mm$^3$ or in case of severe morbidity (graft-versus-host symptoms were observed in some mice).

TABLE 3

Treatment groups

| Treatment group (G) | # of mice (n) | Effector cells | Bi-scFv protein | µg bi-scFv protein/mouse |
|---|---|---|---|---|
| G1 | 4 | — | — | — |
| G2 | 5 | — | 1BiMAB | 5 |
| G3 | 13 | PBMC | — | — |
| G4 | 15 | PBMC | 1BiMAB | 5 | b. Determination of Therapy Influence on Body Weight

The body weight of each mouse was examined twice per week using a laboratory scale. No mouse in any group showed weight loss over the time of treatment (data not shown). Some mice in both "PBMC" groups showed symptoms of a graft-versus-host reaction 4 weeks after PBMC injection and several days after the end of treatment. Effects by 1BiMAB itself on body weight or any other side effects concerning the health of the mice were not observed.

c. Tissue Conservation and Splenocyte Isolation

After killing of mice, tumors were dissected and the tissue was immediately fixed in 10 ml Roti-Histofix 4% (Carl Roth, Karlsruhe, Germany) for immunohistochemical analysis. Moreover, spleens were dissected to detect the engraftment of human cells by flow cytometric analysis. Splenocyte isolation was performed immediately after spleen dissection by mashing the spleens through a 70 µm cell strainer placed into a 50 ml reaction tube with a sterile plunger of a 3-5 ml syringe and repeated flushing of the cell strainer with warm D)PBS. Isolated splenocytes were centrifuged, DPBS decanted and the splenocyte pellets resuspended in 1 ml heat inactivated fetal bovine serum supplemented with 10% DMSO. Samples were immediately frozen at −80° C. and stored until splenocyte samples from all mice were complete.

d. Analysis of Engraftment of Human T Lymphocytes in Mouse Spleens

Figure 10D:
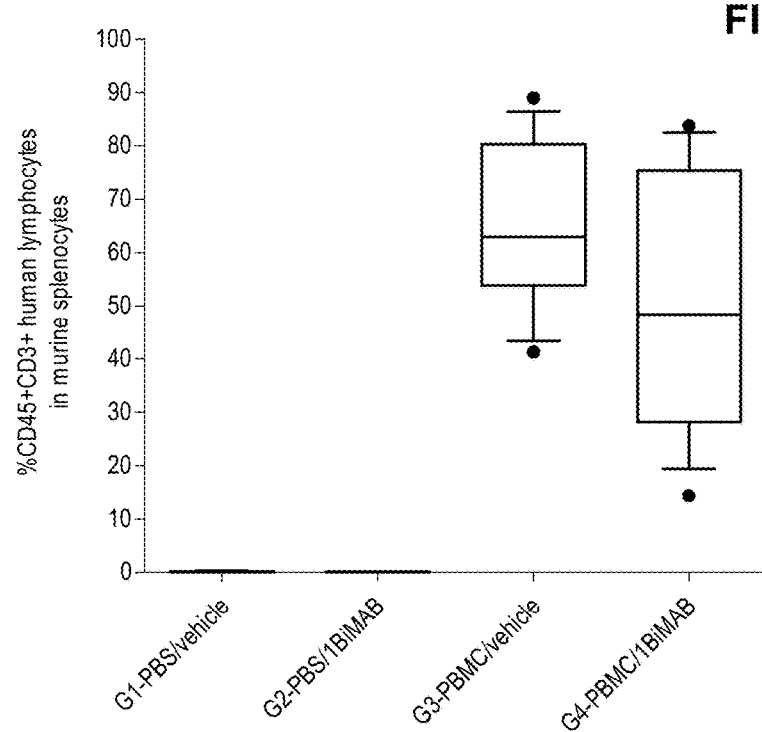

Splenocytes from all mice were collected and frozen as described under Example 8.c The complete collection of splenocyte samples was thawed at one time, all cells were washed twice with warm DPBS and $1 \times 10^6$ splenocytes per sample were incubated with fluorescence-conjugated antibodies for 20 min at 4° C. in the dark to detect the engraftment of human cells by anti-CD45 staining and the percentage of human T cells by anti-CD3, anti-CD4, and anti-CD8 staining. Flow cytometric analysis was conducted with a FACSCalibur (BD Biosciences, Heidelberg, Germany). Human T cell engraftment in both "PBMC" groups could be confirmed by high percentage of CD45-CD3 double positive splenocytes as shown in FIG. 10D.

Example 9

Generation and Testing of Bispecific Binding Agents Targeting CLDN6 and CD3 a. Sequence Origin, Design of Bi-scFv Constructs, and Cloning into Expression Vectors The bispecific tandem single chain antibody constructs (bi-scFv) contained binding domains specific for the human T cell receptor component CD3 and human tumor associated antigens (TAA). The corresponding variable heavy chain regions ($V_H$) and the corresponding variable light chain regions ($V_L$) are for each construct specifically arranged from N- to C-terminus in consecutive order:

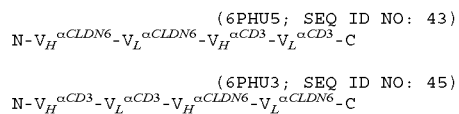

(6PHU5; SEQ ID NO: 43)

(6PHU3; SEQ ID NO: 45)

Table 4 summarizes all bi-scFv constructs specific for the TAA CLDN6 that were generated in the course of the invention. The CLDN18.2 specific bi-scFv construct 1BiMAB was used as control antibody. The bi-scFv constructs were generated by gene synthesis by GeneArt AG (GeneArt/Life Technologies GmbH, Regensburg, Germany) using the $V_H$ and $V_L$ sequences of the corresponding antibodies. Codon optimizations such as *Homo sapiens* (HS) or *Mus musculus* (MM) were implemented by GeneArt's GeneOptimizer® software, and are listed in Table 5. Information on specificity, sequence origin from monoclonal antibodies (mAB), codon usage, additional sequence features and references of all applied domains are summarized in Table 5. Variable domain sequence origin of the respective CD3 antibodies are listed in Table 5. Due to the high homology of human and mouse TAAs, the same anti-TAA $V_H$ and $V_L$ sequences could be used for the generation of bi-scFv constructs for mouse assays, but in combination with the $V_H$, $V_L$ sequences of the mouse specific anti-CD3 antibody clone 145-2C11.

DNA cloning and expression vector construction was carried out according to standard procedures (Sambrook, 1989) well known by the skilled person. Briefly, the bi-scFv DNA sequences were provided with a 5' HindIII and a 3' BamHI restriction for cloning into expression plasmids. A secretion signal sequence was introduced at the 5' end upstream of the bi-scFv sequence for protein secretion from cellular cytoplasm into the culture medium. A sequence coding for a 15 to 18 amino acid flexible glycine-serine peptide linker was inserted to join the $V_H$ and $V_L$ domains for the composition of the single chain variable antibody fragments (scFv) of which one binds to CD3 and the other to the TAA. To form a bispecific single chain antibody, the two scFv domain sequences were connected by a sequence coding for a short peptide linker (GGGGS). Together with this linker sequence a BamHI restriction site was introduced for scFv domain exchanges for the cloning of upcoming bi-scFV constructs. In-depth, 5'scFv-domains could be exchanged by HindIII and BamHI restriction and 3'scFv-domains by BamHI and XhoI restriction.

All used bi-scFv antibody constructs were cloned into the standard mammalian expression vector pcDNA™3.1/myc-His (+) (Invitrogen/Life Technologies GmbH, Darmstadt, Germany). The C-terminal 6×His-tag served for metal affinity purification of the protein and for detection analysis. All constructs were verified by sequencing via MWG's single read sequence service (Eurofins MWG Operon, Ebersberg, Germany). For construct schemata see also FIG. 11.

TABLE 4

Summary of TAA and CD3 specific bispecific single chain antibody constructs

| Internal name | TAA | Specificity | 5'-$V_H$-$V_L$ | 3'-$V_H$-$V_L$ | Codon usage |
|---|---|---|---|---|---|
| 1BiMAB | CLDN18.2 | human | mCLDN18.2ab | TR66 | HS |
| 6PHU5 | CLDN6 | human | mCLDN6ab | TR66 | HS |
| 6PHU3 | CLDN6 | human | TR66 | mCLDN6ab | HS |
| 6PMU5 | CLDN6 | murine | mCLDN6ab | 145-2C11 | MM |
| 6PMU3 | CLDN6 | murine | 145-2C11 | mCLDN6ab | MM |

HS, *Homo sapiens*;
MM, *Mus musculus*;
TAA, tumor associated antigen.

TABLE 5

Summary of bi-scFv construct information

| | CD3 binding moiety | | TAA binding moiety | | Species | | | |
|---|---|---|---|---|---|---|---|---|
| Internal name | mAB origin | Species reactivity | TAA | mAB origin | reactivity | 5'-$V_H$-$V_L$ | 3'-$V_H$-$V_L$ | Short linker |
| 1BiMAB | TR66 | human | CLDN18.2 | mCLDN18.2ab | human, murine | mCLDN18.2ab | TR66 | GGGGS |
| 6PHU5 | TR66 | human | CLDN6 | mCLDN6ab | human, murine | mCLDN6ab | TR66 | SGGGGS |
| 6PHU3 | TR66 | human | CLDN6 | mCLDN6ab | human, murine | TR66 | mCLDN6ab | SGGGGS |

TABLE 5-continued

Summary of bi-scFv construct information

| | | | | | | | | |
|---|---|---|---|---|---|---|---|---|
| 6PMU5 | 145-2C11 | murine | CLDN6 | mCLDN6ab | human, murine | mCLDN6ab | 145-2C11 | SGGGGS |
| 6PMU3 | 145-2C11 | murine | CLDN6 | mCLDN6ab | human, murine | 145-2C11 | mCLDN6ab | SGGGGS |

| Internal name | 5'-long linker | 3'-long linker | Secretion ssignal | Codon usage | Anti-CD3 mAB reference |
|---|---|---|---|---|---|
| 18iMAB | (GGGGS)₃ | VE(GGSGGS)₂GGVD | MGWSCIILFLVATATGVHS | HS | Lanzavecchia & Scheidegger, Eur J Immunol 1987 |
| 6PHU5 | (GGGGS)₃ | VE(GGSGGS)₂GGVD | MGWSCIILFLVATATGVHS | HS | Lanzavecchia & Scheidegger, Eur J Immunol 1987 |
| 6PHU3 | VE(GGSGGS)₂GGVD | (GGGGS)₃ | MGWSCIILFLVATATGVHS | HS | Lanzavecchia & Scheidegger, Eur J Immunol 1987 |
| 6PMU5 | (GGGGS)₃ | VE(GGSGGS)₂GGVD | MGWSCIILFLVATATGVHS | MM | Leo et al., Proc Natl Acad Sci, 1987 |
| 6PMU3 | VE(GGSGGS)₂GGVD | (GGGGS)₃ | MNSGLQLVFFVLTLKGIQG | MM | Leo et al., Proc Natl Acad Sci, 1987 |

HS, Homo sapiens; mAB, monoclonal antibody; MM, Mus musculus; TAA, tumor associated antigen.

b. Generation of Stable Producer Cell Lines

To generate stable producer cell clones of CLDN6 specific bi-scFv proteins the human embryonic kidney cell line HEK293 (ATCC CRL-1573) was used.

$1 \times 10^7$ HEK293 cells were plated two days prior to transfection on 14.5 cm tissue culture dishes in 20 ml complete DMEM medium (DMEM/F-12 GlutaMax supplemented with 10% heat inactivated FBS and 0.5% penicillin-streptomycin; all reagents from Gibco/Life Technologies GmbH, Darmstadt, Germany). Before transfection, cells were washed with DPBS supplemented with 2 mM EDTA, then 20 ml of plain DMEM medium without FBS or antibiotics were added. 20 µg of linearized DNA of the constructs pcDNA3.1/6PHU5 and pcDNA3.1/6PHU3 (described under Example 9.a) were diluted in 0.5 ml plain DMEM/F-12 medium. 75 µl of 1 mg/ml linear PEI solution (Polyethylenimine; Polysciences Europe GmbH, Eppelheim, Germany) were added to the diluted DNA and rigorously vortexed. After 15 min incubation at RT, the DNA/PEI complexes were added dropwise to the cells, cell culture dishes were gently rotated and then incubated at 37° C., 5% $CO_2$. 24 h after transfection the medium was changed. Selection of transfected cells was started 48 h after transfection with G418 sulfate (Gibco/Life Technologies GmbH, Darmstadt, Germany) in a final concentration of 0.8 mg/ml. G418 was added permanently to the culture medium for cell culturing.

c. Small-scale Production of Bi-scFv Proteins 6PHU5 and 6PHU3 with Polyclonal HEK293 Cells Bi-scFv proteins 6PHU5 and 6PHU3 were small-scale produced and purified from polyclonal HEK293 cell supernatants for in vitro comparison.

Briefly, at confluent state, supernatant without FBS was harvested from the polyclonal cell lines described under Example 9.b and filtered with 0.2 µm Minisart syringe filters (Sigma-Aldrich, Germany). Subsequently, bi-scFv proteins were small-scale purified from cell culture supernatants by Ni-NTA spin columns according to the manufacturer's protocol (Qiagen, Hilden, Germany). Bi-scFv protein concentrations were determined by measurement at 280 nm with a NanoDrop 2000c under consideration of the extinction coefficient and molecular weight determined via the ProtParam tool (http://web.expasy.org/protparam/)—of bi-scFv protein 6PHU5 and 6PHU3. Purified proteins were stored at 4° C. for immediate use.

Bi-scFv proteins were tested by polyacrylamid gel electrophoresis followed by coomassie staining and western blot analysis performed by standard procedures (Current Protocols in Protein Science, 2012). Small-scale purified proteins were separated on NuPAGE Novex 4-12% Bis-Tris Gels (Invitrogen/Life Technologies GmbH, Darmstadt, Germany). Subsequently, the gels were stained with Coomassie Brilliant Blue solution according to standard procedures (Current Protocols in Protein Science, 2012) to detect bi-scFv proteins 6PHU5, 6PHU3, and other proteins contained in the cell culture supernatant. Western blot analysis was performed to specifically detect bi-scFv proteins 6PHU5 and 6PHU3 via their 6×His-tag. Briefly, after blotting proteins on PVDF membrane and blocking with PBST/3% milk powder, the membrane was incubated for 1 h at 4° C. with primary antibody Anti-HIS Epitope-Tag (Dianova GmbH, Hamburg, Germany) diluted 1:500 in blocking buffer. After washing with blocking buffer, membranes were incubated with Fc-specific secondary peroxidase-conjugated goat-antimouse IgG antibody (Sigma Aldrich, Germany) diluted 1:10000 in blocking buffer for 1 h at 4° C. After washing with blocking buffer again, the signals were visualized by SuperSignal West Femto Chemiluminescent Substrate (Pierce/Thermo Fisher Scientific, Rockford, Ill., USA) and recorded by an ImageQuant LAS 4000 Imager (GE Healthcare Life Sciences, Munich, Germany). Signals of bi-scFv proteins were detected between 50 and 60 kD as compared to the internal molecular weight standard.

d. Large Scale Production of Bi-scFv Protein 6PHU3 with Polyclonal HEK293 Cells

The polyclonal producer cell line was cultured in a 10-layer Cell Factory (Nunc, Roskilde, Denmark) in DMEM/F-12 GlutaMax supplemented with 10% FBS, 0.5% penicillin-streptomycin and 0.8 mg/ml G418 (all reagents from Gibco/Life Technologies GmbH, Darmstadt, Germany) according to the manufacturer's guidelines. At confluent stage, cells were washed with DPBS and medium was changed to DMEM/F-12 medium with antibiotics but without FBS. Cell supernatant containing bi-scFv protein 6PHU3 was harvested every 3-5 days for up to 3 weeks. Supernatant was filtered with 500 ml Steritop Filter Units (Merck Millipore, Billerica, Mass., USA) and stored at 4° C. until FPLC-purification.

Before FPLC-purification, presence of bi-scFv in the cell culture supernatant was tested by polyacrylamid gel electrophoresis followed by coomassie staining and western blot analysis performed by standard procedures as briefly described under Example 9.c.

e. Purification and Quantification of Bi-scFv Protein 6PHU3

Cell culture supernatant of polyclonal HEK293 cells containing bi-scFv protein 6PHU3 (described under Example 9.b) was subjected to immobilized metal affinity chromatography (IMAC) using standard procedures (Current Protocols in Protein Science, 2012). Briefly, cell culture supernatant was loaded onto a His Trap FF 5 ml column connected to an ÄKTA Purifier 10 FPLC system (both GE Healthcare Life Sciences, Munich, Germany). PBS washing buffer contained 10 mM imidazol, PBS elution buffer contained 500 mM NaCl, 50 mM $NaH_2PO_4$ and 250 mM imidazol, pH of both buffers was adjusted to 7.4. Elution was performed by a stepwise gradient. Eluted bi-scFv protein 6PHU3 was immediately dialyzed against 1×PBS using a Slide-A-Lyzer G2 Dialysis Cassette 10K MWCO (Pierce/Thermo Fisher Scientific, Rockford, Ill., USA). After PBS dialysis, bi-scFv was dialyzed against a 200 mM arginine buffer (L-Arginin-monohydrochloride; Roth, Karlsruhe, Germany) based on $H_2O$.

Bi-scFv concentration was determined by measurement at 280 nm with a NanoDrop 2000c under consideration of the extinction coefficient and molecular weight of bi-scFv protein 6PHU3. Purified protein was aliquoted and stored at −80° C. for long time storage or kept at 4° C. for immediate use.

Quality and purity of bi-scFv protein 6PHU3 was tested by Coomassie staining and western blot analysis as described under Example 9.c. A BSA standard dilution was included in the Coomassie procedure to roughly confirm the concentration measured by NanoDrop (data not shown).

Example 10

Efficiency of CLDN6-targeting Bi-scFv Candidates 6PHU5 and 6PHU3 a. Microscopic Analysis of T Cells Redirected to Target Cells by Bi-scFv Proteins 6PHU5 and 6PHU3

To visualize the redirection of effector cells to CLDN6-expressing target cells by bi-scFv proteins via microscopic analysis, an in vitro cytotox assay was performed. NiNTA column-purified bi-scFv proteins 6PHU3 and 6PHU5 (see Example 9.c) were used to compare these two variants according to their efficiency. As target cell line the ovarian teratocarcinoma cell line PA-1 that endogenously expresses high levels of human CLDN6 was used.

Human effector cells were freshly isolated from human blood from healthy donors according to standard procedures (Current Protocols in Protein Science, 2012): briefly, blood was diluted with DPBS, layered on Ficoll-Paque Plus (GE Healthcare Life Sciences, Munich, Germany) and centrifuged. Peripheral blood mononuclear cells (PBMCs) were collected from the interphase, washed with cold DPBS supplemented with 2 mM EDTA and counted. Human T cells were subsequently separated by magnetic-activated cell separation (MACS) from PBMCs by Pan T Cell Isolation Kit II (Miltenyi Biotec, Teterow, Germany) according to the manufacturer's guidelines.

$1×10^5$ PA-1 cells per well were seeded into tissue culture 6-well plates. Human cells were prepared as described above and added in an effector to target (E:T) ratio of 5:1. MEM medium supplemented with 10% heat inactivated FBS, 0.5% penicillin-streptomycin, 1×NEAA, 1 mM sodium bicarbonate and 1 mM sodium pyruvate (Gibco/Life Technologies GmbH, Darmstadt, Germany) was used for all cells and the final volume per well was adjusted to 2 ml per well. The used bi-scFv protein concentration was 50 ng/ml in this assay. Control samples comprised target or T cells alone without bi-scFv protein. Tissue culture plates were subsequently incubated at 37° C., 5% $CO_2$. The assay was continuously observed with a Wilovert S inverted microscope (Hund, Wetzlar, Germany) from 6h to 24 h of coincubation. Significant effects in terms of T cell clustering on target cells, formation of an immunologic synapse and target cell killing in the presence of bi-scFv protein 6PHU5 and 6PHU3 were seen at 24 h and photographed with a Nikon Eclipse TS100 inverted microscope (Nikon, Japan). Both bi-scFv proteins lead to strong T cell clustering and target cell killing as shown in FIG. 12.

b. T Cell Activation Mediated by Bi-scFv Proteins 6PHU5 and 6PHU3

For the detection of T cell activation and to define differences in the efficiency of the two CLDN6-specific bi-scFv variants, a FACS-based T cell activation assay was used. The early activation marker CD69 and the late activation marker CD25 were selected for staining by fluorescence-conjugated antibodies. For the detection of human T cells in the mixture of target and T cells, CD3 on T cells was stained.

In general, the assay set-up from above was chosen (Example 10.a). Briefly, PA-1 target cells endogenously expressing CLDN6 were seeded with human T cells in an E:T ratio of 5:1 in 2 ml complete medium and bi-scFv proteins 6PHU5 or 6PHU3 were added in a concentration within the range of 5-200 ng/ml. Control samples comprised target or T cells alone with and without bi-scFv proteins. After 24 h and 48 h the T cells were harvested by flushing and transferred to 5 ml round bottom tubes (BD Falcon, Heidelberg, Germany). Cells were centrifuged and washed with DPBS. For cell staining Mouse Anti-Human CD3-FITC, Mouse Anti-Human CD69-APC, and Mouse Anti-Human CD25-PE (all antibodies BD) Biosciences, Heidelberg, Germany) were used. Cell pellets were resuspended in 50 µl FACS-buffer (DPBS supplemented with 5% FBS) containing the fluorescence-conjugated antibodies and 2 µl 7-AAD (BD Biosciences, Heidelberg, Germany). After incubation for 20 min at 4° C. in the dark, samples were washed with 4 ml DPBS and cell pellets were resuspended in 200 µl FACS buffer. Samples were kept on ice and dark throughout the measurement with a FACSCanto II flow cytometer (both BD Biosciences, Heidelberg, Germany). Analysis was evaluated by FlowJo software (Tree Star, San Carlos, Calif., USA).

Both CDLN6-specific bi-scFv variants resulted in efficient T cell activation of up to 60%. Variant 6PHU3 (bi-scFv CD3×CLDN6) was more potent in the low concentration range of 5-10 ng/ml (see also FIG. 13) and was therefore chosen for further studies.

Example 11

Binding Capacity of Bi-scFv 6PHU3

FACS Binding Assay

To assess the binding capacity of the CLDN6- and the CD3-targeting moieties of bi-scFv protein 6PHU3 a flow cytometric assay was used. CLDN6 endogenously expressing PA-1 and OV-90 cells were used to investigate the anti-CLDN6 site and human T cells were used to investigate the anti-CD3 site. CLDN6-negative NugC4 cells were used as control cells.

For the investigation of the anti-CLDN6 binding capacity, CLDN6 positive cells (PA-1, OV-90) and CLDN6 negative cells (NugC4) were trypsinized, washed with complete medium and subsequently with DPBS. All washing steps were conducted by centrifugation at 1200 rpm for 6 min at 4° C. $1 \times 10^5$ cells were transferred to 5 ml round bottom tubes and incubated with 0.01-10 µg/ml µg/ml FPLC-purified 6PHU3 protein or control bi-scFv protein 1BiMAB in FACS-buffer for 30 min at 4° C. Cells were washed with 2 ml FACS-buffer and subsequently incubated with 3.3 µg/ml of monoclonal antibody Anti-HIS Epitope-Tag (Dianova GmbH, Hamburg, Germany) for 30 min at 4° C. After washing with 2 ml FACS-buffer, the cell pellets were incubated with APC-conjugated goat-anti-mouse secondary antibody (Jackson ImmunoResearch Europe, Suffolk, England) in a 1:200 dilution in FACS-buffer for 20 min at 4° C. in the dark. Cells were washed twice with 2 ml FACS-buffer and finally resuspended in 150 µl FACS-buffer supplemented with 1 µg/ml PI (Sigma Aldrich, Germany) to counterstain dead cells. Negative control samples included secondary goat-anti-mouse APC antibody alone. As positive control 10 µg/ml monoclonal CLDN6-specific antibody mCLDN6ab stained with secondary goat-anti-human APC antibody (Jackson ImmunoResearch Europe, Suffolk, England) and the proper secondary antibody only control were implemented.

Samples were measured with a FACSCalibur flow cytometer (RD Biosciences, Heidelberg. Germany) and analyzed by FlowJo Software (Tree Star, San Carlos, Calif., USA). Signal intensity of 10 µg/ml 6PHU3 was 4-9 times lower than the positive control mCLDN6ab (see FIG. 15A). Unspecific binding of 6PHU3 to CLDN6-negative cell line NugC4 was not detected (FIG. 15C).

For investigation of the binding capacity of the anti-CD3 arm of bi-scFv protein 6PHU3, human T cells were used. $5 \times 10^5$ T cells were transferred to 5 ml round bottom tubes and incubated with FPLC-purified 6PHU3 protein within a range of 100 ng/ml-10 µg/ml in FACS-buffer for 30 min at 4° C. Further staining procedure was as described above. Control samples included secondary goat-anti-mouse APC antibody alone and monoclonal antibody Anti-HIS Epitope-Tag plus secondary goat-anti-mouse PE antibody. Measurement and analysis were performed as described above. A significant signal was obtained with 100 ng/ml 6PHU3 (see also FIG. 15B).

Example 12

Investigation of Target Dependent T Cell Activation by Bi-scFv 6PHU3

A cytotox assay as described under Example 10.a and b was performed. Briefly, PA-1 target cells endogenously expressing CLDN6 were seeded with human T cells in an E:T ratio of 5:1 in 2 ml complete medium and bi-scFv protein 6PHU3 was added in a concentration within the range of 0.001-1000 ng/ml. To analyze the target dependency for bi-scFv mediated T cell activation, T cells were seeded without target cells but were incubated with the same bi-scFv 6PHU3 concentrations as the target plus T cell samples. After 24 h and 48 h the T cells were harvested by flushing and transferred to 5 ml round bottom tubes (RD Falcon, Heidelberg, Germany). Cell staining and analysis was conducted as described under Example 10.b.

As shown in FIGS. 16A and B, no 6PHU3 mediated T cell activation is detectable in the absence of target cells underlining the strict target dependency of bi-scFv functionality. A significant T cell activation occurred with only 0.1 ng/ml 6PHU3 after 48 h.

Example 13

Determination of EC50 of Bi-scFv 6PHU3 in an In Vitro Cytotox Assay

Luciferase Cytotox Assay

For the determination of the half maximal effective dose of bi-scFv protein 6PHU3, a titration row of 6PHU3 was tested in an in vitro luciferase cytotox assay.

Stably luciferase-expressing PA-1 cells and human T cells in an E:T ratio of 5:1 were incubated with bi-scFv protein 6PHU3 concentrations within the range of 1 pg/ml to 1 µg/ml (in steps of 10) or without 6PHU3 to determine the $L_{min}$ values.

Cell culture microplates were incubated for 24 h and 48 h at 37° C., 5% $CO_2$. For analysis, 50 µl of a water solution containing 1 mg/ml luciferin (BD Monolight, BD Biosciences, Heidelberg, Germany) and 50 mM HEPES were added per well and plates were subsequently incubated for 30 min in the dark at 37° C. Luminescence arising from oxidation of luciferin by luciferase expressing viable cells was measured with an Inifinite M200 Tecan microplate-reader (Tecan, Männedorf, Switzerland). Percentage of specific target cell lysis was calculated by the following formula: % specific lysis=[1−(luminescence$_{test\ sample}$−$L_{max}$)/($L_{min}$−$L_{max}$)]×100, whereas "L" indicates lysis. $L_{min}$ refers to the minimum lysis in the absence of bi-scFv and $L_{max}$ to the maximum lysis (equal to spontaneous luminescence counts) in the absence of bi-scFv achieved by addition of Triton X-100 (2% final concentration).

Maximum lysis was reached after 48 h with 1-10 ng/ml 6PHU3, the determined EC50 after 48 h is approximately 10 pg/ml (see also FIG. 17). Outcome of this assay strongly depends on the potency of the human T cells which varies according to the immune status of the donor as also reported by others (see e.g. Lutterbucse, R et al., 2010, Proc. Natl. Acad. Sci USA. 2010 Jul. 13; 107(28):12605-10). Thus, an EC50 value variation of bi-scFv protein 6PHU3 by the factor of 3 has been observed during the course of this invention.

Example 14

Efficacy in a Mouse Xenograft Model

To investigate the therapeutic potential of bi-scFv protein 6PHU3 in vivo, the mouse strain NOD.Cg-Prkd$^{scid}$ IL2rg$^{tm1Wjl}$/S$_z$J or short NSG (Jackson laboratory, Bar Harbour, Me., USA) was chosen. For the described study the engraftment of human effector cells and human T lymphocytes in mice is indispensable to study the effects of T cell engaging bi-scFv in vivo. Because of the complete lack of B-, T- and NK cells the mouse strain NSG is suitable for this kind of xenograft studies. A mouse model with mainly engrafted human T cells after PBMC injection was established as part of the invention.

a. Late Onset Treatment of Advanced Highly CLDN6 Expressing Tumors in Mice with Bi-scFv Protein 6PHU3

Figure 18A:
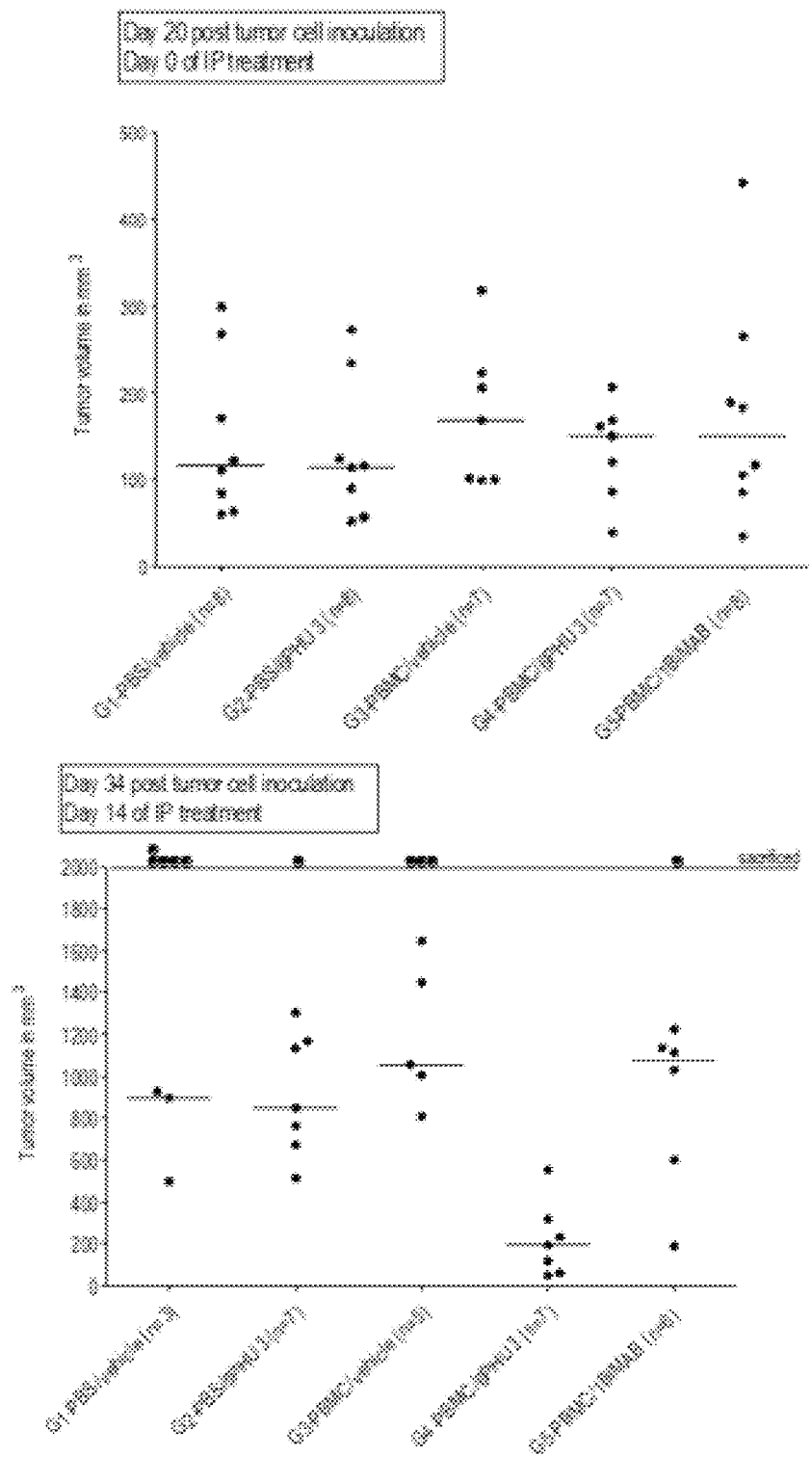
Figure 18A:
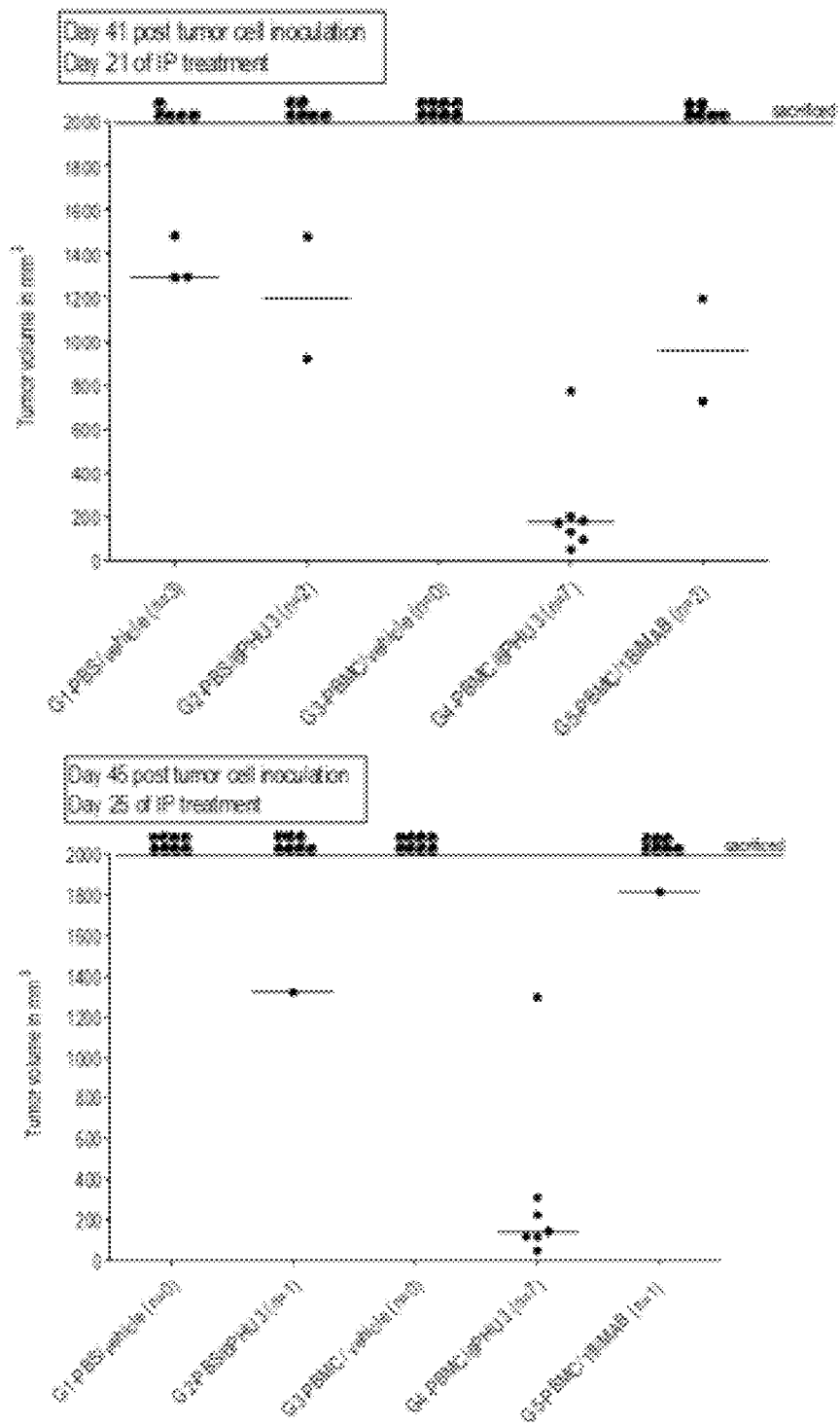
Figure 18B:
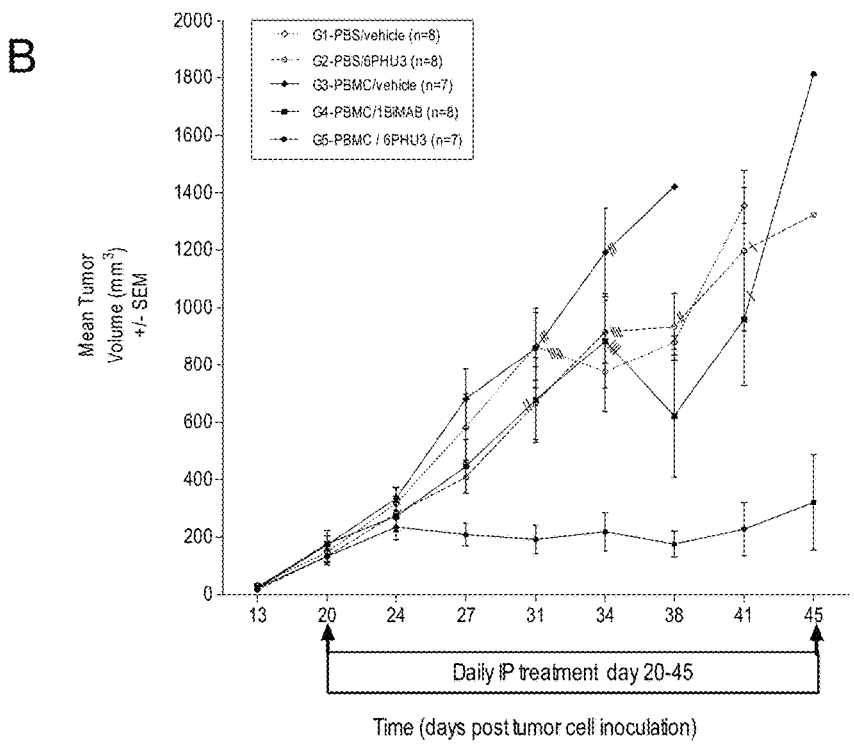
Figure 18C:
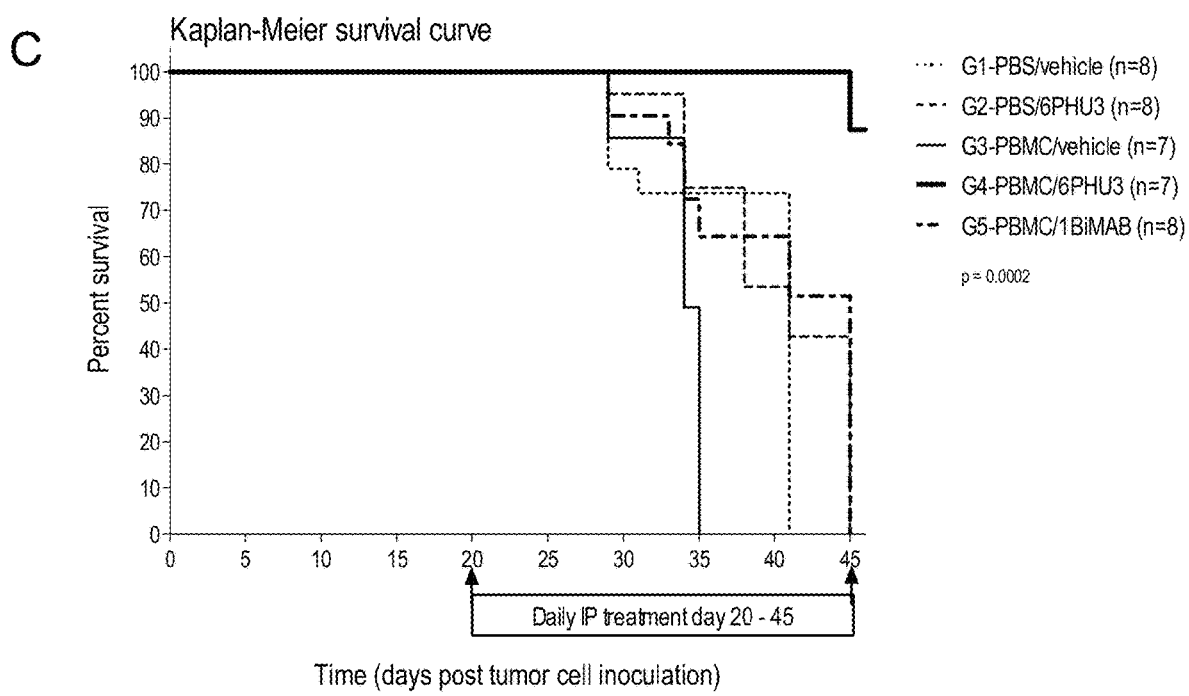

In the exemplified study, 25 female and 25 male NSG mice at the age of 8-11 weeks were subcutaneously inoculated with $1\times10^7$ PA-1 cells endogenously expressing high levels of human CLDN6. 15 days after tumor cell inoculation mice were stratified according to their tumor volume into treatment groups, mice without tumor growth were excluded. At the same day peripheral blood mononuclear cells (PBMCs) were isolated from human blood of healthy donors by Ficoll density gradient technique and used as effector cells in vivo. $2\times10^7$ PBMCs diluted in 200 µl DPBS were injected intraperitoneally at the day of isolation to the experimental treatment groups designated with "PBMC". With "PBS" designated treatment groups received 200 µl plain DPBS intraperitoneally instead and served as control without human effector cells. With the "PBS" control groups the investigation of a potential effect on tumor growth by 6PHU3 itself or any potential side effects which are caused by 6PHU3 or vehicle and not by human effector cells against mouse tissue (i.e. graft-versus-host reaction exerted by human effector cells against murine tissue) could be examined. Group "PBS/vehicle" comprised 8 mice (n=8), "PBS/6PHU3" 8 mice (n=8), "PBMC/vehicle" 7 mice (n=7), "PBMC/6PHU3" 7 mice (n=7) and "PBMC/1BiMAB" 8 mice (n=8). The therapy was started 7 days after DPBS or PBMC application: groups "PBS/6PHU3", "PBMC/6PHU3" and "PBMC/1 BiMAB" received intraperitoneally 5 µg purified bi-scFv protein 6PHU3 or 1BiMAB diluted in 200 µl of DPBS per animal. Groups "PBS/vehicle" and "PBMC/vehicle" received intraperitoneally 200 µl of vehicle buffer (200 mM L-Arginin-monohydrochloride dissolved in $H_2O$, sterile filtered) diluted in DPBS. Treatment groups are summarized in Table 6. Therapy was conducted on a daily basis for 26 days. Twice per week tumor dimensions were measured with a digital calibrated caliper and the tumor volume calculated according to the formula $mm^3$=length×width×width/2. FIGS. 18A and B exemplify the inhibition of tumor growth in all mice of the "PBMC/6PHU3" group by the antibody in the presence of human effector cells. Mice were sacrificed by cervical dislocation when the tumor volume reached 1500 $mm^3$ or in case of severe morbidity (graft-versus-host symptoms were observed in some mice).

TABLE 6

| Treatment group (G) | # of mice (n) | Effector cells | Bi-scFv protein | µg bi-scFv protein/mouse |
|---|---|---|---|---|
| G1 | 8 | — | — | — |
| G2 | 8 | — | 6PHU3 | 5 |
| G3 | 7 | PBMC | — | — |
| G4 | 7 | PBMC | 6PHU3 | 5 |
| G5 | 8 | PBMC | 1BiMAB | 5 | b. Determination of Therapy Influence on Body Weight

The body weight of each mouse was examined twice per week using a laboratory scale. No mouse in any group showed weight loss over the time of treatment (data not shown).

c. Tissue Conservation and Splenocyte Isolation

After killing of mice, tumors were dissected and the tissue was immediately fixed in 10 ml Roti-Histofix 4% (Carl Roth, Karlsruhe, Germany) for immunohistochemical analysis. Moreover, spleens were dissected to detect the engraftment of human cells by flow cytometric analysis. Splenocyte isolation was performed immediately after spleen dissection by mashing the spleens through a 70 µm cell strainer placed into a 50 ml reaction tube with a sterile plunger of a 3-5 ml syringe and repeated flushing of the cell strainer with warm DPBS. Isolated splenocytes were centrifuged, DPBS decanted and the splenocyte pellets resuspended in 1 ml heat inactivated fetal bovine serum supplemented with 10% DMSO. Samples were immediately frozen at −80° C. and stored until splenocyte samples from all mice were complete.

d. Analysis of Engraftment of Human T Lymphocytes in Mouse Spleens

Figure 18D:
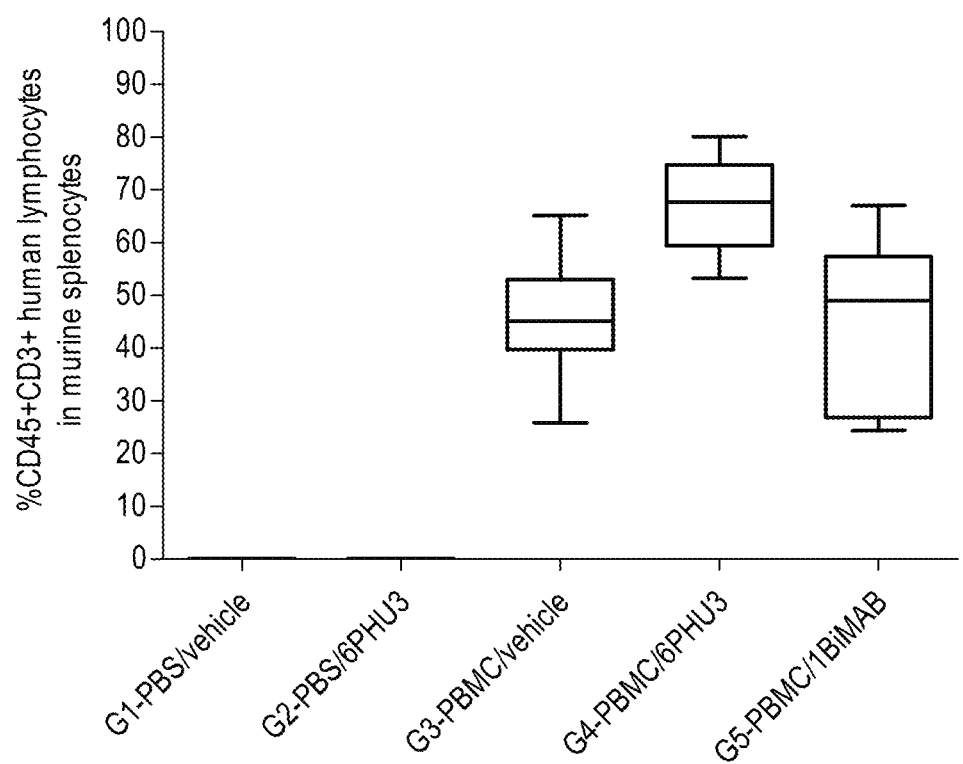
Figure 19A:
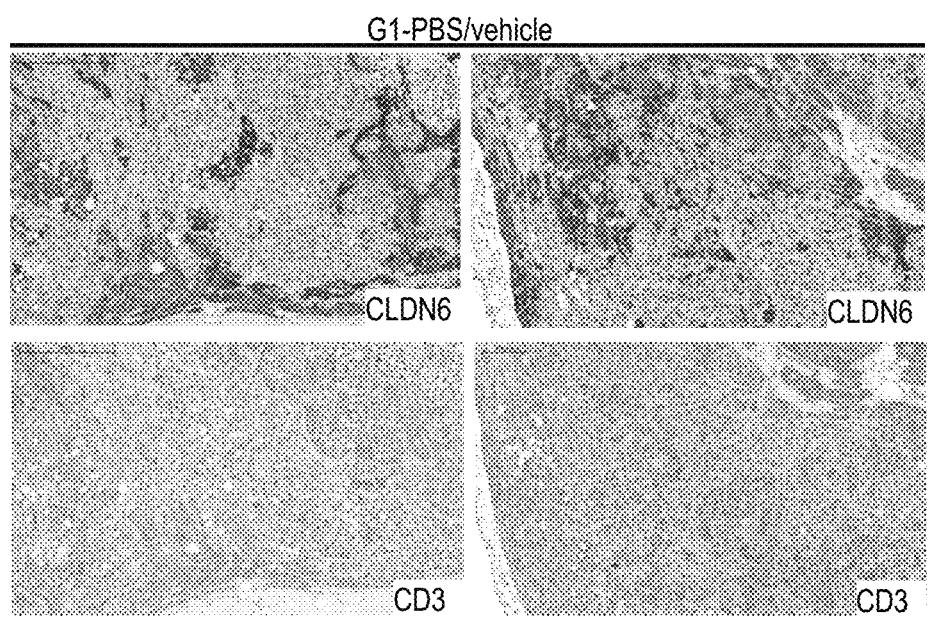
Figure 19B:
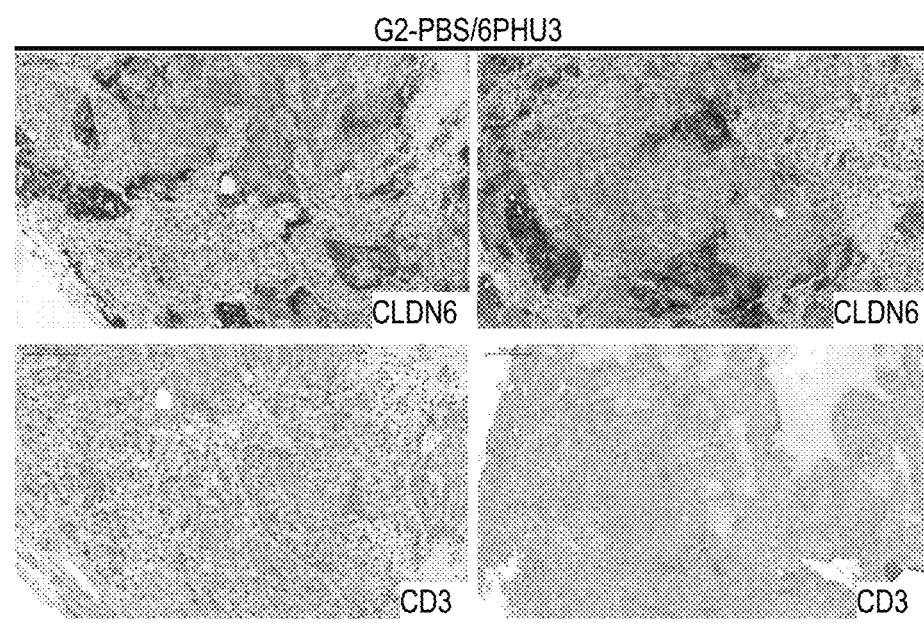
Figure 19C:
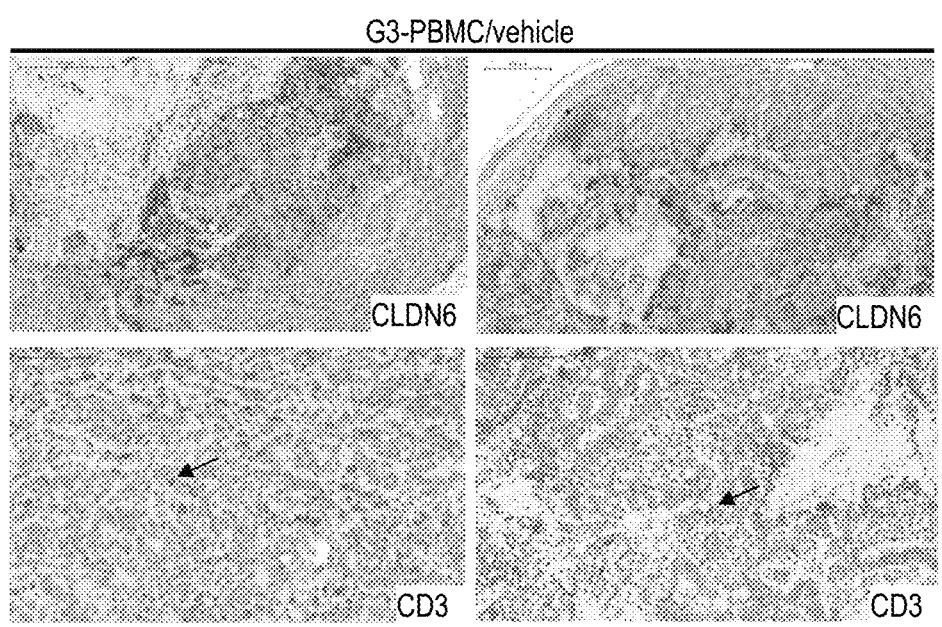
Figure 19D:
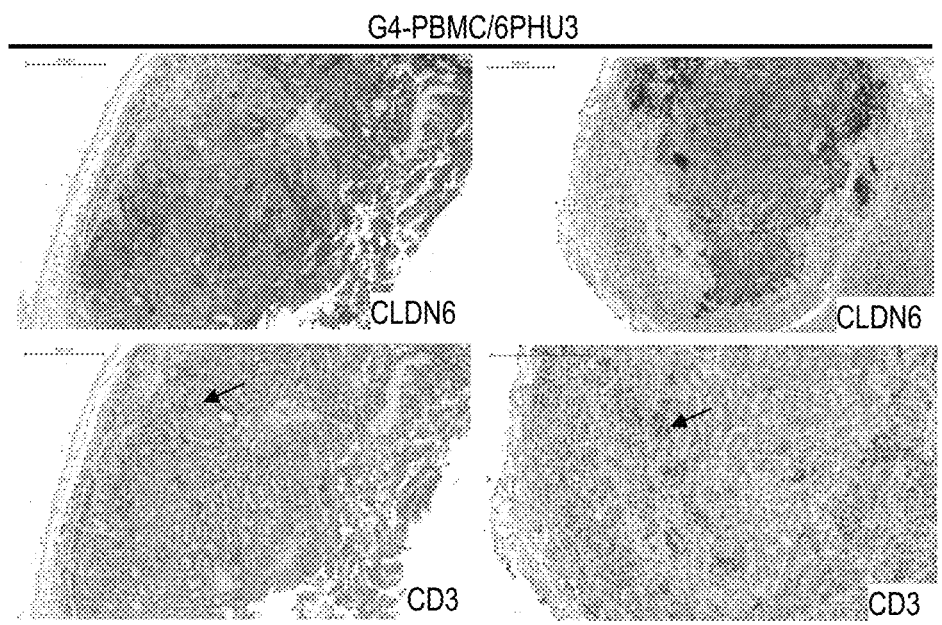
Figure 19E:
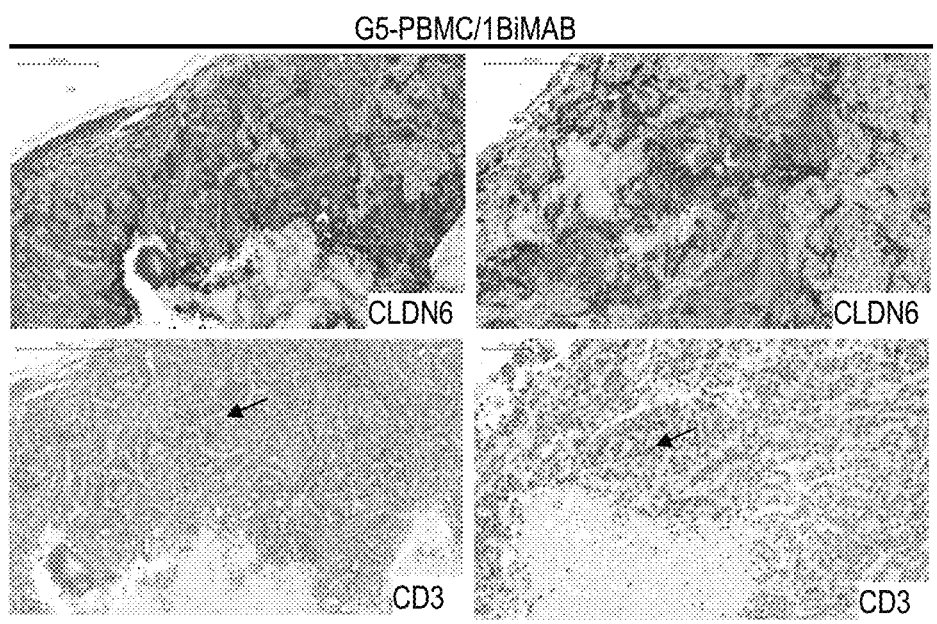

Splenocytes from all mice were collected and frozen as described under Example 14.c. The complete collection of splenocyte samples was thawed at one time, all cells were washed twice with warm DPBS and $1\times10^6$ splenocytes per sample were incubated with fluorescence-conjugated antibodies for 20 min at 4° C. in the dark to detect the engraftment of human cells by anti-CD45 staining and the percentage of human T cells by anti-CD3, anti-CD4, and anti-CD8 staining. Flow cytometric analysis was conducted with a FACSCalibur (BD Biosciences, Heidelberg, Germany). Human T cell engraftment in both "PBMC" groups could be confirmed by high percentage of CD45-CD3 double positive splenocytes as shown in FIG. 18D.

e. Immunohistochemistry for the Determination of Target Expression and T Cell Infiltration Tumors were fixed after dissection using 4% buffered formaldehyde-solution (Roti-Histofix, Carl Roth, Karlsruhe, Germany) for 48 h at 4° C. The fixed tumors were divided into two parts and transferred into the automated vacuum tissue processor ASP200 for dehydration (Leica Microsystems GmbH, Wetzlar, Germany) followed by embedding into paraffin (Paraplast, Carl Roth, Karlsruhe, Germany) via the paraffin dispenser station MPS/C (Slee Medical GmbH, Mainz, Germany). For immunohistochemical stainings, 3 µm thick sections of the formalin-fixed and paraffin-embedded tissues were generated using the rotary microtome RM2255 (Leica Microsystems GmbH, Wetzlar, Germany). Deparaffinization and re-hydrations were conducted in the bi-linear batch stainer StainMate Max (Thermo Fisher Scientific, Rockford, Ill., USA) followed by heat-induced epitope retrieval in 10 mM citric buffer, pH6 with 0.05% Tween20 for 10 min at 120° C. Endogenous peroxidases were quenched subsequently using 0.3% $H_2O_2$ solution in PBS for 15 min (Carl Roth), followed by incubation with 10% goat serum in PBS (PAA Laboratories GmbH/GE Healthcare, Pasching, Austria) for 30 min to block unspecific antibody binding sites. TAA Claudin 6 was detected by incubation with the polyclonal primary antibody Anti-Mouse Claudin 6 (C) Rabbit (IBL-America, Minneapolis, Minn., USA) at 4° C. over night; T cells were detected on consecutive sections using the polyclonal anti-CD3 AB (Abcam, Cambridge, UK) at 4° C. over night followed by incubation with a BrightVision polymer HRP-conjugated anti-rabbit secondary antibody (ImmunoLogic, Duiven, Netherlands). Binding reactions were visualized using the Vector NovaRED kit (Vector Laboratories Ltd., Peterborough, UK) according to the manufacturer's instructions, followed by hematoxylin counterstaining (Carl Roth), dehydration and mounting. Analysis and documentation were performed using either the Axio Imager M2 or the Mirax scanner (both Carl Zeiss Microscopy GmbH, Goettingen, Germany).

As shown in FIG. 19, highest T cell infiltration was detected in the tumors of the "PBMC/6PHU3" group by CD3 staining, especially in the border areas of CLDN6 expression. The heterogeneous expression pattern of TAA CLDN6 in the control groups (FIGS. 19A, B, C, and D) changed to more compact areas of CLDN6 expression in the tumors of the "PBMC/6PHU3" group as a result of the therapy (FIG. 19D).

Example 15

Generation and Testing of Bispecific Binding Agents Targeting CLDN18.2 and CD3 a. Sequence Origin, Design of Bi-scFv Constructs, and Cloning into Template Vectors Bispecific tandem single chain antibody constructs (bi-scFv) containing binding domains specific for the human T cell receptor component CD3 epsylon and human tumor associated antigens (TAA) were prepared. The corresponding variable heavy chain regions ($V_H$) and the corresponding variable light chain regions ($V_L$) for each construct were specifically arranged from 5'- to 3'-end in consecutive order:

pST1-hAgKozak-$V_H^{\alpha CLDN18.2}$-$V_L^{\alpha CLDN18.2}$-$V_H^{\alpha CD3}$-

$V_L^{\alpha CD3}$-His-2hBgUTR-A120
(1BiMAB, 18RHU5, no. 1-5)

pST1-hAgKozak-$V_H^{\alpha CD3}$-$V_L^{\alpha CD3}$-$V_H^{\alpha CLDN18.2}$-

$V_L^{\alpha CLDN18.2}$-His-2hBgUTR-A120
(18RHU3, no. 6-10)

Table 7 summarizes all bi-scFv constructs specific for the TAA CLDN18.2 and PLAC1 that were generated in the course of the invention. The bi-scFv constructs were generated by gene synthesis by GeneArt AG (GeneArt/Life Technologies GmbH, Regensburg, Germany) using the $V_H$ and $V_L$ sequences of the corresponding antibodies. Codon optimizations such as Homo sapiens (HS), Mus musculus (MM), or Chinese Hamster Ovary (CHO) were implemented by GeneArt's GeneOptimizer® software, and are listed in Table 7. Information on specificity, sequence origin from monoclonal antibodies (mAB), codon usage, additional sequence features and references of all applied domains are summarized in Table 8. Variable domain sequence origin of the respective CD3 antibodies are listed in Table 8. Due to the high homology of human and mouse TAAs, the same anti-TAA $V_H$ and $V_L$ sequences could be used for the generation of bi-scFv constructs for mouse assays, but in combination with the $V_H$, $V_L$ sequences of the mouse specific anti-CD3 antibody clone 145-2C11.

DNA cloning and expression vector construction was carried out according to standard procedures (Green/Sambrook, Molecular Cloning, 2012) well known by the skilled person. Briefly, the leadoff bi-scFv DNA sequences were provided with a 5'-BsmBI and a 3'-XhoI restriction site for cloning into pST1 plasmids. A secretion signal sequence was introduced at the 5' end upstream of the bi-scFv sequence for bi-scFv secretion. A sequence coding for a 15 to 18 amino acid flexible glycine-serine peptide linker was inserted to join the $V_H$ and $V_L$ domains for the composition of the single chain variable antibody fragments (scFv) of which one binds to CD3 and the other to the TAA. To form a bispecific single chain antibody, the two scFv domain sequences were connected by a sequence coding for a short peptide linker (GGGGS). Together with this linker sequence a BamHI restriction site was introduced for scFv domain exchanges for the cloning of upcoming bi-scFv constructs. Briefly, 5'scFv-domains were exchanged by BsmBI and BamHI restriction and 3'scFv-domains by BamHI and XhoI restriction. A C-terminal 6xHis-tag was implemented for detection analysis of the translated protein. Untranslated regions of human alpha globin 5' and of human beta globin 3' of the bi-scFv sequence were present in the pST1 vector (for details see WO02007/036366A2; Waggoner, S. et al. (2003) Exp. Biol. Med. (Maywood) 228 (4), pp. 387-395).

For 1BiMAB replicon vector production, the full 1 BiMAB sequence including secretion signal and 6xHis-tag was subcloned 3' to the subgenomic promoter of the Semliki forest virus replicon vector (pSFV) kindly provided by K. Lundström (Lundstrom, K. et al. (2001) Histochem. Cell Biol. 115 (1), pp. 83-91; Ebrengruber, M. U. et al. (1999) Proc. Natl. Acad. Sci. U.S.A. 96 (12), pp. 7041-7046).

All constructs were verified by sequencing via MWG's single read sequence service (Eurofins MWG Operon, Ebersberg, Germany) and only those with correct sequence and a poly(A) tail of more than 100 adenines were used for in vitro RNA transcription.

For construct schemata see also FIG. 20 A.

TABLE 7

Summary of TAA and CD3 specific bispecific single chain antibody mRNA-template constructs

| Internal name | TAA | Specificity | 5'-$V_H$-$V_L$ | 3'-$V_H$-$V_L$ | Codon usage |
|---|---|---|---|---|---|
| 1BiMAB | CLDN18.2 | human | mCLDN18.2ab | TR66 | HS |
| no. 1 | CLDN18.2 | murine | mCLDN18.2ab | 145-2C11 | CHO |
| no. 2 | CLDN18.2 | human | mCLDN18.2ab | UCHT1-1HU | CHO |
| no. 3 | CLDN18.2 | human | mCLDN18.2ab | UCHT1 | CHO |
| no. 4 | CLDN18.2 | human | mCLDN18.2ab | CLB-T3 | CHO |
| no. 5 | CLDN18.2 | human | mCLDN18.2ab | TR66 | CHO |
| no. 6 | CLDN18.2 | murine | 145-2C11 | mCLDN18.2ab | CHO |
| no. 7 | CLDN18.2 | human | UCHT1-HU | mCLDN18.2ab | CHO |
| no. 8 | CLDN18.2 | human | UCHT1 | mCLDN18.2ab | CHO |
| no. 9 | CLDN18.2 | human | CLB-T3 | mCLDN18.2ab | CHO |
| no. 10 | CLDN18.2 | human | TR66 | mCLDN18.2ab | CHO |
| 18RHU5 | CLDN18.2 | human | mCLDN18.2ab | TR66 | HS |
| 18RHU3 | CLDN18.2 | human | TR66 | mCLDN18.2ab | HS |

TABLE 7-continued

Summary of TAA and CD3 specific bispecific
single chain antibody mRNA-template constructs

| Internal name | TAA | Specificity | 5'-$V_H$-$V_L$ | 3'-$V_H$-$V_L$ | Codon usage |
|---|---|---|---|---|---|
| 18RMU5 | CLDN18.2 | murine | mCLDN18.2ab | 145-2C11 | MM |
| 18RMU3 | CLDN18.2 | murine | 145-2C11 | mCLDN18.2ab | MM |
| control bi-scFv | | | | | |
| no. 25 | PLAC1 | human | 78H11 | TR66 | CHO |

Bi-seFv indicates bispecific single chain variable fragment;
CHO, Chinese Hamster Ovary;
HS, *Homo sapiens*;
HU, humanized;
MM. *Mus musculus*;
TAA, tumor associated antigen;
$V_H$, variable heavy chain domain,
$V_L$, variable light chain domain.

TABLE 8

Summary of bi-scFv mRNA-template construct information

| | CD3 binding moiety | | TAA binding moiety | | | | | |
|---|---|---|---|---|---|---|---|---|
| Internal name | mAB origin | Species reactivity | TAA | mAB origin | Species reactivity | 5'-$V_H$-$V_L$ | 3'-$V_H$-$V_L$ | Short linker |
| 1BiMAB | -TR66 | human | CLDN18.2 | mCLDN18.2ab | human, murine | mCLDN18.2ab | TR66 | GGGGS |
| no.1 | 145-2C11 | murine | CLDN18.2 | mCLDN18.2ah | human, murine | mCLDN18.2ab | 145-2C11 | SGGGGS |
| no.2 | UCHT1-HU | human | CLDN18.2 | mCLDN18.2ab | human, murine | mCLDN18.2ab | UCHT1-HU | SGGGGS |
| no.3 | UCHT1 | human | CLDN18.2 | mCLDN18.2ab | human, murine | mCLDN18.2ab | UCHT1 | SGGGGS |
| no.4 | CLB-T3 | human | CLDN18.2 | mCLDN18.2ab | human, murine | mCLDN18.2ab | CLB-T3 | SGGGGS |
| no.5 | TR66 | human | CLDN18.2 | mCLDN18.2ab | human, murine | mCLDN18.2ab | TR66 | SGGGGS |
| no.6 | 145-2C11 | murine | CLDN18.2 | mCLDN18.2ab | human, murine | 145-2C11 | mCLDN18.2ab | SGGGGS |
| no.7 | UCHT1-HU | human | CLDN18.2 | mCLDN18.2ab | human, murine | UCHT1-HU | mCLDN18.2ab | SGGGGS |
| no.8 | UCHT1 | human | CLDN18.2 | mCLDN18.2ab | human, murine | UCHT1 | mCLDN18.2ab | SGGGGS |
| no.9 | CLB-T3 | human | CLDN18.2 | mCLDN18.2ab | human, murine | CLB-T3 | mCLDN18.2ab | SGGGGS |
| no.10 | TR66 | human | CLDN18.2 | mCLDN18.2ab | human, murine | TR66 | mCLDN18.2ab | SGGGGS |
| 18RHU5 | TR66 | human | CLDN18.2 | mCLDN18.2ab | human, murine | mCLDN18.2ab | TR66 | SGGGGS |
| 18RHU3 | TR66 | human | CLDN18.2 | mCLDN18.2ab | human, murine | TR66 | mCLDN18.2ab | SGGGGS |
| 18RMU5 | 145-2C11 | murine | CLDN18.2 | mCLDN18.2ab | human, murine | mCLDN18.2ab | 145-2C11 | SGGGGS |
| 18RMU3 | 145-2C11 | murine | CLDN18.2 | mCLDN18.2ab | human, murine | 145-2C11 | mCLDN18.2ab | SGGGGS |

TABLE 8-continued

Summary of bi-scFv mRNA-template construct information

| | | | | | | | | |
|---|---|---|---|---|---|---|---|---|
| no.25 | TR66 | human | PLAC1 | 78H11 | human, murine | 78H11 | TR66 | SGGGGS |

| Internal name | 5'-long linker | 3'-long linker | Secretion signal | Codon usage | Anti-CD3 mAB reference | |
|---|---|---|---|---|---|---|
| 1BiMAB | (GGGGS)$_3$ | VE(GGSGGS)$_2$ GGVD | MGWSCIILFLVAT ATGVHS | HS | Lanzavecchia & Scheidegger, Eur J Immunol 1987 | |
| no.1 | (GGGGS)$_3$ | (GGGGS)$_3$ | MGWSCIILFLVAT ATGVHS | CHO | Leo et al., Proc Natl Acad Sci, 1987 | |
| no.2 | (GGGGS)$_3$ | (GGGGS)$_3$ | MGWSCIILFLVAT ATGVHS | CHO | Shalaby et al., J Exp Med 1992 | |
| no.3 | (GGGGS)$_3$ | (GGGGS)$_3$ | MGWSCIILFLVAT ATGVHS | CHO | Beverley et al., Eur J Immunol 1981 | |
| no.4 | (GGGGS)$_3$ | (GGGGS)$_3$ | MGWSCIILFLVAT ATGVHS | CHO | Van Lier et al., Immunology 1989 | |
| no.5 | (GGGGG)$_3$ | (GGGGS)$_3$ | MGWSCIILFLVAT ATGVHS | CHO | Lanzavecchia & Scheidegger, Eur J Immunol 1987 | |
| no.6 | (GGGGS)$_3$ | (GGGGS)$_3$ | MNSGLQLVFFVL TLKGIQG | CHO | Leo et al., Proc Nal Acad Sci, 1987 | |
| no.7 | (GGGGS)$_3$ | (GGGGS)$_3$ | MGWSCIILFLVAT ATGVHS | CHO | Shalaby et al., J Exp Med 1992 | |
| no.8 | (GGGGS)$_3$ | (GGGGS)$_3$ | MNSGLQLVFFVL TLKGIQG | CHO | Beverley et al., Eur J Immunol 1981 | |
| no.9 | (GGGGS)$_3$ | (GGGGS)$_3$ | MNFGLSLIFLALI LKGVQC | CHO | Van Lier at al., Immunology 1989 | |
| no.10 | (GGGGS)$_3$ | (GGGGS)$_3$ | MEWSWIFLFLLS VTTGVHS | CHO | Lanzavecchia & Scheidegger, Eur J Immunol 1987 | |
| 18RHU5 | (GGGGS)$_3$ | VE(GGSGGS)$_2$ GGVD | MGWSCHIILFLVAT ATGVHS | HS | Lanzavecchia & Scheidegger, Eur J Immunol 1987 | |
| 18RHU3 | VE(GGSGGS)$_2$ GGVD | (GGGGS)$_3$ | MGWSCIILFLVAT ATGVHS | HS | Lanzavecchia & Scheidegger, Eur J Immunol 1987 | |
| 18RMU5 | (GGGGS)$_3$ | VE(GGSGGS)$_2$ GGVD | MGWSCIILFLVAT ATGVHS | MM | Leo et al., Proc Natl Acad Sci, 1987 | |
| 18RMU3 | VE(GGSGGS)$_2$ GGVD | (GGGGS)$_3$ | MNSGLQLVFFVL TLKGIQG | MM | Leo et al., Proc Natl Acad Sci, 1987 | |
| no.25 | (GGGGS)$_3$ | (GGGGS)$_3$ | MGWLWNLLFLM AAAQSAQA | CHO | Lanzavecchia & Scheidegger, Eur J Immunol 1987 | |

CHO indicates Chinese Hamster Ovary; HS, Homo sapiens; mAB, monoclonal antibody; MM, Mus musculus; TAA, tumor associated antigen.

b. IVT-RNA Synthesis

For the generation of anti-CLDN18.2-specific bi-scFv IVT templates, plasmids were linearized downstream the poly(A)-tail using a class IIs endonuclease Linearized template DNA was purified by phenol/chloroform extraction and sodium acetate precipitation as described elsewhere (Holtkamp, S. et al. (2006) Blood 108 (13), pp. 4009-4017).

Linearized DNA templates were subjected to in vitro transcription using MEGAscript Kits (Ambion/Life Technologies, Darmstadt, Germany) according to the manufacturer's guidelines: pST1 templates were transcribed with the MEGAscript T7 Kit and pSFV templates with the MEGAscript SP6 Kit. For reactions with cap analoga, the GTP concentration was lowered to 1.5 mM, and 6 mM of ARCA, beta-S-ARCA(D1), or beta-S-ARCA(D2), synthesized as described elsewhere (Kowalska, J. et al. (2008) RNA 14 (6), pp. 1119-1131; Grudzien, E. et al. (2004) RNA 10 (9), pp. 1479-1487; Stepinski, J. et al. (2001) RNA 7 (10), pp. 1486-1495) was added to the reaction. Purification of IVT-mRNA was carried out with the MEGAclear Kit (Ambion/Life Technologies, Darmstadt, Germany) according to the manual. Concentration and quality of the IVT-RNA were assessed by spectrophotometry and analysis on a 2100 Bioanalyzer (Agilent Technologies, Santa Clara, Calif., USA).

Example 16

T Cell Activation in Response to Bi-scFv Secretion by Target Cells Transfected with Various CLDN18.2-specific IVT-mRNAs For the examination of CLDN18.2-specific bi-scFv IVT-RNA functionality, the gastric carcinoma cell line NugC4 that endogenously expresses relatively high levels of human CLDN18.2 (Sahin, U. et al. (2008) *Clin. Cancer Res.* 14 (23), pp. 7624-7634) was used as target cell line.

NugC4 target cells—that are routinely tested for TAA expression by FACS analysis before every assay—were washed twice with ice cold X-Vivo 15 medium (LONZA, Basel, Switzerland) and resuspended to a density of $2 \times 10^7$ cells/ml. 250 µl cell suspension was transferred to pre-cooled 0.4 cm Gene Pulser/MicroPulser Cuvettes (Bio-Rad, Dreieich, Germany) and 20 µg/ml IVT-mRNA was added. IVT-mRNAs used were: 1BiMAB, no. 2, no. 3, no. 4, no. 5, no. 7, no. 8, no. 9 and no. 10. For detailed information on bi-scFv variants see Tables 7 and 8. After careful mixing, cells were transfected with a BTX ECM 830 electroporator (Harvard Apparatus, Holliston, Mass., USA) using the following conditions: 250 V, 2 pulses, 12 ms pulse length, 400 ms interval length. Immediately after electroporation, cuvettes were shortly put on ice and then the cell suspensions were transferred into RT warm assay medium (RPMI 1640 medium supplemented with 5% heat inactivated human AB serum, 0.5% penicillin-streptomycin, 1×NEAA and 1 mM sodium pyruvate (Gibco/Life Technologies GmbH, Darmstadt, Germany)) in 15 ml tubes. Transfected target cells were counted and adjusted to $1 \times 10^5$ cells per ml.

Human effector cells were freshly isolated from human blood of healthy donors according to standard procedures (Current Protocols in Immunology, 2012): briefly, blood was diluted with DPBS, layered on Ficoll-Paque Plus (GE Healthcare Life Sciences, Munich, Germany) and centrifuged. Peripheral blood mononuclear cells (PBMCs) were collected from the interphase, washed with cold DPBS supplemented with 2 mM EDTA and counted. Human cytotoxic T cells were isolated by magnetic-activated cell separation (MACS) from PBMCs by CD8 T Cell Isolation Kit, human (Miltenyi Biotec, Teterow, Germany) according to the manufacturer's guidelines. Effector cell separations were routinely tested for successful T cell isolation via FACS analysis (CD4, CD8 staining). T cells were adjusted to $5 \times 10^5$ cells per ml in assay medium.

$1 \times 10^5$ target cells were seeded per well of a 6-well plate and human cytotoxic T cells were added to an E:T ratio of 5:1. The final volume per well was 2 ml. Control samples containing effector and target cells comprised target cells secreting no. 25, the parental IgG mAB chCLDN18.2ab and 1BiMAB protein as positive control in a final concentration of 5 ng/ml. Controls included electroporated target cells alone or T cells alone with and without 1BiMAB protein. After 48 h T cells and target cells were harvested, labeled and analyzed by flow cytometry. Briefly, all cells were harvested by gentle scraping with Cell Scrapers (Sarstedt AG & Co, Nürmbrecht, Germany) and transferred to 5 ml round bottom tubes (BD) Falcon, Heidelberg, Germany). Cells were centrifuged and washed with DPBS. For cell staining Mouse Anti-Human CD3-FITC, Mouse Anti-Human CD69-APC, and Mouse Anti-Human CD25-PE (all antibodies BD Biosciences, Heidelberg, Germany) were used. Cell pellets were resuspended in 50 µl FACS-buffer (DPBS supplemented with 5% FBS) containing the fluorescence-conjugated antibodies. After incubation for 20 min at 4° C. in the dark, samples were washed with 4 ml DPBS and cell pellets were resuspended in 200 µl FACS buffer containing propidium iodide (PI) (Sigma Aldrich, Germany) in a final dilution of 1:1000 for the detection of dead cells. Samples were kept on ice and dark until measured. Establishment of the assay was performed with a FACSCalibur (BD Biosciences, Heidelberg, Germany). Analysis was evaluated by FlowJo software (Tree Star, San Carlos, Calif., USA).

As shown in FIG. 21 A, each CLDN18.2-specific IVT-mRNA resulted in secretion of bi-scFv protein as seen in the efficient T cell activation. The most potent variants with only marginal differences in T cell activation were no. 5>no. 8>no. 10>no. 3>1BiMAB in descending order. All of these variants led to a total T cell activation of above 55% whereas variants no. 2, no. 4, no. 7 and no. 9 led to a total T cell activation of 40 to 50%.

Specific target cell lysis was calculated by the formula: % lysis=(% $PI^+$ target cells$_{sample}$−% $PI^+$ target cells $_{EP\ reference}$) where "sample" specifies coincubated effector and target cells and "EP reference" electroporated target cells of each individual IVT-mRNA electroporation alone. As shown in FIG. 21 B, target cell lysis above 65% was achieved by the variants 1BiMAB>no. 5>no. 8>no. 3 in descending order. The other variants mediated a target cell lysis of 55-64%. The most potent CLDN18.2-specific bi-scFv carry the $V_H$ and $V_L$ domains of TR66 (1BiMAB, no. 5, no. 10) or UCHT1 (no. 3, no. 8). Regarding the domain orientations, no significant difference was observed in contrast to the protein bi-scFv variants (see example 3). In accordance with the protein studies IVT-mRNA encoding 1BiMAB was chosen for further studies.

Constructs 18RHU5 and 18RHU3 (see Tables 7 and 8) were compared at a later time point to 1BiMAB. Efficiency of 18RHU5 was equivalent to 1BiMAB, 18RHU3 was less potent (data not shown).

Example 17

Microscopic Analysis of T Cells Redirected to Target Cells Secreting CLDN18.2-specific bi-scFv 1BiMAB The assay set-up was essentially as described under example 2.a.

Human cytotoxic T cells were isolated by MACS from freshly isolated PBMCs by $CD8^+$ T Cell Isolation Kit, human (Miltenyi Biotec, Teterow, Germany) according to the manufacturer's guidelines.

NugC4 target cells were prepared and transfected as described under example 16 with the exception that 80 µg/ml 1BiMAB IVT-mRNA or 80 µg/ml no. 25 ctrl IVT-mRNA was used. Transfected target cells were counted and adjusted to $2 \times 10^5$ cells per ml. $1 \times 10^4$ target cells were seeded per well of a 96-well plate and human cytotoxic T cells were added according to an E:T ratio of 5:1. The final volume per well was 100 µl. Control samples comprised transfected target cells alone to proof healthiness after electroporation and control bi-scFv transfected target cells with effector cells. Tissue culture plates were subsequently incubated at 37° C., 5% $CO_2$. Significant effects in terms of T cell clustering on target cells, formation of an immunologic synapse and target cell killing in samples containing 1BiMAB transfected target cells were seen at 24 h and recorded with a Nikon Eclipse TS100 inverted microscope (Nikon, Japan). No T cell clustering or target cell lysis was observed in the control sample with no. 25 transfected target cells implying the strict dependency on TAA expression to induce an activation of T cells. See also FIG. 22.

Example 18

Flow Cytometric Analysis of Concentration Dependent T Cell Activation by CLDN18.2-specific bi-scFv 1BiMAB To investigate a bi-scFv concentration dependent activation of T cells in the presence of TAA-expressing target cells a three-fold dilution series was applied to the transfection process. NugC4 target cells were prepared and transfected as described under example 16 but with a final IVT-mRNA concentration of 40 µg/ml. 1BiMAB IVT-mRNA concentrations ranged from 0.4-40 µg/ml and were filled up with appropriate amounts of luciferase IVT-mRNA with the purpose to expose all samples to the same stress level regarding IVT-mRNA amounts.

$1 \times 10^5$ transfected target cells and human cytotoxic T cells (isolated as described under example 16) were seeded in an E:T ratio of 10:1 in 2 ml assay medium in a 6-well format. Control samples contained target cells transfected with 40 µg/ml luciferase IVT-mRNA but not with 1BiMAB IVT-mRNA. After 24 h and 48 h of target and effector cell coincubation, cells were harvested, stained and analyzed as described under example 16.

As shown in FIGS. 23 A and B, significant T cell activation was observed in samples containing target cells transfected with 4 µg/ml 1BiMAB IVT-mRNA. Maximum T cell activation in this assay was reached with 40 µg/ml 1BiMAB IVT-mRNA. Expression of CD69 and CD25 varied with the coincubation time (FIG. 23 A to B) and the IVT-mRNA concentration. Higher 1BiMAB IVT-mRNA amounts (12 and 40 µg/ml) led to faster initiation of the T cell activation mechanism as visible e.g. at the increased expression of CD25 compared to that of CD69 in FIG. 23 B. Total T cell activation did not exceed ~40%.

Example 19

Flow Cytometric Analysis of Concentration Dependent T Cell Mediated Target Cell Lysis by CLDN18.2-specific Bi-scFv 1BiMAB To investigate a bi-scFv concentration dependent T cell mediated target cell lysis the experimental set-up described under example 18 was used. Besides the effector and target cell coincubation samples ("sample") also the individually electroporated target cells alone were seeded. The latter served as reference samples ("EP reference") to subtract target cells killed by the electroporation process itself from target cells lysed by T cells.

Harvest and staining was performed according to example 18. Target cells were finally analysed via their incorporation of propidium iodide with a FACSCalibur (BD Biosciences, Heidelberg, Germany).

Percentage of specific target cell lysis was determined by a two-step subtraction of background dead cells:
1. % T cell mediated lysis=(% PI$^+$ target cells $_{sample}$-% PI$^+$ target cells $_{EP\ reference}$)
2. % specific lysis=(% T cell mediated lysis $_{sample}$-% T cell mediated lysis$_{ctrl}$)

"T cell mediated lysis$_{ctrl}$" is deduced from the difference of PI$^+$ target cells of control samples (40 µg/ml luciferase IVT-mRNA only) with and without effector cells.

By this calculation a maximum specific lysis of 55.5%+/−5.6% is reached with 12 µg/ml 1BiMAB IVT-mRNA in this experiment. Due to the sensitivity of NugC4 target cells to electroporation stress and the therewith unavoidable dead background target cells that are subtracted, the plotted specific target cell lysis might be lower in this experimental set-up than the actual lysis percentage.

Example 20

T Cell Proliferation in Response to 1BiMAB IVT-mRNA Transfection

T cell proliferation is an indicator of T cell activation. To show specific T cell proliferation in response to bi-scFv encoding IVT-mRNA 1BiMAB in the presence of CLDN18.2 positive target cells, a flow cytometric assay was used. Briefly, $1 \times 10^7$ human T cells isolated as described under example 16 were stained with 1 µM carboxyfluorescein diacetate succinimidyl ester (CellTrace CFSE, Invitrogen/Life Technologies GmbH, Germany) dissolved in DPBS in the dark at RT for 5 min. Cells were washed twice with DPBS/5% FCS and resuspended in assay medium to $2 \times 10^6$ cells per ml. As target cells, NugC4 cells lentivirally transduced with human CLDN18.2 and—for specificity testing—the CLDN18.2-negative breast cancer cell line MDA-MB-231 were chosen. 20 µg/ml of IVT-mRNAs 1BiMAB or a non-targeting control were used for electroporation. Electroporation of NugC4 was performed as described under example 16. MDA-MB-231 electroporation was conducted using the following conditions: 400 V, 3 ms pulse length, 1 pulse, 400 ms interval length in 0.4 cm Gene Pulser/ MicroPulser Cuvettes (Bio-Rad, Dreieich, Germany). A cytotox assay as described under example 16 was set up with the transfected target cells and human CFSE-labeled T cells as effector cells. T cells alone and untransfected or control transfected target cells plus T cells were used as negative controls. T cells alone stimulated with 5 µg/ml OKT3 (Bio X Cell, West Lebanon, N.H., USA) and 2 µg/ml anti-CD28 (BioLegend, Fell, Germany) served as positive control. 1BiMAB protein in a concentration of 5 ng/ml was applied to untransfected target plus T cells to confirm the assay validity. Samples combined with the non-targeting bi-scFv protein 6PHU3 were included as specificity control. All samples were set up in triplicates in a total volume of 0.2 ml assay medium in 96 wells. After 72 h of coincubation, T cells were harvested, collected in 5 ml round bottom tubes, washed and stained at 4° C. for 30 min with 2 µl anti-CD45-APC to differentiate human T cells from tumor cells and 0.25 µl eFluor506 (BD Biosciences, Heidelberg, Germany) to counterstain dead cells in 200 µl DPBS. After washing with DPBS, cells were resuspended in FACS-buffer and analyzed with a FACSCanto II (BD Biosciences, Heidelberg, Germany).

Proliferation of T cells was detected by decreasing CFSE-signal only in the presence of CLDN18.2 positive target cells and bi-scFv 1BiMAB (see also FIG. 25). Besides the positive control, T cell proliferation of 42-48% could be observed in the presence of CDLN18.2 positive target cells in combination with 1BiMAB protein. Target positive cells transfected with 1BiMAB IVT-mRNA led to 22%+/−3%. The lower proliferation in response to IVT-mRNA than to protein is probably due to the low transfection efficiency achievable with NugC4 target cells. T cells incubated with CLDN18.2 negative target cells MDA-MB-231 do not show a significant proliferation in any constellation as well as T cells without target cells except for the positive control.

Example 21

Titration of Effector to Target Ratios to Determine a Potent Ratio

For the determination of a suitable E:T ratio in the setting of the in vitro cytotox assay based on FACS analysis, E:T ratios ranging from 0.3:1 to 10:1 in 3-fold steps were chosen.

NugC4 target cells were prepared and transfected as described under example 16 with an IVT-mRNA concentration of 40 µg/ml. One preparation of 1BiMAB IVT-mRNA transfected cells was used for all test samples. Transfection of 40 µg/ml luciferase IVT-mRNA was selected as negative control.

Human cytotoxic T cells were separated from freshly isolated PBMCs as described under example 16 and served as effector cells. $1 \times 10^5$ transfected target cells were coincubated with cytotoxic T cells in 6-well plates in duplicates in the following effector to target ratios: 0.3:1-1:1-3:1-10:1. Additionally, human cytotoxic T cells were cultured in the absence of target cells to determine background T cell activation. Target cells transfected with control IVT-mRNA or 1BiMAB IVT-mRNA were also cultured in the absence of effector cells to define background dead cells by electroporation stress. The luciferase negative control was only seeded in the maximum E:T ratio of 10:1. After 48 h of coincubation cells were harvested, labeled and analyzed as described under example 16.

FIG. 26 A shows a specific activation of cytotoxic T cells in response to 1BiMAB secretion by NugC4 target cells. Independent of the number of T cells in the samples, a total activation of 50-60% was detected. Moreover, the distribution of CD25 and CD69 expression in the samples is highly comparable. This indicates that there is a given percentage of T cells in the cytotoxic T cell population that can be activated.

In FIG. 26 B the dependency of efficient target cell lysis of the cytotoxic T cell number becomes obvious. Even though target cells are lysed in an E:T ratio of only 0.3:1 a potent lysis starts with a ratio of 3:1.

Example 22

Analysis of T Cell Activation and Target Cell Lysis in a FACS-based Assay with 1BiMAB IVT-mRNA Transfected Effector Cells In this experiment the aim was to test whether also human effector cells are capable to produce and secrete 1BiMAB after IVT-mRNA transfection. The rational behind this was a hypothetical patient's scenario in which the patient's own T cells could be transfected with bi-scFv followed by a retransfer into the patient.

Human cytotoxic T cells—isolated as described under example 16—were washed twice with X-Vivo 15 medium (LONZA, Basel, Switzerland) and resuspended to a density of $2 \times 10^7$ cells/ml. 250 µl cell suspension was transferred to pre-cooled 0.4 cm Gene Pulser/MicroPulser Cuvettes (Rio-Rad, Dreicich, Germany) and 80 or 240 µg/ml IVT-mRNA was added. IVT-mRNAs used were 1BiMAB and cGFP as control. After careful mixing, cells were electroporated with a BTX ECM 830 (Harvard Apparatus, Holliston, Mass., USA) electroporator using the following conditions: 500 V, 1 pulse, 3 ms pulse length, 400 ms interval length. Immediately after electroporation, cuvettes were shortly put on ice and then the cell suspensions were transferred into assay medium (RPMI 1640 medium supplemented with 5% heat inactivated human AB serum, 0.5% penicillin-streptomycin, 1×NEAA and 1 mM sodium pyruvate (Gibco/Life Technologies GmbH, Darmstadt, Germany)) containing 10 U/ml IL-2. Transfected effector cells were cultivated over night at 37° C., 5% $CO_2$. The next day, the transfection efficiency was analyzed by FACS revealing a transfection efficiency above 70% for both eGFP IVT-mRNA concentrations. Each effector cell sample was counted and adjusted to $5 \times 10^5$ cells per ml. NugC4 target cells were harvested by trypsinization, washed with assay medium, counted and adjusted to $1 \times 10^5$ cells per ml. Effector and target cells were mixed and seeded to 6-wells in duplicates with a final E:T ratio of 5:1 and a final volume of 2 ml. Untreated T cells were seeded without target cells for determination of background activation signals. Assay analysis was performed as described under example 16 after 48 h of coincubation at 37° C., 5% $CO_2$.

A significant activation of cytotoxic T cells transfected with 1BiMAB IVT-mRNA and coincubated with target cells was achieved as shown in FIG. 27 A. Target cell lysis by 1BiMAB IVT-mRNA transfected T cells was above 60% as plotted in FIG. 27 B. The effects of 80 µg/ml 1BiMAB IVT-mRNA could not be increased with higher RNA amounts.

Concluding from this experiment, effector cells could theoretically be used as bi-scFv producing and secreting recipient cells.

Example 23

Investigation of Target Specificity of 1BiMAB IVT-mRNA in a Luciferase-based Cytotox Assay Using CLDN18.2 Negative Target Cells Strict target specificity is an important issue to avoid unwanted adverse effects in patients. In this preliminary study, a CLDN8.2 negative cell line—the teratocarcinoma cell line PA-1 (ATCC CRL-1572)—has been chosen to examine an unspecific cytolytic potential of 1BiMAB introduced as IVT-mRNA.

The PA-1 cell line used had been stably transduced with a lentiviral luciferase vector and could therefore be applied in a luciferase-based cytotox assay. PA-1/luc target cells were prepared for electroporation as described under example 16. A total of 40 µg/ml IVT-mRNA was transfected per sample. IVT-mRNAs used were: 1BiMAB, no. 25 and 6RHU3. No. 25 targets the non-expressed TAA PLAC-1 and 6RHU3 targets the highly expressed target CLDN6 in PA-1/luc cells. For detailed information on bi-scFv variants see Tables 7 and 8. No. 25 was used as fill-up IVT-mRNA in electroporation samples with 4 µg/ml IVT-mRNA to ensure the same stress level caused by RNA transfection for all target cell samples. After careful mixing, cells were transfected with a BTX ECM 830 electroporator (Harvard Apparatus, Holliston, Mass., USA) using the following conditions for a 0.4 cm cuvette: 200 V, 2 pulses, 12 ms pulse length, 400 ms interval length. Immediately after electroporation, cuvettes were shortly put on ice and then the cell suspensions were transferred into RT warm PA-1 assay medium (MEM medium supplemented with 10% heat inactivated FCS, 0.5% penicillin-streptomycin, 1×NEAA, 1.5 g/l sodium bicarbonate and 1 mM sodium pyruvate (Gibco/Life Technologies GmbH, Darmstadt, Germany)) in 15 ml tubes. Transfected target cells were counted and adjusted to $1 \times 10^5$ cells per ml.

Human effector cells were isolated as described under example 16. Human cytotoxic T cells were isolated by magnetic-activated cell separation (MACS) from PBMCs by Pan T Cell Isolation Kit II, human (Miltenyi Biotec, Teterow, Germany) according to the manufacturer's guidelines. T cells were adjusted to 5×10$^5$ cells per ml in PA-1 assay medium. 1×10$^4$ target cells were seeded per well of a 96-well plate and human cytotoxic T cells were added to an E:T ratio of 5:1. The final volume per well was 100 µl. Control samples containing effector and target cells comprised target cells secreting no. 25 as negative control, 6RHU3 or 6PHU3 protein as positive control and 1BiMAB protein. Protein concentrations were set to a final concentration of 100 ng/ml and were combined with no. 25-transfected target cells to ensure the same condition for the used target cells. Minimal lysis controls ($L_{min}$) included each electroporated target cell sample alone. Spontaneous lysis controls ($L_{max}$) consisted of untreated target and effector cells ($L_{max1}$) for subtraction from $L_{test\ sample}$ or untreated target cells alone ($L_{max2}$) for subtraction from $L_{min}$. Each sample was seeded in triplicate. Assay analysis was undertaken after 72 h incubation at 37° C., 5% CO$_2$. Spontaneous lysis controls ($L_{max}$) were treated with Triton X-100 in a final concentration of 2%.

For analysis, 50 µl of a water solution containing 1 mg/ml luciferin (BD Monolight, BD Biosciences, Heidelberg, Germany) and 50 mM HEPES were added per well and plates subsequently incubated for 30 min in the dark at 37° C. Luminescence arising from oxidation of luciferin by luciferase expressing viable cells was measured in a microplate-reader (Infinite M200, Tecan, Männedorf, Switzerland). Percentage of specific target cell lysis was calculated by the following formula: % specific lysis=[1−(luminescence$_{test\ sample}$−$L_{max1}$)/($L_{min}$−$L_{max2}$)]×100.

FIG. 28 shows the percentage of specific target cell lysis. CLDN18.2 negative PA-1/luc cells transfected with the negative control no. 25 or with 1BiMAB do not show significant lysis even after an incubation of 72 h. Also 100 ng/ml 1BiMAB protein do not result in significant lysis, whereas lysis by bi-scFv secretion of TAA-targeting 6RHU13 or by 100 ng/ml 6PHU3 protein was between 85-93%. 24 h and 48 h time points were analyzed as well and show equivalent results (data not shown).

Example 24

Qualitative Analysis of 1BiMAB Protein Production after IVT-RNA Transfection of Mammalian Cells For the investigation of RNA translation into protein in mammalian cells the cell line BHK21 (ATCC CRL-13001) was chosen as expression system. 2×10$^7$ BHK21 cells per ml were transfected by electroporation as described under example 16 with the difference that all steps were conducted at RT. 250 µl cell suspension was transferred to 0.4 cm Gene Pulser/MicroPulser Cuvettes (Bio-Rad, Dreieich, Germany) and 40 µg/ml 1 BiMAB IVT-mRNA or IVT-replicon RNA was added. Electroporation conditions were as follows: 300 V, 16 ms pulse length, 1 pulse, 400 ms interval length.

Electroporated cells were resuspended in RT culture medium (RPMI1640, 10% FCS) and transferred into 15 cm culture dishes. 5 h after seeding, medium containing FCS was replaced by FCS-free medium. In case of examples 24 a and b, cell culture supernatant and cells were harvested separately 18 h after electroporation. Cell pellets were lysed in 1×LDS sample buffer (cat. no. NP0008; Life technologies, Darmstadt, Germany) and heated at 72° C. for 15 min. For ELISA analysis non-concentrated and approximately 50-fold concentrated supernatant was used. Concentration was carried out with Amicon ultra-15 centrifugal filter units (Merck Millipore, Billerica, Mass., USA) according to the manufacturer's protocol. In case of example 24 c (IVT-mRNA only), supernatant was harvested 48 h post transfection and subjected to 40-fold concentration as described above.

a. ELISA Using Supernatant

For ELISA analysis Nickel coated plates (Thermo Fisher Scientific, Bonn, Germany) were used for capturing the analyte via its His-Tag. First, the plate was washed three times with 200 µl wash buffer (0.01% Tween-20 in 1×PBS) per well. As standard, purified 1BiMAB protein was diluted into 1.75% Na-Casein in 1×PBS(=diluent). The dilution row ranged from 2.34 to 37.50 ng/ml in steps of 2. 100 µl per standard dilution was transferred to the wells in triplicates of each concentration. Accordingly, 100 µl of the samples was transferred in triplicates. The plate was sealed with an adhesive film and incubated at 37° C. for 30 minutes. Afterwards, the plate was washed three times with 200 µl wash buffer per well. For the detection of 1BiMAB the anti-idiotypic monoclonal IgG 8B1F3 that specifically binds to $V_H$-$V_L$ of mCLDN18.2ab and therefore also to 1BiMAB was used. 8B1F3 was mixed into the diluent to a final concentration of 1 µg/ml. 100 µl of the anti-idiotypic antibody solution was transferred to each well followed by an incubation time of 30 min at 37° C. Subsequently, the plate was washed 3× with 200 µl wash buffer per well and 100 µl of an AP-conjugated anti-mouse detection antibody (Jackson Immuno Research laboratories, West Grove, Pa., USA)—diluted 1:500 in diluent—was added to each well followed by 30 min incubation at 37° C. After a final wash step (3×200 µl wash buffer), 1.5 mg/ml of the substrate pNPP in appropriate substrate buffer (1 M Diethanolamine, 0.5 mM MgCl$_2$, 0.01% Na-azide, pH 9.8) was added to each well, followed by incubation for 30 min at RT in the dark. 100 µl of 3 M KOH was used for each well to stop the enzymatic reaction. Absorbance was measured with a microplate-reader (Infinite M200, Tecan, Männedorf, Switzerland). For dual wavelength analysis 405 nm was set as measurement wavelength and 492 nm as reference wavelength. Absorbance values were calculated by subtraction of reference wavelength from measurement wavelength.

In FIG. 29A the mean absorbance values at 405 nm including standard deviations are plotted. Concentrated supernatant from 1 BiMAB IVT-mRNA and IVT-replicon transfected cells led to significant signals proving the translation of bi-scFv encoding IVT-RNA. Concentrated supernatant from mock transfected cells did not result in any signal. Actual protein concentrations cannot be proposed because of different toxicity of the IVT-mRNA and IVT-replicon constructs and slightly different x-fold concentrates. Estimation of approximate protein concentration in unconcentrated supernatant was in the range of 1.5 ng/ml for IVT-replicon samples and 2.4 ng/ml for IVT-mRNA samples.

b. Western Blot Analysis of Supernatant and Cell Lysate (IVT-mRNA and IVT-Replicon Samples)

For analysis by Western blot, concentrated supernatants and cell lysates were separated on NuPAGE Novex 4-12% Bis-iris Gels (Invitrogen/Life Technologies GmbH, Darmstadt, Germany). Supernatant and cell lysate of BHK21 cells transfected with 1BiMAB IVT-mRNA, IVT-replicon RNA or of untreated cells and a positive control—0.1 µg purified 1BiMAB protein—were loaded. Western blot analysis was performed by standard procedures (Current Protocols in Protein Science, 2012). Briefly, after blotting proteins on PVDF membrane and blocking with PBST/3% milk powder, the membrane was incubated for 1 h at 4° C. with primary antibody Anti-HIS Epitope-Tag (Dianova GmbH, Hamburg, Germany) diluted 1:500 in blocking buffer. After repeated washing with blocking buffer, membranes were incubated with Fc-specific secondary peroxidase-conjugated goat-anti-mouse IgG antibody (Sigma Aldrich, Germany) diluted 1:10000 in blocking buffer for 1 h at 4° C. After repeated washing with blocking buffer, the signals were visualized by SuperSignal West Femto Chemiluminescent Substrate (Pierce/Thermo Fisher Scientific, Rockford, Ill., USA) and recorded by an ImageQuant LAS 4000 Imager (GE Healthcare Life Sciences, Munich, Germany). Signals of 1BiMAB were detected between 50 and 60 kD as compared to the internal molecular weight standard.

As shown in FIG. 29 B weak signals were detected in supernatant of IVT-mRNA (lane 2) and IVT-replicon RNA (lane 3) transfected cells, whereas lane 4 with supernatant from untreated cells is without signal. Strong signals could be generated with cell lysates of IVT-mRNA (lane 5) and IVT-replicon RNA (lane 6) transfected cells. Cell lysate from untreated cells (lane 7) led again to no signal. All signals appeared at the same height as the purified 1BiMAB protein control (lane 8). The weak signal in the supernatant and with it the weak 1BiMAB secretion is probably owed to the relatively short incubation time after transfection. Due to the toxic effect of the replicon RNA longer incubation times could not be tested.

Both analyses are of qualitative nature and do not serve for protein concentration determinations.

c. Western Blot Analysis of Supernatant (IVT-mRNA Samples)

Supernatant collected 48 h post transfection was separated by SDS-PAGE followed by Western blot analysis as described under example 24 b. As shown in FIG. 29 C, no. 25 and 1 BiMAB translated from IVT-mRNA and secreted into the supernatant were detected via their His-tag. Herewith, the production and secretion of 1BiMAB as well as of no. 25 that has been used as bi-scFv specificity control could be proven.

Example 25

Detection of In Vivo Translated and Functional 1BiMAB Protein after Intramuscular RNA Injection Female and male NSG mice at an age of 8-16 weeks were selected and distributed into 4 groups A 5 mice. 40 µl RNA solution was injected per mouse and femoral muscle. 40 µl RNA solution consisted of 1×PBS, 5 µg D2-capped 1 BiMAB IVT-mRNA or replicon, 2 µg D1-capped luciferase IVT-mRNA and 0 or 15 µg D1-capped EBK IVT-mRNA. The EBK IVT-mRNA encoding the vaccinia virus proteins E3L, BI 8R and K3L, (EBK) was coinjected to inhibit IFN response and to counteract PKR activation for the purpose of RNA translation enhancement(Patent Application PCT/EP2012/04673). Luciferase signal was monitored 24 h post injection with a Xenogen IVIS 2000 to exclude mice without signal from sample b collections.

Blood was collected 2, 4 and 7 days post injection. Serum was harvested and subsequently frozen at −80° C. Muscles of mice with strong luminescence signal were dissected and histofixed for IHC or shock-frozen for Western blot analysis 4 days post RNA injection.

Cytotox Assay

Sera of NSG mice were analyzed in an in vitro cytotox assay. NugC4 target cells stably transduced with firefly luciferase and human CLDN18.2 for better target expression were seeded with human T cells (isolated as described under example 16) in an E:T ratio of 30 to 1 for maximum sensitivity. Assay medium consisted of RPMI 1640 medium supplemented with 10% heat inactivated FCS, 0.5% penicillin-streptomycin, 1×NEAA and 1 mM sodium pyruvate (Gibco/Life Technologies GmbH, Darmstadt, Germany). 20 µl of thawed test serum was added per test sample well. Standard 1BiMAB protein control wells, $L_{min}$ and $L_{max}$ wells were completed with 20 µl serum of untreated NSG mice. Final volume per well was 100 µl. $L_{min}$ was seeded twelvefold, $L_{max}$ sixfold and test samples in triplicates. After 48 h incubation at 37° C. and 5% $CO_2$ $L_{max}$ wells were mixed with 10 µl 2% Triton X-100 solution and incubated for 10 min. To all other wells 10 µl assay medium was added. 50 µl luciferin solution (see example 23) were added and plates were measured—after a 30 min incubation step at 37° C. in the dark—in an Infinite M200 microplate reader (TECAN, Männedorf, Switzerland). Calculation of specific target cell lysis was performed as described under example 23.

In FIG. 30 the percent specific lysis is plotted. Significant cytotoxic effects were detected in each group. Cytolytic effects were increased by factor 1.7 in the wells containing serum of mice injected with EBK and 1BiMAB IVT-mRNA and harvested 2 days post injection. Significantly lower effects were achieved by samples harvested 4 or 7 days post injection. In the case of 1BiMAB-replicon samples, sera harvested at later time points also generated strong cytolytic effects.

These data prove the in vivo translation of 1BiMAB from IVT-mRNA or -replicon and the secretion into the blood stream after intramuscular injection.

Example 26

Generation and Testing of Bispecific Binding Agents Targeting CLDN6 and CD3 a. Sequence Origin, Design of Bi-scFv Constructs, and Cloning into Template Vectors Bispecific tandem single chain antibody constructs (bi-scFv) containing binding domains specific for the human T cell receptor component CD3 and human tumor associated antigens (TAA) were prepared. The corresponding variable heavy chain regions ($V_H$) and the corresponding variable light chain regions ($V_L$) for each construct were specifically arranged from 5'- to 3'-end in consecutive order:

pST1-5'hAgKozak-$V_H^{\alpha CLDN6}$-$V_L^{\alpha CLDN6}$-$V_H^{\alpha CD3}$-$V_L^{\alpha CD3}$-His-2hBgUTR-A120 (6RHU5)

pST1-5'hAgKozak-$V_H^{\alpha CD3}$-$V_L^{\alpha CD3}$-$V_H^{\alpha CLDN6}$-$V_L^{\alpha CLDN6}$-His-2hBgUTR-A120 (6RHU3)

Table 9 summarizes all bi-scFv constructs specific for the TAA CLDN6 that were generated in the course of the invention. The CLDN18.2-specific bi-scFv construct 1BiMAB was used as control antibody. The bi-scFv constructs were generated by gene synthesis by GeneArt AG (GeneArt/Life Technologies GmbH, Regensburg, Germany) using the $V_H$ and $V_L$ sequences of the corresponding antibodies. Codon optimizations such as Homo sapiens (HS) or Mus musculus (MM) were implemented by GeneArt's GeneOptimizer® software, and are listed in Table 9. Information on specificity, sequence origin from monoclonal antibodies (mAB), codon usage, additional sequence features and references of all applied domains are summarized in Table 10. Variable domain sequence origin of the respective CD3 antibodies are listed in Table 10. Due to the high homology of human and mouse TAAs, the same anti-TAA $V_H$ and $V_L$ sequences could be used for the generation of bi-scFv constructs for mouse assays, but in combination with the $V_H$, $V_L$ sequences of the mouse specific anti-CD3 antibody clone 145-2C11.

DNA cloning and expression vector construction was carried out according to standard procedures (Green/Sambrook, Molecular Cloning, 2012) well known by the skilled person. Briefly, the leadoff bi-scFv DNA sequences were provided with a 5'-BsmBI and a 3'-XhoI restriction site for cloning into pST1 plasmids. A secretion signal sequence was introduced at the 5' end upstream of the bi-scFv sequence for bi-scFv secretion. A sequence coding for a 15 to 18 amino acid flexible glycine-serine peptide linker was inserted to join the $V_H$ and $V_L$ domains for the composition of the single chain variable antibody fragments (scFv) of which one binds to CD3 and the other to the TAA. To form a bispecific single chain antibody, the two scFv domain sequences were connected by a sequence coding for a short peptide linker (GGGGS). Together with this linker sequence a BamHI restriction site was introduced for scFv domain exchanges for the cloning of upcoming bi-scFV constructs. Briefly, 5'scFv-domains could be exchanged by BsmBI and BamHI restriction and 3'scFv-domains by BamHI and XhoI restriction. A C-terminal 6×His-tag served for detection analysis of the translated protein. For 6RHU3 replicon vector b production, the full 6RHU3 sequence including secretion signal and 6×His-tag was subcloned 3' to the subgenomic promoter of the Semliki forest virus replicon vector (pSFV) kindly provided by K. Lundström (Lundstrom, K. et al. (2001) Histochem. Cell Biol. 115 (1), pp. 83-91; Ebrengruber, M. U. et al. (1999) Proc. Natl. Acad. Sci. U.S.A. 96 (12), pp. 7041-7046).

All constructs were verified by sequencing via MWG's single read sequence service (Eurofins MWG Operon, Ebersberg, Germany) and only those with correct sequence and a Poly(A) tail of more than 100 adenines were used for in vitro RNA transcription.

For construct schemata see also FIG. 31 A.

TABLE 9

Summary of TAA and CD3 specific bispecific single chain antibody mRNA-template constructs

| Internal name | TAA | Specificity | 5'-$V_H$-$V_L$ | 3'-$V_H$-$V_L$ | Codon usage |
|---|---|---|---|---|---|
| 1BiMAB | CLDN18.2 | human | mCLDN18.2ab | TR66 | HS |
| 6RHU5 | CLDN6 | human | mCLDN6ab | TR66 | HS |
| 6RHU3 | CLDN6 | human | TR66 | mCLDN6ab | HS |
| 6RMU5 | CLDN6 | murine | mCLDN6ab | 145-2C11 | MM |
| 6RMU3 | CLDN6 | murine | 145-2C11 | mCLDN6ab | MM |

Bi-scFv indicates bispecific single chain variable fragment;
HS, Homo sapiens;
MM, Mus musculus;
TAA, tumor associated antigen;
$V_H$, variable heavy chain domain,
$V_L$, variable light chain domain.

TABLE 10

Summary of bi-scFv mRNA-template construct information

| Internal name | CD3 binding moiety | | TAA binding moiety | | Species reactivity | 5'-$V_H$-$V_L$ | 3'-$V_H$-$V_L$ | Short linker |
|---|---|---|---|---|---|---|---|---|
| | mAB origin | Species reactivity | TAA | mAB origin | | | | |
| 1BiMAB | TR66 | human | CLDN18.2 | mCLDN18.2ab | human, murine | mCLDN18.2ab | TR66 | GGGGS |
| 6RHU5 | TR66 | human | CLDN6 | mCLDN6ab | human, murine | mCLDNC6ab | TR66 | SGGGGS |
| 6RHU3 | TR66 | human | CLDN6 | mCLDN6ab | human, murine | TR66 | mCLDN6ab | SGGGGS |
| 6RMU5 | 145-2C11 | murine | CLDN6 | mCLDN6ab | human, murine | mCLDN6ab | 145-2C11 | SGGGGS |
| 6RMU3 | 145-2C11 | murine | CLDN6 | mCLDN6ab | human, murine | 145-2C11 | mCLDN6ab | SGGGGS |

| Internal name | 5'-long linker | 3'-long linker | Secretion ssignal | Codon usage | Anti-CD3 mAB reference |
|---|---|---|---|---|---|
| 1BiMAB | (GGGGS)₃ | VE(GGSGGS)₂ GGVD | MGWSCIILFL VATATGVHS | HS | Lanzavecchia & Scheidegger, Eur J Immunol 1987 |
| 6RHU5 | (GGGGS)₃ | VE(GGSGGS)₂ GGVD | MGWSCIILFL VATATGVHS | HS | Lanzavecchia & Scheidegger, Eur J Immunol 1987 |
| 6RHU3 | VE(GGSGGS)₂ GGVD | (GGGGS)₃ | MGWSCIILFL VATATGVHS | HS | Lanzavecchia & Scheidegger, Eur J Immunol 1987 |
| 6RMU5 | (GGGGS)₃ | VE(GGSGGS)₂ GGVD | MGWSCIILFL VATATGVHS | MM | Leo et al., Proc Natl Acad Sci, 1987 |

TABLE 10-continued

Summary of bi-scFv mRNA-template construct information

| 6RMU3 | VE(GGSGGS)₂ (GGGGS)₃ GGVD | MNSGLQLVF FVLTLKGIQG | MM | Leo et al., Proc Natl Acad Sci, 1987 |

HS, Homo sapiens; mAB, monoclonal antibody; MM, Mus musculus; TAA, tumor associated antigen.

b. IVT-RNA Synthesis

For the generation of anti-CLDN6-specific bi-scFv IVT templates, plasmids were linearized downstream the poly (A)-tail using a class IIs endonuclease. Linearized template DNA was purified by phenol/chloroform extraction and sodium acetate precipitation as described elsewhere (Holtkamp, S. et al. (2006) *Blood* 108 (13), pp. 4009-4017).

Linearized DNA templates were subjected to in vitro transcription using MEGAscript Kits (Ambion/Life Technologies, Darmstadt, Germany) according to the manufacturer's guidelines: pST1 templates were transcribed with the MEGAscript T7 Kit and pSFV templates with the MEGAscript SP6 Kit. For reactions with cap analoga, the GTP concentration was lowered to 1.5 mM, and 6 mM of ARCA, beta-S-ARCA(D1), or beta-S-ARCA(D2), synthesized as described elsewhere (Grudzien, E. et al. (2004) *RNA* 10 (9), pp. 1479-1487; Kowalska, J. et al. (2008) *RNA* 14 (6), pp. 1119-1131; Stepinski, J. et al. (2001) *RNA* 7 (10), pp. 1486-1495) was added to the reaction. Purification of IVT-RNA was carried out with the MEGAclear Kit (Ambion/Life Technologies, Darmstadt, Germany) according to the manual. Concentration and quality of the IVT-RNA were assessed by spectrophotometry and analysis on a 2100 Bioanalyzer (Agilent Technologies, Santa Clara, Calif., USA).

Example 27

Microscopic Analysis of T Cells Redirected to Target Cells Secreting CLDN6-specific bi-scFv 1BiMAB The assay set-up was in principle performed as described under example 2.a.

As target cell line a subclone of the ovarian teratocarcinoma cell line PA-1 (ATCC CRL-1572) that endogenously expresses high levels of human CLDN6 was used. Human cytotoxic T cells were isolated by MACS from freshly isolated PBMCs by Pan T Cell Isolation Kit II, human (Miltenyi Biotec, Teterow, Germany) according to the manufacturer's guidelines.

PA-1 target cells—that are routinely tested for TAA expression by FACS analysis before every assay—were washed twice with ice cold X-Vivo 15 medium (LONZA, Basel, Switzerland) and resuspended to a density of $2\times10^7$ cells/ml. 250 µl cell suspension was transferred to pre-cooled 0.4 cm Gene Pulser/MicroPulser Cuvettes (Bio-Rad, Dreieich, Germany) and 20 µg/ml IVT-mRNA was added. Conditions using a BTX ECM 830 electroporator (Harvard Apparatus, Holliston, Mass., USA) were: 200 V, 12 ms pulse length, 2 pulses, 400 ms interval length. IVT-mRNAs used were: 6RHU5, 6RHU3, no. 25 (for details see tables 9 and 10). Transfected target cells were counted and adjusted to $1\times10^5$ cells per ml. $1\times10^5$ target cells were seeded per well of a 6-well plate and human cytotoxic T cells were added according to an E:T ratio of 5:1. The final volume per well was 2 ml. Control samples comprised transfected target cells alone to proof healthiness after electroporation and control bi-scFv transfected target cells with effector cells. As positive controls the corresponding CLDN6-specific bi-scFv proteins 6PHU5 and 6PHU3 were implemented in a concentration of 50 µg/ml. Therefore, untreated PA-1 cells with human T cells were used. Tissue culture plates were subsequently incubated at 37° C., 5% $CO_2$. Significant effects in terms of T cell clustering on target cells, formation of an immunologic synapse and target cell killing in samples containing 6RHU5 or 6RHU3 transfected target cells were seen after 24 h and recorded with a Nikon Eclipse TS100 inverted microscope (Nikon, Japan). As shown in FIG. 32, no T cell clustering or target cell lysis was observed in the control sample with no. 25 transfected target cells implying the strict dependency on TAA expression to induce an activation of T cells. The mock control without bi-scFv shows also no T cell clustering. Protein controls instead led to strong T cell clustering and target cell lysis.

Example 28

T Cell Activation Induced by CLDN6-targeting Bi-scFv Candidates 6RHU5 and 6RHU3

For the detection of T cell activation and to define differences in the efficiency of the two CLDN6-specific bi-scFv variants, a FACS-based T cell activation assay was conducted. The early activation marker CD69 and the late activation marker CD25 were selected for staining by fluorescence-conjugated antibodies. For the detection of human T cells in the mixture of target and T cells, CD3 expressed by all T cells was stained.

Target and effector cells were prepared as described above (example 27). Briefly, PA-1 target cells endogenously expressing CLDN6 were transfected by electroporation with 20 µg/ml of the following IVT-mRNAs: 6RHU5, 6RHU3 and no. 25. No. 25, targeting a non-expressed TAA, served as specificity control, untreated target cells as mock control. As positive control 50 ng/ml 6PHU5 protein was used. Further, T cells were seeded without target cells with or without 6PHU5 protein as background activation references. Each sample was seeded in duplicate in 6-well plates and incubated at 37° C., 5% $CO_2$. After 24 h and 48 h T cells were harvested by scraping and transferred to 5 ml round bottom tubes (BD Falcon, Heidelberg, Germany). Cells were centrifuged and washed with DPBS. For cell staining Mouse Anti-Human CD3-FITC, Mouse Anti-Human CD69-APC, and Mouse Anti-Human CD25-PE (all antibodies BD Biosciences, Heidelberg, Germany) were used. Cell pellets were resuspended in 50 µl FACS-buffer (DPBS supplemented with 5% FBS) containing the fluorescence-conjugated antibodies and 2 µl 7-AAD (RD Biosciences, Heidelberg, Germany). After incubation for 20 min at 4° C. in the dark, samples were washed with 4 ml DPBS and cell pellets were resuspended in 200 µl FACS buffer. Samples were kept on ice and dark throughout the measurement with a FACSCanto II flow cytometer (both BD Biosciences, Heidelberg, Germany). Analysis was evaluated by FlowJo software (Tree Star, San Carlos, Calif., USA).

As shown in FIGS. 33 A and B both variants led to T cell activation, whereas none of the negative controls showed significant expression of T cell activation markers CD69 or CD25.

Total T cell activation in response to 6RHU3 was 1.53-fold higher after 24 h (A) and 1.35-fold higher after 48 h (B) of coincubation than in response to 6RHU5. Based on these findings all further studies were conducted with variant 6RHU3 only.

Example 29

Concentration Dependent T Cell Activation by Coincubation with 6RHU3 Transfected Target Cells For the determination of the lowest 6RHU3 IVT-mRNA concentration necessary to induce a target-dependent T cell activation a dilution range from 0.2-20 µg/ml IVT-mRNA was transfected into PA-1 target cells. To expose all samples to the same stress level by RNA electroporation, a total concentration of 20 µpg/ml IVT-mRNA was transfected. No. 25—targeting a non-expressed TAA—was used as fill-up IVT-mRNA. Accordingly, 0 µg/ml 6RHU3 correlates to 20 µg/ml no. 25. Electroporation was performed as described under example 27. Human T cells were used as effector cells. Isolation from PBMCs was performed following the manufacturers manual (Pan T Cell Isolation Kit II, Miltenyi, Teterow, Germany). Effector and target cells were mixed in a 5:1 ratio. Untreated target cells with T cells served as mock control. Further, T cells were seeded without target cells with or without 6PHU5 protein as background activation references. As positive control, untreated target cells were mixed with T cells and 50 ng/ml 6PHU5 protein. All samples were prepared in duplicates in 6-well plates.

Target and effector cells were coincubated for 48 h at 37° C., 5% $CO_2$. Samples were prepared for flow cytometric analysis as described under example 28.

In FIG. 34 the percentage of CD3-positive T cells that express activation markers is plotted. No T cell activation was observed in the controls. Detection of a significant T cell activation started at a concentration of 0.7 µg/ml 6RHU3 IVT-mRNA. Effects in response to 2.0 µg/ml 6RHU3 IVT-mRNA were comparable to those mediated by 50 ng/ml 6PHU5 protein control. Hence, protein translation and secretion from transfected IVT-mRNA seems to be an efficient process.

Example 30

Determination of $EC_{50}$ for 6RHU3

For the determination of the half maximal effective dose of bi-scFv encoding IVT-mRNA 6RHU3, a titration row of 6RHU3 was tested in an in vitro luciferase cytotox assay. Stably luciferase-expressing PA-1 cells were transiently transfected by electroporation as described under example 27. 6RHU3 IVT-mRNA concentrations used ranged from 0.004-13.3 µg/ml in 6 dilution steps. Total IVT-mRNA concentration was constantly set to 13.3 µg/ml, no. 25 was used as fill-up IVT-mRNA. As minimum lysis controls ($L_{min}$) all transfected target cell samples were seeded without effector cells. By this procedure the background dead cells of each individual electroporation sample is subtracted and only T cell mediated lysis effects will be obtained.

Transfected target cells were seeded with human T cells in an effector to target ratio of 5:1 in triplicates in a 96-well format and incubated at 37° C., 5% $CO_2$. Maximum lysis ($L_{max}$) for the normalization to spontaneous luminescence counts was achieved by addition of Triton X-100 to control wells containing effector and non-treated target cells shortly prior to luciferin addition. After addition of luciferin solution—per well 50 µl of a water solution containing 1 mg/ml luciferin (BD Monolight, BD Biosciences, Heidelberg, Germany) and 50 mM HEPES—the luminescence was measured in an Infinite M200 Tecan microplate reader after 24 h and 48 h. Specific target cell lysis was calculated by the formula: % specific lysis=[1−(luminescence$_{test\ sample}$−$L_{max}$)/($L_{min\_test\ sample}$−$L_{max}$)]×100.

FIG. 35 depicts the concentration-dependent curve for specific target cell lysis in response to 6RHU3. Using GraphPad Prism equation "log(agonist) vs. response—Variable slope" for calculation of $EC_{50}$ values revealed an $EC_{50}$ (24 h)=548.0 ng/ml, and an $EC_{50}$ (48 h)=194.5 ng/ml. The outcome of this assay strongly depends on the potency of the human T cells which varies according to the immune status of the donor as also reported by others (see e.g. (Lutterbuese, R. et al. (2010) *Proc. Natl. Acad. Sci. U.S.A.* 107 (28), pp. 12605-12610). Therefore, results can differ with each donor.

Example 31

T Cell Proliferation in Response to 6RHU3 IVT-mRNA Transfection

T cell proliferation is an indicator of T cell activation. To show specific T cell proliferation in response to bi-scFv encoding IVT-mRNA 1BiMAB in the presence of CLDN6 positive target cells, a flow cytometric assay was used. Briefly, 1×10$^7$ human T cells isolated as described under example 16 were stained with 1 µM carboxyfluorescein diacetate succinimidyl ester (CellTrace CFSE, Invitrogen/Life Technologies GmbH, Germany) dissolved in DPBS in the dark at RT for 5 min. Cells were washed twice with DPBS/5% FCS and resuspended in assay medium to 2×10$^6$ cells per ml. As target cells, PA-1 endogenously expressing CLDN6 and—for specificity testing—the CLDN6-negative breast cancer cell line MDA-MB-231 were chosen. 20 µg/ml of IVT-mRNAs 6RHU3 or a non-targeting control were used for electroporation. Electroporation of PA-1 was performed as described under example 27. MDA-MB-231 electroporation was conducted using the following conditions: 400 V, 3 ms pulse length, 1 pulse, 400 ms interval length in 0.4 cm Gene Pulser/MicroPulser Cuvettes (Bio-Rad, Dreieich, Germany). A cytotox assay as described under example 27 was set up with the transfected target cells and human CFSE-labeled T cells as effector cells. T cells alone and untransfected or control transfected target cells plus T cells were used as negative controls. T cells alone stimulated with 5 µg/ml OKT3 (Bio X Cell, West Lebanon, N.H., USA) and 2 µg/ml anti-CD28 (BioLegend, Fell, Germany) served as positive control. 6PHU3 protein in a concentration of 5 ng/ml was applied to untransfected target plus T cells to confirm the assay validity. Samples combined with the non-targeting bi-scFv protein 1BiMAB were included as specificity control. All samples were set up in triplicates in a total volume of 0.2 ml assay medium in 96 wells. After 72 h of coincubation, T cells were harvested, collected in 5 ml round bottom tubes, washed and stained at 4° C. for 30 min with 2 µl anti-CD45-APC to differentiate human T cells from tumor cells and 0.25 µl eFluor506 (BD Biosciences, Heidelberg, Germany) to counterstain dead cells in 200 µl DPBS. After washing with DPBS, cells were resuspended in FACS-buffer and analyzed with a FACSCanto II (BD) Biosciences, Heidelberg, Germany).

Proliferation of T cells was detected by decreasing CFSE-signal only in the presence of CLDN6 positive target cells and anti-CLDN6-specific bi-scFv (see also FIG. 36). Besides the positive control, T cell proliferation of 49-61% could be observed in the presence of CDLN6 positive target cells in combination with 6PHU3 protein. Target positive cells transfected with 6RHU3 IVT-mRNA led to 62%+/−2%. T cells incubated with CLDN6 negative target cells MDA-MB-231 do not show a significant proliferation in any constellation as well as T cells without target cells except for the positive control.

Example 32

Qualitative Analysis of Protein Production after 6RHU3 IVT-RNA Transfection of Mammalian Cells For the investigation of RNA translation into protein in mammalian cells the cell line BHK21 (ATCC CRL-3001) was chosen as expression system. $2 \times 10^7$ BHK21 cells per ml were transfected by electroporation as described under example 16 with the difference that all steps were conducted at RT. 250 µl cell suspension was transferred to 0.4 cm Gene Pulser/MicroPulser Cuvettes (Bio-Rad, Dreieich, Germany) and 40 µg/ml no. 25 IVT-mRNA, 6RHU3 IVT-mRNA or 6RHU3 IVT-replicon RNA was added. Electroporation conditions were as follows: 300 V, 16 ms pulse length, 1 pulse, 400 ms interval length.

Electroporated cells were resuspended in RT culture medium (RPMI1640, 10% FCS) and transferred into 15 cm culture dishes. 5 h after seeding, medium containing FCS was replaced by FCS-free medium. In case of examples 32 a and b, 18 h after electroporation cell culture supernatant and cells were harvested separately. Cell pellets were lysed in 1×LDS sample buffer (cat. no. NP0008; Life technologies, Darmstadt, Germany) and heated at 72° C. for 15 min. For ELISA analysis non-concentrated and approximately 50-fold concentrated supernatant was used. Concentration was carried out with Amicon ultra-15 centrifugal filter units (Merck Millipore, Billerica, Mass., USA) according to the manufacturer's protocol. In case of example 32 c (IVT-mRNA only), supernatant was harvested 48 h post transfection and subjected to 40× concentration as described above.

a. ELISA Using Supernatant

For ELISA analysis Nickel coated plates (Thermo Fisher Scientific, Bonn, Germany) were used for capturing the analyte via its His-Tag. First, the plate was washed three times with 200 µl wash buffer (0.01% Tween-20 in 1×PBS) per well. As standard, purified 6PHU3 protein was diluted into 1.75% Na-Casein in 1×PBS(=diluent). The dilution row ranged from 2.34 to 150 ng/ml in steps of 2. 100 µl per standard dilution was transferred to the wells in triplicates of each concentration. Accordingly, 100 µl of the samples was transferred in triplicates. The plate was sealed with an adhesive film and incubated at 37° C. for 30 minutes. Afterwards, the plate was washed three times with 200 µl wash buffer per well. For the detection of 6PHU3/6RHU3, the anti-idiotypic monoclonal IgG 4F9 that specifically binds to $V_H$-$V_L$ of mCLDN6ab and therefore also to 6PHU3/6RHU3, was used. 4F9 was mixed into the diluent to a final concentration of 2.5 pg/ml. 100 µl of the anti-idiotypic antibody solution was transferred to each well followed by an incubation time of 30 min at 37° C. Subsequently, the plate was washed 3× with 200 µl wash buffer per well and 100 µl of an AP-conjugated anti-mouse detection antibody (Jackson Immuno Research Laboratories, West Grove, Pa., USA) diluted 1:500 in diluent was added to each well followed by 30 min incubation at 37° C. After a final wash step (3×200 µl wash buffer), 1.5 mg/ml of the substrate pNPP in appropriate substrate buffer (1 M Diethanolamine, 0.5 mM $MgCl_2$, 0.01% Na-azide, pH 9.8) was added to each well, followed by incubation for 30 min at RT in the dark. 100 µl of 3 M KOH was used for each well to stop the enzymatic reaction. Absorbance was measured with a microplate-reader (Infinite M200, Tecan, Männedorf, Switzerland). For dual wavelength analysis 405 nm was chosen as measurement wavelength and 492 nm as reference wavelength. Absorbance values were calculated by subtraction of reference wavelength from measurement wavelength.

In FIG. 37 A the mean absorbance values including standard deviations are plotted. Concentrated supernatant from 6RHU3 IVT-mRNA and IVT-replicon transfected cells led to significant signals proving the translation of bi-scFv encoding IVT-RNA. Concentrated supernatant from mock and no. 25 control (−ctrl) transfected cells did not result in any signal as expected. Actual protein concentrations cannot be proposed because of different toxicity of the IVT-mRNA and IVT-replicon constructs and slightly different x-fold concentrates. Estimation of approximate protein concentration in non-concentrated supernatant was in the range of 1.4 ng/ml for IVT-replicon and 5.9 ng/ml for IVT-mRNA samples.

b. Western Blot Analysis of Supernatant and Cell Lysates (IVT-mRNA and -replicon Samples)

For analysis by Western blot, concentrated supernatants and cell lysates were separated on NuPAGE Novex 4-12% Bis-Tris Gels (Invitrogen/Life Technologies GmbH, Darmstadt, Germany). Supernatant and cell lysate of BHK21 cells transfected with 6RHU3 IVT-mRNA, IVT-replicon RNA, no. 25 IVT-mRNA or of untreated cells and a positive control—0.1 µg purified 6PHU3 protein—were loaded. Western blot analysis was performed by standard procedures (Current Protocols in Protein Science, 2012). Briefly, after blotting proteins on PVDF membrane and blocking with PBST/3% milk powder, the membrane was incubated for 1 h at 4° C. with primary antibody Anti-HIS Epitope-Tag (Dianova GmbH, Hamburg, Germany) diluted 1:500 in blocking buffer. After repeated washing with blocking buffer, membranes were incubated with Fc-specific secondary peroxidase-conjugated goat-anti-mouse IgG antibody (Sigma Aldrich, Germany) diluted 1:10000 in blocking buffer for 1 h at 4° C. After repeated washing again with blocking buffer, the signals were visualized by SuperSignal West Femto Chemiluminescent Substrate (Pierce/Thermo Fisher Scientific, Rockford, Ill., USA) and recorded by an ImageQuant LAS 4000 Imager (GE Healthcare Life Sciences, Munich, Germany). Signals of 6PHU3 were detected between 50 and 60 kD as compared to the internal molecular weight standard.

As shown in FIG. 37 B signals were detected in supernatants of no. 25 IVT-mRNA (lane 1), 6RHU3 IVT-mRNA (lane 4) and 6RHU3 IVT-replicon RNA (lane 5) transfected cells, whereas lane 6 with supernatant from untreated cells is without signal. Strong signals could be generated with cell lysates of 6RHU3 IVT-mRNA (lane 8) and IVT-replicon RNA (lane 9) transfected cells. Cell lysate from no. 25 transfected cells led to a very weak signal (lane 2), untreated cells (lane 10) showed no signal. Purified 6PHU3 protein control (lane 11) could be detected. The relatively weak signals in the supernatant and with it the weak 6RHU3 secretion are probably owed to the relatively short incubation time after transfection. Due to the toxic effect of the replicon RNA longer incubation times could not be tested.

Both analyses—ELISA and Western blot—are of qualitative nature and do not serve as protein concentration determinations.

c. Western Blot Analysis of Supernatant (IVT-mRNA Samples)

Supernatant collected 48 h post transfection was separated by SDS-PAGE followed by Western blot analysis as described under example 32 b. As shown in FIG. 37 C, no. 25 and 6RHU3 translated from IVT-mRNA and secreted into the supernatant were detected via their His-tag. Herewith, the production and secretion of 6RHU3 as well as of no. 25 that has been used as bi-scFv specificity control could be proven.

Example 33

Detection of In Vive Translated and Functional CLDN6-specific Bi-scFv Protein after Intramuscular RNA Injection Female and male NSG mice at an age of 8-16 weeks were selected and distributed into 4 groups a 5 mice. 40 µl RNA solution was injected per mouse and femoral muscle. 40 µl RNA solution consisted of 1×PBS, 5 pg D2-capped 6RHU3 IVT-mRNA or replicon, 2 µg D1-capped luciferase IVT-mRNA and 0 or 15 µg D1-capped EBK IVT-mRNA. The EBK IVT-mRNA encoding the vaccinia virus proteins E3L, B18R and K3L. (EBK) were coinjected to inhibit IFN response and to counteract PKR activation for the purpose of RNA translation enhancement(Patent Application PCT/EP2012/04673). Luciferase signal was monitored 24 h post injection with a Xenogen IVIS 2000 to exclude mice without signal from sample collections.

Blood was collected 7 days post injection. Serum was harvested and subsequently frozen at −80° C.

Cytotox Assay

Sera of NSG mice were analyzed in an in vitro cytotox assay. PA-1 target cells stably transduced with firefly luciferase and endogenously expressing CLDN6 were seeded with human T cells (isolated as described under example 16) in an E:T ratio of 30 to 1 for maximum sensitivity. Assay medium consisted of RPMI 1640 medium supplemented with 10% heat inactivated FCS, 0.5% penicillin-streptomycin, lx NEAA and 1 mM sodium pyruvate (Gibco/Life Technologies GmbH, Darmstadt, Germany). 20 µl of thawed test serum was added per test sample well. 6PHU3 protein standard control wells, $L_{min}$ and $L_{max}$ wells were completed with 20 µl serum of untreated NSG mice. Final volume per well was 100 µl. $L_{min}$ was seeded twelvefold, $L_{max}$ sixfold and test samples in triplicates. After 48 h incubation at 37° C., 5% $CO_2$ $L_{max}$ wells were mixed with 10 µl 2% Triton X-100 solution and incubated for 10 min. To all other wells 10 µl assay medium was added. 50 µl luciferin solution (see example 23) were added and plates were measured—after a 30 min incubation step at 37° C. in the dark—in an Infinite M200 microplate reader (TECAN, Männedorf, Switzerland). Calculation of specific target cell lysis was performed as described under example 23.

In FIG. 38 the percentage of specific lysis is plotted. Significant cytotoxic effects were detected in each group. CLDN6-specific bi-scFv protein concentration was significantly increased by EBK coinjection in the case of 6RHU3 IVT-mRNA.

These data prove the in vivo translation of 6RHU3 from IVT-mRNA or -replicon and the secretion into the blood stream after intramuscular injection.

Example 34

Generation and Testing of Bispecific Binding Agents Targeting CLDN18.2 or CLDN6 and CD3

In the further development of anti-CLDN18.2 and anti-CLDN6 specific bi-scFv antibody fragments different aspects for an optimization of the original protein were addressed. These aspects referred mainly towards obtaining preparations with higher homogeneity with respect to different folding species, disulfide isomers, and oligomers which might form upon recombinant protein production. These modifications should not be prejudicial to the functional activity of the bi-scFv proteins.

Substitution of the Extra (Unpaired) Cysteine Residue in the Anti-CD3 Binding Domain of the Bi-scFv Proteins In order to investigate whether unpaired cysteine residues occurring within the primary sequence of an Ig domain might interfere with the correct formation of the intrachain and/or interchain disulphide bounds which are essential for the proper folding and the stability of the resulting antibody fragment or not, several synthetic constructs were generated. Such unpaired cysteines might compromise efficacy, homogeneity, productivity and stability of the final protein product and should therefore be avoided. In addition to the "standard" set of cysteines involved in disulfide pairing free cysteine residues can be present in the variable domains.

For example in the VH domain from the OKT3 antibody, three residues before the start of CDR-H3 a conserved cysteine at position H92 is present and forms a structural disulfide bond with position H22. But in this molecule at the position H100A (CDR-H3), another Cysteine (Cys) could allow mis-folding where H100A instead of I192 is involved in forming the disulfide bond with H22, thereby generating a mis-folded, insoluble and non-functional product. To overcome this possible mis-pairing of the cysteine residues, site directed substitution of the free cysteine was performed (Kipriyanov, Protein Engineering 10:445-453, 1997). By this single substitution a significant increase of productivity and stability of the scFv derived from OKT3 was achieved maintaining the overall binding activity.

The VH domain of the anti-CD3 antibody TR66 (SEQ ID NO: 36) used in the present study contains such a free cysteine at position H103 of the primary sequence as shown in SEQ ID NO: 36. Sequence comparison of the VH domain of the anti-CD3 antibody TR66 (SEQ ID NO: 36) with the VH domain of the anti-CD3 antibody OKT3 shows 96.6% sequence homology.

Following these results, a substitution of the free cysteine by a serine residue within the CDR-H3 of the VH domain of the anti-CD3 antibody TR66 was performed for bi-scFv proteins targeting CD3 (SEQ ID NO: 94) and either for CLDN18.2 or CLDN6. The introduction of such substitutions results in the design of the bi-scFv proteins 1-BiMAB-S(SEQ ID NO: 103) and 6-PHU3-S(SEQ ID) NO: 101) (sec Tables 11 and 12, respectively).

Substitution of the Extra (Unpaired) Cysteine Residues in Anti-CLDN6 Bi-scFv Proteins The parental anti-CLDN6 antibody mCLDN6ab, whose variable domains were used for the assembly of the corresponding bi-scFv proteins 6PHU3 (SEQ ID NO: 45) and 6PHU5 (SEQ ID NO: 43), contains an unpaired cysteine residue within the flanking region of the CDR-L2 of the VL domain at position 46 of the corresponding primary sequence. This corresponds to position 45 within SEQ ID NO: 23 where the first amino acid of the VL has been omitted. Different substitutions were performed to substitute this free cysteine by:
- a serine residue in analogy to the substitution in the VH domain of the anti-CD3 antibody TR66 (SEQ ID NO: 100).
- a leucine residue, by comparison with the amino acid sequence of other anti-CLDN6 antibodies (SEQ ID NO: 97 and 98).
- a tryptophan residue, by amino acid sequence comparison with the germline database (SEQ ID NO: 99).

Evaluation of Linker Length, Order of V-domains and Artificial Interface Disulfide Bonds in Anti-CLDN18.2 hi-scFv Proteins As another example Arndt et al. (Biochemistry 37:12918-12926, 1998) describe the so called domain swapping as a possible explanation for the appearance of non-covalently linked oligomers of scFv fragments. Under this model the protein state is subjected to a possible thermodynamic equilibrium between a monomeric and a dimeric/oligomeric form due to a constantly occurring intra- and intermolecular exchange of the VL/VH interface contacts. These oligomers could be present already in the cell culture supernatant and should be eliminated during the purification process. However these molecular species could be also formed during the storage of purified monomeric species.

The preferred energetic status of the protein is strongly influenced by its overall design (primary sequence, linker length, VL/VH orientation etc.).

Wörn and Plückthun (JMB 305:989-1010, 1999) mentioned that forms with higher content of monomeric species could be obtained by using a linker of 20 or more residues. Desplaneq et al., (Protein Eng. 7:1027-1033, 1994) indicated that the variable domain orientation could also have an impact on the formation of dimers and high molecular forms. In the same publication Desplaneq showed that a linker of 25 or 30 amino acids (aa) gave the best ratio of monomer over dimer for their particular antibody. The distance between the C-terminus of VL and the N-terminus of VH is around 39-43 Å, and the distance between the C-terminus of VH and N-terminus of VL is 32-34 Å (Plückthun et al., From PCR to fermentation. (J. McCafferty, H. R. Hoogenboom, & D. J. Chriswell, Eds.). In: (IRL Press., pp. 203-252, 1996). To obtain similar molecular properties, a linker for the orientation VL-VH has to be longer than a VH-VL linker. Plückthun et al., (From PCR to fermentation. (J. McCafferty, H. R. Hoogenboom, & D. J. Chriswell, Eds.). In: (IRL Press., pp. 203-252, 1996) recommended using linkers with a length of 15 or 20 amino acids in the orientation VH/VL and linkers with a length of 20 or 25 amino acids in the orientation VL/VH.

Another possibility to force the formation of monomers and to stabilize the VH/VL domain interaction is to engineer an interface disulfide bond into the contact surface between the two domains. The introduction of a disulfide bridge at the position H44-L100 (Kabat numbering) has been the most frequently used in scFvs with satisfactory results (Brinkmann et al., PNAS. 90:7538-7542, 1993; Worn and Plückthun, Biochemistry 38: 8739-8750, 1999; Weatherill et al., PEDS. 25:321-329, 2012). This strategy has been used successfully to stabilize IgG-like bispecific antibodies combining scFv fused to full length IgG (Michaelson et al., mAbs 1: 128-141, 2009; Schanzer et al., Antimicrob. Agents. Chemother. 55:2369-2378, 2011).

Weatherill et al., (PEDS 25:321-239, 2012) stabilized human scFvs (VH-(CG4S)$_4$-VL and VL-(G4S)$_4$—VH) with a disulfide bond between the position $V_H$44 and $V_L$-100. Moreover this publication address the problem of possible domain swapping with scFv containing no interface disulfide bond by performing different SE-HPLC experiments at different load volume and concentration. The assays gave different results depending on the sample loading conditions for the non-stabilized scFv, but independent of the conditions used the disulfide stabilized molecules eluted like a monomer. Zhao et al., (Int. J. Mol. Sci. 12:1-11, 2011) introduced the same mutation in a scFv and observed higher stability of the stabilized molecule after storage for 20 h at 37° C.

For the bispecific format using scFv fused to full length IgG, Schanzer et al., (Antimicrob. Agents Chemother. 55:2369-2378 2011) compared the effect of the linker length and interface disulfide bond. They fused the parental scFv or scdFv (VH-(G4S)$_3$-VL) either at the C- or N-terminal part of the heavy chain or light chains. For the different linker length (20, 25 and 30 amino acids) they fused the parental scFv to the C-terminal part either of the heavy or light chains. The results obtained with the different linker length identified the 30 as peptide as the more preferable linker for the production of stable monomers. The level of aggregates after 7 days storage at 40° C. was 50% for scFv$_{15}$, 18% for scFv$_{20}$, 8% for scFv$_{25}$ and 6% for scFv$_{30}$. But the disulfide scFv$_{15}$ stabilized with the interface disulfide bond was slightly superior to the scFv$_{30}$. The same approach was used by Michaelson et al., (mAbs, 1:128-141 2009), and they improved their parental IgG-like bispecific antibody containing scFv with 15 aa linker in VH/VL orientation (generating 40% aggregates), by increasing the linker length to 20 aa of the scFv and introducing the interface disulfide bond between the position $V_H$44 and $V_L$-100. The resulting molecule yielded more than 98% monomers that were stable after three months at 4° C. The authors took the decision to work on the improvement of the scFv molecule before going to the bispecific format.

In the case of anti-CLDN18.2 specific bi-scFv proteins, it is not known if the formation of dimers and high molecular forms could occur and what is the implication on the anti-Claudin and/or the anti-CD3 scFv molecules. In order to assess an optimal overall molecule for the anti-CLDN18.2 specific bi-scFv protein for each separate scFv the following modifications have been evaluated:
- domain orientation
- linker length
- introduction of an interface disulfide bond
- Combination of the three modifications For the anti-Claudin 18.2 binding domain, in addition to the variable domains derived from the mCLDN18.2ah (VH: SEQ ID NO: 8; VL: SEQ ID NO: 15), the sequences derived from the mCLDN18.2ab1 (VH: SEQ ID NO: 6; VL: SEQ ID NO: 11) have been used for the construction of anti-CLDN18.2 specific bi-scFv proteins.

Table 11 in section A.a "Sequence origin, design of 32 anti-CLDN18.2 specific bi-scFv constructs, and cloning into expression vectors" describes the different constructs.

A. Generation and Testing of Bispecific Binding Agents Targeting CLDN18.2 and CD3 a. Sequence Origin, Design of 32 Anti-CLDN8.2 Specific Bi-scFv Constructs, and Cloning into Expression Vectors The bispecific tandem single chain antibody constructs bi-scFv presented herein contain two distinct binding domains from which the first is specific for a human tumor associated antigen (TAA), whereas the second is specific for the a-chain of human T cell receptor (CD3). Each of the two binding domains of the bispecific molecule comprises two antibody variable domains, arranged as scFv moiety in either VH-VL or VL-VH orientation. The antibody variable domains are connected via a flexible glycin-serine peptide linker consisting of four or five repeats of a $G_4S$ subunit, dependent on the orientation. Thus, the scFv moieties arranged in the VH-VL orientation are connected by a 20 amino acid linker (named "LL4"), the VL-VH is connected by a 25 amino acid linker (named "LL5"). The two scFv moities on the other hand are connected via a six amino acids long $SG_4S$ linker (named "SL"). Information on sequence origin from monoclonal antibodies (mAB) and domain organization are summarized in Table 11.

The variants 5504, 5505, 5506, 5507, 5512, 5513, 5514, 5515, 5520, 5521, 5522, 5523, 5528, 5529, 5530, 5531, 5536, 5537, 5538, 5539, 5544, 5545, 5546, 5547, 5552, 5553, 5554, 5555, 5560, 5561, 5562 and 5563 comprises the VH anti-CD3 with the SEQ ID NO: 95 and the VL anti-CD3 with the SEQ ID NO: 96.

In the particular case of the 1-BiMAB-S, only the substitution of the free cysteine by a serine in the VH anti-CD3 (SEQ ID NO: 94) is done in comparison to the amino acid sequence of the 1-BiMAB sequence (SEQ ID NO: 39). It should be noted that SEQ ID NO: 39 still contains the amino acid sequence of an N-terminal signal sequence which mediates the secretion of the 1-BiMAB bi-scFv protein into the cell culture supernatant upon mammalian expression. This signal sequence is not part of the secreted recombinant protein since it is cleaved off by a signal peptidase in the lumen of the reticulum endoplasmic reticulum.

The genes encoding the bi-scFv constructs were generated via GeneArt® gene synthesis (Life Technologies GmbH, Darmstadt, Germany) using the GencOptimizer® software to optimize the codon usage for expression in CHO cells. Besides a common secretion signal, all DNA constructs contain the same Kozak sequence and a HindIII restriction at the 5' end. At the 3' end BsiWI and XhoI recognition sites were added to allow for flexible subcloning into different expression vectors. Subcloning into the expression vector of choice pCEP4 (Life Technologies GmbH, Darmstadt, Germany) was performed by Life Technologies using the HindIII and XhoI restriction sites.

TABLE 11

Summary of the bi-scFv anti-CLDN18.2 constructs

| Variant Identification | Anti-CLDN18.2 origin | Anti-CD3 origin | Substitution at pos. H103 of TR66 | Domain order (from N- to C-terminal) | Domain organization* | SEQ ID NO: |
|---|---|---|---|---|---|---|
| 1 BiMAB-S | mCLDN18.2ab | TR66 | Serine | scFv-anti-CLDN18.2-scFv anti-CD3 | See 1 BiMAB in Example 1 | 103 |
| 5504 | mCLDN18.2ab1 | TR66 | Serine | scFv-anti-CLDN18.2-scFv anti-CD3 | VH-LL4-VL-SL-VH-LL4-VL | 66 |
| 5505 | mCLDN18.2ab1 | TR66 | Serine | scFv-anti-CLDN18.2-scFv anti-CD3 | ds-(VH-LL4-VL)-SL-VH-LL4-VL | 67 |
| 5506 | mCLDN18.2ab | TR66 | Serine | scFv-anti-CLDN18.2-scFv anti-CD3 | VH-LL4-VL-SL-VH-LL4-VL | 68 |
| 5507 | mCLDN18.2ab | TR66 | Serine | scFv-anti-CLDN18.2-scFv anti-CD3 | ds-(VH-LL4-VL)-SL-VH-LL4-VL | 69 |
| 5512 | mCLDN18.2ab1 | TR66 | Serine | scFv-anti-CLDN18.2-scFv anti-CD3 | VH-LL4-VL-SL-ds(VH-LL4-VL) | 70 |
| 5513 | mCLDN18.2ab1 | TR66 | Serine | scFv-anti-CLDN18.2-scFv anti-CD3 | ds-VH-LL4-VL-SL-ds(VH-LL4-VL) | 71 |
| 5514 | mCLDN18.2ab | TR66 | Serine | scFv-anti-CLDN18.2-scFv anti-CD3 | VH-LL4-VL-SL-ds(VH-LL4-VL) | 72 |
| 5515 | mCLDN18.2ab | TR66 | Serine | scFv-anti-CLDN18.2-scFv anti-CD3 | ds-VH-LL4-VL-SL-ds(VH-LL4-VL) | 73 |
| 5520 | mCLDN18.2ab1 | TR66 | Serine | scFv-anti-CLDN18.2-scFv anti-CD3 | VH-LL4-VL-SL-VL-LL5-VH | 74 |
| 5521 | mCLDN18.2ab1 | TR66 | Serine | scFv-anti-CLDN18.2-scFv anti-CD3 | ds-(VH-LL4-VL)-SL-VL-LL5-VH | 75 |
| 5522 | mCLDN18.2ab | TR66 | Serine | scFv-anti-CLDN18.2-scFv anti-CD3 | VH-LL4-VL-SL-VL-LL5-VH | 76 |
| 5523 | mCLDN18.2ab | TR66 | Serine | scFv-anti-CLDN18.2-scFv anti-CD3 | ds-(VH-LL4-VL)-SL-VL-LL5-VH | 77 |
| 5528 | mCLDN18.2ab1 | TR66 | Serine | scFv-anti-CLDN18.2-scFv ant-CD3 | VH-LL4-VL-SL-ds(VL-LL5-VH) | 78 |
| 5529 | mCLDN18.2ab1 | TR66 | Serine | scFv-anti-CLDN18.2-scFv anti-CD3 | ds-VH-LL4-VL-SL-ds(VL-LL5-VH) | 79 |

TABLE 11-continued

Summary of the bi-scFv anti-CLDN18.2 constructs

| Variant Identification | Anti-CLDN18.2 origin | Anti-CD3 origin | Substitution at pos. H103 of TR66 | Domain order (from N- to C-terminal) | Domain organization* | SEQ ID NO: |
|---|---|---|---|---|---|---|
| 5530 | mCLDN18.2ab | TR66 | Serine | scFv-anti-CLDN18.2-scFv anti-CD3 | VH-LL4-VL-SL-ds(VL-LL5-VH) | 80 |
| 5531 | mCLDN18.2ab | TR66 | Serine | scFv-anti-CLDN18.2-scFv anti-CD3 | ds-VH-LL4-VL-SL-ds(VL-LL5-VH) | 81 |
| 5536 | mCLDN18.2ab1 | TR66 | Serine | scFv-anti-CLDN18.2-scFv anti-CD3 | VL-LL5-VH-SL-VH-LL4-VL | 82 |
| 5537 | mCLDN18.2ab1 | TR66 | Serine | scFv-anti-CLDN18.2-scFv anti-CD3 | ds-(VL-LL5-VH)-SL-VH-LL4-VL | 83 |
| 5538 | mCLDN18.2ab | TR66 | Serine | scFv-anti-CLDN18.2-scFv anti-CD3 | VL-L5-VH-SL-VH-LL4-VL | 84 |
| 5539 | mCLDN18.2ab | TR66 | Serine | scFv-anti-CLDN18.2-scFv anti-CD3 | ds-(VL-LL5-VH)-SL-VH-LL4-VL | 85 |
| 5544 | mCLDN18.2ab1 | TR66 | Serine | scFv-anti-CLDN18.2-scFv anti-CD3 | VL-LL5-VH-SL-ds(VH-LL4-VL) | 86 |
| 5545 | mCLDN18.2ab1 | TR66 | Serine | scFv-anti-CLDN18.2-scFv anti-CD3 | ds-VL-LL5-VH-SL-ds(VH-LL4-VL) | 87 |
| 5546 | mCLDN18.2ab | TR66 | Serine | scFv-anti-CLDN18.2-scFv anti-CD3 | VL-L5-VH-SL-ds(VH-LL4-VL) | 88 |
| 5547 | mCLDN18.2ab | TR66 | Serine | scFv-anti-CLDN18.2-scFv anti-CD3 | ds-VL-LL5-VH-SL-ds(VH-LL4-VL) | 89 |
| 5552 | mCLDN18.2ab1 | TR66 | Serine | scFv-anti-CLDN18.2-scFv anti-CD3 | VL-LL5-VH-SL-VL-LL5-VH | — |
| 5553 | mCLDN18.2ab1 | TR66 | Serine | scFv-anti-CLDN18.2-scFv anti-CD3 | ds-(VL-LL5-VH)-SL-VL-LL5-VH | — |
| 5554 | mCLDN18.2ab | TR66 | Serine | scFv-anti-CLDN18.2-scFv anti-CD3 | VL-LL5-VH-SL-VL-LL5-VH | — |
| 5555 | mCLDN18.2ab | TR66 | Serine | scFv-anti-CLDN18.2-scFv anti-CD3 | ds-(VL-LL5-VH)-SL-VL-LL5-VH | — |
| 5560 | mCLDN18.2ab1 | TR66 | Serine | scFv-anti-CLDN18.2-scFv anti-CD3 | VL-LL5-VH-SL-ds(VL-LL5-VH) | 90 |
| 5561 | mCLDN18.2ab1 | TR66 | Serine | scFv-anti-CLDN18.2-scFv anti-CD3 | ds-VL-LL5-VH-SL-ds(VL-LL5-VH) | 91 |
| 5562 | mCLDN18.2ab | TR66 | Serine | scFv-anti-CLDN18.2-scFv anti-CD3 | VL-LL5-VH-SL-ds(VL-LL5-VH) | 92 |
| 5563 | mCLDN18.2ab | TR66 | Serine | scFv-anti-CLDN18.2-scFv anti-CD3 | ds-VL-LL5-VH-SL-ds(VL-LL5-VH) | 93 |

*LL4, $(G_4S)_4$; LL5, $(G_4S)_5$; SL, $SG_4S$

It should be noted that SEQ ID NOs: 66 to 93 still contain the amino acid sequence of an N-terminal signal sequence which mediates the secretion of the 1-BiMAB bi-scFv protein into the cell culture supernatant upon mammalian expression. This signal sequence is not part of the secreted recombinant protein since it is cleaved off by a signal peptidase in the lumen of the endoplasmic reticulum.

b. Production and Purification of 32 Anti CLDN18.2 Specific Bi-scFv Proteins by Transient Transfection Suspension adapted CHO-cells were sub-cultivated in serum-free media in a humidified C02 shaker. One day prior transfection, cells were seeded in serum-free media in shaker flasks. On the day of transfection cells were centrifuged (5 min at 200×g) and resuspended in fresh DMEM-Medium (Invitrogen, 4 1965-039) in shaker flasks. DNA and transfection reagent were added to the cells and gently mixed by shaking. After static incubation in a $CO_2$-incubator, the cells were diluted with serum free growth media and further cultivated for expression in an incubation shaker. Cells were fed according to nutritional requirement with CHO CD EfficientFeed™ C (Invitrogen, A13275). Bi-scFv proteins were harvested after the viability of the cells starts to decrease. The antibody constructs were purified by Capto L sepharose. The protein concentration was determined by absorbance at 280 nm.

c. Luciferase Cytotoxicity Assay with 32 Anti-CLDN18.2-specific Bi-scFv Proteins For the functional screening of the 32 anti-CLDN18.2-specific bi-scFv proteins, four point titrations (5000, 1000, 200 and 40 ng/ml) were tested in an in vitro luciferase cytotoxicity assay, as described in Example 2.c.

Stable luciferase-expressing NugC4 cells described in Example 2.c were incubated with human T cells and bi-scFv proteins or without bi-scFv protein to determine the $L_{min}$ values. Luminescence of viable cells was measured with an Infinite M200 Tecan plate reader 24 h and 48 h after assay set up. Specific target cell lysis was calculated by the formula exemplified in Example 2.c.

By performing a qualitative analysis of the cytotoxic results (FIGS. 39 a, b, c and d) based on the scFv anti-CD3 TR66 binding domains the following observation could be drawn.

The best performing anti-CLDN18.2-specific bi-scFv proteins in the luciferase cytotoxic assay contain the anti-CD3 moiety in the VH/VL domain orientation connected by the "LL4" linker with or without the interface disulfide bridge (5504, 5505, 5506, 5507, 5536, 5537, 5538, 5539, 5512, 5513, 5514, 5515, 5544, 5545, 5546, 5547; FIGS. 39 a and b). A lower cytotoxic activity is obtained with the variants containing the anti-CD3 moiety in the VL/VH domain orientation with the peptide linker "LL5" and containing the interface disulfide bridge (5528, 5529, 5530, 5531, 5560, 5561, 5562, 5563; FIG. 39 d). The lowest cytotoxic activity is obtained with the variant containing the anti-CD3 moiety in the VL/VH domain orientation with the peptide linker "LL5" without interface disulfide bridge (5520, 5521, 5522, 5523, 5552, 5553, 5554, 5555; FIG. 39 c).

B. Generation and Testing of Bispecific Binding Agents Targeting CLDN6 and CD3 a. Sequence Origin, Design of Bi-scFv Constructs, and Cloning into Expression Vectors The bispecific tandem single chain antibody constructs bi-scFv presented herein contain two distinct binding domains from which one is specific for a human tumor associated antigen (TAA), whereas the other is specific for the a-chain of human T cell receptor (CD3). Each of the two binding domains of the bispecific molecule comprises two antibody variable domains, arranged as scFv moiety in either VH-VL or VL-VH orientation. The antibody variable domains are connected via a flexible glycin-serine peptide linker. The scFv moieties targeting the TAA C are arranged in the VH-VL orientation and are connected by a 15 amino acid linker (named "LL3") consisting of three identical repeats of a $G_4S$ subunit. The scFv moieties targeting CD3 are also arranged in the VH-VL orientation, but are connected by a 18 amino acid linker (named LLv1) with the sequence $G_4S(G_2S)_3G_3S$. The two scFv moieties on the other hand are connected via a six amino acid long $SG_4S$ linker (named "SL"). Information on sequence origin from monoclonal antibodies (mAB) and domain organization are summarized in Table 12. The variants 5454, 5456, 5458, 5460, 5462 and 5464 comprise for the anti-CD3 binding domain the VH anti-CD3 with the SEQ ID NO: 95 and the VL anti-CD3 with the SEQ ID NO: 96. The variants 5454 and 5458 comprise the VL anti-CLDN6 with the SEQ ID NO: 98; the variants 5456 and 5460 comprise the VL anti-CLDN6 with the SEQ ID NO: 99; the variants 5462 and 5464 comprise the VL anti-CLDN6 with the SEQ ID NO: 100.

In the particular case of the 6PHU3-S(SEQ ID NO: 101), only the substitution of the free cysteine by a serine residue in the VH anti-CD3 (SEQ ID NO: 94) is done in comparison to the amino acid sequence of the 6-PHU3 sequence (SEQ ID NO: 45). It should be noted that SEQ ID) NO: 45 still contains the amino acid sequence of an N-terminal signal sequence which mediates the secretion of the 6-PHU-3 bi-scFv protein into the cell culture supernatant upon mammalian expression. This signal sequence is not part of the secreted recombinant protein since it is cleaved off by a signal peptidase in the lumen of the endoplasmic reticulum. Moreover for the 6PHU3-SI, (SEQ ID NO: 102), the substitution of the free cysteine by a leucine residue in the VL anti-CLDN6 (SEQ ID NO: 97) at position 46 of the corresponding primary sequence is performed in comparison to the amino acid sequence of the 6PHU3-S. This corresponds to position 45 within SEQ ID NO: 23 where the first amino acid of the VL has been omitted.

The genes encoding the bi-scFv constructs were generated via GeneArt® gene synthesis (Life Technologies GmbH, Darmstadt, Germany) using the GeneOptimizer® software to optimize the codon usage for expression in CHO cells. Besides a common secretion signal, all DNA constructs contain the same Kozak sequence and a HindIII restriction at the 5' end. At the 3' end BsiWI and XhoI recognition sites were added to allow for flexible subcloning into different expression vectors. Subcloning into the expression vector of choice pEE12.4 (Lonza Group Ltd, Basel, Switzerland) was performed using standard techniques using the HindIII and BsiWI restriction sites.

TABLE 12

Summary of the bi-scFv anti-CLDN6 constructs

| Variant Identification | Anti-CLDN6 origin | Substitution at pos L46 of mCLDN6ab | Anti-CD3 origin | Substitution at pos. H103 of TR66 | Domain order (from N- to C-terminal) | Domain organization* | SEQ ID NO: |
|---|---|---|---|---|---|---|---|
| 5454 | mCLDN6ab | Leucine | TR66 | Serine | scFvanti-CLDN6-scFvanti-CD3 | VH-LL3-VL-SL-VH-LLv1-VL | 60 |
| 5456 | mCLDN6ab | Tryptophan | TR66 | Serine | scFvanti-CLDN6-scFvanti-CD3 | VHLL3VL-SL-VH-LLv1-VL | 61 |
| 5462 | mCLDN6ab | Serine | TR66 | Serine | scFvanti-CLDN6-scFvanti-CD3 | VH-LL3-VL-SL-VH-LLv1-VL | 62 |
| 6PHU3-S | mCLDN6ab | NA | TR66 | Serine | scFvanti-CD3-scFvanti-CLDN6 | See 6PHU3 in Example 9 | 101 |

TABLE 12-continued

Summary of the bi-scFv anti-CLDN6 constructs

| Variant Identification | Anti-CLDN6 origin | Substitution at pos L46 of mCLDN6ab | Anti-CD3 origin | Substitution at pos. H103 of TR66 | Domain order (from N- to C-terminal) | Domain organization* | SEQ ID NO: |
|---|---|---|---|---|---|---|---|
| 6PHU3-SL | mCLDN6ab | Leucine | TR66 | Serine | scFvanti-CD3-scFvanti-CLDN6 | See 6PHU3 in Example 9 | 102 |
| 5458 | mCLDN6ab | LeucMe | TR66 | Serine | scFvanti-CD3-scFvanti-CLDN6 | VH-LLv1-VL-SL-VH-LL3-VL | 63 |
| 5460 | mCLDN6ab | Tryptophan | TR66 | Serine | scFvanti-CD3-scFvanti-CLDN6 | VH-LLv1-VL-SL-VH-LL3-VL | 64 |
| 5464 | mCLDN6ab | Serine | TR66 | Serine | scFvanti-CD3-scFvanti-CLDN6 | VH-LLv1-VL-SL-VH-LL3-VL | 65 |

*LL3, $(G_4S)_3$; LLv1, $G_4S(G_2S)_3G_3S$; SL, $SG_4S$ b. Production and Purification of 6 Anti CLDN6 Specific Bi-scFv Proteins by Transient Transfection Suspension adapted CHO-cells were sub-cultivated in serum-free media in a humidified CO2 shaker. One day prior transfection, cells were seeded in serum-free media in shaker flasks. On the day of transfection cells were centrifuged (5 min at 200×g) and resuspended in fresh DMEM-Medium (Invitrogen, 41965-039) in shaker flasks. DNA and transfection reagent were added to the cells and gently mixed by shaking. After static incubation in a CO2-incubator, the cells were diluted with serum free growth media and further cultivated for expression in an incubation shaker. Cells were feeded according to nutritional requirement with CHO CD EfficientFeed™ C (Invitrogen, A13275). Bi-scFv proteins were harvested after the viability of the cells starts to decrease. The antibody constructs were purified by FPLC using Capto L sepharose. The protein concentration was determined by absorbance at 280 nm.

c. Determination of EC50 of 6 Anti-CLDN6-specific Bi-scFv Proteins

For the determination of the half maximal effective dose of anti-CLDN6-specific bi-scFv proteins, a titration row of bi-scFv proteins was tested in an in vitro luciferase cytotoxic assay as described in Example 13.

Stable luciferase-expressing PA-1 cells and human T cells in an E:T ratio of 5:1 were incubated with bi-scFv protein concentrations within the range of 2.5 pg/ml to 5 µg/ml (in steps of 10) or without anti-CLDN6-specific bi-scFv proteins to determine the Lmin values.

Three independent assays were performed with different human donors for the preparation of the human T cells. The results are illustrated in FIG. 40.

By performing a quantitative comparison of the cytotoxic results based on the cysteine residue substitution within the flanking region of the CDR-L2 by either a serine, leucine or tryptophan and on anti-CLDN6 and anti-CD3 binding domain position the following observation could be drawn.

The best performing anti-CLDN6-specific bi-scFv proteins in the luciferase cytotoxic assay contain the cysteine to tryptophan substitution with the anti-CLDN6 binding domain in the N-terminal part of the bi-scFv protein (variant 5456). A slightly lower cytotoxic activity is obtained with the variants containing the anti-CLDN6 in the C-terminal part with either the substitution of the cysteine by a tryptophan (variant 5460) or a serine (variant 5464). For the variants containing the substitution of the cysteine by a leucine with the anti-CLDN6 in the N--terminal part (variant 5454) or C-terminal part (variant 5458) of the bi-scFv proteins lower cytotoxic activity is measured in comparison with the previous variants. Surprisingly, the variant containing the substitution of the cysteine by a serine with the anti-CLDN6 in the N-terminal part (variant 5462) of the bi-scFv protein has the lowest cytotoxic activity.

The invention claimed is:

1. A method of treating a cancer disease characterized by cancer cells expressing claudin 6 (CLDN6), the method comprising administering to a patient a pharmaceutical composition, wherein the pharmaceutical composition comprises a binding agent, wherein the binding agent is a bispecific single chain antibody (bi-scFv) comprising a first binding domain and a second binding domain, wherein the first binding domain binds to CD3 and the second binding domain binds to CLDN6, wherein the first binding domain and the second binding domain each comprise a combination of a variable domain of a heavy chain of an immunoglobulin (VH) and a variable domain of a light chain of an immunoglobulin (VL) as defined in SEQ ID NO:45.

2. The method of claim 1, wherein said second binding domain binds to an extracellular domain of said CLDN6.

3. The method of claim 1, wherein said first binding domain binds to the epsilon-chain of CD3.

4. The method of claim 1, wherein said CD3 is expressed on the surface of a T cell.

5. The method of claim 1, wherein binding of said binding agent to CD3 on T cells results in proliferation and/or activation of said T cells, wherein said activated T cells preferably release cytotoxic factors, e.g. perforins and granzymes, and initiate cytolysis and apoptosis of cancer cells.

6. The method of claim 1, wherein the bispecific single chain antibody consists of two scFv molecules connected via a linker peptide.

7. The method of claim 1, wherein said cancer is selected from the group consisting of urinary bladder cancer, ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, uterine cancer, germ cell tumors such as a teratocarcinoma or an embryonal carcinoma, in particular germ cell tumors of the testis, and the metastatic forms thereof.

8. The method of claim 1, wherein the VH comprises an amino acid sequence represented by SEQ ID NO: 22 and the VL comprises an amino acid sequence represented by SEQ ID NO: 23.

9. The method of claim 1, wherein the binding agent comprises an amino acid sequence according to SEQ ID NO:42.

10. The method of claim 1, wherein the binding agent comprises an amino acid sequence according to SEQ ID NO:43.

11. The method of claim 1, wherein the binding agent comprises an amino acid sequence according to SEQ ID NO:44.

12. The method of claim 1, wherein the binding agent comprises an amino acid sequence according to SEQ ID NO:45.

* * * * *

SEQUENCE LISTING

<160> NUMBER OF SEQ ID NOS: 108

<210> SEQ ID NO 1
<211> LENGTH: 261
<212> TYPE: PRT
<213> ORGANISM: Homo sapiens

<400> SEQUENCE: 1

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

```
Leu Trp Arg Ser Cys Val Arg Glu Ser Ser Gly Phe Thr Glu Cys Arg
     50                  55                  60

Gly Tyr Phe Thr Leu Leu Gly Leu Pro Ala Met Leu Gln Ala Val Arg
 65                  70                  75                  80

Ala Leu Met Ile Val Gly Ile Val Leu Gly Ala Ile Gly Leu Leu Val
                     85                  90                  95

Ser Ile Phe Ala Leu Lys Cys Ile Arg Ile Gly Ser Met Glu Asp Ser
                    100                 105                 110

Ala Lys Ala Asn Met Thr Leu Thr Ser Gly Ile Met Phe Ile Val Ser
                115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                    165                 170                 175

Val Gly Trp Val Ala Gly Gly Leu Thr Leu Ile Gly Gly Val Met Met
                180                 185                 190

Cys Ile Ala Cys Arg Gly Leu Ala Pro Glu Glu Thr Asn Tyr Lys Ala
            195                 200                 205

Val Ser Tyr His Ala Ser Gly His Ser Val Ala Tyr Lys Pro Gly Gly
        210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                    245                 250                 255

Lys His Asp Tyr Val
                260

<210> SEQ ID NO 2
<211> LENGTH: 220
<212> TYPE: PRT
<213> ORGANISM: Homo sapiens

<400> SEQUENCE: 2

Met Ala Ser Ala Gly Met Gln Ile Leu Gly Val Val Leu Thr Leu Leu
 1               5                  10                  15

Gly Trp Val Asn Gly Leu Val Ser Cys Ala Leu Pro Met Trp Lys Val
                 20                  25                  30

Thr Ala Phe Ile Gly Asn Ser Ile Val Val Ala Gln Val Val Trp Glu
                 35                  40                  45

Gly Leu Trp Met Ser Cys Val Val Gln Ser Thr Gly Gln Met Gln Cys
 50                  55                  60

Lys Val Tyr Asp Ser Leu Leu Ala Leu Pro Gln Asp Leu Gln Ala Ala
 65                  70                  75                  80

Arg Ala Leu Cys Val Ile Ala Leu Leu Val Ala Leu Phe Gly Leu Leu
                     85                  90                  95

Val Tyr Leu Ala Gly Ala Lys Cys Thr Thr Cys Val Glu Glu Lys Asp
                    100                 105                 110

Ser Lys Ala Arg Leu Val Leu Thr Ser Gly Ile Val Phe Val Ile Ser
                115                 120                 125

Gly Val Leu Thr Leu Ile Pro Val Cys Trp Thr Ala His Ala Ile Ile
    130                 135                 140

Arg Asp Phe Tyr Asn Pro Leu Val Ala Glu Ala Gln Lys Arg Glu Leu
145                 150                 155                 160
```

```
Gly Ala Ser Leu Tyr Leu Gly Trp Ala Ala Ser Gly Leu Leu Leu Leu
                165                 170                 175

Gly Gly Gly Leu Leu Cys Cys Thr Cys Pro Ser Gly Ser Gln Gly
            180                 185                 190

Pro Ser His Tyr Met Ala Arg Tyr Ser Thr Ser Ala Pro Ala Ile Ser
            195                 200                 205

Arg Gly Pro Ser Glu Tyr Pro Thr Lys Asn Tyr Val
    210                 215                 220

<210> SEQ ID NO 3
<211> LENGTH: 220
<212> TYPE: PRT
<213> ORGANISM: Homo sapiens

<400> SEQUENCE: 3

Met Ala Ser Ala Gly Met Gln Ile Leu Gly Val Val Leu Thr Leu Leu
1               5                   10                  15

Gly Trp Val Asn Gly Leu Val Ser Cys Ala Leu Pro Met Trp Lys Val
            20                  25                  30

Thr Ala Phe Ile Gly Asn Ser Ile Val Val Ala Gln Val Val Trp Glu
        35                  40                  45

Gly Leu Trp Met Ser Cys Val Val Gln Ser Thr Gly Gln Met Gln Cys
    50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Val Ala Leu Phe Gly Leu Leu
                85                  90                  95

Val Tyr Leu Ala Gly Ala Lys Cys Thr Thr Cys Val Glu Glu Lys Asp
            100                 105                 110

Ser Lys Ala Arg Leu Val Leu Thr Ser Gly Ile Val Phe Val Ile Ser
        115                 120                 125

Gly Val Leu Thr Leu Ile Pro Val Cys Trp Thr Ala His Ala Val Ile
    130                 135                 140

Arg Asp Phe Tyr Asn Pro Leu Val Ala Glu Ala Gln Lys Arg Glu Leu
145                 150                 155                 160

Gly Ala Ser Leu Tyr Leu Gly Trp Ala Ala Ser Gly Leu Leu Leu Leu
                165                 170                 175

Gly Gly Gly Leu Leu Cys Cys Thr Cys Pro Ser Gly Ser Gln Gly
            180                 185                 190

Pro Ser His Tyr Met Ala Arg Tyr Ser Thr Ser Ala Pro Ala Ile Ser
            195                 200                 205

Arg Gly Pro Ser Glu Tyr Pro Thr Lys Asn Tyr Val
    210                 215                 220

<210> SEQ ID NO 4
<211> LENGTH: 207
<212> TYPE: PRT
<213> ORGANISM: Homo sapiens

<400> SEQUENCE: 4

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45
```

```
Cys Pro Gln Tyr Pro Gly Ser Glu Ile Leu Trp Gln His Asn Asp Lys
     50                   55                  60

Asn Ile Gly Gly Asp Glu Asp Lys Asn Ile Gly Ser Asp Glu Asp
 65              70                  75                  80

His Leu Ser Leu Lys Glu Phe Ser Glu Leu Glu Gln Ser Gly Tyr Tyr
                 85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
         115                 120                 125

Ser Val Ala Thr Ile Val Ile Val Asp Ile Cys Ile Thr Gly Gly Leu
     130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                 165                 170                 175

Lys Glu Arg Pro Pro Val Pro Asn Pro Asp Tyr Glu Pro Ile Arg
             180                 185                 190

Lys Gly Gln Arg Asp Leu Tyr Ser Gly Leu Asn Gln Arg Arg Ile
             195                 200                 205

<210> SEQ ID NO 5
<211> LENGTH: 117
<212> TYPE: PRT
<213> ORGANISM: Artificial Sequence
<220> FEATURE:
<223> OTHER INFORMATION: Antibody fragment

<400> SEQUENCE: 5

Gln Val Gln Leu Gln Gln Ser Gly Ala Glu Leu Met Lys Pro Gly Ala
 1               5                  10                  15

Ser Val Lys Ile Ser Cys Lys Ala Thr Gly Tyr Thr Phe Ser Ser Tyr
             20                  25                  30

Trp Ile Glu Trp Val Lys Gln Arg Pro Gly His Gly Leu Glu Trp Ile
         35                  40                  45

Gly Glu Ile Leu Pro Gly Ser Gly Ser Thr Asn Tyr Asn Glu Lys Phe
     50                  55                  60

Lys Gly Lys Ala Thr Phe Thr Ala Asp Thr Ser Ser Asn Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Asp Tyr Pro Trp Phe Ala Tyr Trp Gly Gln Gly Thr Leu
            100                 105                 110

Val Thr Val Ser Ala
        115

<210> SEQ ID NO 6
<211> LENGTH: 118
<212> TYPE: PRT
<213> ORGANISM: Artificial Sequence
<220> FEATURE:
<223> OTHER INFORMATION: Antibody fragment

<400> SEQUENCE: 6

Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Asn Tyr
```

```
            20                  25                  30
Gly Met Asn Trp Val Lys Gln Ala Pro Gly Lys Gly Leu Lys Trp Met
        35                  40                  45

Gly Trp Ile Asn Thr Asn Thr Gly Glu Pro Thr Tyr Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Leu Gly Phe Gly Asn Ala Met Asp Tyr Trp Gly Gln Gly Thr
            100                 105                 110

Ser Val Thr Val Ser Ser
        115

<210> SEQ ID NO 7
<211> LENGTH: 116
<212> TYPE: PRT
<213> ORGANISM: Artificial Sequence
<220> FEATURE:
<223> OTHER INFORMATION: Antibody fragment

<400> SEQUENCE: 7

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Asp Tyr
            20                  25                  30

Tyr Ile Asn Trp Val Lys Gln Arg Thr Gly Gln Gly Leu Glu Trp Ile
        35                  40                  45

Gly Glu Ile Tyr Pro Gly Ser Gly Asn Thr Tyr Tyr Asn Glu Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ser Tyr Gly Ala Phe Asp Tyr Trp Gly Gln Gly Thr Thr Leu
            100                 105                 110

Thr Val Ser Ser
        115

<210> SEQ ID NO 8
<211> LENGTH: 118
<212> TYPE: PRT
<213> ORGANISM: Artificial Sequence
<220> FEATURE:
<223> OTHER INFORMATION: Antibody fragment

<400> SEQUENCE: 8

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Lys Ser Ser Ser Thr Ala Tyr
65                  70                  75                  80
```

```
Met Gln Leu Ser Ser Pro Thr Ser Glu Asp Ser Ala Val Tyr Tyr Cys
                85                  90                  95

Thr Arg Ser Trp Arg Gly Asn Ser Phe Asp Tyr Trp Gly Gln Gly Thr
            100                 105                 110

Thr Leu Thr Val Ser Ser
        115

<210> SEQ ID NO 9
<211> LENGTH: 118
<212> TYPE: PRT
<213> ORGANISM: Artificial Sequence
<220> FEATURE:
<223> OTHER INFORMATION: Antibody fragment

<400> SEQUENCE: 9

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile Ser Trp Val Lys Gln Arg Thr Gly Gln Gly Leu Glu Trp Ile
        35                  40                  45

Gly Glu Ile Tyr Pro Gly Ser Gly Ser Thr Tyr Tyr Asn Glu Lys Phe
    50                  55                  60

Lys Gly Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Phe Cys
                85                  90                  95

Ala Arg Gly Val Leu Leu Arg Ala Met Asp Tyr Trp Gly Gln Gly Thr
            100                 105                 110

Ser Val Thr Val Ser Ser
        115

<210> SEQ ID NO 10
<211> LENGTH: 120
<212> TYPE: PRT
<213> ORGANISM: Artificial Sequence
<220> FEATURE:
<223> OTHER INFORMATION: Antibody fragment

<400> SEQUENCE: 10

Gln Val His Leu Gln Gln Ser Gly Ser Glu Leu Arg Ser Pro Gly Ser
1               5                   10                  15

Ser Val Lys Leu Ser Cys Lys Asp Phe Asp Ser Glu Val Phe Pro Phe
            20                  25                  30

Ala Tyr Met Ser Trp Ile Arg Gln Lys Pro Gly His Gly Phe Glu Trp
        35                  40                  45

Ile Gly Asp Ile Leu Pro Ser Ile Gly Arg Thr Ile Tyr Gly Glu Lys
    50                  55                  60

Phe Glu Asp Lys Ala Thr Leu Asp Ala Asp Thr Val Ser Asn Thr Ala
65                  70                  75                  80

Tyr Leu Glu Leu Asn Ser Leu Thr Ser Glu Asp Ser Ala Ile Tyr Tyr
                85                  90                  95

Cys Ala Arg Gly Glu Tyr Gly Ala Trp Phe Ala Tyr Trp Gly Gln
            100                 105                 110

Gly Thr Leu Val Thr Val Ser Ala
        115                 120

<210> SEQ ID NO 11
```

<211> LENGTH: 113
<212> TYPE: PRT
<213> ORGANISM: Artificial Sequence
<220> FEATURE:
<223> OTHER INFORMATION: Antibody fragment

<400> SEQUENCE: 11

Asp Ile Val Met Thr Gln Ser Pro Ser Ser Leu Thr Val Thr Ala Gly
1               5                   10                  15

Glu Lys Val Thr Met Ser Cys Lys Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys

<210> SEQ ID NO 12
<211> LENGTH: 106
<212> TYPE: PRT
<213> ORGANISM: Artificial Sequence
<220> FEATURE:
<223> OTHER INFORMATION: Antibody fragment

<400> SEQUENCE: 12

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Pro Thr
                85                  90                  95

Phe Gly Gly Gly Thr Lys Leu Glu Ile Lys
            100                 105

<210> SEQ ID NO 13
<211> LENGTH: 107
<212> TYPE: PRT
<213> ORGANISM: Artificial Sequence
<220> FEATURE:
<223> OTHER INFORMATION: Antibody fragment

<400> SEQUENCE: 13

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Arg Thr Ala
            20                  25                  30

Val Ala Trp Tyr Gln Gln Lys Pro Gly Gln Ser Pro Lys Ala Leu Ile

```
                35                  40                  45

Tyr Leu Ala Ser Asn Arg His Thr Gly Val Pro Asp Arg Phe Thr Gly
 50                  55                  60

Ser Gly Ser Gly Thr Asp Phe Thr Leu Thr Ile Ser Asn Val Gln Ser
 65                  70                  75                  80

Glu Asp Leu Ala Asp Tyr Phe Cys Leu Gln His Trp Asn Tyr Pro Leu
                 85                  90                  95

Thr Phe Gly Gly Gly Thr Lys Leu Glu Ile Lys
            100                 105

<210> SEQ ID NO 14
<211> LENGTH: 113
<212> TYPE: PRT
<213> ORGANISM: Artificial Sequence
<220> FEATURE:
<223> OTHER INFORMATION: Antibody fragment

<400> SEQUENCE: 14

Asp Ile Val Met Ser Gln Ser Pro Ser Ser Leu Ala Val Ser Val Gly
 1               5                  10                  15

Glu Lys Val Thr Met Ser Cys Lys Ser Gln Ser Leu Leu Tyr Ser
                20                  25                  30

Ser Asn Gln Lys Asn Tyr Leu Ala Trp Tyr Gln Gln Lys Pro Gly Gln
             35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                 85                  90                  95

Tyr Tyr Ser Tyr Pro Leu Thr Phe Gly Ala Gly Thr Lys Leu Glu Leu
            100                 105                 110

Lys

<210> SEQ ID NO 15
<211> LENGTH: 113
<212> TYPE: PRT
<213> ORGANISM: Artificial Sequence
<220> FEATURE:
<223> OTHER INFORMATION: Antibody fragment

<400> SEQUENCE: 15

Asp Ile Val Met Thr Gln Ser Pro Ser Ser Leu Thr Val Thr Ala Gly
 1               5                  10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
             35                  40                  45

Pro Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp Tyr Ser Tyr Pro Phe Thr Phe Gly Ser Gly Thr Lys Leu Glu Ile
            100                 105                 110

Lys
```

<210> SEQ ID NO 16
<211> LENGTH: 112
<212> TYPE: PRT
<213> ORGANISM: Artificial Sequence
<220> FEATURE:
<223> OTHER INFORMATION: Antibody fragment

<400> SEQUENCE: 16

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Tyr Thr Phe Gly Gly Gly Thr Lys Leu Glu Ile Lys
            100                 105                 110

<210> SEQ ID NO 17
<211> LENGTH: 113
<212> TYPE: PRT
<213> ORGANISM: Artificial Sequence
<220> FEATURE:
<223> OTHER INFORMATION: Antibody fragment

<400> SEQUENCE: 17

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Ala Thr Asp Phe Thr Leu Thr
65                  70                  75                  80

Ile Ser Ser Val Gln Ala Glu Asp Leu Ala Asp Tyr His Cys Gly Gln
                85                  90                  95

Gly Tyr Ser Tyr Pro Tyr Thr Phe Gly Gly Gly Thr Lys Leu Glu Ile
            100                 105                 110

Lys

<210> SEQ ID NO 18
<211> LENGTH: 113
<212> TYPE: PRT
<213> ORGANISM: Artificial Sequence
<220> FEATURE:
<223> OTHER INFORMATION: Antibody fragment

<400> SEQUENCE: 18

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser

```
                 20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
         50                  55                  60

Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                 85                  90                  95

Tyr Tyr Ser Tyr Pro Leu Thr Phe Gly Ala Gly Thr Lys Leu Glu Leu
            100                 105                 110

Lys

<210> SEQ ID NO 19
<211> LENGTH: 107
<212> TYPE: PRT
<213> ORGANISM: Artificial Sequence
<220> FEATURE:
<223> OTHER INFORMATION: Antibody fragment

<400> SEQUENCE: 19

Asn Ile Val Met Thr Gln Ser Pro Lys Ser Met Ser Met Ser Val Gly
 1               5                  10                  15

Glu Arg Val Thr Leu Thr Cys Lys Ala Ser Glu Asn Val Val Thr Tyr
                 20                  25                  30

Val Ser Trp Tyr Gln Gln Lys Pro Glu Gln Ser Pro Lys Leu Leu Ile
            35                  40                  45

Tyr Gly Ala Ser Asn Arg Tyr Thr Gly Val Pro Asp Arg Phe Thr Gly
         50                  55                  60

Ser Gly Ser Ala Thr Asp Phe Thr Leu Thr Ile Ser Ser Val Lys Ala
 65                  70                  75                  80

Glu Asp Leu Ala Val Tyr Tyr Cys Gln Gln Tyr Tyr Ser Tyr Pro Leu
                 85                  90                  95

Thr Phe Gly Ala Gly Thr Lys Leu Glu Leu Lys
            100                 105

<210> SEQ ID NO 20
<211> LENGTH: 117
<212> TYPE: PRT
<213> ORGANISM: Artificial Sequence
<220> FEATURE:
<223> OTHER INFORMATION: Antibody fragment

<400> SEQUENCE: 20

Glu Val Gln Leu Gln Gln Ser Gly Pro Glu Leu Val Lys Pro Gly Ala
 1               5                  10                  15

Ser Met Lys Ile Ser Cys Lys Ala Ser Gly Tyr Ser Phe Thr Gly Tyr
                 20                  25                  30

Thr Met Asn Trp Val Lys Gln Ser His Gly Lys Asn Leu Glu Trp Ile
            35                  40                  45

Gly Leu Ile Asn Pro Tyr Asn Gly Gly Thr Ser Tyr Asn Gln Lys Phe
         50                  55                  60

Lys Gly Lys Ala Thr Leu Thr Ile Asp Lys Ser Ser Ser Thr Ala Tyr
 65                  70                  75                  80

Met Glu Leu Leu Ser Leu Thr Ser Glu Asp Ser Ala Val Tyr Tyr Cys
                 85                  90                  95

Ala Arg Asp Tyr Gly Tyr Val Leu Asp Tyr Trp Gly Gln Gly Thr Thr
```

Leu Thr Val Ser Ser
        115

<210> SEQ ID NO 21
<211> LENGTH: 106
<212> TYPE: PRT
<213> ORGANISM: Artificial Sequence
<220> FEATURE:
<223> OTHER INFORMATION: Antibody fragment

<400> SEQUENCE: 21

Ile Val Leu Thr Gln Ser Pro Ala Ile Met Ser Ala Ser Pro Gly Glu
1               5                   10                  15

Lys Val Thr Ile Thr Cys Ser Ala Ser Ser Ser Val Ser Tyr Leu His
            20                  25                  30

Trp Phe Gln Gln Lys Pro Gly Thr Ser Pro Lys Leu Trp Val Tyr Ser
        35                  40                  45

Thr Ser Asn Leu Pro Ser Gly Val Pro Ala Arg Phe Gly Gly Ser Gly
    50                  55                  60

Ser Gly Thr Ser Tyr Ser Leu Thr Ile Ser Arg Met Glu Ala Glu Asp
65                  70                  75                  80

Ala Ala Thr Tyr Tyr Cys Gln Gln Arg Ser Ile Tyr Pro Pro Trp Thr
                85                  90                  95

Phe Gly Gly Gly Thr Lys Leu Glu Ile Lys
            100                 105

<210> SEQ ID NO 22
<211> LENGTH: 117
<212> TYPE: PRT
<213> ORGANISM: Artificial Sequence
<220> FEATURE:
<223> OTHER INFORMATION: Antibody fragment

<400> SEQUENCE: 22

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Thr Ile Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Asp Tyr Gly Phe Val Leu Asp Tyr Trp Gly Gln Gly Thr Thr
            100                 105                 110

Leu Thr Val Ser Ser
        115

<210> SEQ ID NO 23
<211> LENGTH: 106
<212> TYPE: PRT
<213> ORGANISM: Artificial Sequence
<220> FEATURE:
<223> OTHER INFORMATION: Antibody fragment

<400> SEQUENCE: 23

Ile Val Leu Thr Gln Ser Pro Ser Ile Met Ser Val Ser Pro Gly Glu
1               5                   10                  15

Lys Val Thr Ile Thr Cys Ser Ala Ser Ser Val Ser Tyr Met His
            20                  25                  30

Trp Phe Gln Gln Lys Pro Gly Thr Ser Pro Lys Leu Cys Ile Tyr Ser
        35                  40                  45

Thr Ser Asn Leu Ala Ser Gly Val Pro Ala Arg Phe Ser Gly Arg Gly
    50                  55                  60

Ser Gly Thr Ser Tyr Ser Leu Thr Ile Ser Arg Val Ala Ala Glu Asp
65              70                  75                  80

Ala Ala Thr Tyr Tyr Cys Gln Gln Arg Ser Asn Tyr Pro Pro Trp Thr
                85                  90                  95

Phe Gly Gly Gly Thr Lys Leu Glu Ile Lys
            100                 105

<210> SEQ ID NO 24
<211> LENGTH: 117
<212> TYPE: PRT
<213> ORGANISM: Artificial Sequence
<220> FEATURE:
<223> OTHER INFORMATION: Antibody fragment

<400> SEQUENCE: 24

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Ile Ile Tyr Asn Gln Lys Phe
    50                  55                  60

Lys Gly Lys Ala Thr Leu Thr Val Asp Lys Ser Ser Ser Thr Ala Tyr
65              70                  75                  80

Met Glu Leu Leu Ser Leu Thr Ser Glu Asp Ser Ala Val Phe Tyr Cys
                85                  90                  95

Ala Arg Asp Phe Gly Tyr Val Leu Asp Tyr Trp Gly Gln Gly Thr Thr
            100                 105                 110

Leu Thr Val Ser Ser
        115

<210> SEQ ID NO 25
<211> LENGTH: 106
<212> TYPE: PRT
<213> ORGANISM: Artificial Sequence
<220> FEATURE:
<223> OTHER INFORMATION: Antibody fragment

<400> SEQUENCE: 25

Ile Val Leu Thr Gln Ser Pro Ala Ile Met Ser Ala Ser Pro Gly Glu
1               5                   10                  15

Lys Val Thr Ile Thr Cys Ser Ala Ser Ser Val Ser Tyr Met His
            20                  25                  30

Trp Phe Gln Gln Lys Pro Gly Thr Ser Pro Lys Leu Trp Ile Tyr Ser
        35                  40                  45

Thr Ser Asn Leu Ala Ser Gly Val Pro Ala Arg Phe Ser Gly Ser Gly
    50                  55                  60

Ser Gly Thr Ser Tyr Ser Leu Thr Ile Ser Arg Val Ala Ala Glu Asp

```
                    65                  70                  75                  80
Ala Ala Thr Tyr Tyr Cys Gln Gln Arg Ser Thr Tyr Pro Pro Trp Thr
                        85                  90                  95

Phe Gly Gly Gly Thr Lys Leu Glu Ile Lys
                100                 105

<210> SEQ ID NO 26
<211> LENGTH: 117
<212> TYPE: PRT
<213> ORGANISM: Artificial Sequence
<220> FEATURE:
<223> OTHER INFORMATION: Antibody fragment

<400> SEQUENCE: 26

Glu Val Gln Leu Gln Gln Ser Arg Pro Glu Leu Val Lys Pro Gly Ala
1               5                   10                  15

Ser Met Lys Ile Ser Cys Lys Ala Ser Gly Tyr Ser Phe Thr Gly Tyr
                20                  25                  30

Thr Leu Asn Trp Val Lys Gln Ser His Gly Lys Asn Leu Glu Trp Ile
            35                  40                  45

Gly Leu Ile Asn Pro Tyr Asn Gly Gly Ser Ser Tyr Asn Gln Lys Phe
        50                  55                  60

Lys Asp Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Asp Tyr Gly Tyr Val Phe Asp Tyr Trp Gly Gln Gly Thr Thr
                100                 105                 110

Leu Thr Val Ser Ser
        115

<210> SEQ ID NO 27
<211> LENGTH: 106
<212> TYPE: PRT
<213> ORGANISM: Artificial Sequence
<220> FEATURE:
<223> OTHER INFORMATION: Antibody fragment

<400> SEQUENCE: 27

Ile Val Leu Thr Gln Ser Pro Ala Ile Met Ser Ala Ser Pro Gly Glu
1               5                   10                  15

Lys Val Thr Ile Thr Cys Ser Ala Ser Ser Val Asn Tyr Met His
                20                  25                  30

Trp Phe Gln Leu Lys Pro Gly Thr Ser Pro Lys Leu Leu Ile Tyr Ser
            35                  40                  45

Thr Ser Asn Leu Ala Ser Gly Val Pro Ala Arg Phe Ser Gly Arg Gly
        50                  55                  60

Ser Gly Thr Ser Tyr Ser Leu Thr Ile Ser Arg Met Glu Ala Glu Asp
65                  70                  75                  80

Ala Ala Thr Tyr Tyr Cys Gln Gln Arg Asn Asn Tyr Pro Pro Trp Thr
                85                  90                  95

Phe Gly Gly Gly Thr Lys Leu Glu Ile Lys
                100                 105

<210> SEQ ID NO 28
<211> LENGTH: 106
<212> TYPE: PRT
<213> ORGANISM: Artificial Sequence
<220> FEATURE:
```

<223> OTHER INFORMATION: Antibody fragment

<400> SEQUENCE: 28

Ile Val Leu Thr Gln Ser Pro Ser Ile Met Ser Val Ser Pro Gly Glu
1               5                   10                  15

Lys Val Thr Ile Thr Cys Ser Ala Ser Ser Val Ser Tyr Met His
            20                  25                  30

Trp Phe Gln Gln Lys Pro Gly Thr Ser Pro Lys Leu Gly Ile Tyr Ser
        35                  40                  45

Thr Ser Asn Leu Ala Ser Gly Val Pro Ala Arg Phe Ser Gly Arg Gly
    50                  55                  60

Ser Gly Thr Ser Tyr Ser Leu Thr Ile Ser Arg Val Ala Ala Glu Asp
65                  70                  75                  80

Ala Ala Thr Tyr Tyr Cys Gln Gln Arg Ser Asn Tyr Pro Pro Trp Thr
                85                  90                  95

Phe Gly Gly Gly Thr Lys Leu Glu Ile Lys
            100                 105

<210> SEQ ID NO 29
<211> LENGTH: 106
<212> TYPE: PRT
<213> ORGANISM: Artificial Sequence
<220> FEATURE:
<223> OTHER INFORMATION: Antibody fragment

<400> SEQUENCE: 29

Ile Val Leu Thr Gln Ser Pro Ser Ile Met Ser Val Ser Pro Gly Glu
1               5                   10                  15

Lys Val Thr Ile Thr Cys Ser Ala Ser Ser Val Ser Tyr Met His
            20                  25                  30

Trp Phe Gln Gln Lys Pro Gly Thr Ser Pro Lys Leu Ser Ile Tyr Ser
        35                  40                  45

Thr Ser Asn Leu Ala Ser Gly Val Pro Ala Arg Phe Ser Gly Arg Gly
    50                  55                  60

Ser Gly Thr Ser Tyr Ser Leu Thr Ile Ser Arg Val Ala Ala Glu Asp
65                  70                  75                  80

Ala Ala Thr Tyr Tyr Cys Gln Gln Arg Ser Asn Tyr Pro Pro Trp Thr
                85                  90                  95

Phe Gly Gly Gly Thr Lys Leu Glu Ile Lys
            100                 105

<210> SEQ ID NO 30
<211> LENGTH: 119
<212> TYPE: PRT
<213> ORGANISM: Artificial Sequence
<220> FEATURE:
<223> OTHER INFORMATION: Antibody fragment

<400> SEQUENCE: 30

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Tyr Thr Lys Tyr Asn Gln Lys Phe
    50                  55                  60

Lys Asp Lys Ala Thr Leu Thr Ala Asp Lys Ser Ser Ser Thr Ala Tyr

```
                65                  70                  75                  80
Met Gln Leu Ser Ser Leu Thr Ser Glu Asp Ser Ala Val Tyr Tyr Cys
                    85                  90                  95

Ala Arg Trp Gln Asp Tyr Asp Val Tyr Phe Asp Tyr Trp Gly Gln Gly
                100                 105                 110

Thr Thr Leu Thr Val Ser Ser
            115

<210> SEQ ID NO 31
<211> LENGTH: 107
<212> TYPE: PRT
<213> ORGANISM: Artificial Sequence
<220> FEATURE:
<223> OTHER INFORMATION: Antibody fragment

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys
            100                 105

<210> SEQ ID NO 32
<211> LENGTH: 122
<212> TYPE: PRT
<213> ORGANISM: Artificial Sequence
<220> FEATURE:
<223> OTHER INFORMATION: Antibody fragment

<400> SEQUENCE: 32

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
                20                  25                  30

Thr Met Asn Trp Val Lys Gln Ser His Gly Lys Asn Leu Glu Trp Met
            35                  40                  45

Gly Leu Ile Asn Pro Tyr Lys Gly Val Ser Thr Tyr Asn Gln Lys Phe
    50                  55                  60

Lys Asp Lys Ala Thr Phe Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Ser Gly Tyr Tyr Gly Asp Ser Asp Trp Tyr Phe Asp Val Trp
                100                 105                 110

Gly Ala Gly Thr Thr Val Thr Val Ser Ser
            115                 120

<210> SEQ ID NO 33
<211> LENGTH: 107
```

```
<212> TYPE: PRT
<213> ORGANISM: Artificial Sequence
<220> FEATURE:
<223> OTHER INFORMATION: Antibody fragment

<400> SEQUENCE: 33

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Arg Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Lys Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Ala Gly Gly Thr Lys Leu Glu Ile Lys
            100                 105

<210> SEQ ID NO 34
<211> LENGTH: 119
<212> TYPE: PRT
<213> ORGANISM: Artificial Sequence
<220> FEATURE:
<223> OTHER INFORMATION: Antibody fragment

<400> SEQUENCE: 34

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Phe Trp Val Arg Gln Thr Pro Asp Lys Arg Leu Glu Trp Val
        35                  40                  45

Ala Thr Ile Ser Arg Tyr Ser Arg Tyr Ile Tyr Tyr Pro Asp Ser Val
50                  55                  60

Lys Gly Arg Phe Thr Ile Ser Arg Asp Asn Val Lys Asn Thr Leu Tyr
65                  70                  75                  80

Leu Gln Met Ser Ser Leu Lys Ser Glu Asp Thr Ala Ile Tyr Tyr Cys
                85                  90                  95

Ala Arg Arg Pro Leu Tyr Gly Ser Ser Pro Asp Tyr Trp Gly Gln Gly
            100                 105                 110

Thr Thr Leu Thr Val Ser Ser
        115

<210> SEQ ID NO 35
<211> LENGTH: 108
<212> TYPE: PRT
<213> ORGANISM: Artificial Sequence
<220> FEATURE:
<223> OTHER INFORMATION: Antibody fragment

<400> SEQUENCE: 35

Asp Ile Glu Asn Val Leu Thr Gln Ser Pro Ala Ile Met Ser Ala Ser
1               5                   10                  15

Pro Gly Glu Lys Val Thr Met Thr Cys Ser Ala Ser Ser Ser Val Thr
            20                  25                  30

Tyr Val His Trp Tyr Gln Gln Lys Ser Asn Thr Ser Pro Lys Leu Trp
```

```
                35                  40                  45
Ile Tyr Asp Thr Ser Lys Leu Ala Ser Gly Val Pro Gly Arg Val Ser
 50                  55                  60
Gly Ser Gly Ser Gly Asn Ser Tyr Ser Leu Thr Ile Ser Ser Met Glu
 65                  70                  75                  80
Ala Glu Asp Val Ala Thr Tyr Tyr Cys Phe Gln Gly Ser Gly Tyr Pro
                 85                  90                  95
Leu Thr Phe Gly Ser Gly Thr Lys Leu Glu Met Arg
            100                 105

<210> SEQ ID NO 36
<211> LENGTH: 117
<212> TYPE: PRT
<213> ORGANISM: Artificial Sequence
<220> FEATURE:
<223> OTHER INFORMATION: Antibody fragment

<400> SEQUENCE: 36

Lys Leu Gln Gln Ser Gly Ala Glu Leu Ala Arg Pro Gly Ala Ser Val
  1               5                  10                  15
Lys Met Ser Cys Lys Thr Ser Gly Tyr Thr Phe Thr Arg Tyr Thr Met
                 20                  25                  30
His Trp Val Lys Gln Arg Pro Gly Gln Gly Leu Glu Trp Ile Gly Tyr
             35                  40                  45
Ile Asn Pro Ser Arg Gly Tyr Thr Asn Tyr Asn Gln Lys Phe Lys Asp
 50                  55                  60
Lys Ala Thr Leu Thr Thr Asp Lys Ser Ser Thr Ala Tyr Met Gln
 65                  70                  75                  80
Leu Ser Ser Leu Thr Ser Glu Asp Ser Ala Val Tyr Tyr Cys Ala Arg
                 85                  90                  95
Tyr Tyr Asp Asp His Tyr Cys Leu Asp Tyr Trp Gly Gln Gly Thr Thr
            100                 105                 110
Leu Thr Val Ser Ser
            115

<210> SEQ ID NO 37
<211> LENGTH: 106
<212> TYPE: PRT
<213> ORGANISM: Artificial Sequence
<220> FEATURE:
<223> OTHER INFORMATION: Antibody fragment

<400> SEQUENCE: 37

Asp Ile Gln Leu Thr Gln Ser Pro Ala Ile Met Ser Ala Ser Pro Gly
  1               5                  10                  15
Glu Lys Val Thr Met Thr Cys Arg Ala Ser Ser Ser Val Ser Tyr Met
                 20                  25                  30
Asn Trp Tyr Gln Gln Lys Ser Gly Thr Ser Pro Lys Arg Trp Ile Tyr
             35                  40                  45
Asp Thr Ser Lys Val Ala Ser Gly Val Pro Tyr Arg Phe Ser Gly Ser
 50                  55                  60
Gly Ser Gly Thr Ser Tyr Ser Leu Thr Ile Ser Ser Met Glu Ala Glu
 65                  70                  75                  80
Asp Ala Ala Thr Tyr Tyr Cys Gln Gln Trp Ser Ser Asn Pro Leu Thr
                 85                  90                  95
Phe Gly Ala Gly Thr Lys Leu Glu Leu Lys
            100                 105
```

```
<210> SEQ ID NO 38
<211> LENGTH: 495
<212> TYPE: PRT
<213> ORGANISM: Artificial Sequence
<220> FEATURE:
<223> OTHER INFORMATION: Bispecific molecule

<400> SEQUENCE: 38

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Ser Trp Arg Gly Asn Ser Phe Asp Tyr Trp Gly Gln Gly Thr
            100                 105                 110

Thr Leu Thr Val Ser Ser Gly Gly Gly Gly Ser Gly Gly Gly Gly Ser
        115                 120                 125

Gly Gly Gly Gly Ser Asp Ile Val Met Thr Gln Ser Pro Ser Ser Leu
    130                 135                 140

Thr Val Thr Ala Gly Glu Lys Val Thr Met Ser Cys Lys Ser Ser Gln
145                 150                 155                 160

Ser Leu Leu Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Thr Gly Ser Gly Ser Gly Thr
        195                 200                 205

Asp Phe Thr Leu Thr Ile Ser Ser Val Gln Ala Glu Asp Leu Ala Val
    210                 215                 220

Tyr Tyr Cys Gln Asn Asp Tyr Ser Tyr Pro Phe Thr Phe Gly Ser Gly
225                 230                 235                 240

Thr Lys Leu Glu Ile Lys Ser Gly Gly Gly Ser Asp Ile Lys Leu
                245                 250                 255

Gln Gln Ser Gly Ala Glu Leu Ala Arg Pro Gly Ala Ser Val Lys Met
            260                 265                 270

Ser Cys Lys Thr Ser Gly Tyr Thr Phe Thr Arg Tyr Thr Met His Trp
        275                 280                 285

Val Lys Gln Arg Pro Gly Gln Gly Leu Glu Trp Ile Gly Tyr Ile Asn
    290                 295                 300

Pro Ser Arg Gly Tyr Thr Asn Tyr Asn Gln Lys Phe Lys Asp Lys Ala
305                 310                 315                 320

Thr Leu Thr Thr Asp Lys Ser Ser Ser Thr Ala Tyr Met Gln Leu Ser
                325                 330                 335

Ser Leu Thr Ser Glu Asp Ser Ala Val Tyr Tyr Cys Ala Arg Tyr Tyr
            340                 345                 350

Asp Asp His Tyr Cys Leu Asp Tyr Trp Gly Gln Gly Thr Thr Leu Thr
        355                 360                 365
```

Val Ser Ser Val Glu Gly Gly Ser Gly Gly Ser Gly Gly
370                 375             380

Ser Gly Gly Val Asp Asp Ile Gln Leu Thr Gln Ser Pro Ala Ile Met
385                 390                 395                 400

Ser Ala Ser Pro Gly Glu Lys Val Thr Met Thr Cys Arg Ala Ser Ser
                405                 410                 415

Ser Val Ser Tyr Met Asn Trp Tyr Gln Gln Lys Ser Gly Thr Ser Pro
            420                 425                 430

Lys Arg Trp Ile Tyr Asp Thr Ser Lys Val Ala Ser Gly Val Pro Tyr
        435                 440                 445

Arg Phe Ser Gly Ser Gly Ser Gly Thr Ser Tyr Ser Leu Thr Ile Ser
    450                 455                 460

Ser Met Glu Ala Glu Asp Ala Ala Thr Tyr Tyr Cys Gln Gln Trp Ser
465                 470                 475                 480

Ser Asn Pro Leu Thr Phe Gly Ala Gly Thr Lys Leu Glu Leu Lys
                485                 490                 495

<210> SEQ ID NO 39
<211> LENGTH: 520
<212> TYPE: PRT
<213> ORGANISM: Artificial Sequence
<220> FEATURE:
<223> OTHER INFORMATION: Bispecific molecule

<400> SEQUENCE: 39

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Thr Phe
        35                  40                  45

Thr Ser Tyr Trp Ile Asn Trp Val Lys Gln Arg Pro Gly Gln Gly Leu
    50                  55                  60

Glu Trp Ile Gly Asn Ile Tyr Pro Ser Asp Ser Tyr Thr Asn Tyr Asn
65                  70                  75                  80

Gln Lys Phe Lys Asp Lys Ala Thr Leu Thr Val Asp Lys Ser Ser Ser
                85                  90                  95

Thr Ala Tyr Met Gln Leu Ser Ser Pro Thr Ser Glu Asp Ser Ala Val
            100                 105                 110

Tyr Tyr Cys Thr Arg Ser Trp Arg Gly Asn Ser Phe Asp Tyr Trp Gly
        115                 120                 125

Gln Gly Thr Thr Leu Thr Val Ser Ser Gly Gly Gly Gly Ser Gly Gly
    130                 135                 140

Gly Gly Ser Gly Gly Gly Gly Ser Asp Ile Val Met Thr Gln Ser Pro
145                 150                 155                 160

Ser Ser Leu Thr Val Thr Ala Gly Glu Lys Val Thr Met Ser Cys Lys
                165                 170                 175

Ser Ser Gln Ser Leu Leu Asn Ser Gly Asn Gln Lys Asn Tyr Leu Thr
            180                 185                 190

Trp Tyr Gln Gln Lys Pro Gly Gln Pro Pro Lys Leu Leu Ile Tyr Trp
        195                 200                 205

Ala Ser Thr Arg Glu Ser Gly Val Pro Asp Arg Phe Thr Gly Ser Gly
    210                 215                 220

Ser Gly Thr Asp Phe Thr Leu Thr Ile Ser Ser Val Gln Ala Glu Asp
225                 230                 235                 240

```
Leu Ala Val Tyr Tyr Cys Gln Asn Asp Tyr Ser Tyr Pro Phe Thr Phe
                245                 250                 255

Gly Ser Gly Thr Lys Leu Glu Ile Lys Ser Gly Gly Gly Gly Ser Asp
        260                 265                 270

Ile Lys Leu Gln Gln Ser Gly Ala Glu Leu Ala Arg Pro Gly Ala Ser
        275                 280                 285

Val Lys Met Ser Cys Lys Thr Ser Gly Tyr Thr Phe Thr Arg Tyr Thr
        290                 295                 300

Met His Trp Val Lys Gln Arg Pro Gly Gln Gly Leu Glu Trp Ile Gly
305                 310                 315                 320

Tyr Ile Asn Pro Ser Arg Gly Tyr Thr Asn Tyr Asn Gln Lys Phe Lys
                325                 330                 335

Asp Lys Ala Thr Leu Thr Thr Asp Lys Ser Ser Ser Thr Ala Tyr Met
                340                 345                 350

Gln Leu Ser Ser Leu Thr Ser Glu Asp Ser Ala Val Tyr Tyr Cys Ala
                355                 360                 365

Arg Tyr Tyr Asp Asp His Tyr Cys Leu Asp Tyr Trp Gly Gln Gly Thr
        370                 375                 380

Thr Leu Thr Val Ser Ser Val Glu Gly Gly Ser Gly Gly Ser Gly Gly
385                 390                 395                 400

Ser Gly Gly Ser Gly Gly Val Asp Asp Ile Gln Leu Thr Gln Ser Pro
                405                 410                 415

Ala Ile Met Ser Ala Ser Pro Gly Glu Lys Val Thr Met Thr Cys Arg
                420                 425                 430

Ala Ser Ser Ser Val Ser Tyr Met Asn Trp Tyr Gln Gln Lys Ser Gly
                435                 440                 445

Thr Ser Pro Lys Arg Trp Ile Tyr Asp Thr Ser Lys Val Ala Ser Gly
        450                 455                 460

Val Pro Tyr Arg Phe Ser Gly Ser Gly Ser Gly Thr Ser Tyr Ser Leu
465                 470                 475                 480

Thr Ile Ser Ser Met Glu Ala Glu Asp Ala Ala Thr Tyr Tyr Cys Gln
                485                 490                 495

Gln Trp Ser Ser Asn Pro Leu Thr Phe Gly Ala Gly Thr Lys Leu Glu
                500                 505                 510

Leu Lys His His His His His His
        515                 520

<210> SEQ ID NO 40
<211> LENGTH: 490
<212> TYPE: PRT
<213> ORGANISM: Artificial Sequence
<220> FEATURE:
<223> OTHER INFORMATION: Bispecific molecule

<400> SEQUENCE: 40

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
                20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
        50                  55                  60

Lys Asp Lys Ala Thr Leu Thr Val Asp Lys Ser Ser Ser Thr Ala Tyr
65                  70                  75                  80
```

```
Met Gln Leu Ser Ser Pro Thr Ser Glu Asp Ser Ala Val Tyr Tyr Cys
                85                  90                  95

Thr Arg Ser Trp Arg Gly Asn Ser Phe Asp Tyr Trp Gly Gln Gly Thr
            100                 105                 110

Thr Leu Thr Val Ser Ser Gly Gly Gly Gly Ser Gly Gly Gly Gly Ser
        115                 120                 125

Gly Gly Gly Gly Ser Asp Ile Val Met Thr Gln Ser Pro Ser Ser Leu
    130                 135                 140

Thr Val Thr Ala Gly Glu Lys Val Thr Met Ser Cys Lys Ser Ser Gln
145                 150                 155                 160

Ser Leu Leu Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Thr Gly Ser Gly Ser Gly Thr
        195                 200                 205

Asp Phe Thr Leu Thr Ile Ser Ser Val Gln Ala Glu Asp Leu Ala Val
    210                 215                 220

Tyr Tyr Cys Gln Asn Asp Tyr Ser Tyr Pro Phe Thr Phe Gly Ser Gly
225                 230                 235                 240

Thr Lys Leu Glu Ile Lys Ser Gly Gly Gly Ser Lys Leu Gln Gln
                245                 250                 255

Ser Gly Ala Glu Leu Ala Arg Pro Gly Ala Ser Val Lys Met Ser Cys
                260                 265                 270

Lys Thr Ser Gly Tyr Thr Phe Thr Arg Tyr Thr Met His Trp Val Lys
            275                 280                 285

Gln Arg Pro Gly Gln Gly Leu Glu Trp Ile Gly Tyr Ile Asn Pro Ser
        290                 295                 300

Arg Gly Tyr Thr Asn Tyr Asn Gln Lys Phe Lys Asp Lys Ala Thr Leu
305                 310                 315                 320

Thr Thr Asp Lys Ser Ser Thr Ala Tyr Met Gln Leu Ser Ser Leu
                325                 330                 335

Thr Ser Glu Asp Ser Ala Val Tyr Tyr Cys Ala Arg Tyr Tyr Asp Asp
            340                 345                 350

His Tyr Cys Leu Asp Tyr Trp Gly Gln Gly Thr Thr Leu Thr Val Ser
        355                 360                 365

Ser Gly Gly Gly Gly Ser Gly Gly Gly Gly Ser Gly Gly Gly Gly Ser
    370                 375                 380

Asp Ile Gln Leu Thr Gln Ser Pro Ala Ile Met Ser Ala Ser Pro Gly
385                 390                 395                 400

Glu Lys Val Thr Met Thr Cys Arg Ala Ser Ser Ser Val Ser Tyr Met
                405                 410                 415

Asn Trp Tyr Gln Gln Lys Ser Gly Thr Ser Pro Lys Arg Trp Ile Tyr
            420                 425                 430

Asp Thr Ser Lys Val Ala Ser Gly Val Pro Tyr Arg Phe Ser Gly Ser
        435                 440                 445

Gly Ser Gly Thr Ser Tyr Ser Leu Thr Ile Ser Ser Met Glu Ala Glu
    450                 455                 460

Asp Ala Ala Thr Tyr Tyr Cys Gln Gln Trp Ser Ser Asn Pro Leu Thr
465                 470                 475                 480

Phe Gly Ala Gly Thr Lys Leu Glu Leu Lys
                485                 490
```

```
<210> SEQ ID NO 41
<211> LENGTH: 515
<212> TYPE: PRT
<213> ORGANISM: Artificial Sequence
<220> FEATURE:
<223> OTHER INFORMATION: Bispecific molecule

<400> SEQUENCE: 41

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Thr Phe
        35                  40                  45

Thr Ser Tyr Trp Ile Asn Trp Val Lys Gln Arg Pro Gly Gln Gly Leu
    50                  55                  60

Glu Trp Ile Gly Asn Ile Tyr Pro Ser Asp Ser Tyr Thr Asn Tyr Asn
65                  70                  75                  80

Gln Lys Phe Lys Asp Lys Ala Thr Leu Thr Val Asp Lys Ser Ser Ser
                85                  90                  95

Thr Ala Tyr Met Gln Leu Ser Ser Pro Thr Ser Glu Asp Ser Ala Val
            100                 105                 110

Tyr Tyr Cys Thr Arg Ser Trp Arg Gly Asn Ser Phe Asp Tyr Trp Gly
        115                 120                 125

Gln Gly Thr Thr Leu Thr Val Ser Ser Gly Gly Gly Gly Ser Gly Gly
    130                 135                 140

Gly Gly Ser Gly Gly Gly Ser Asp Ile Val Met Thr Gln Ser Pro
145                 150                 155                 160

Ser Ser Leu Thr Val Thr Ala Gly Glu Lys Val Thr Met Ser Cys Lys
                165                 170                 175

Ser Ser Gln Ser Leu Leu Asn Ser Gly Asn Gln Lys Asn Tyr Leu Thr
            180                 185                 190

Trp Tyr Gln Gln Lys Pro Gly Gln Pro Pro Lys Leu Leu Ile Tyr Trp
        195                 200                 205

Ala Ser Thr Arg Glu Ser Gly Val Pro Asp Arg Phe Thr Gly Ser Gly
    210                 215                 220

Ser Gly Thr Asp Phe Thr Leu Thr Ile Ser Ser Val Gln Ala Glu Asp
225                 230                 235                 240

Leu Ala Val Tyr Tyr Cys Gln Asn Asp Tyr Ser Tyr Pro Phe Thr Phe
                245                 250                 255

Gly Ser Gly Thr Lys Leu Glu Ile Lys Ser Gly Gly Gly Gly Ser Lys
            260                 265                 270

Leu Gln Gln Ser Gly Ala Glu Leu Ala Arg Pro Gly Ala Ser Val Lys
        275                 280                 285

Met Ser Cys Lys Thr Ser Gly Tyr Thr Phe Thr Arg Tyr Thr Met His
    290                 295                 300

Trp Val Lys Gln Arg Pro Gly Gln Gly Leu Glu Trp Ile Gly Tyr Ile
305                 310                 315                 320

Asn Pro Ser Arg Gly Tyr Thr Asn Tyr Asn Gln Lys Phe Lys Asp Lys
                325                 330                 335

Ala Thr Leu Thr Thr Asp Lys Ser Ser Ser Thr Ala Tyr Met Gln Leu
            340                 345                 350

Ser Ser Leu Thr Ser Glu Asp Ser Ala Val Tyr Tyr Cys Ala Arg Tyr
        355                 360                 365

Tyr Asp Asp His Tyr Cys Leu Asp Tyr Trp Gly Gln Gly Thr Thr Leu
```

```
            370                 375                 380
Thr Val Ser Ser Gly Gly Gly Ser Gly Gly Gly Ser Gly Gly
385                 390                 395                 400

Gly Gly Ser Asp Ile Gln Leu Thr Gln Ser Pro Ala Ile Met Ser Ala
                405                 410                 415

Ser Pro Gly Glu Lys Val Thr Met Thr Cys Arg Ala Ser Ser Ser Val
            420                 425                 430

Ser Tyr Met Asn Trp Tyr Gln Gln Lys Ser Gly Thr Ser Pro Lys Arg
        435                 440                 445

Trp Ile Tyr Asp Thr Ser Lys Val Ala Ser Gly Val Pro Tyr Arg Phe
    450                 455                 460

Ser Gly Ser Gly Ser Gly Thr Ser Tyr Ser Leu Thr Ile Ser Ser Met
465                 470                 475                 480

Glu Ala Glu Asp Ala Ala Thr Tyr Tyr Cys Gln Gln Trp Ser Ser Asn
                485                 490                 495

Pro Leu Thr Phe Gly Ala Gly Thr Lys Leu Glu Leu Lys His His His
                500                 505                 510

His His His
        515

<210> SEQ ID NO 42
<211> LENGTH: 487
<212> TYPE: PRT
<213> ORGANISM: Artificial Sequence
<220> FEATURE:
<223> OTHER INFORMATION: Bispecific molecule

<400> SEQUENCE: 42

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
                20                  25                  30

Thr Met Asn Trp Val Lys Gln Ser His Gly Lys Asn Leu Glu Trp Ile
            35                  40                  45

Gly Leu Ile Asn Pro Tyr Asn Gly Gly Thr Ile Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Asp Tyr Gly Phe Val Leu Asp Tyr Trp Gly Gln Gly Thr Thr
            100                 105                 110

Leu Thr Val Ser Ser Gly Gly Gly Gly Ser Gly Gly Gly Gly Ser Gly
        115                 120                 125

Gly Gly Ser Asp Ile Val Leu Thr Gln Ser Pro Ser Ile Met Ser
    130                 135                 140

Val Ser Pro Gly Glu Lys Val Thr Ile Thr Cys Ser Ala Ser Ser Ser
145                 150                 155                 160

Val Ser Tyr Met His Trp Phe Gln Gln Lys Pro Gly Thr Ser Pro Lys
                165                 170                 175

Leu Cys Ile Tyr Ser Thr Ser Asn Leu Ala Ser Gly Val Pro Ala Arg
            180                 185                 190

Phe Ser Gly Arg Gly Ser Gly Thr Ser Tyr Ser Leu Thr Ile Ser Arg
        195                 200                 205

Val Ala Ala Glu Asp Ala Ala Thr Tyr Tyr Cys Gln Gln Arg Ser Asn
```

```
            210                 215                 220
Tyr Pro Pro Trp Thr Phe Gly Gly Thr Lys Leu Glu Ile Lys Ser
225                 230                 235                 240

Gly Gly Gly Gly Ser Asp Ile Lys Leu Gln Gln Ser Gly Ala Glu Leu
                245                 250                 255

Ala Arg Pro Gly Ala Ser Val Lys Met Ser Cys Lys Thr Ser Gly Tyr
            260                 265                 270

Thr Phe Thr Arg Tyr Thr Met His Trp Val Lys Gln Arg Pro Gly Gln
        275                 280                 285

Gly Leu Glu Trp Ile Gly Tyr Ile Asn Pro Ser Arg Gly Tyr Thr Asn
    290                 295                 300

Tyr Asn Gln Lys Phe Lys Asp Lys Ala Thr Leu Thr Thr Asp Lys Ser
305                 310                 315                 320

Ser Ser Thr Ala Tyr Met Gln Leu Ser Ser Leu Thr Ser Glu Asp Ser
                325                 330                 335

Ala Val Tyr Tyr Cys Ala Arg Tyr Tyr Asp Asp His Tyr Cys Leu Asp
            340                 345                 350

Tyr Trp Gly Gln Gly Thr Thr Leu Thr Val Ser Ser Val Glu Gly Gly
        355                 360                 365

Ser Gly Gly Ser Gly Gly Ser Gly Gly Ser Gly Gly Val Asp Asp Ile
    370                 375                 380

Gln Leu Thr Gln Ser Pro Ala Ile Met Ser Ala Ser Pro Gly Glu Lys
385                 390                 395                 400

Val Thr Met Thr Cys Arg Ala Ser Ser Val Ser Tyr Met Asn Trp
                405                 410                 415

Tyr Gln Gln Lys Ser Gly Thr Ser Pro Lys Arg Trp Ile Tyr Asp Thr
            420                 425                 430

Ser Lys Val Ala Ser Gly Val Pro Tyr Arg Phe Ser Gly Ser Gly Ser
        435                 440                 445

Gly Thr Ser Tyr Ser Leu Thr Ile Ser Ser Met Glu Ala Glu Asp Ala
    450                 455                 460

Ala Thr Tyr Tyr Cys Gln Gln Trp Ser Ser Asn Pro Leu Thr Phe Gly
465                 470                 475                 480

Ala Gly Thr Lys Leu Glu Leu
                485

<210> SEQ ID NO 43
<211> LENGTH: 513
<212> TYPE: PRT
<213> ORGANISM: Artificial Sequence
<220> FEATURE:
<223> OTHER INFORMATION: Bispecific molecule

<400> SEQUENCE: 43

Met Gly Trp Ser Cys Ile Ile Leu Phe Leu Val Ala Thr Ala Thr Gly
1               5                   10                  15

Val His Ser Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Met Asn Trp Val Lys Gln Ser His Gly Lys Asn Leu
    50                  55                  60

Glu Trp Ile Gly Leu Ile Asn Pro Tyr Asn Gly Gly Thr Ile Tyr Asn
65                  70                  75                  80

Gln Lys Phe Lys Gly Lys Ala Thr Leu Thr Val Asp Lys Ser Ser Ser
```

```
                    85                  90                  95
Thr Ala Tyr Met Glu Leu Leu Ser Leu Thr Ser Glu Asp Ser Ala Val
                100                 105                 110
Tyr Tyr Cys Ala Arg Asp Tyr Gly Phe Val Leu Asp Tyr Trp Gly Gln
                115                 120                 125
Gly Thr Thr Leu Thr Val Ser Ser Gly Gly Gly Ser Gly Gly Gly
            130                 135                 140
Gly Ser Gly Gly Gly Ser Asp Ile Val Leu Thr Gln Ser Pro Ser
145                 150                 155                 160
Ile Met Ser Val Ser Pro Gly Glu Lys Val Thr Ile Thr Cys Ser Ala
                165                 170                 175
Ser Ser Ser Val Ser Tyr Met His Trp Phe Gln Gln Lys Pro Gly Thr
                180                 185                 190
Ser Pro Lys Leu Cys Ile Tyr Ser Thr Ser Asn Leu Ala Ser Gly Val
                195                 200                 205
Pro Ala Arg Phe Ser Gly Arg Gly Ser Gly Thr Ser Tyr Ser Leu Thr
                210                 215                 220
Ile Ser Arg Val Ala Ala Glu Asp Ala Ala Thr Tyr Tyr Cys Gln Gln
225                 230                 235                 240
Arg Ser Asn Tyr Pro Pro Trp Thr Phe Gly Gly Gly Thr Lys Leu Glu
                245                 250                 255
Ile Lys Ser Gly Gly Gly Gly Ser Asp Ile Lys Leu Gln Gln Ser Gly
                260                 265                 270
Ala Glu Leu Ala Arg Pro Gly Ala Ser Val Lys Met Ser Cys Lys Thr
                275                 280                 285
Ser Gly Tyr Thr Phe Thr Arg Tyr Thr Met His Trp Val Lys Gln Arg
                290                 295                 300
Pro Gly Gln Gly Leu Glu Trp Ile Gly Tyr Ile Asn Pro Ser Arg Gly
305                 310                 315                 320
Tyr Thr Asn Tyr Asn Gln Lys Phe Lys Asp Lys Ala Thr Leu Thr Thr
                325                 330                 335
Asp Lys Ser Ser Ser Thr Ala Tyr Met Gln Leu Ser Ser Leu Thr Ser
                340                 345                 350
Glu Asp Ser Ala Val Tyr Tyr Cys Ala Arg Tyr Tyr Asp Asp His Tyr
                355                 360                 365
Cys Leu Asp Tyr Trp Gly Gln Gly Thr Thr Leu Thr Val Ser Ser Val
                370                 375                 380
Glu Gly Gly Ser Gly Gly Ser Gly Gly Ser Gly Gly Ser Gly Gly Val
385                 390                 395                 400
Asp Asp Ile Gln Leu Thr Gln Ser Pro Ala Ile Met Ser Ala Ser Pro
                405                 410                 415
Gly Glu Lys Val Thr Met Thr Cys Arg Ala Ser Ser Ser Val Ser Tyr
                420                 425                 430
Met Asn Trp Tyr Gln Gln Lys Ser Gly Thr Ser Pro Lys Arg Trp Ile
                435                 440                 445
Tyr Asp Thr Ser Lys Val Ala Ser Gly Val Pro Tyr Arg Phe Ser Gly
                450                 455                 460
Ser Gly Ser Gly Thr Ser Tyr Ser Leu Thr Ile Ser Ser Met Glu Ala
465                 470                 475                 480
Glu Asp Ala Ala Thr Tyr Tyr Cys Gln Gln Trp Ser Ser Asn Pro Leu
                485                 490                 495
Thr Phe Gly Ala Gly Thr Lys Leu Glu Leu Lys His His His His
                500                 505                 510
```

His

```
<210> SEQ ID NO 44
<211> LENGTH: 488
<212> TYPE: PRT
<213> ORGANISM: Artificial Sequence
<220> FEATURE:
<223> OTHER INFORMATION: Bispecific molecule

<400> SEQUENCE: 44
```

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Ser Gly Gly Gly Ser Glu Val Gln Leu Gln Gln Ser
                245                 250                 255

Gly Pro Glu Leu Val Lys Pro Gly Ala Ser Met Lys Ile Ser Cys Lys
            260                 265                 270

Ala Ser Gly Tyr Ser Phe Thr Gly Tyr Thr Met Asn Trp Val Lys Gln
        275                 280                 285

Ser His Gly Lys Asn Leu Glu Trp Ile Gly Leu Ile Asn Pro Tyr Asn
    290                 295                 300

Gly Gly Thr Ile Tyr Asn Gln Lys Phe Lys Gly Lys Ala Thr Leu Thr
305                 310                 315                 320

Val Asp Lys Ser Ser Ser Thr Ala Tyr Met Glu Leu Leu Ser Leu Thr
                325                 330                 335

Ser Glu Asp Ser Ala Val Tyr Tyr Cys Ala Arg Asp Tyr Gly Phe Val
            340                 345                 350

Leu Asp Tyr Trp Gly Gln Gly Thr Leu Thr Val Ser Ser Gly Gly
            355                 360                 365

Gly Gly Ser Gly Gly Gly Ser Gly Gly Gly Ser Asp Ile Val
370                 375                 380

Leu Thr Gln Ser Pro Ser Ile Met Ser Val Ser Pro Gly Glu Lys Val
385                 390                 395                 400

Thr Ile Thr Cys Ser Ala Ser Ser Val Ser Tyr Met His Trp Phe
                405                 410                 415

Gln Gln Lys Pro Gly Thr Ser Pro Lys Leu Cys Ile Tyr Ser Thr Ser
                420                 425                 430

Asn Leu Ala Ser Gly Val Pro Ala Arg Phe Ser Gly Arg Gly Ser Gly
            435                 440                 445

Thr Ser Tyr Ser Leu Thr Ile Ser Arg Val Ala Ala Glu Asp Ala Ala
    450                 455                 460

Thr Tyr Tyr Cys Gln Gln Arg Ser Asn Tyr Pro Pro Trp Thr Phe Gly
465                 470                 475                 480

Gly Gly Thr Lys Leu Glu Ile Lys
                485

<210> SEQ ID NO 45
<211> LENGTH: 513
<212> TYPE: PRT
<213> ORGANISM: Artificial Sequence
<220> FEATURE:
<223> OTHER INFORMATION: Bispecific molecule

<400> SEQUENCE: 45

Met Gly Trp Ser Cys Ile Ile Leu Phe Leu Val Ala Thr Ala Thr Gly
1               5                   10                  15

Val His Ser Asp Ile Lys Leu Gln Gln Ser Gly Ala Glu Leu Ala Arg
                20                  25                  30

Pro Gly Ala Ser Val Lys Met Ser Cys Lys Thr Ser Gly Tyr Thr Phe
            35                  40                  45

Thr Arg Tyr Thr Met His Trp Val Lys Gln Arg Pro Gly Gln Gly Leu
    50                  55                  60

Glu Trp Ile Gly Tyr Ile Asn Pro Ser Arg Gly Tyr Thr Asn Tyr Asn
65                  70                  75                  80

Gln Lys Phe Lys Asp Lys Ala Thr Leu Thr Thr Asp Lys Ser Ser Ser
                85                  90                  95

Thr Ala Tyr Met Gln Leu Ser Ser Leu Thr Ser Glu Asp Ser Ala Val
                100                 105                 110

Tyr Tyr Cys Ala Arg Tyr Tyr Asp Asp His Tyr Cys Leu Asp Tyr Trp
            115                 120                 125

Gly Gln Gly Thr Thr Leu Thr Val Ser Val Glu Gly Gly Ser Gly
130                 135                 140

Gly Ser Gly Gly Ser Gly Gly Ser Gly Gly Val Asp Asp Ile Gln Leu
145                 150                 155                 160

Thr Gln Ser Pro Ala Ile Met Ser Ala Ser Pro Gly Glu Lys Val Thr
                165                 170                 175

Met Thr Cys Arg Ala Ser Ser Ser Val Ser Tyr Met Asn Trp Tyr Gln
            180                 185                 190

Gln Lys Ser Gly Thr Ser Pro Lys Arg Trp Ile Tyr Asp Thr Ser Lys
        195                 200                 205

Val Ala Ser Gly Val Pro Tyr Arg Phe Ser Gly Ser Gly Ser Gly Thr
    210                 215                 220

Ser Tyr Ser Leu Thr Ile Ser Ser Met Glu Ala Glu Asp Ala Ala Thr
225                 230                 235                 240

Tyr Tyr Cys Gln Gln Trp Ser Ser Asn Pro Leu Thr Phe Gly Ala Gly
            245                 250                 255

Thr Lys Leu Glu Leu Lys Ser Gly Gly Gly Ser Glu Val Gln Leu
        260                 265                 270

Gln Gln Ser Gly Pro Glu Leu Val Lys Pro Gly Ala Ser Met Lys Ile
        275                 280                 285

Ser Cys Lys Ala Ser Gly Tyr Ser Phe Thr Gly Tyr Thr Met Asn Trp
        290                 295                 300

Val Lys Gln Ser His Gly Lys Asn Leu Glu Trp Ile Gly Leu Ile Asn
305                 310                 315                 320

Pro Tyr Asn Gly Gly Thr Ile Tyr Asn Gln Lys Phe Lys Gly Lys Ala
            325                 330                 335

Thr Leu Thr Val Asp Lys Ser Ser Thr Ala Tyr Met Glu Leu Leu
        340                 345                 350

Ser Leu Thr Ser Glu Asp Ser Ala Val Tyr Tyr Cys Ala Arg Asp Tyr
        355                 360                 365

Gly Phe Val Leu Asp Tyr Trp Gly Gln Gly Thr Thr Leu Thr Val Ser
370                 375                 380

Ser Gly Gly Gly Gly Ser Gly Gly Gly Ser Gly Gly Gly Ser
385                 390                 395                 400

Asp Ile Val Leu Thr Gln Ser Pro Ser Ile Met Ser Val Ser Pro Gly
                405                 410                 415

Glu Lys Val Thr Ile Thr Cys Ser Ala Ser Ser Ser Val Ser Tyr Met
            420                 425                 430

His Trp Phe Gln Gln Lys Pro Gly Thr Ser Pro Lys Leu Cys Ile Tyr
            435                 440                 445

Ser Thr Ser Asn Leu Ala Ser Gly Val Pro Ala Arg Phe Ser Gly Arg
        450                 455                 460

Gly Ser Gly Thr Ser Tyr Ser Leu Thr Ile Ser Arg Val Ala Ala Glu
465                 470                 475                 480

Asp Ala Ala Thr Tyr Tyr Cys Gln Gln Arg Ser Asn Tyr Pro Pro Trp
            485                 490                 495

Thr Phe Gly Gly Gly Thr Lys Leu Glu Ile Lys His His His His His
            500                 505                 510

His

<210> SEQ ID NO 46
<211> LENGTH: 15
<212> TYPE: PRT
<213> ORGANISM: Artificial Sequence
<220> FEATURE:
<223> OTHER INFORMATION: Linker

<400> SEQUENCE: 46

Gly Gly Gly Gly Ser Gly Gly Gly Gly Ser Gly Gly Gly Gly Ser
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Linker

<400> SEQUENCE: 47

```
Val Glu Gly Gly Gly Ser Gly Gly Gly Ser Gly Gly Val Asp
1               5                   10                  15

<210> SEQ ID NO 48
<211> LENGTH: 6
<212> TYPE: PRT
<213> ORGANISM: Artificial Sequence
<220> FEATURE:
<223> OTHER INFORMATION: Linker

<400> SEQUENCE: 48

Ser Gly Gly Gly Gly Ser
1               5

<210> SEQ ID NO 49
<211> LENGTH: 5
<212> TYPE: PRT
<213> ORGANISM: Artificial Sequence
<220> FEATURE:
<223> OTHER INFORMATION: Linker

<400> SEQUENCE: 49

Gly Gly Gly Gly Ser
1               5

<210> SEQ ID NO 50
<211> LENGTH: 18
<212> TYPE: PRT
<213> ORGANISM: Artificial Sequence
<220> FEATURE:
<223> OTHER INFORMATION: Linker

<400> SEQUENCE: 50

Val Glu Gly Gly Ser Gly Gly Ser Gly Gly Ser Gly Gly
1               5                   10                  15

Val Asp

<210> SEQ ID NO 51
<211> LENGTH: 19
<212> TYPE: PRT
<213> ORGANISM: Artificial Sequence
<220> FEATURE:
<223> OTHER INFORMATION: Secretion signal

<400> SEQUENCE: 51

Met Gly Trp Ser Cys Ile Ile Leu Phe Leu Val Ala Thr Ala Thr Gly
1               5                   10                  15

Val His Ser

<210> SEQ ID NO 52
<211> LENGTH: 19
<212> TYPE: PRT
<213> ORGANISM: Artificial Sequence
<220> FEATURE:
<223> OTHER INFORMATION: Secretion signal

<400> SEQUENCE: 52

Met Asn Ser Gly Leu Gln Leu Val Phe Phe Val Leu Thr Leu Lys Gly
1               5                   10                  15

Ile Gln Gly

<210> SEQ ID NO 53
<211> LENGTH: 19
<212> TYPE: PRT
<213> ORGANISM: Artificial Sequence
```

<220> FEATURE:
<223> OTHER INFORMATION: Secretion signal

<400> SEQUENCE: 53

Met Asn Phe Gly Leu Ser Leu Ile Phe Leu Ala Leu Ile Leu Lys Gly
1               5                   10                  15

Val Gln Cys

<210> SEQ ID NO 54
<211> LENGTH: 19
<212> TYPE: PRT
<213> ORGANISM: Artificial Sequence
<220> FEATURE:
<223> OTHER INFORMATION: Secretion signal

<400> SEQUENCE: 54

Met Glu Trp Ser Trp Ile Phe Leu Phe Leu Leu Ser Val Thr Thr Gly
1               5                   10                  15

Val His Ser

<210> SEQ ID NO 55
<211> LENGTH: 19
<212> TYPE: PRT
<213> ORGANISM: Artificial Sequence
<220> FEATURE:
<223> OTHER INFORMATION: Secretion signal

<400> SEQUENCE: 55

Met Gly Trp Leu Trp Asn Leu Leu Phe Leu Met Ala Ala Ala Gln Ser
1               5                   10                  15

Ala Gln Ala

<210> SEQ ID NO 56
<211> LENGTH: 21
<212> TYPE: DNA
<213> ORGANISM: Artificial Sequence
<220> FEATURE:
<223> OTHER INFORMATION: Oligonucleotide

<400> SEQUENCE: 56
tggctctgtg tcgacactgt g                                     21

<210> SEQ ID NO 57
<211> LENGTH: 21
<212> TYPE: DNA
<213> ORGANISM: Artificial Sequence
<220> FEATURE:
<223> OTHER INFORMATION: Oligonucleotide

<400> SEQUENCE: 57
gtgtacatgt tagctgtgga c                                     21

<210> SEQ ID NO 58
<211> LENGTH: 21
<212> TYPE: DNA
<213> ORGANISM: Artificial Sequence
<220> FEATURE:
<223> OTHER INFORMATION: Oligonucleotide

<400> SEQUENCE: 58
tgacactggc aaaacaatgc a                                     21

<210> SEQ ID NO 59
<211> LENGTH: 21

```
<212> TYPE: DNA
<213> ORGANISM: Artificial Sequence
<220> FEATURE:
<223> OTHER INFORMATION: Oligonucleotide

<400> SEQUENCE: 59
ggtccttttc accagcaagc t                                      21

<210> SEQ ID NO 60
<211> LENGTH: 507
<212> TYPE: PRT
<213> ORGANISM: artificial
<220> FEATURE:
<223> OTHER INFORMATION: artificial Antibody

<400> SEQUENCE: 60
```

Met Gly Trp Ser Cys Ile Ile Leu Phe Leu Val Ala Thr Ala Thr Gly
1               5                   10                  15

Val His Ser Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Met Asn Trp Val Lys Gln Ser His Gly Lys Asn Leu
    50                  55                  60

Glu Trp Ile Gly Leu Ile Asn Pro Tyr Asn Gly Gly Thr Ile Tyr Asn
65              70                  75                  80

Gln Lys Phe Lys Gly Lys Ala Thr Leu Thr Val Asp Lys Ser Ser Ser
                85                  90                  95

Thr Ala Tyr Met Glu Leu Leu Ser Leu Thr Ser Glu Asp Ser Ala Val
            100                 105                 110

Tyr Tyr Cys Ala Arg Asp Tyr Gly Phe Val Leu Asp Tyr Trp Gly Gln
        115                 120                 125

Gly Thr Thr Leu Thr Val Ser Ser Gly Gly Gly Ser Gly Gly Gly
    130                 135                 140

Gly Ser Gly Gly Gly Gly Ser Gln Ile Val Leu Thr Gln Ser Pro Ser
145                 150                 155                 160

Ile Met Ser Val Ser Pro Gly Glu Lys Val Thr Ile Thr Cys Ser Ala
                165                 170                 175

Ser Ser Ser Val Ser Tyr Met His Trp Phe Gln Gln Lys Pro Gly Thr
            180                 185                 190

Ser Pro Lys Leu Leu Ile Tyr Ser Thr Ser Asn Leu Ala Ser Gly Val
        195                 200                 205

Pro Ala Arg Phe Ser Gly Arg Gly Ser Gly Thr Ser Tyr Ser Leu Thr
    210                 215                 220

Ile Ser Arg Val Ala Ala Glu Asp Ala Ala Thr Tyr Tyr Cys Gln Gln
225                 230                 235                 240

Arg Ser Asn Tyr Pro Pro Trp Thr Phe Gly Gly Gly Thr Lys Leu Glu
                245                 250                 255

Ile Lys Ser Gly Gly Gly Gly Ser Gln Val Gln Leu Gln Gln Ser Gly
            260                 265                 270

Ala Glu Leu Ala Arg Pro Gly Ala Ser Val Lys Met Ser Cys Lys Thr
        275                 280                 285

Ser Gly Tyr Thr Phe Thr Arg Tyr Thr Met His Trp Val Lys Gln Arg
    290                 295                 300

Pro Gly Gln Gly Leu Glu Trp Ile Gly Tyr Ile Asn Pro Ser Arg Gly
305                 310                 315                 320

-continued

```
Tyr Thr Asn Tyr Asn Gln Lys Phe Lys Asp Lys Ala Thr Leu Thr Thr
                325                 330                 335

Asp Lys Ser Ser Thr Ala Tyr Met Gln Leu Ser Ser Leu Thr Ser
    340                 345                 350

Glu Asp Ser Ala Val Tyr Tyr Cys Ala Arg Tyr Tyr Asp Asp His Tyr
            355                 360                 365

Ser Leu Asp Tyr Trp Gly Gln Gly Thr Thr Leu Thr Val Ser Ser Gly
    370                 375                 380

Gly Gly Gly Ser Gly Gly Ser Gly Gly Ser Gly Gly Ser Gly Gly Gly
385                 390                 395                 400

Ser Gln Ile Val Leu Thr Gln Ser Pro Ala Ile Met Ser Ala Ser Pro
            405                 410                 415

Gly Glu Lys Val Thr Met Thr Cys Arg Ala Ser Ser Ser Val Ser Tyr
            420                 425                 430

Met Asn Trp Tyr Gln Gln Lys Ser Gly Thr Ser Pro Lys Arg Trp Ile
    435                 440                 445

Tyr Asp Thr Ser Lys Val Ala Ser Gly Val Pro Tyr Arg Phe Ser Gly
    450                 455                 460

Ser Gly Ser Gly Thr Ser Tyr Ser Leu Thr Ile Ser Ser Met Glu Ala
465                 470                 475                 480

Glu Asp Ala Ala Thr Tyr Tyr Cys Gln Gln Trp Ser Ser Asn Pro Leu
            485                 490                 495

Thr Phe Gly Ala Gly Thr Lys Leu Glu Leu Lys
            500                 505

<210> SEQ ID NO 61
<211> LENGTH: 507
<212> TYPE: PRT
<213> ORGANISM: artificial
<220> FEATURE:
<223> OTHER INFORMATION: artificial Antibody

<400> SEQUENCE: 61

Met Gly Trp Ser Cys Ile Ile Leu Phe Leu Val Ala Thr Ala Thr Gly
1               5                   10                  15

Val His Ser Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Met Asn Trp Val Lys Gln Ser His Gly Lys Asn Leu
    50                  55                  60

Glu Trp Ile Gly Leu Ile Asn Pro Tyr Asn Gly Thr Ile Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Leu Ser Leu Thr Ser Glu Asp Ser Ala Val
            100                 105                 110

Tyr Tyr Cys Ala Arg Asp Tyr Gly Phe Val Leu Asp Tyr Trp Gly Gln
        115                 120                 125

Gly Thr Thr Leu Thr Val Ser Ser Gly Gly Gly Gly Ser Gly Gly Gly
    130                 135                 140

Gly Ser Gly Gly Gly Ser Gln Ile Val Leu Thr Gln Ser Pro Ser
145                 150                 155                 160

Ile Met Ser Val Ser Pro Gly Glu Lys Val Thr Ile Thr Cys Ser Ala
                165                 170                 175
```

Ser Ser Ser Val Ser Tyr Met His Trp Phe Gln Gln Lys Pro Gly Thr
            180                 185                 190

Ser Pro Lys Leu Trp Ile Tyr Ser Thr Ser Asn Leu Ala Ser Gly Val
        195                 200                 205

Pro Ala Arg Phe Ser Gly Arg Gly Ser Gly Thr Ser Tyr Ser Leu Thr
    210                 215                 220

Ile Ser Arg Val Ala Ala Glu Asp Ala Ala Thr Tyr Tyr Cys Gln Gln
225                 230                 235                 240

Arg Ser Asn Tyr Pro Pro Trp Thr Phe Gly Gly Gly Thr Lys Leu Glu
                245                 250                 255

Ile Lys Ser Gly Gly Gly Gly Ser Gln Val Gln Leu Gln Gln Ser Gly
            260                 265                 270

Ala Glu Leu Ala Arg Pro Gly Ala Ser Val Lys Met Ser Cys Lys Thr
        275                 280                 285

Ser Gly Tyr Thr Phe Thr Arg Tyr Thr Met His Trp Val Lys Gln Arg
    290                 295                 300

Pro Gly Gln Gly Leu Glu Trp Ile Gly Tyr Ile Asn Pro Ser Arg Gly
305                 310                 315                 320

Tyr Thr Asn Tyr Asn Gln Lys Phe Lys Asp Lys Ala Thr Leu Thr Thr
                325                 330                 335

Asp Lys Ser Ser Ser Thr Ala Tyr Met Gln Leu Ser Ser Leu Thr Ser
            340                 345                 350

Glu Asp Ser Ala Val Tyr Tyr Cys Ala Arg Tyr Tyr Asp Asp His Tyr
        355                 360                 365

Ser Leu Asp Tyr Trp Gly Gln Gly Thr Thr Leu Thr Val Ser Ser Gly
    370                 375                 380

Gly Gly Gly Ser Gly Gly Ser Gly Gly Ser Gly Ser Gly Gly Gly
385                 390                 395                 400

Ser Gln Ile Val Leu Thr Gln Ser Pro Ala Ile Met Ser Ala Ser Pro
                405                 410                 415

Gly Glu Lys Val Thr Met Thr Cys Arg Ala Ser Ser Ser Val Ser Tyr
            420                 425                 430

Met Asn Trp Tyr Gln Gln Lys Ser Gly Thr Ser Pro Lys Arg Trp Ile
        435                 440                 445

Tyr Asp Thr Ser Lys Val Ala Ser Gly Val Pro Tyr Arg Phe Ser Gly
    450                 455                 460

Ser Gly Ser Gly Thr Ser Tyr Ser Leu Thr Ile Ser Ser Met Glu Ala
465                 470                 475                 480

Glu Asp Ala Ala Thr Tyr Tyr Cys Gln Gln Trp Ser Ser Asn Pro Leu
                485                 490                 495

Thr Phe Gly Ala Gly Thr Lys Leu Glu Leu Lys
            500                 505

<210> SEQ ID NO 62
<211> LENGTH: 507
<212> TYPE: PRT
<213> ORGANISM: artificial
<220> FEATURE:
<223> OTHER INFORMATION: artificial Antibody

<400> SEQUENCE: 62

Met Gly Trp Ser Cys Ile Ile Leu Phe Leu Val Ala Thr Ala Thr Gly
1               5                   10                  15

Val His Ser Glu Val Gln Leu Gln Gln Ser Gly Pro Glu Leu Val Lys
            20                  25                  30

```
Pro Gly Ala Ser Met Lys Ile Ser Cys Lys Ala Ser Gly Tyr Ser Phe
             35                  40                  45

Thr Gly Tyr Thr Met Asn Trp Val Lys Gln Ser His Gly Lys Asn Leu
 50                  55                  60

Glu Trp Ile Gly Leu Ile Asn Pro Tyr Asn Gly Gly Thr Ile Tyr Asn
 65                  70                  75                  80

Gln Lys Phe Lys Gly Lys Ala Thr Leu Thr Val Asp Lys Ser Ser Ser
                 85                  90                  95

Thr Ala Tyr Met Glu Leu Leu Ser Leu Thr Ser Glu Asp Ser Ala Val
                100                 105                 110

Tyr Tyr Cys Ala Arg Asp Tyr Gly Phe Val Leu Asp Tyr Trp Gly Gln
                115                 120                 125

Gly Thr Thr Leu Thr Val Ser Ser Gly Gly Gly Gly Ser Gly Gly Gly
            130                 135                 140

Gly Ser Gly Gly Gly Gly Ser Gln Ile Val Leu Thr Gln Ser Pro Ser
145                 150                 155                 160

Ile Met Ser Val Ser Pro Gly Glu Lys Val Thr Ile Thr Cys Ser Ala
                165                 170                 175

Ser Ser Ser Val Ser Tyr Met His Trp Phe Gln Gln Lys Pro Gly Thr
            180                 185                 190

Ser Pro Lys Leu Ser Ile Tyr Ser Thr Ser Asn Leu Ala Ser Gly Val
        195                 200                 205

Pro Ala Arg Phe Ser Gly Arg Gly Ser Gly Thr Ser Tyr Ser Leu Thr
    210                 215                 220

Ile Ser Arg Val Ala Ala Glu Asp Ala Ala Thr Tyr Tyr Cys Gln Gln
225                 230                 235                 240

Arg Ser Asn Tyr Pro Pro Trp Thr Phe Gly Gly Gly Thr Lys Leu Glu
                245                 250                 255

Ile Lys Ser Gly Gly Gly Gly Ser Gln Val Gln Leu Gln Gln Ser Gly
            260                 265                 270

Ala Glu Leu Ala Arg Pro Gly Ala Ser Val Lys Met Ser Cys Lys Thr
        275                 280                 285

Ser Gly Tyr Thr Phe Thr Arg Tyr Thr Met His Trp Val Lys Gln Arg
    290                 295                 300

Pro Gly Gln Gly Leu Glu Trp Ile Gly Tyr Ile Asn Pro Ser Arg Gly
305                 310                 315                 320

Tyr Thr Asn Tyr Asn Gln Lys Phe Lys Asp Lys Ala Thr Leu Thr Thr
                325                 330                 335

Asp Lys Ser Ser Ser Thr Ala Tyr Met Gln Leu Ser Ser Leu Thr Ser
            340                 345                 350

Glu Asp Ser Ala Val Tyr Tyr Cys Ala Arg Tyr Tyr Asp Asp His Tyr
        355                 360                 365

Ser Leu Asp Tyr Trp Gly Gln Gly Thr Thr Leu Thr Val Ser Ser Gly
    370                 375                 380

Gly Gly Gly Ser Gly Gly Ser Gly Gly Ser Gly Gly Ser Gly Gly Gly
385                 390                 395                 400

Ser Gln Ile Val Leu Thr Gln Ser Pro Ala Ile Met Ser Ala Ser Pro
                405                 410                 415

Gly Glu Lys Val Thr Met Thr Cys Arg Ala Ser Ser Ser Val Ser Tyr
            420                 425                 430

Met Asn Trp Tyr Gln Gln Lys Ser Gly Thr Ser Pro Lys Arg Trp Ile
        435                 440                 445

Tyr Asp Thr Ser Lys Val Ala Ser Gly Val Pro Tyr Arg Phe Ser Gly
```

```
                  450                 455                 460
Ser Gly Ser Gly Thr Ser Tyr Ser Leu Thr Ile Ser Ser Met Glu Ala
465                 470                 475                 480

Glu Asp Ala Ala Thr Tyr Tyr Cys Gln Gln Trp Ser Ser Asn Pro Leu
                485                 490                 495

Thr Phe Gly Ala Gly Thr Lys Leu Glu Leu Lys
                500                 505

<210> SEQ ID NO 63
<211> LENGTH: 507
<212> TYPE: PRT
<213> ORGANISM: artificial
<220> FEATURE:
<223> OTHER INFORMATION: artificial Antibody

<400> SEQUENCE: 63

Met Gly Trp Ser Cys Ile Ile Leu Phe Leu Val Ala Thr Ala Thr Gly
1               5                  10                  15

Val His Ser Gln Val Gln Leu Gln Gln Ser Gly Ala Glu Leu Ala Arg
                20                  25                  30

Pro Gly Ala Ser Val Lys Met Ser Cys Lys Thr Ser Gly Tyr Thr Phe
            35                  40                  45

Thr Arg Tyr Thr Met His Trp Val Lys Gln Arg Pro Gly Gln Gly Leu
        50                  55                  60

Glu Trp Ile Gly Tyr Ile Asn Pro Ser Arg Gly Tyr Thr Asn Tyr Asn
65                  70                  75                  80

Gln Lys Phe Lys Asp Lys Ala Thr Leu Thr Thr Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Tyr Tyr Asp Asp His Tyr Ser Leu Asp Tyr Trp
        115                 120                 125

Gly Gln Gly Thr Thr Leu Thr Val Ser Ser Gly Gly Gly Gly Ser Gly
    130                 135                 140

Gly Ser Gly Gly Ser Gly Gly Ser Gly Gly Ser Gln Ile Val Leu
145                 150                 155                 160

Thr Gln Ser Pro Ala Ile Met Ser Ala Ser Pro Gly Glu Lys Val Thr
                165                 170                 175

Met Thr Cys Arg Ala Ser Ser Val Ser Tyr Met Asn Trp Tyr Gln
            180                 185                 190

Gln Lys Ser Gly Thr Ser Pro Lys Arg Trp Ile Tyr Asp Thr Ser Lys
        195                 200                 205

Val Ala Ser Gly Val Pro Tyr Arg Phe Ser Gly Ser Gly Ser Gly Thr
    210                 215                 220

Ser Tyr Ser Leu Thr Ile Ser Ser Met Glu Ala Glu Asp Ala Ala Thr
225                 230                 235                 240

Tyr Tyr Cys Gln Gln Trp Ser Ser Asn Pro Leu Thr Phe Gly Ala Gly
                245                 250                 255

Thr Lys Leu Glu Leu Lys Ser Gly Gly Gly Gly Ser Glu Val Gln Leu
            260                 265                 270

Gln Gln Ser Gly Pro Glu Leu Val Lys Pro Gly Ala Ser Met Lys Ile
        275                 280                 285

Ser Cys Lys Ala Ser Gly Tyr Ser Phe Thr Gly Tyr Thr Met Asn Trp
    290                 295                 300

Val Lys Gln Ser His Gly Lys Asn Leu Glu Trp Ile Gly Leu Ile Asn
```

```
                305                 310                 315                 320
        Pro Tyr Asn Gly Gly Thr Ile Tyr Asn Gln Lys Phe Lys Gly Lys Ala
                        325                 330                 335

Thr Leu Thr Val Asp Lys Ser Ser Thr Ala Tyr Met Glu Leu Leu
                        340                 345                 350

Ser Leu Thr Ser Glu Asp Ser Ala Val Tyr Tyr Cys Ala Arg Asp Tyr
                        355                 360                 365

Gly Phe Val Leu Asp Tyr Trp Gly Gln Gly Thr Thr Leu Thr Val Ser
                        370                 375                 380

Ser Gly Gly Gly Gly Ser Gly Gly Gly Ser Gly Gly Gly Gly Ser
        385                 390                 395                 400

Gln Ile Val Leu Thr Gln Ser Pro Ser Ile Met Ser Val Ser Pro Gly
                        405                 410                 415

Glu Lys Val Thr Ile Thr Cys Ser Ala Ser Ser Ser Val Ser Tyr Met
                        420                 425                 430

His Trp Phe Gln Gln Lys Pro Gly Thr Ser Pro Lys Leu Leu Ile Tyr
                        435                 440                 445

Ser Thr Ser Asn Leu Ala Ser Gly Val Pro Ala Arg Phe Ser Gly Arg
                        450                 455                 460

Gly Ser Gly Thr Ser Tyr Ser Leu Thr Ile Ser Arg Val Ala Ala Glu
        465                 470                 475                 480

Asp Ala Ala Thr Tyr Tyr Cys Gln Gln Arg Ser Asn Tyr Pro Pro Trp
                        485                 490                 495

Thr Phe Gly Gly Gly Thr Lys Leu Glu Ile Lys
                        500                 505

<210> SEQ ID NO 64
<211> LENGTH: 507
<212> TYPE: PRT
<213> ORGANISM: artificial
<220> FEATURE:
<223> OTHER INFORMATION: artificial Antibody

<400> SEQUENCE: 64

Met Gly Trp Ser Cys Ile Ile Leu Phe Leu Val Ala Thr Ala Thr Gly
        1               5                   10                  15

Val His Ser Gln Val Gln Leu Gln Gln Ser Gly Ala Glu Leu Ala Arg
                        20                  25                  30

Pro Gly Ala Ser Val Lys Met Ser Cys Lys Thr Ser Gly Tyr Thr Phe
                        35                  40                  45

Thr Arg Tyr Thr Met His Trp Val Lys Gln Arg Pro Gly Gln Gly Leu
                        50                  55                  60

Glu Trp Ile Gly Tyr Ile Asn Pro Ser Arg Gly Tyr Thr Asn Tyr Asn
        65                  70                  75                  80

Gln Lys Phe Lys Asp Lys Ala Thr Leu Thr Thr Asp Lys Ser Ser Ser
                        85                  90                  95

Thr Ala Tyr Met Gln Leu Ser Ser Leu Thr Ser Glu Asp Ser Ala Val
                        100                 105                 110

Tyr Tyr Cys Ala Arg Tyr Tyr Asp Asp His Tyr Ser Leu Asp Tyr Trp
                        115                 120                 125

Gly Gln Gly Thr Thr Leu Thr Val Ser Ser Gly Gly Gly Gly Ser Gly
                        130                 135                 140

Gly Ser Gly Gly Ser Gly Gly Ser Gly Gly Ser Gln Ile Val Leu
        145                 150                 155                 160

Thr Gln Ser Pro Ala Ile Met Ser Ala Ser Pro Gly Glu Lys Val Thr
```

```
                165                 170                 175
Met Thr Cys Arg Ala Ser Ser Val Ser Tyr Met Asn Trp Tyr Gln
            180                 185                 190

Gln Lys Ser Gly Thr Ser Pro Lys Arg Trp Ile Tyr Asp Thr Ser Lys
        195                 200                 205

Val Ala Ser Gly Val Pro Tyr Arg Phe Ser Gly Ser Gly Ser Gly Thr
    210                 215                 220

Ser Tyr Ser Leu Thr Ile Ser Ser Met Glu Ala Glu Asp Ala Ala Thr
225                 230                 235                 240

Tyr Tyr Cys Gln Gln Trp Ser Ser Asn Pro Leu Thr Phe Gly Ala Gly
                245                 250                 255

Thr Lys Leu Glu Leu Lys Ser Gly Gly Gly Ser Glu Val Gln Leu
            260                 265                 270

Gln Gln Ser Gly Pro Glu Leu Val Lys Pro Gly Ala Ser Met Lys Ile
        275                 280                 285

Ser Cys Lys Ala Ser Gly Tyr Ser Phe Thr Gly Tyr Thr Met Asn Trp
    290                 295                 300

Val Lys Gln Ser His Gly Lys Asn Leu Glu Trp Ile Gly Leu Ile Asn
305                 310                 315                 320

Pro Tyr Asn Gly Gly Thr Ile Tyr Asn Gln Lys Phe Lys Gly Lys Ala
                325                 330                 335

Thr Leu Thr Val Asp Lys Ser Ser Thr Ala Tyr Met Glu Leu Leu
            340                 345                 350

Ser Leu Thr Ser Glu Asp Ser Ala Val Tyr Tyr Cys Ala Arg Asp Tyr
        355                 360                 365

Gly Phe Val Leu Asp Tyr Trp Gly Gln Gly Thr Thr Leu Thr Val Ser
    370                 375                 380

Ser Gly Gly Gly Gly Ser Gly Gly Gly Ser Gly Gly Gly Gly Ser
385                 390                 395                 400

Gln Ile Val Leu Thr Gln Ser Pro Ser Ile Met Ser Val Ser Pro Gly
                405                 410                 415

Glu Lys Val Thr Ile Thr Cys Ser Ala Ser Ser Ser Val Ser Tyr Met
            420                 425                 430

His Trp Phe Gln Gln Lys Pro Gly Thr Ser Pro Lys Leu Trp Ile Tyr
        435                 440                 445

Ser Thr Ser Asn Leu Ala Ser Gly Val Pro Ala Arg Phe Ser Gly Arg
    450                 455                 460

Gly Ser Gly Thr Ser Tyr Ser Leu Thr Ile Ser Arg Val Ala Ala Glu
465                 470                 475                 480

Asp Ala Ala Thr Tyr Tyr Cys Gln Gln Arg Ser Asn Tyr Pro Pro Trp
                485                 490                 495

Thr Phe Gly Gly Gly Thr Lys Leu Glu Ile Lys
            500                 505

<210> SEQ ID NO 65
<211> LENGTH: 507
<212> TYPE: PRT
<213> ORGANISM: artificial
<220> FEATURE:
<223> OTHER INFORMATION: artificial Antibody

<400> SEQUENCE: 65

Met Gly Trp Ser Cys Ile Ile Leu Phe Leu Val Ala Thr Ala Thr Gly
1               5                   10                  15

Val His Ser Gln Val Gln Leu Gln Gln Ser Gly Ala Glu Leu Ala Arg
```

```
                  20                  25                  30
Pro Gly Ala Ser Val Lys Met Ser Cys Lys Thr Ser Gly Tyr Thr Phe
                35                  40                  45
Thr Arg Tyr Thr Met His Trp Val Lys Gln Arg Pro Gly Gln Gly Leu
    50                  55                  60
Glu Trp Ile Gly Tyr Ile Asn Pro Ser Arg Gly Tyr Thr Asn Tyr Asn
65                  70                  75                  80
Gln Lys Phe Lys Asp Lys Ala Thr Leu Thr Thr Asp Lys Ser Ser Ser
                85                  90                  95
Thr Ala Tyr Met Gln Leu Ser Ser Leu Thr Ser Glu Asp Ser Ala Val
                100                 105                 110
Tyr Tyr Cys Ala Arg Tyr Tyr Asp Asp His Tyr Ser Leu Asp Tyr Trp
                115                 120                 125
Gly Gln Gly Thr Thr Leu Thr Val Ser Ser Gly Gly Gly Gly Ser Gly
            130                 135                 140
Gly Ser Gly Gly Ser Gly Gly Ser Gly Gly Gly Ser Gln Ile Val Leu
145                 150                 155                 160
Thr Gln Ser Pro Ala Ile Met Ser Ala Ser Pro Gly Glu Lys Val Thr
                165                 170                 175
Met Thr Cys Arg Ala Ser Ser Ser Val Ser Tyr Met Asn Trp Tyr Gln
                180                 185                 190
Gln Lys Ser Gly Thr Ser Pro Lys Arg Trp Ile Tyr Asp Thr Ser Lys
            195                 200                 205
Val Ala Ser Gly Val Pro Tyr Arg Phe Ser Gly Ser Gly Ser Gly Thr
            210                 215                 220
Ser Tyr Ser Leu Thr Ile Ser Ser Met Glu Ala Glu Asp Ala Ala Thr
225                 230                 235                 240
Tyr Tyr Cys Gln Gln Trp Ser Ser Asn Pro Leu Thr Phe Gly Ala Gly
                245                 250                 255
Thr Lys Leu Glu Leu Lys Ser Gly Gly Gly Gly Ser Glu Val Gln Leu
                260                 265                 270
Gln Gln Ser Gly Pro Glu Leu Val Lys Pro Gly Ala Ser Met Lys Ile
            275                 280                 285
Ser Cys Lys Ala Ser Gly Tyr Ser Phe Thr Gly Tyr Thr Met Asn Trp
            290                 295                 300
Val Lys Gln Ser His Gly Lys Asn Leu Glu Trp Ile Gly Leu Ile Asn
305                 310                 315                 320
Pro Tyr Asn Gly Gly Thr Ile Tyr Asn Gln Lys Phe Lys Gly Lys Ala
                325                 330                 335
Thr Leu Thr Val Asp Lys Ser Ser Ser Thr Ala Tyr Met Glu Leu Leu
                340                 345                 350
Ser Leu Thr Ser Glu Asp Ser Ala Val Tyr Tyr Cys Ala Arg Asp Tyr
            355                 360                 365
Gly Phe Val Leu Asp Tyr Trp Gly Gln Gly Thr Thr Leu Thr Val Ser
            370                 375                 380
Ser Gly Gly Gly Gly Ser Gly Gly Gly Gly Ser Gly Gly Gly Gly Ser
385                 390                 395                 400
Gln Ile Val Leu Thr Gln Ser Pro Ser Ile Met Ser Val Ser Pro Gly
                405                 410                 415
Glu Lys Val Thr Ile Thr Cys Ser Ala Ser Ser Ser Val Ser Tyr Met
                420                 425                 430
His Trp Phe Gln Gln Lys Pro Gly Thr Ser Pro Lys Leu Ser Ile Tyr
            435                 440                 445
```

```
Ser Thr Ser Asn Leu Ala Ser Gly Val Pro Ala Arg Phe Ser Gly Arg
    450                 455                 460

Gly Ser Gly Thr Ser Tyr Ser Leu Thr Ile Ser Arg Val Ala Ala Glu
465                 470                 475                 480

Asp Ala Ala Thr Tyr Tyr Cys Gln Gln Arg Ser Asn Tyr Pro Pro Trp
            485                 490                 495

Thr Phe Gly Gly Gly Thr Lys Leu Glu Ile Lys
            500                 505

<210> SEQ ID NO 66
<211> LENGTH: 530
<212> TYPE: PRT
<213> ORGANISM: artificial
<220> FEATURE:
<223> OTHER INFORMATION: artificial Antibody

<400> SEQUENCE: 66

Met Gly Trp Ser Cys Ile Ile Leu Phe Leu Val Ala Thr Ala Thr Gly
1               5                   10                  15

Val His Ser Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Asn Thr Gly Glu Pro Thr Tyr Ala
65                  70                  75                  80

Glu Glu Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Leu Gly Phe Gly Asn Ala Met Asp Tyr Trp Gly
        115                 120                 125

Gln Gly Thr Ser Val Thr Val Ser Ser Gly Gly Gly Ser Gly Gly
    130                 135                 140

Gly Gly Ser Gly Gly Gly Ser Gly Gly Gly Ser Asp Ile Val
145                 150                 155                 160

Met Thr Gln Ser Pro Ser Ser Leu Thr Val Thr Ala Gly Glu Lys Val
                165                 170                 175

Thr Met Ser Cys Lys Ser Ser Gln Ser Leu Leu Asn Ser Gly Asn Gln
            180                 185                 190

Lys Asn Tyr Leu Thr Trp Tyr Gln Gln Lys Pro Gly Gln Pro Pro Lys
        195                 200                 205

Leu Leu Ile Tyr Trp Ala Ser Thr Arg Glu Ser Gly Val Pro Asp Arg
    210                 215                 220

Phe Thr Gly Ser Gly Ser Gly Thr Asp Phe Thr Leu Thr Ile Ser Ser
225                 230                 235                 240

Val Gln Ala Glu Asp Leu Ala Val Tyr Tyr Cys Gln Asn Asp Tyr Ser
                245                 250                 255

Tyr Pro Leu Thr Phe Gly Ala Gly Thr Lys Leu Glu Leu Lys Ser Gly
            260                 265                 270

Gly Gly Gly Ser Gln Val Gln Leu Gln Gln Ser Gly Ala Glu Leu Ala
        275                 280                 285

Arg Pro Gly Ala Ser Val Lys Met Ser Cys Lys Thr Ser Gly Tyr Thr
    290                 295                 300
```

```
Phe Thr Arg Tyr Thr Met His Trp Val Lys Gln Arg Pro Gly Gln Gly
305                 310                 315                 320

Leu Glu Trp Ile Gly Tyr Ile Asn Pro Ser Arg Gly Tyr Thr Asn Tyr
            325                 330                 335

Asn Gln Lys Phe Lys Asp Lys Ala Thr Leu Thr Thr Asp Lys Ser Ser
        340                 345                 350

Ser Thr Ala Tyr Met Gln Leu Ser Ser Leu Thr Ser Glu Asp Ser Ala
    355                 360                 365

Val Tyr Tyr Cys Ala Arg Tyr Tyr Asp Asp His Tyr Ser Leu Asp Tyr
370                 375                 380

Trp Gly Gln Gly Thr Thr Leu Thr Val Ser Ser Gly Gly Gly Gly Ser
385                 390                 395                 400

Gly Gly Gly Gly Ser Gly Gly Gly Ser Gly Gly Gly Gly Ser Gln
                405                 410                 415

Ile Val Leu Thr Gln Ser Pro Ala Ile Met Ser Ala Ser Pro Gly Glu
            420                 425                 430

Lys Val Thr Met Thr Cys Arg Ala Ser Ser Val Ser Tyr Met Asn
                435                 440                 445

Trp Tyr Gln Gln Lys Ser Gly Thr Ser Pro Lys Arg Trp Ile Tyr Asp
    450                 455                 460

Thr Ser Lys Val Ala Ser Gly Val Pro Tyr Arg Phe Ser Gly Ser Gly
465                 470                 475                 480

Ser Gly Thr Ser Tyr Ser Leu Thr Ile Ser Ser Met Glu Ala Glu Asp
                485                 490                 495

Ala Ala Thr Tyr Tyr Cys Gln Gln Trp Ser Ser Asn Pro Leu Thr Phe
            500                 505                 510

Gly Ala Gly Thr Lys Leu Glu Leu Lys Gly Gly Ser His His His His
        515                 520                 525

His His
    530

<210> SEQ ID NO 67
<211> LENGTH: 530
<212> TYPE: PRT
<213> ORGANISM: artificial
<220> FEATURE:
<223> OTHER INFORMATION: artificial Antibody

<400> SEQUENCE: 67

Met Gly Trp Ser Cys Ile Ile Leu Phe Leu Val Ala Thr Ala Thr Gly
1               5                   10                  15

Val His Ser Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Cys Leu
    50                  55                  60

Lys Trp Met Gly Trp Ile Asn Thr Asn Thr Gly Glu Pro Thr Tyr Ala
65                  70                  75                  80

Glu Glu Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Leu Gly Phe Gly Asn Ala Met Asp Tyr Trp Gly
        115                 120                 125
```

```
Gln Gly Thr Ser Val Thr Val Ser Ser Gly Gly Gly Ser Gly Gly
    130                 135                 140
Gly Gly Ser Gly Gly Gly Ser Gly Gly Gly Ser Asp Ile Val
145                 150                 155                 160
Met Thr Gln Ser Pro Ser Ser Leu Thr Val Thr Ala Gly Glu Lys Val
                165                 170                 175
Thr Met Ser Cys Lys Ser Ser Gln Ser Leu Leu Asn Ser Gly Asn Gln
            180                 185                 190
Lys Asn Tyr Leu Thr Trp Tyr Gln Gln Lys Pro Gly Gln Pro Pro Lys
        195                 200                 205
Leu Leu Ile Tyr Trp Ala Ser Thr Arg Glu Ser Gly Val Pro Asp Arg
    210                 215                 220
Phe Thr Gly Ser Gly Ser Gly Thr Asp Phe Thr Leu Thr Ile Ser Ser
225                 230                 235                 240
Val Gln Ala Glu Asp Leu Ala Val Tyr Tyr Cys Gln Asn Asp Tyr Ser
                245                 250                 255
Tyr Pro Leu Thr Phe Gly Cys Gly Thr Lys Leu Glu Leu Lys Ser Gly
            260                 265                 270
Gly Gly Gly Ser Gln Val Gln Leu Gln Gln Ser Gly Ala Glu Leu Ala
        275                 280                 285
Arg Pro Gly Ala Ser Val Lys Met Ser Cys Lys Thr Ser Gly Tyr Thr
    290                 295                 300
Phe Thr Arg Tyr Thr Met His Trp Val Lys Gln Arg Pro Gly Gln Gly
305                 310                 315                 320
Leu Glu Trp Ile Gly Tyr Ile Asn Pro Ser Arg Gly Tyr Thr Asn Tyr
                325                 330                 335
Asn Gln Lys Phe Lys Asp Lys Ala Thr Leu Thr Thr Asp Lys Ser Ser
            340                 345                 350
Ser Thr Ala Tyr Met Gln Leu Ser Ser Leu Thr Ser Glu Asp Ser Ala
        355                 360                 365
Val Tyr Tyr Cys Ala Arg Tyr Tyr Asp Asp His Tyr Ser Leu Asp Tyr
    370                 375                 380
Trp Gly Gln Gly Thr Thr Leu Thr Val Ser Ser Gly Gly Gly Gly Ser
385                 390                 395                 400
Gly Gly Gly Gly Ser Gly Gly Gly Ser Gly Gly Gly Ser Gln
                405                 410                 415
Ile Val Leu Thr Gln Ser Pro Ala Ile Met Ser Ala Ser Pro Gly Glu
            420                 425                 430
Lys Val Thr Met Thr Cys Arg Ala Ser Ser Ser Val Ser Tyr Met Asn
        435                 440                 445
Trp Tyr Gln Gln Lys Ser Gly Thr Ser Pro Lys Arg Trp Ile Tyr Asp
    450                 455                 460
Thr Ser Lys Val Ala Ser Gly Val Pro Tyr Arg Phe Ser Gly Ser Gly
465                 470                 475                 480
Ser Gly Thr Ser Tyr Ser Leu Thr Ile Ser Ser Met Glu Ala Glu Asp
                485                 490                 495
Ala Ala Thr Tyr Tyr Cys Gln Gln Trp Ser Ser Asn Pro Leu Thr Phe
            500                 505                 510
Gly Ala Gly Thr Lys Leu Glu Leu Lys Gly Gly Ser His His His His
        515                 520                 525
His His
    530
```

<210> SEQ ID NO 68
<211> LENGTH: 530
<212> TYPE: PRT
<213> ORGANISM: artificial
<220> FEATURE:
<223> OTHER INFORMATION: artificial Antibody

<400> SEQUENCE: 68

```
Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Thr Phe
        35                  40                  45

Thr Ser Tyr Trp Ile Asn Trp Val Lys Gln Arg Pro Gly Gln Gly Leu
    50                  55                  60

Glu Trp Ile Gly Asn Ile Tyr Pro Ser Asp Ser Tyr Thr Asn Tyr Asn
65                  70                  75                  80

Gln Lys Phe Lys Asp Lys Ala Thr Leu Thr Val Asp Lys Ser Ser Ser
                85                  90                  95

Thr Ala Tyr Met Gln Leu Ser Ser Pro Thr Ser Glu Asp Ser Ala Val
            100                 105                 110

Tyr Tyr Cys Thr Arg Ser Trp Arg Gly Asn Ser Phe Asp Tyr Trp Gly
        115                 120                 125

Gln Gly Thr Thr Leu Thr Val Ser Gly Gly Gly Gly Ser Gly Gly
    130                 135                 140

Gly Gly Ser Gly Gly Gly Ser Gly Gly Gly Gly Ser Asp Ile Val
145                 150                 155                 160

Met Thr Gln Ser Pro Ser Ser Leu Thr Val Thr Ala Gly Glu Lys Val
                165                 170                 175

Thr Met Ser Cys Lys Ser Ser Gln Ser Leu Leu Asn Ser Gly Asn Gln
            180                 185                 190

Lys Asn Tyr Leu Thr Trp Tyr Gln Gln Lys Pro Gly Gln Pro Pro Lys
        195                 200                 205

Leu Leu Ile Tyr Trp Ala Ser Thr Arg Glu Ser Gly Val Pro Asp Arg
    210                 215                 220

Phe Thr Gly Ser Gly Ser Gly Thr Asp Phe Thr Leu Thr Ile Ser Ser
225                 230                 235                 240

Val Gln Ala Glu Asp Leu Ala Val Tyr Tyr Cys Gln Asn Asp Tyr Ser
                245                 250                 255

Tyr Pro Phe Thr Phe Gly Ser Gly Thr Lys Leu Glu Ile Lys Ser Gly
            260                 265                 270

Gly Gly Gly Ser Gln Val Gln Leu Gln Gln Ser Gly Ala Glu Leu Ala
        275                 280                 285

Arg Pro Gly Ala Ser Val Lys Met Ser Cys Lys Thr Ser Gly Tyr Thr
    290                 295                 300

Phe Thr Arg Tyr Thr Met His Trp Val Lys Gln Arg Pro Gly Gln Gly
305                 310                 315                 320

Leu Glu Trp Ile Gly Tyr Ile Asn Pro Ser Arg Gly Tyr Thr Asn Tyr
                325                 330                 335

Asn Gln Lys Phe Lys Asp Lys Ala Thr Leu Thr Thr Asp Lys Ser Ser
            340                 345                 350

Ser Thr Ala Tyr Met Gln Leu Ser Ser Leu Thr Ser Glu Asp Ser Ala
        355                 360                 365
```

Val Tyr Tyr Cys Ala Arg Tyr Asp Asp His Tyr Ser Leu Asp Tyr
370                 375                 380

Trp Gly Gln Gly Thr Thr Leu Thr Val Ser Ser Gly Gly Gly Ser
385                 390                 395                 400

Gly Gly Gly Gly Ser Gly Gly Gly Ser Gly Gly Gly Ser Gln
            405                 410                 415

Ile Val Leu Thr Gln Ser Pro Ala Ile Met Ser Ala Ser Pro Gly Glu
                420                 425                 430

Lys Val Thr Met Thr Cys Arg Ala Ser Ser Val Ser Tyr Met Asn
                435                 440                 445

Trp Tyr Gln Gln Lys Ser Gly Thr Ser Pro Lys Arg Trp Ile Tyr Asp
450                 455                 460

Thr Ser Lys Val Ala Ser Gly Val Pro Tyr Arg Phe Ser Gly Ser Gly
465                 470                 475                 480

Ser Gly Thr Ser Tyr Ser Leu Thr Ile Ser Ser Met Glu Ala Glu Asp
                485                 490                 495

Ala Ala Thr Tyr Tyr Cys Gln Gln Trp Ser Ser Asn Pro Leu Thr Phe
                500                 505                 510

Gly Ala Gly Thr Lys Leu Glu Leu Lys Gly Gly Ser His His His His
                515                 520                 525

His His
    530

<210> SEQ ID NO 69
<211> LENGTH: 530
<212> TYPE: PRT
<213> ORGANISM: artificial
<220> FEATURE:
<223> OTHER INFORMATION: artificial Antibody

<400> SEQUENCE: 69

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Arg
                20                  25                  30

Pro Gly Ala Ser Val Lys Leu Ser Cys Lys Ala Ser Gly Tyr Thr Phe
            35                  40                  45

Thr Ser Tyr Trp Ile Asn Trp Val Lys Gln Arg Pro Gly Gln Cys Leu
    50                  55                  60

Glu Trp Ile Gly Asn Ile Tyr Pro Ser Asp Ser Tyr Thr Asn Tyr Asn
65                  70                  75                  80

Gln Lys Phe Lys Asp Lys Ala Thr Leu Thr Val Asp Lys Ser Ser Ser
                85                  90                  95

Thr Ala Tyr Met Gln Leu Ser Ser Pro Thr Ser Glu Asp Ser Ala Val
            100                 105                 110

Tyr Tyr Cys Thr Arg Ser Trp Arg Gly Asn Ser Phe Asp Tyr Trp Gly
        115                 120                 125

Gln Gly Thr Thr Leu Thr Val Ser Ser Gly Gly Gly Gly Ser Gly Gly
    130                 135                 140

Gly Gly Ser Gly Gly Gly Gly Ser Gly Gly Gly Gly Ser Asp Ile Val
145                 150                 155                 160

Met Thr Gln Ser Pro Ser Ser Leu Thr Val Thr Ala Gly Glu Lys Val
                165                 170                 175

Thr Met Ser Cys Lys Ser Ser Gln Ser Leu Leu Asn Ser Gly Asn Gln
            180                 185                 190

```
Lys Asn Tyr Leu Thr Trp Tyr Gln Gln Lys Pro Gly Gln Pro Pro Lys
                195                 200                 205

Leu Leu Ile Tyr Trp Ala Ser Thr Arg Glu Ser Gly Val Pro Asp Arg
    210                 215                 220

Phe Thr Gly Ser Gly Ser Gly Thr Asp Phe Thr Leu Thr Ile Ser Ser
225                 230                 235                 240

Val Gln Ala Glu Asp Leu Ala Val Tyr Tyr Cys Gln Asn Asp Tyr Ser
                245                 250                 255

Tyr Pro Phe Thr Phe Gly Cys Gly Thr Lys Leu Glu Ile Lys Ser Gly
                260                 265                 270

Gly Gly Gly Ser Gln Val Gln Leu Gln Gln Ser Gly Ala Glu Leu Ala
            275                 280                 285

Arg Pro Gly Ala Ser Val Lys Met Ser Cys Lys Thr Ser Gly Tyr Thr
        290                 295                 300

Phe Thr Arg Tyr Thr Met His Trp Val Lys Gln Arg Pro Gly Gln Gly
305                 310                 315                 320

Leu Glu Trp Ile Gly Tyr Ile Asn Pro Ser Arg Gly Tyr Thr Asn Tyr
                325                 330                 335

Asn Gln Lys Phe Lys Asp Lys Ala Thr Leu Thr Thr Asp Lys Ser Ser
                340                 345                 350

Ser Thr Ala Tyr Met Gln Leu Ser Ser Leu Thr Ser Glu Asp Ser Ala
            355                 360                 365

Val Tyr Tyr Cys Ala Arg Tyr Tyr Asp Asp His Tyr Ser Leu Asp Tyr
        370                 375                 380

Trp Gly Gln Gly Thr Thr Leu Thr Val Ser Ser Gly Gly Gly Gly Ser
385                 390                 395                 400

Gly Gly Gly Gly Ser Gly Gly Gly Ser Gly Gly Gly Gly Ser Gln
                405                 410                 415

Ile Val Leu Thr Gln Ser Pro Ala Ile Met Ser Ala Ser Pro Gly Glu
            420                 425                 430

Lys Val Thr Met Thr Cys Arg Ala Ser Ser Ser Val Ser Tyr Met Asn
        435                 440                 445

Trp Tyr Gln Gln Lys Ser Gly Thr Ser Pro Lys Arg Trp Ile Tyr Asp
450                 455                 460

Thr Ser Lys Val Ala Ser Gly Val Pro Tyr Arg Phe Ser Gly Ser Gly
465                 470                 475                 480

Ser Gly Thr Ser Tyr Ser Leu Thr Ile Ser Ser Met Glu Ala Glu Asp
                485                 490                 495

Ala Ala Thr Tyr Tyr Cys Gln Gln Trp Ser Ser Asn Pro Leu Thr Phe
            500                 505                 510

Gly Ala Gly Thr Lys Leu Glu Leu Lys Gly Gly Ser His His His His
        515                 520                 525

His His
    530

<210> SEQ ID NO 70
<211> LENGTH: 530
<212> TYPE: PRT
<213> ORGANISM: artificial
<220> FEATURE:
<223> OTHER INFORMATION: artificial Antibody

<400> SEQUENCE: 70

Met Gly Trp Ser Cys Ile Ile Leu Phe Leu Val Ala Thr Ala Thr Gly
1               5                   10                  15
```

Val His Ser Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Asn Thr Gly Glu Pro Thr Tyr Ala
65                  70                  75                  80

Glu Glu Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Leu Gly Phe Gly Asn Ala Met Asp Tyr Trp Gly
        115                 120                 125

Gln Gly Thr Ser Val Thr Val Ser Gly Gly Gly Ser Gly Gly
    130                 135                 140

Gly Gly Ser Gly Gly Gly Ser Gly Gly Gly Ser Asp Ile Val
145                 150                 155                 160

Met Thr Gln Ser Pro Ser Ser Leu Thr Val Thr Ala Gly Glu Lys Val
                165                 170                 175

Thr Met Ser Cys Lys Ser Ser Gln Ser Leu Leu Asn Ser Gly Asn Gln
            180                 185                 190

Lys Asn Tyr Leu Thr Trp Tyr Gln Gln Lys Pro Gly Gln Pro Pro Lys
        195                 200                 205

Leu Leu Ile Tyr Trp Ala Ser Thr Arg Glu Ser Gly Val Pro Asp Arg
    210                 215                 220

Phe Thr Gly Ser Gly Ser Gly Thr Asp Phe Thr Leu Thr Ile Ser Ser
225                 230                 235                 240

Val Gln Ala Glu Asp Leu Ala Val Tyr Tyr Cys Gln Asn Asp Tyr Ser
                245                 250                 255

Tyr Pro Leu Thr Phe Gly Ala Gly Thr Lys Leu Glu Leu Lys Ser Gly
            260                 265                 270

Gly Gly Gly Ser Gln Val Gln Leu Gln Gln Ser Gly Ala Glu Leu Ala
        275                 280                 285

Arg Pro Gly Ala Ser Val Lys Met Ser Cys Lys Thr Ser Gly Tyr Thr
    290                 295                 300

Phe Thr Arg Tyr Thr Met His Trp Val Lys Gln Arg Pro Gly Gln Cys
305                 310                 315                 320

Leu Glu Trp Ile Gly Tyr Ile Asn Pro Ser Arg Gly Tyr Thr Asn Tyr
                325                 330                 335

Asn Gln Lys Phe Lys Asp Lys Ala Thr Leu Thr Thr Asp Lys Ser Ser
            340                 345                 350

Ser Thr Ala Tyr Met Gln Leu Ser Ser Leu Thr Ser Glu Asp Ser Ala
        355                 360                 365

Val Tyr Tyr Cys Ala Arg Tyr Tyr Asp Asp His Tyr Ser Leu Asp Tyr
    370                 375                 380

Trp Gly Gln Gly Thr Thr Leu Thr Val Ser Ser Gly Gly Gly Gly Ser
385                 390                 395                 400

Gly Gly Gly Gly Ser Gly Gly Gly Gly Gly Gly Gly Ser Gln
                405                 410                 415

Ile Val Leu Thr Gln Ser Pro Ala Ile Met Ser Ala Ser Pro Gly Glu
            420                 425                 430

Lys Val Thr Met Thr Cys Arg Ala Ser Ser Ser Val Ser Tyr Met Asn

```
                        435                 440                 445
Trp Tyr Gln Gln Lys Ser Gly Thr Ser Pro Lys Arg Trp Ile Tyr Asp
450                 455                 460

Thr Ser Lys Val Ala Ser Gly Val Pro Tyr Arg Phe Ser Gly Ser Gly
465                 470                 475                 480

Ser Gly Thr Ser Tyr Ser Leu Thr Ile Ser Ser Met Glu Ala Glu Asp
                485                 490                 495

Ala Ala Thr Tyr Tyr Cys Gln Gln Trp Ser Ser Asn Pro Leu Thr Phe
                500                 505                 510

Gly Cys Gly Thr Lys Leu Glu Leu Lys Gly Gly Ser His His His His
            515                 520                 525

His His
    530

<210> SEQ ID NO 71
<211> LENGTH: 530
<212> TYPE: PRT
<213> ORGANISM: artificial
<220> FEATURE:
<223> OTHER INFORMATION: artificial Antibody

<400> SEQUENCE: 71

Met Gly Trp Ser Cys Ile Ile Leu Phe Leu Val Ala Thr Ala Thr Gly
1               5                  10                  15

Val His Ser Gln Ile Gln Leu Val Gln Ser Gly Pro Glu Leu Lys Lys
                20                  25                  30

Pro Gly Glu Thr Val Lys Ile Ser Cys Lys Ala Ser Gly Tyr Thr Phe
            35                  40                  45

Thr Asn Tyr Gly Met Asn Trp Val Lys Gln Ala Pro Gly Lys Cys Leu
        50                  55                  60

Lys Trp Met Gly Trp Ile Asn Thr Asn Thr Gly Glu Pro Thr Tyr Ala
65                  70                  75                  80

Glu Glu Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Leu Gly Phe Gly Asn Ala Met Asp Tyr Trp Gly
        115                 120                 125

Gln Gly Thr Ser Val Thr Val Ser Ser Gly Gly Gly Gly Ser Gly Gly
    130                 135                 140

Gly Gly Ser Gly Gly Gly Gly Ser Gly Gly Gly Gly Ser Asp Ile Val
145                 150                 155                 160

Met Thr Gln Ser Pro Ser Ser Leu Thr Val Thr Ala Gly Glu Lys Val
                165                 170                 175

Thr Met Ser Cys Lys Ser Ser Gln Ser Leu Leu Asn Ser Gly Asn Gln
            180                 185                 190

Lys Asn Tyr Leu Thr Trp Tyr Gln Gln Lys Pro Gly Gln Pro Pro Lys
        195                 200                 205

Leu Leu Ile Tyr Trp Ala Ser Thr Arg Glu Ser Gly Val Pro Asp Arg
    210                 215                 220

Phe Thr Gly Ser Gly Ser Gly Thr Asp Phe Thr Leu Thr Ile Ser Ser
225                 230                 235                 240

Val Gln Ala Glu Asp Leu Ala Val Tyr Tyr Cys Gln Asn Asp Tyr Ser
                245                 250                 255

Tyr Pro Leu Thr Phe Gly Cys Gly Thr Lys Leu Glu Leu Lys Ser Gly
```

```
                    260                 265                 270
Gly Gly Gly Ser Gln Val Gln Leu Gln Gln Ser Gly Ala Glu Leu Ala
            275                 280                 285
Arg Pro Gly Ala Ser Val Lys Met Ser Cys Lys Thr Ser Gly Tyr Thr
        290                 295                 300
Phe Thr Arg Tyr Thr Met His Trp Val Lys Gln Arg Pro Gly Gln Cys
305                 310                 315                 320
Leu Glu Trp Ile Gly Tyr Ile Asn Pro Ser Arg Gly Tyr Thr Asn Tyr
                325                 330                 335
Asn Gln Lys Phe Lys Asp Lys Ala Thr Leu Thr Thr Asp Lys Ser Ser
            340                 345                 350
Ser Thr Ala Tyr Met Gln Leu Ser Ser Leu Thr Ser Glu Asp Ser Ala
        355                 360                 365
Val Tyr Tyr Cys Ala Arg Tyr Tyr Asp Asp His Tyr Ser Leu Asp Tyr
    370                 375                 380
Trp Gly Gln Gly Thr Thr Leu Thr Val Ser Ser Gly Gly Gly Gly Ser
385                 390                 395                 400
Gly Gly Gly Gly Ser Gly Gly Gly Ser Gly Gly Gly Gly Ser Gln
                405                 410                 415
Ile Val Leu Thr Gln Ser Pro Ala Ile Met Ser Ala Ser Pro Gly Glu
            420                 425                 430
Lys Val Thr Met Thr Cys Arg Ala Ser Ser Ser Val Ser Tyr Met Asn
        435                 440                 445
Trp Tyr Gln Gln Lys Ser Gly Thr Ser Pro Lys Arg Trp Ile Tyr Asp
    450                 455                 460
Thr Ser Lys Val Ala Ser Gly Val Pro Tyr Arg Phe Ser Gly Ser Gly
465                 470                 475                 480
Ser Gly Thr Ser Tyr Ser Leu Thr Ile Ser Ser Met Glu Ala Glu Asp
                485                 490                 495
Ala Ala Thr Tyr Tyr Cys Gln Gln Trp Ser Ser Asn Pro Leu Thr Phe
            500                 505                 510
Gly Cys Gly Thr Lys Leu Glu Leu Lys Gly Gly Ser His His His His
        515                 520                 525
His His
    530

<210> SEQ ID NO 72
<211> LENGTH: 530
<212> TYPE: PRT
<213> ORGANISM: artificial
<220> FEATURE:
<223> OTHER INFORMATION: artificial Antibody

<400> SEQUENCE: 72

Met Gly Trp Ser Cys Ile Ile Leu Phe Leu Val Ala Thr Ala Thr Gly
1               5                   10                  15
Val His Ser Gln Val Gln Leu Gln Gln Pro Gly Ala Glu Leu Val Arg
                20                  25                  30
Pro Gly Ala Ser Val Lys Leu Ser Cys Lys Ala Ser Gly Tyr Thr Phe
            35                  40                  45
Thr Ser Tyr Trp Ile Asn Trp Val Lys Gln Arg Pro Gly Gln Gly Leu
        50                  55                  60
Glu Trp Ile Gly Asn Ile Tyr Pro Ser Asp Ser Tyr Thr Asn Tyr Asn
65                  70                  75                  80
Gln Lys Phe Lys Asp Lys Ala Thr Leu Thr Val Asp Lys Ser Ser Ser
```

```
              85              90              95
Thr Ala Tyr Met Gln Leu Ser Ser Pro Thr Ser Glu Asp Ser Ala Val
            100             105             110

Tyr Tyr Cys Thr Arg Ser Trp Arg Gly Asn Ser Phe Asp Tyr Trp Gly
            115             120             125

Gln Gly Thr Thr Leu Thr Val Ser Ser Gly Gly Gly Ser Gly Gly
            130             135             140

Gly Gly Ser Gly Gly Gly Ser Gly Gly Gly Ser Asp Ile Val
145             150             155             160

Met Thr Gln Ser Pro Ser Ser Leu Thr Val Thr Ala Gly Glu Lys Val
            165             170             175

Thr Met Ser Cys Lys Ser Ser Gln Ser Leu Leu Asn Ser Gly Asn Gln
            180             185             190

Lys Asn Tyr Leu Thr Trp Tyr Gln Gln Lys Pro Gly Gln Pro Pro Lys
            195             200             205

Leu Leu Ile Tyr Trp Ala Ser Thr Arg Glu Ser Gly Val Pro Asp Arg
            210             215             220

Phe Thr Gly Ser Gly Ser Gly Thr Asp Phe Thr Leu Thr Ile Ser Ser
225             230             235             240

Val Gln Ala Glu Asp Leu Ala Val Tyr Tyr Cys Gln Asn Asp Tyr Ser
            245             250             255

Tyr Pro Phe Thr Phe Gly Ser Gly Thr Lys Leu Glu Ile Lys Ser Gly
            260             265             270

Gly Gly Gly Ser Gln Val Gln Leu Gln Gln Ser Gly Ala Glu Leu Ala
            275             280             285

Arg Pro Gly Ala Ser Val Lys Met Ser Cys Lys Thr Ser Gly Tyr Thr
            290             295             300

Phe Thr Arg Tyr Thr Met His Trp Val Lys Gln Arg Pro Gly Gln Cys
305             310             315             320

Leu Glu Trp Ile Gly Tyr Ile Asn Pro Ser Arg Gly Tyr Thr Asn Tyr
            325             330             335

Asn Gln Lys Phe Lys Asp Lys Ala Thr Leu Thr Thr Asp Lys Ser Ser
            340             345             350

Ser Thr Ala Tyr Met Gln Leu Ser Ser Leu Thr Ser Glu Asp Ser Ala
            355             360             365

Val Tyr Tyr Cys Ala Arg Tyr Tyr Asp Asp His Tyr Ser Leu Asp Tyr
            370             375             380

Trp Gly Gln Gly Thr Thr Leu Thr Val Ser Ser Gly Gly Gly Gly Ser
385             390             395             400

Gly Gly Gly Gly Ser Gly Gly Gly Ser Gly Gly Gly Ser Gln
            405             410             415

Ile Val Leu Thr Gln Ser Pro Ala Ile Met Ser Ala Ser Pro Gly Glu
            420             425             430

Lys Val Thr Met Thr Cys Arg Ala Ser Ser Ser Val Ser Tyr Met Asn
            435             440             445

Trp Tyr Gln Gln Lys Ser Gly Thr Ser Pro Lys Arg Trp Ile Tyr Asp
            450             455             460

Thr Ser Lys Val Ala Ser Gly Val Pro Tyr Arg Phe Ser Gly Ser Gly
465             470             475             480

Ser Gly Thr Ser Tyr Ser Leu Thr Ile Ser Ser Met Glu Ala Glu Asp
            485             490             495

Ala Ala Thr Tyr Tyr Cys Gln Gln Trp Ser Ser Asn Pro Leu Thr Phe
            500             505             510
```

```
Gly Cys Gly Thr Lys Leu Glu Leu Lys Gly Gly Ser His His His His
            515                 520                 525
His His
    530

<210> SEQ ID NO 73
<211> LENGTH: 530
<212> TYPE: PRT
<213> ORGANISM: artificial
<220> FEATURE:
<223> OTHER INFORMATION: artificial Antibody

<400> SEQUENCE: 73

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Thr Phe
        35                  40                  45

Thr Ser Tyr Trp Ile Asn Trp Val Lys Gln Arg Pro Gly Gln Cys Leu
    50                  55                  60

Glu Trp Ile Gly Asn Ile Tyr Pro Ser Asp Ser Tyr Thr Asn Tyr Asn
65                  70                  75                  80

Gln Lys Phe Lys Asp Lys Ala Thr Leu Thr Val Asp Lys Ser Ser Ser
                85                  90                  95

Thr Ala Tyr Met Gln Leu Ser Ser Pro Thr Ser Glu Asp Ser Ala Val
            100                 105                 110

Tyr Tyr Cys Thr Arg Ser Trp Arg Gly Asn Ser Phe Asp Tyr Trp Gly
        115                 120                 125

Gln Gly Thr Thr Leu Thr Val Ser Ser Gly Gly Gly Ser Gly Gly
    130                 135                 140

Gly Gly Ser Gly Gly Gly Ser Gly Gly Gly Gly Ser Asp Ile Val
145                 150                 155                 160

Met Thr Gln Ser Pro Ser Ser Leu Thr Val Thr Ala Gly Glu Lys Val
                165                 170                 175

Thr Met Ser Cys Lys Ser Ser Gln Ser Leu Leu Asn Ser Gly Asn Gln
            180                 185                 190

Lys Asn Tyr Leu Thr Trp Tyr Gln Gln Lys Pro Gly Gln Pro Pro Lys
        195                 200                 205

Leu Leu Ile Tyr Trp Ala Ser Thr Arg Glu Ser Gly Val Pro Asp Arg
    210                 215                 220

Phe Thr Gly Ser Gly Ser Gly Thr Asp Phe Thr Leu Thr Ile Ser Ser
225                 230                 235                 240

Val Gln Ala Glu Asp Leu Ala Val Tyr Tyr Cys Gln Asn Asp Tyr Ser
                245                 250                 255

Tyr Pro Phe Thr Phe Gly Cys Gly Thr Lys Leu Glu Ile Lys Ser Gly
            260                 265                 270

Gly Gly Gly Ser Gln Val Gln Leu Gln Gln Ser Gly Ala Glu Leu Ala
        275                 280                 285

Arg Pro Gly Ala Ser Val Lys Met Ser Cys Lys Thr Ser Gly Tyr Thr
    290                 295                 300

Phe Thr Arg Tyr Thr Met His Trp Val Lys Gln Arg Pro Gly Gln Cys
305                 310                 315                 320

Leu Glu Trp Ile Gly Tyr Ile Asn Pro Ser Arg Gly Tyr Thr Asn Tyr
                325                 330                 335
```

-continued

Asn Gln Lys Phe Lys Asp Lys Ala Thr Leu Thr Thr Asp Lys Ser Ser
            340                 345                 350

Ser Thr Ala Tyr Met Gln Leu Ser Ser Leu Thr Ser Glu Asp Ser Ala
            355                 360                 365

Val Tyr Tyr Cys Ala Arg Tyr Tyr Asp Asp His Tyr Ser Leu Asp Tyr
370                 375                 380

Trp Gly Gln Gly Thr Thr Leu Thr Val Ser Ser Gly Gly Gly Gly Ser
385                 390                 395                 400

Gly Gly Gly Gly Ser Gly Gly Gly Ser Gly Gly Gly Gly Ser Gln
                405                 410                 415

Ile Val Leu Thr Gln Ser Pro Ala Ile Met Ser Ala Ser Pro Gly Glu
            420                 425                 430

Lys Val Thr Met Thr Cys Arg Ala Ser Ser Ser Val Ser Tyr Met Asn
            435                 440                 445

Trp Tyr Gln Gln Lys Ser Gly Thr Ser Pro Lys Arg Trp Ile Tyr Asp
            450                 455                 460

Thr Ser Lys Val Ala Ser Gly Val Pro Tyr Arg Phe Ser Gly Ser Gly
465                 470                 475                 480

Ser Gly Thr Ser Tyr Ser Leu Thr Ile Ser Ser Met Glu Ala Glu Asp
                485                 490                 495

Ala Ala Thr Tyr Tyr Cys Gln Gln Trp Ser Ser Asn Pro Leu Thr Phe
            500                 505                 510

Gly Cys Gly Thr Lys Leu Glu Leu Lys Gly Gly Ser His His His His
            515                 520                 525

His His
    530

<210> SEQ ID NO 74
<211> LENGTH: 535
<212> TYPE: PRT
<213> ORGANISM: artificial
<220> FEATURE:
<223> OTHER INFORMATION: artificial Antibody

<400> SEQUENCE: 74

Met Gly Trp Ser Cys Ile Ile Leu Phe Leu Val Ala Thr Ala Thr Gly
1               5                   10                  15

Val His Ser Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
            35                  40                  45

Thr Asn Tyr Gly Met Asn Trp Val Lys Gln Ala Pro Gly Lys Gly Leu
    50                  55                  60

Lys Trp Met Gly Trp Ile Asn Thr Asn Thr Gly Glu Pro Thr Tyr Ala
65                  70                  75                  80

Glu Glu Phe Lys Gly Arg Phe Ala Phe Ser Leu Glu Thr Ser Ala Ser
            85                  90                  95

Thr Ala Tyr Leu Gln Ile Asn Asn Leu Lys Asn Glu Asp Thr Ala Thr
            100                 105                 110

Tyr Phe Cys Ala Arg Leu Gly Phe Gly Asn Ala Met Asp Tyr Trp Gly
            115                 120                 125

Gln Gly Thr Ser Val Thr Val Ser Ser Gly Gly Gly Gly Ser Gly Gly
            130                 135                 140

Gly Gly Ser Gly Gly Gly Gly Ser Gly Gly Gly Gly Ser Asp Ile Val
145                 150                 155                 160

Met Thr Gln Ser Pro Ser Ser Leu Thr Val Thr Ala Gly Glu Lys Val
            165                 170                 175

Thr Met Ser Cys Lys Ser Ser Gln Ser Leu Leu Asn Ser Gly Asn Gln
            180                 185                 190

Lys Asn Tyr Leu Thr Trp Tyr Gln Gln Lys Pro Gly Gln Pro Pro Lys
            195                 200                 205

Leu Leu Ile Tyr Trp Ala Ser Thr Arg Glu Ser Gly Val Pro Asp Arg
210                 215                 220

Phe Thr Gly Ser Gly Ser Gly Thr Asp Phe Thr Leu Thr Ile Ser Ser
225                 230                 235                 240

Val Gln Ala Glu Asp Leu Ala Val Tyr Tyr Cys Gln Asn Asp Tyr Ser
            245                 250                 255

Tyr Pro Leu Thr Phe Gly Ala Gly Thr Lys Leu Glu Leu Lys Ser Gly
            260                 265                 270

Gly Gly Gly Ser Gln Ile Val Leu Thr Gln Ser Pro Ala Ile Met Ser
            275                 280                 285

Ala Ser Pro Gly Glu Lys Val Thr Met Thr Cys Arg Ala Ser Ser Ser
            290                 295                 300

Val Ser Tyr Met Asn Trp Tyr Gln Gln Lys Ser Gly Thr Ser Pro Lys
305                 310                 315                 320

Arg Trp Ile Tyr Asp Thr Ser Lys Val Ala Ser Gly Val Pro Tyr Arg
            325                 330                 335

Phe Ser Gly Ser Gly Ser Gly Thr Ser Tyr Ser Leu Thr Ile Ser Ser
            340                 345                 350

Met Glu Ala Glu Asp Ala Ala Thr Tyr Tyr Cys Gln Gln Trp Ser Ser
            355                 360                 365

Asn Pro Leu Thr Phe Gly Ala Gly Thr Lys Leu Glu Leu Lys Gly Gly
            370                 375                 380

Gly Gly Ser Gly Gly Gly Ser Gly Gly Gly Ser Gly Gly Gly
385                 390                 395                 400

Gly Ser Gly Gly Gly Gly Ser Gln Val Gln Leu Gln Gln Ser Gly Ala
            405                 410                 415

Glu Leu Ala Arg Pro Gly Ala Ser Val Lys Met Ser Cys Lys Thr Ser
            420                 425                 430

Gly Tyr Thr Phe Thr Arg Tyr Thr Met His Trp Val Lys Gln Arg Pro
            435                 440                 445

Gly Gln Gly Leu Glu Trp Ile Gly Tyr Ile Asn Pro Ser Arg Gly Tyr
            450                 455                 460

Thr Asn Tyr Asn Gln Lys Phe Lys Asp Lys Ala Thr Leu Thr Thr Asp
465                 470                 475                 480

Lys Ser Ser Ser Thr Ala Tyr Met Gln Leu Ser Ser Leu Thr Ser Glu
            485                 490                 495

Asp Ser Ala Val Tyr Tyr Cys Ala Arg Tyr Tyr Asp Asp His Tyr Ser
            500                 505                 510

Leu Asp Tyr Trp Gly Gln Gly Thr Thr Leu Thr Val Ser Ser Gly Gly
            515                 520                 525

Ser His His His His His His
    530                 535

<210> SEQ ID NO 75
<211> LENGTH: 535
<212> TYPE: PRT
<213> ORGANISM: artificial
<220> FEATURE:

<223> OTHER INFORMATION: artificial Antibody

<400> SEQUENCE: 75

```
Met Gly Trp Ser Cys Ile Ile Leu Phe Leu Val Ala Thr Ala Thr Gly
 1               5                  10                  15

Val His Ser Gln Ile Gln Leu Val Gln Ser Gly Pro Glu Leu Lys Lys
             20                  25                  30

Pro Gly Glu Thr Val Lys Ile Ser Cys Lys Ala Ser Gly Tyr Thr Phe
         35                  40                  45

Thr Asn Tyr Gly Met Asn Trp Val Lys Gln Ala Pro Gly Lys Cys Leu
     50                  55                  60

Lys Trp Met Gly Trp Ile Asn Thr Asn Thr Gly Glu Pro Thr Tyr Ala
 65                  70                  75                  80

Glu Glu Phe Lys Gly Arg Phe Ala Phe Ser Leu Glu Thr Ser Ala Ser
                 85                  90                  95

Thr Ala Tyr Leu Gln Ile Asn Asn Leu Lys Asn Glu Asp Thr Ala Thr
            100                 105                 110

Tyr Phe Cys Ala Arg Leu Gly Phe Gly Asn Ala Met Asp Tyr Trp Gly
        115                 120                 125

Gln Gly Thr Ser Val Thr Val Ser Ser Gly Gly Gly Ser Gly Gly
    130                 135                 140

Gly Gly Ser Gly Gly Gly Ser Gly Gly Gly Ser Asp Ile Val
145                 150                 155                 160

Met Thr Gln Ser Pro Ser Ser Leu Thr Val Thr Ala Gly Glu Lys Val
                165                 170                 175

Thr Met Ser Cys Lys Ser Ser Gln Ser Leu Leu Asn Ser Gly Asn Gln
            180                 185                 190

Lys Asn Tyr Leu Thr Trp Tyr Gln Gln Lys Pro Gly Gln Pro Pro Lys
        195                 200                 205

Leu Leu Ile Tyr Trp Ala Ser Thr Arg Glu Ser Gly Val Pro Asp Arg
    210                 215                 220

Phe Thr Gly Ser Gly Ser Gly Thr Asp Phe Thr Leu Thr Ile Ser Ser
225                 230                 235                 240

Val Gln Ala Glu Asp Leu Ala Val Tyr Tyr Cys Gln Asn Asp Tyr Ser
                245                 250                 255

Tyr Pro Leu Thr Phe Gly Cys Gly Thr Lys Leu Glu Leu Lys Ser Gly
            260                 265                 270

Gly Gly Gly Ser Gln Ile Val Leu Thr Gln Ser Pro Ala Ile Met Ser
        275                 280                 285

Ala Ser Pro Gly Glu Lys Val Thr Met Thr Cys Arg Ala Ser Ser Ser
    290                 295                 300

Val Ser Tyr Met Asn Trp Tyr Gln Gln Lys Ser Gly Thr Ser Pro Lys
305                 310                 315                 320

Arg Trp Ile Tyr Asp Thr Ser Lys Val Ala Ser Gly Val Pro Tyr Arg
                325                 330                 335

Phe Ser Gly Ser Gly Ser Gly Thr Ser Tyr Ser Leu Thr Ile Ser Ser
            340                 345                 350

Met Glu Ala Glu Asp Ala Ala Thr Tyr Tyr Cys Gln Gln Trp Ser Ser
        355                 360                 365

Asn Pro Leu Thr Phe Gly Ala Gly Thr Lys Leu Glu Leu Lys Gly Gly
    370                 375                 380

Gly Gly Ser Gly Gly Gly Gly Ser Gly Gly Gly Ser Gly Gly Gly
385                 390                 395                 400
```

```
Gly Ser Gly Gly Gly Ser Gln Val Gln Leu Gln Ser Gly Ala
            405                 410                 415
Glu Leu Ala Arg Pro Gly Ala Ser Val Lys Met Ser Cys Lys Thr Ser
            420                 425                 430
Gly Tyr Thr Phe Thr Arg Tyr Thr Met His Trp Val Lys Gln Arg Pro
            435                 440                 445
Gly Gln Gly Leu Glu Trp Ile Gly Tyr Ile Asn Pro Ser Arg Gly Tyr
            450                 455                 460
Thr Asn Tyr Asn Gln Lys Phe Lys Asp Lys Ala Thr Leu Thr Thr Asp
465                 470                 475                 480
Lys Ser Ser Ser Thr Ala Tyr Met Gln Leu Ser Ser Leu Thr Ser Glu
                485                 490                 495
Asp Ser Ala Val Tyr Tyr Cys Ala Arg Tyr Tyr Asp Asp His Tyr Ser
                500                 505                 510
Leu Asp Tyr Trp Gly Gln Gly Thr Thr Leu Thr Val Ser Ser Gly Gly
                515                 520                 525
Ser His His His His His His
                530                 535

<210> SEQ ID NO 76
<211> LENGTH: 535
<212> TYPE: PRT
<213> ORGANISM: artificial
<220> FEATURE:
<223> OTHER INFORMATION: artificial Antibody

<400> SEQUENCE: 76

Met Gly Trp Ser Cys Ile Ile Leu Phe Leu Val Ala Thr Ala Thr Gly
1               5                   10                  15
Val His Ser Gln Val Gln Leu Gln Gln Pro Gly Ala Glu Leu Val Arg
                20                  25                  30
Pro Gly Ala Ser Val Lys Leu Ser Cys Lys Ala Ser Gly Tyr Thr Phe
                35                  40                  45
Thr Ser Tyr Trp Ile Asn Trp Val Lys Gln Arg Pro Gly Gln Gly Leu
            50                  55                  60
Glu Trp Ile Gly Asn Ile Tyr Pro Ser Asp Ser Tyr Thr Asn Tyr Asn
65                  70                  75                  80
Gln Lys Phe Lys Asp Lys Ala Thr Leu Thr Val Asp Lys Ser Ser Ser
                85                  90                  95
Thr Ala Tyr Met Gln Leu Ser Ser Pro Thr Ser Glu Asp Ser Ala Val
                100                 105                 110
Tyr Tyr Cys Thr Arg Ser Trp Arg Gly Asn Ser Phe Asp Tyr Trp Gly
            115                 120                 125
Gln Gly Thr Thr Leu Thr Val Ser Ser Gly Gly Gly Gly Ser Gly Gly
            130                 135                 140
Gly Gly Ser Gly Gly Gly Gly Ser Gly Gly Gly Gly Ser Asp Ile Val
145                 150                 155                 160
Met Thr Gln Ser Pro Ser Ser Leu Thr Val Thr Ala Gly Glu Lys Val
                165                 170                 175
Thr Met Ser Cys Lys Ser Ser Gln Ser Leu Leu Asn Ser Gly Asn Gln
            180                 185                 190
Lys Asn Tyr Leu Thr Trp Tyr Gln Gln Lys Pro Gly Gln Pro Pro Lys
            195                 200                 205
Leu Leu Ile Tyr Trp Ala Ser Thr Arg Glu Ser Gly Val Pro Asp Arg
            210                 215                 220
```

Phe Thr Gly Ser Gly Ser Gly Thr Asp Phe Thr Leu Thr Ile Ser Ser
225                 230                 235                 240

Val Gln Ala Glu Asp Leu Ala Val Tyr Tyr Cys Gln Asn Asp Tyr Ser
            245                 250                 255

Tyr Pro Phe Thr Phe Gly Ser Gly Thr Lys Leu Glu Ile Lys Ser Gly
        260                 265                 270

Gly Gly Gly Ser Gln Ile Val Leu Thr Gln Ser Pro Ala Ile Met Ser
    275                 280                 285

Ala Ser Pro Gly Glu Lys Val Thr Met Thr Cys Arg Ala Ser Ser Ser
290                 295                 300

Val Ser Tyr Met Asn Trp Tyr Gln Gln Lys Ser Gly Thr Ser Pro Lys
305                 310                 315                 320

Arg Trp Ile Tyr Asp Thr Ser Lys Val Ala Ser Gly Val Pro Tyr Arg
                325                 330                 335

Phe Ser Gly Ser Gly Ser Gly Thr Ser Tyr Ser Leu Thr Ile Ser Ser
            340                 345                 350

Met Glu Ala Glu Asp Ala Ala Thr Tyr Tyr Cys Gln Gln Trp Ser Ser
        355                 360                 365

Asn Pro Leu Thr Phe Gly Ala Gly Thr Lys Leu Glu Leu Lys Gly Gly
    370                 375                 380

Gly Gly Ser Gly Gly Gly Ser Gly Gly Gly Ser Gly Gly Gly Gly Gly
385                 390                 395                 400

Gly Ser Gly Gly Gly Ser Gln Val Gln Leu Gln Gln Ser Gly Ala
                405                 410                 415

Glu Leu Ala Arg Pro Gly Ala Ser Val Lys Met Ser Cys Lys Thr Ser
            420                 425                 430

Gly Tyr Thr Phe Thr Arg Tyr Thr Met His Trp Val Lys Gln Arg Pro
        435                 440                 445

Gly Gln Gly Leu Glu Trp Ile Gly Tyr Ile Asn Pro Ser Arg Gly Tyr
    450                 455                 460

Thr Asn Tyr Asn Gln Lys Phe Lys Asp Lys Ala Thr Leu Thr Thr Asp
465                 470                 475                 480

Lys Ser Ser Ser Thr Ala Tyr Met Gln Leu Ser Ser Leu Thr Ser Glu
                485                 490                 495

Asp Ser Ala Val Tyr Tyr Cys Ala Arg Tyr Tyr Asp Asp His Tyr Ser
            500                 505                 510

Leu Asp Tyr Trp Gly Gln Gly Thr Thr Leu Thr Val Ser Ser Gly Gly
        515                 520                 525

Ser His His His His His His
    530                 535

<210> SEQ ID NO 77
<211> LENGTH: 535
<212> TYPE: PRT
<213> ORGANISM: artificial
<220> FEATURE:
<223> OTHER INFORMATION: artificial Antibody

<400> SEQUENCE: 77

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Thr Phe
        35                  40                  45

```
Thr Ser Tyr Trp Ile Asn Trp Val Lys Gln Arg Pro Gly Gln Cys Leu
     50                  55                  60
Glu Trp Ile Gly Asn Ile Tyr Pro Ser Asp Ser Tyr Thr Asn Tyr Asn
 65              70                  75                      80
Gln Lys Phe Lys Asp Lys Ala Thr Leu Thr Val Asp Lys Ser Ser Ser
             85                  90                  95
Thr Ala Tyr Met Gln Leu Ser Ser Pro Thr Ser Glu Asp Ser Ala Val
            100                 105                 110
Tyr Tyr Cys Thr Arg Ser Trp Arg Gly Asn Ser Phe Asp Tyr Trp Gly
            115                 120                 125
Gln Gly Thr Thr Leu Thr Val Ser Ser Gly Gly Gly Ser Gly Gly
        130                 135                 140
Gly Gly Ser Gly Gly Gly Ser Gly Gly Gly Ser Asp Ile Val
145                 150                 155                 160
Met Thr Gln Ser Pro Ser Ser Leu Thr Val Thr Ala Gly Glu Lys Val
                165                 170                 175
Thr Met Ser Cys Lys Ser Ser Gln Ser Leu Leu Asn Ser Gly Asn Gln
            180                 185                 190
Lys Asn Tyr Leu Thr Trp Tyr Gln Gln Lys Pro Gly Gln Pro Pro Lys
            195                 200                 205
Leu Leu Ile Tyr Trp Ala Ser Thr Arg Glu Ser Gly Val Pro Asp Arg
210                 215                 220
Phe Thr Gly Ser Gly Ser Gly Thr Asp Phe Thr Leu Thr Ile Ser Ser
225                 230                 235                 240
Val Gln Ala Glu Asp Leu Ala Val Tyr Tyr Cys Gln Asn Asp Tyr Ser
                245                 250                 255
Tyr Pro Phe Thr Phe Gly Cys Gly Thr Lys Leu Glu Ile Lys Ser Gly
            260                 265                 270
Gly Gly Gly Ser Gln Ile Val Leu Thr Gln Ser Pro Ala Ile Met Ser
            275                 280                 285
Ala Ser Pro Gly Glu Lys Val Thr Met Thr Cys Arg Ala Ser Ser Ser
    290                 295                 300
Val Ser Tyr Met Asn Trp Tyr Gln Gln Lys Ser Gly Thr Ser Pro Lys
305                 310                 315                 320
Arg Trp Ile Tyr Asp Thr Ser Lys Val Ala Ser Gly Val Pro Tyr Arg
            325                 330                 335
Phe Ser Gly Ser Gly Ser Gly Thr Ser Tyr Ser Leu Thr Ile Ser Ser
            340                 345                 350
Met Glu Ala Glu Asp Ala Ala Thr Tyr Tyr Cys Gln Gln Trp Ser Ser
            355                 360                 365
Asn Pro Leu Thr Phe Gly Ala Gly Thr Lys Leu Glu Leu Lys Gly Gly
    370                 375                 380
Gly Gly Ser Gly Gly Gly Ser Gly Gly Gly Ser Gly Gly
385                 390                 395                 400
Gly Ser Gly Gly Gly Ser Gln Val Gln Leu Gln Gln Ser Gly Ala
            405                 410                 415
Glu Leu Ala Arg Pro Gly Ala Ser Val Lys Met Ser Cys Lys Thr Ser
            420                 425                 430
Gly Tyr Thr Phe Thr Arg Tyr Thr Met His Trp Val Lys Gln Arg Pro
            435                 440                 445
Gly Gln Gly Leu Glu Trp Ile Gly Tyr Ile Asn Pro Ser Arg Gly Tyr
    450                 455                 460
Thr Asn Tyr Asn Gln Lys Phe Lys Asp Lys Ala Thr Leu Thr Thr Asp
```

465                 470                 475                 480
Lys Ser Ser Thr Ala Tyr Met Gln Leu Ser Ser Leu Thr Ser Glu
                485                 490                 495

Asp Ser Ala Val Tyr Tyr Cys Ala Arg Tyr Tyr Asp Asp His Tyr Ser
                500                 505                 510

Leu Asp Tyr Trp Gly Gln Gly Thr Leu Thr Val Ser Ser Gly Gly
                515                 520                 525

Ser His His His His His
                530                 535

<210> SEQ ID NO 78
<211> LENGTH: 535
<212> TYPE: PRT
<213> ORGANISM: artificial
<220> FEATURE:
<223> OTHER INFORMATION: artificial Antibody

<400> SEQUENCE: 78

Met Gly Trp Ser Cys Ile Ile Leu Phe Leu Val Ala Thr Ala Thr Gly
1               5                   10                  15

Val His Ser Gln Ile Gln Leu Val Gln Ser Gly Pro Glu Leu Lys Lys
                20                  25                  30

Pro Gly Glu Thr Val Lys Ile Ser Cys Lys Ala Ser Gly Tyr Thr Phe
                35                  40                  45

Thr Asn Tyr Gly Met Asn Trp Val Lys Gln Ala Pro Gly Lys Gly Leu
        50                  55                  60

Lys Trp Met Gly Trp Ile Asn Thr Asn Thr Gly Glu Pro Thr Tyr Ala
65                  70                  75                  80

Glu Glu Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
                100                 105                 110

Tyr Phe Cys Ala Arg Leu Gly Phe Gly Asn Ala Met Asp Tyr Trp Gly
                115                 120                 125

Gln Gly Thr Ser Val Thr Val Ser Ser Gly Gly Gly Ser Gly Gly
        130                 135                 140

Gly Gly Ser Gly Gly Gly Ser Gly Gly Gly Ser Asp Ile Val
145                 150                 155                 160

Met Thr Gln Ser Pro Ser Ser Leu Thr Val Thr Ala Gly Glu Lys Val
                165                 170                 175

Thr Met Ser Cys Lys Ser Ser Gln Ser Leu Leu Asn Ser Gly Asn Gln
                180                 185                 190

Lys Asn Tyr Leu Thr Trp Tyr Gln Gln Lys Pro Gly Gln Pro Pro Lys
                195                 200                 205

Leu Leu Ile Tyr Trp Ala Ser Thr Arg Glu Ser Gly Val Pro Asp Arg
        210                 215                 220

Phe Thr Gly Ser Gly Ser Gly Thr Asp Phe Thr Leu Thr Ile Ser Ser
225                 230                 235                 240

Val Gln Ala Glu Asp Leu Ala Val Tyr Tyr Cys Gln Asn Asp Tyr Ser
                245                 250                 255

Tyr Pro Leu Thr Phe Gly Ala Gly Thr Lys Leu Glu Leu Lys Ser Gly
                260                 265                 270

Gly Gly Gly Ser Gln Ile Val Leu Thr Gln Ser Pro Ala Ile Met Ser
                275                 280                 285

Ala Ser Pro Gly Glu Lys Val Thr Met Thr Cys Arg Ala Ser Ser Ser

Val Ser Tyr Met Asn Trp Tyr Gln Gln Lys Ser Gly Thr Ser Pro Lys
305                 310                 315                 320

Arg Trp Ile Tyr Asp Thr Ser Lys Val Ala Ser Gly Val Pro Tyr Arg
                325                 330                 335

Phe Ser Gly Ser Gly Ser Gly Thr Ser Tyr Ser Leu Thr Ile Ser Ser
            340                 345                 350

Met Glu Ala Glu Asp Ala Ala Thr Tyr Tyr Cys Gln Gln Trp Ser Ser
        355                 360                 365

Asn Pro Leu Thr Phe Gly Cys Gly Thr Lys Leu Glu Leu Lys Gly Gly
    370                 375                 380

Gly Gly Ser Gly Gly Gly Ser Gly Gly Gly Ser Gly Gly Gly
385                 390                 395                 400

Gly Ser Gly Gly Gly Ser Gln Val Gln Leu Gln Gln Ser Gly Ala
                405                 410                 415

Glu Leu Ala Arg Pro Gly Ala Ser Val Lys Met Ser Cys Lys Thr Ser
        420                 425                 430

Gly Tyr Thr Phe Thr Arg Tyr Thr Met His Trp Val Lys Gln Arg Pro
            435                 440                 445

Gly Gln Cys Leu Glu Trp Ile Gly Tyr Ile Asn Pro Ser Arg Gly Tyr
    450                 455                 460

Thr Asn Tyr Asn Gln Lys Phe Lys Asp Lys Ala Thr Leu Thr Thr Asp
465                 470                 475                 480

Lys Ser Ser Ser Thr Ala Tyr Met Gln Leu Ser Ser Leu Thr Ser Glu
                485                 490                 495

Asp Ser Ala Val Tyr Tyr Cys Ala Arg Tyr Tyr Asp Asp His Tyr Ser
        500                 505                 510

Leu Asp Tyr Trp Gly Gln Gly Thr Thr Leu Thr Val Ser Ser Gly Gly
            515                 520                 525

Ser His His His His His His
    530                 535

<210> SEQ ID NO 79
<211> LENGTH: 535
<212> TYPE: PRT
<213> ORGANISM: artificial
<220> FEATURE:
<223> OTHER INFORMATION: artificial Antibody

<400> SEQUENCE: 79

Met Gly Trp Ser Cys Ile Ile Leu Phe Leu Val Ala Thr Ala Thr Gly
1               5                   10                  15

Val His Ser Gln Ile Gln Leu Val Gln Ser Gly Pro Glu Leu Lys Lys
                20                  25                  30

Pro Gly Glu Thr Val Lys Ile Ser Cys Lys Ala Ser Gly Tyr Thr Phe
            35                  40                  45

Thr Asn Tyr Gly Met Asn Trp Val Lys Gln Ala Pro Gly Lys Cys Leu
        50                  55                  60

Lys Trp Met Gly Trp Ile Asn Thr Asn Thr Gly Glu Pro Thr Tyr Ala
65                  70                  75                  80

Glu Glu Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Leu Gly Phe Gly Asn Ala Met Asp Tyr Trp Gly

```
            115                 120                 125
Gln Gly Thr Ser Val Thr Val Ser Ser Gly Gly Gly Gly
    130                 135                 140
Gly Gly Ser Gly Gly Gly Ser Gly Gly Gly Ser Asp Ile Val
145                 150                 155                 160
Met Thr Gln Ser Pro Ser Ser Leu Thr Val Thr Ala Gly Glu Lys Val
                165                 170                 175
Thr Met Ser Cys Lys Ser Ser Gln Ser Leu Leu Asn Ser Gly Asn Gln
                180                 185                 190
Lys Asn Tyr Leu Thr Trp Tyr Gln Gln Lys Pro Gly Gln Pro Pro Lys
                195                 200                 205
Leu Leu Ile Tyr Trp Ala Ser Thr Arg Glu Ser Gly Val Pro Asp Arg
            210                 215                 220
Phe Thr Gly Ser Gly Ser Gly Thr Asp Phe Thr Leu Thr Ile Ser Ser
225                 230                 235                 240
Val Gln Ala Glu Asp Leu Ala Val Tyr Tyr Cys Gln Asn Asp Tyr Ser
                245                 250                 255
Tyr Pro Leu Thr Phe Gly Cys Gly Thr Lys Leu Glu Leu Lys Ser Gly
                260                 265                 270
Gly Gly Gly Ser Gln Ile Val Leu Thr Gln Ser Pro Ala Ile Met Ser
            275                 280                 285
Ala Ser Pro Gly Glu Lys Val Thr Met Thr Cys Arg Ala Ser Ser Ser
            290                 295                 300
Val Ser Tyr Met Asn Trp Tyr Gln Gln Lys Ser Gly Thr Ser Pro Lys
305                 310                 315                 320
Arg Trp Ile Tyr Asp Thr Ser Lys Val Ala Ser Gly Val Pro Tyr Arg
                325                 330                 335
Phe Ser Gly Ser Gly Ser Gly Thr Ser Tyr Ser Leu Thr Ile Ser Ser
                340                 345                 350
Met Glu Ala Glu Asp Ala Ala Thr Tyr Tyr Cys Gln Gln Trp Ser Ser
                355                 360                 365
Asn Pro Leu Thr Phe Gly Cys Gly Thr Lys Leu Glu Leu Lys Gly Gly
            370                 375                 380
Gly Gly Ser Gly Gly Gly Ser Gly Gly Gly Ser Gly Gly Gly
385                 390                 395                 400
Gly Ser Gly Gly Gly Ser Gln Val Gln Leu Gln Ser Gly Ala
                405                 410                 415
Glu Leu Ala Arg Pro Gly Ala Ser Val Lys Met Ser Cys Lys Thr Ser
                420                 425                 430
Gly Tyr Thr Phe Thr Arg Tyr Thr Met His Trp Val Lys Gln Arg Pro
            435                 440                 445
Gly Gln Cys Leu Glu Trp Ile Gly Tyr Ile Asn Pro Ser Arg Gly Tyr
            450                 455                 460
Thr Asn Tyr Asn Gln Lys Phe Lys Asp Lys Ala Thr Leu Thr Thr Asp
465                 470                 475                 480
Lys Ser Ser Ser Thr Ala Tyr Met Gln Leu Ser Ser Leu Thr Ser Glu
                485                 490                 495
Asp Ser Ala Val Tyr Tyr Cys Ala Arg Tyr Tyr Asp Asp His Tyr Ser
                500                 505                 510
Leu Asp Tyr Trp Gly Gln Gly Thr Thr Leu Thr Val Ser Ser Gly Gly
            515                 520                 525
Ser His His His His His His
    530                 535
```

<210> SEQ ID NO 80
<211> LENGTH: 535
<212> TYPE: PRT
<213> ORGANISM: artificial
<220> FEATURE:
<223> OTHER INFORMATION: artificial Antibody

<400> SEQUENCE: 80

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Thr Phe
        35                  40                  45

Thr Ser Tyr Trp Ile Asn Trp Val Lys Gln Arg Pro Gly Gln Gly Leu
    50                  55                  60

Glu Trp Ile Gly Asn Ile Tyr Pro Ser Asp Ser Tyr Thr Asn Tyr Asn
65                  70                  75                  80

Gln Lys Phe Lys Asp Lys Ala Thr Leu Thr Val Asp Lys Ser Ser Ser
                85                  90                  95

Thr Ala Tyr Met Gln Leu Ser Ser Pro Thr Ser Glu Asp Ser Ala Val
            100                 105                 110

Tyr Tyr Cys Thr Arg Ser Trp Arg Gly Asn Ser Phe Asp Tyr Trp Gly
        115                 120                 125

Gln Gly Thr Thr Leu Thr Val Ser Ser Gly Gly Gly Ser Gly Gly
    130                 135                 140

Gly Gly Ser Gly Gly Gly Ser Gly Gly Gly Ser Asp Ile Val
145                 150                 155                 160

Met Thr Gln Ser Pro Ser Ser Leu Thr Val Thr Ala Gly Glu Lys Val
                165                 170                 175

Thr Met Ser Cys Lys Ser Ser Gln Ser Leu Leu Asn Ser Gly Asn Gln
            180                 185                 190

Lys Asn Tyr Leu Thr Trp Tyr Gln Gln Lys Pro Gly Gln Pro Pro Lys
        195                 200                 205

Leu Leu Ile Tyr Trp Ala Ser Thr Arg Glu Ser Gly Val Pro Asp Arg
    210                 215                 220

Phe Thr Gly Ser Gly Ser Gly Thr Asp Phe Thr Leu Thr Ile Ser Ser
225                 230                 235                 240

Val Gln Ala Glu Asp Leu Ala Val Tyr Tyr Cys Gln Asn Asp Tyr Ser
                245                 250                 255

Tyr Pro Phe Thr Phe Gly Ser Gly Thr Lys Leu Glu Ile Lys Ser Gly
            260                 265                 270

Gly Gly Gly Ser Gln Ile Val Leu Thr Gln Ser Pro Ala Ile Met Ser
        275                 280                 285

Ala Ser Pro Gly Glu Lys Val Thr Met Thr Cys Arg Ala Ser Ser Ser
    290                 295                 300

Val Ser Tyr Met Asn Trp Tyr Gln Gln Lys Ser Gly Thr Ser Pro Lys
305                 310                 315                 320

Arg Trp Ile Tyr Asp Thr Ser Lys Val Ala Ser Gly Val Pro Tyr Arg
                325                 330                 335

Phe Ser Gly Ser Gly Ser Gly Thr Ser Tyr Ser Leu Thr Ile Ser Ser
            340                 345                 350

Met Glu Ala Glu Asp Ala Ala Thr Tyr Tyr Cys Gln Gln Trp Ser Ser
        355                 360                 365

```
Asn Pro Leu Thr Phe Gly Cys Gly Thr Lys Leu Glu Leu Lys Gly Gly
    370                 375                 380

Gly Gly Ser Gly Gly Gly Ser Gly Gly Gly Ser Gly Gly Gly
385                 390                 395                 400

Gly Ser Gly Gly Gly Ser Gln Val Gln Leu Gln Gln Ser Gly Ala
            405                 410                 415

Glu Leu Ala Arg Pro Gly Ala Ser Val Lys Met Ser Cys Lys Thr Ser
            420                 425                 430

Gly Tyr Thr Phe Thr Arg Tyr Thr Met His Trp Val Lys Gln Arg Pro
            435                 440                 445

Gly Gln Cys Leu Glu Trp Ile Gly Tyr Ile Asn Pro Ser Arg Gly Tyr
    450                 455                 460

Thr Asn Tyr Asn Gln Lys Phe Lys Asp Lys Ala Thr Leu Thr Thr Asp
465                 470                 475                 480

Lys Ser Ser Ser Thr Ala Tyr Met Gln Leu Ser Ser Leu Thr Ser Glu
                485                 490                 495

Asp Ser Ala Val Tyr Tyr Cys Ala Arg Tyr Tyr Asp Asp His Tyr Ser
            500                 505                 510

Leu Asp Tyr Trp Gly Gln Gly Thr Thr Leu Thr Val Ser Ser Gly Gly
    515                 520                 525

Ser His His His His His His
    530                 535

<210> SEQ ID NO 81
<211> LENGTH: 535
<212> TYPE: PRT
<213> ORGANISM: artificial
<220> FEATURE:
<223> OTHER INFORMATION: artificial Antibody

<400> SEQUENCE: 81

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Arg
                20                  25                  30

Pro Gly Ala Ser Val Lys Leu Ser Cys Lys Ala Ser Gly Tyr Thr Phe
            35                  40                  45

Thr Ser Tyr Trp Ile Asn Trp Val Lys Gln Arg Pro Gly Gln Cys Leu
    50                  55                  60

Glu Trp Ile Gly Asn Ile Tyr Pro Ser Asp Ser Tyr Thr Asn Tyr Asn
65                  70                  75                  80

Gln Lys Phe Lys Asp Lys Ala Thr Leu Thr Val Asp Lys Ser Ser Ser
                85                  90                  95

Thr Ala Tyr Met Gln Leu Ser Ser Pro Thr Ser Glu Asp Ser Ala Val
            100                 105                 110

Tyr Tyr Cys Thr Arg Ser Trp Arg Gly Asn Ser Phe Asp Tyr Trp Gly
            115                 120                 125

Gln Gly Thr Thr Leu Thr Val Ser Ser Gly Gly Gly Gly Ser Gly Gly
    130                 135                 140

Gly Gly Ser Gly Gly Gly Gly Ser Gly Gly Gly Gly Ser Asp Ile Val
145                 150                 155                 160

Met Thr Gln Ser Pro Ser Ser Leu Thr Val Thr Ala Gly Glu Lys Val
                165                 170                 175

Thr Met Ser Cys Lys Ser Ser Gln Ser Leu Leu Asn Ser Gly Asn Gln
            180                 185                 190
```

Lys Asn Tyr Leu Thr Trp Tyr Gln Gln Lys Pro Gly Gln Pro Pro Lys
            195                 200                 205

Leu Leu Ile Tyr Trp Ala Ser Thr Arg Glu Ser Gly Val Pro Asp Arg
    210                 215                 220

Phe Thr Gly Ser Gly Ser Gly Thr Asp Phe Thr Leu Thr Ile Ser Ser
225                 230                 235                 240

Val Gln Ala Glu Asp Leu Ala Val Tyr Tyr Cys Gln Asn Asp Tyr Ser
            245                 250                 255

Tyr Pro Phe Thr Phe Gly Cys Gly Thr Lys Leu Glu Ile Lys Ser Gly
            260                 265                 270

Gly Gly Gly Ser Gln Ile Val Leu Thr Gln Ser Pro Ala Ile Met Ser
        275                 280                 285

Ala Ser Pro Gly Glu Lys Val Thr Met Thr Cys Arg Ala Ser Ser Ser
        290                 295                 300

Val Ser Tyr Met Asn Trp Tyr Gln Gln Lys Ser Gly Thr Ser Pro Lys
305                 310                 315                 320

Arg Trp Ile Tyr Asp Thr Ser Lys Val Ala Ser Gly Val Pro Tyr Arg
            325                 330                 335

Phe Ser Gly Ser Gly Ser Gly Thr Ser Tyr Ser Leu Thr Ile Ser Ser
            340                 345                 350

Met Glu Ala Glu Asp Ala Ala Thr Tyr Tyr Cys Gln Gln Trp Ser Ser
            355                 360                 365

Asn Pro Leu Thr Phe Gly Cys Gly Thr Lys Leu Glu Leu Lys Gly Gly
        370                 375                 380

Gly Gly Ser Gly Gly Gly Gly Ser Gly Gly Gly Gly Ser Gly Gly Gly
385                 390                 395                 400

Gly Ser Gly Gly Gly Gly Ser Gln Val Gln Leu Gln Gln Ser Gly Ala
            405                 410                 415

Glu Leu Ala Arg Pro Gly Ala Ser Val Lys Met Ser Cys Lys Thr Ser
            420                 425                 430

Gly Tyr Thr Phe Thr Arg Tyr Thr Met His Trp Val Lys Gln Arg Pro
        435                 440                 445

Gly Gln Cys Leu Glu Trp Ile Gly Tyr Ile Asn Pro Ser Arg Gly Tyr
        450                 455                 460

Thr Asn Tyr Asn Gln Lys Phe Lys Asp Lys Ala Thr Leu Thr Thr Asp
465                 470                 475                 480

Lys Ser Ser Ser Thr Ala Tyr Met Gln Leu Ser Ser Leu Thr Ser Glu
            485                 490                 495

Asp Ser Ala Val Tyr Tyr Cys Ala Arg Tyr Tyr Asp Asp His Tyr Ser
            500                 505                 510

Leu Asp Tyr Trp Gly Gln Gly Thr Thr Leu Thr Val Ser Ser Gly Gly
        515                 520                 525

Ser His His His His His His
    530                 535

<210> SEQ ID NO 82
<211> LENGTH: 535
<212> TYPE: PRT
<213> ORGANISM: artificial
<220> FEATURE:
<223> OTHER INFORMATION: artificial Antibody

<400> SEQUENCE: 82

Met Gly Trp Ser Cys Ile Ile Leu Phe Leu Val Ala Thr Ala Thr Gly
1               5                   10                  15

Val His Ser Asp Ile Val Met Thr Gln Ser Pro Ser Leu Thr Val
            20                  25                  30

Thr Ala Gly Glu Lys Val Thr Met Ser Cys Lys Ser Ser Gln Ser Leu
        35                  40                  45

Leu Asn Ser Gly Asn Gln Lys Asn Tyr Leu Thr Trp Tyr Gln Gln Lys
50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ser Ser Val Gln Ala Glu Asp Leu Ala Val Tyr Tyr
            100                 105                 110

Cys Gln Asn Asp Tyr Ser Tyr Pro Leu Thr Phe Gly Ala Gly Thr Lys
        115                 120                 125

Leu Glu Leu Lys Gly Gly Gly Ser Gly Gly Gly Gly Ser Gly Gly
130                 135                 140

Gly Gly Ser Gly Gly Gly Ser Gly Gly Gly Ser Gln Ile Gln
145                 150                 155                 160

Leu Val Gln Ser Gly Pro Glu Leu Lys Lys Pro Gly Glu Thr Val Lys
                165                 170                 175

Ile Ser Cys Lys Ala Ser Gly Tyr Thr Phe Thr Asn Tyr Gly Met Asn
            180                 185                 190

Trp Val Lys Gln Ala Pro Gly Lys Gly Leu Lys Trp Met Gly Trp Ile
        195                 200                 205

Asn Thr Asn Thr Gly Glu Pro Thr Tyr Ala Glu Glu Phe Lys Gly Arg
210                 215                 220

Phe Ala Phe Ser Leu Glu Thr Ser Ala Ser Thr Ala Tyr Leu Gln Ile
225                 230                 235                 240

Asn Asn Leu Lys Asn Glu Asp Thr Ala Thr Tyr Phe Cys Ala Arg Leu
                245                 250                 255

Gly Phe Gly Asn Ala Met Asp Tyr Trp Gly Gln Gly Thr Ser Val Thr
            260                 265                 270

Val Ser Ser Gly Gly Gly Gly Ser Gln Val Gln Leu Gln Gln Ser
        275                 280                 285

Gly Ala Glu Leu Ala Arg Pro Gly Ala Ser Val Lys Met Ser Cys Lys
290                 295                 300

Thr Ser Gly Tyr Thr Phe Thr Arg Tyr Thr Met His Trp Val Lys Gln
305                 310                 315                 320

Arg Pro Gly Gln Gly Leu Glu Trp Ile Gly Tyr Ile Asn Pro Ser Arg
                325                 330                 335

Gly Tyr Thr Asn Tyr Asn Gln Lys Phe Lys Asp Lys Ala Thr Leu Thr
            340                 345                 350

Thr Asp Lys Ser Ser Ser Thr Ala Tyr Met Gln Leu Ser Ser Leu Thr
        355                 360                 365

Ser Glu Asp Ser Ala Val Tyr Tyr Cys Ala Arg Tyr Tyr Asp Asp His
370                 375                 380

Tyr Ser Leu Asp Tyr Trp Gly Gln Gly Thr Thr Leu Thr Val Ser Ser
385                 390                 395                 400

Gly Gly Gly Gly Ser Gly Gly Gly Ser Gly Gly Gly Gly Ser Gly
                405                 410                 415

Gly Gly Ser Gln Ile Val Leu Thr Gln Ser Pro Ala Ile Met Ser
            420                 425                 430

```
Ala Ser Pro Gly Glu Lys Val Thr Met Thr Cys Arg Ala Ser Ser Ser
            435                 440                 445

Val Ser Tyr Met Asn Trp Tyr Gln Gln Lys Ser Gly Thr Ser Pro Lys
    450                 455                 460

Arg Trp Ile Tyr Asp Thr Ser Lys Val Ala Ser Gly Val Pro Tyr Arg
465                 470                 475                 480

Phe Ser Gly Ser Gly Ser Gly Thr Ser Tyr Ser Leu Thr Ile Ser Ser
                485                 490                 495

Met Glu Ala Glu Asp Ala Ala Thr Tyr Tyr Cys Gln Gln Trp Ser Ser
            500                 505                 510

Asn Pro Leu Thr Phe Gly Ala Gly Thr Lys Leu Glu Leu Lys Gly Gly
        515                 520                 525

Ser His His His His His
    530                 535

<210> SEQ ID NO 83
<211> LENGTH: 535
<212> TYPE: PRT
<213> ORGANISM: artificial
<220> FEATURE:
<223> OTHER INFORMATION: artificial Antibody

<400> SEQUENCE: 83

Met Gly Trp Ser Cys Ile Ile Leu Phe Leu Val Ala Thr Ala Thr Gly
1               5                   10                  15

Val His Ser Asp Ile Val Met Thr Gln Ser Pro Ser Ser Leu Thr Val
            20                  25                  30

Thr Ala Gly Glu Lys Val Thr Met Ser Cys Lys Ser Ser Gln Ser Leu
        35                  40                  45

Leu Asn Ser Gly Asn Gln Lys Asn Tyr Leu Thr Trp Tyr Gln Gln Lys
    50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ser Ser Val Gln Ala Glu Asp Leu Ala Val Tyr Tyr
            100                 105                 110

Cys Gln Asn Asp Tyr Ser Tyr Pro Leu Thr Phe Gly Cys Gly Thr Lys
        115                 120                 125

Leu Glu Leu Lys Gly Gly Gly Ser Gly Gly Gly Ser Gly Gly
    130                 135                 140

Gly Gly Ser Gly Gly Gly Ser Gly Gly Gly Ser Gln Ile Gln
145                 150                 155                 160

Leu Val Gln Ser Gly Pro Glu Leu Lys Lys Pro Gly Glu Thr Val Lys
                165                 170                 175

Ile Ser Cys Lys Ala Ser Gly Tyr Thr Phe Thr Asn Tyr Gly Met Asn
            180                 185                 190

Trp Val Lys Gln Ala Pro Gly Lys Cys Leu Lys Trp Met Gly Trp Ile
        195                 200                 205

Asn Thr Asn Thr Gly Glu Pro Thr Tyr Ala Glu Glu Phe Lys Gly Arg
    210                 215                 220

Phe Ala Phe Ser Leu Glu Thr Ser Ala Ser Thr Ala Tyr Leu Gln Ile
225                 230                 235                 240

Asn Asn Leu Lys Asn Glu Asp Thr Ala Thr Tyr Phe Cys Ala Arg Leu
                245                 250                 255
```

Gly Phe Gly Asn Ala Met Asp Tyr Trp Gly Gln Gly Thr Ser Val Thr
                260                 265                 270

Val Ser Ser Ser Gly Gly Gly Ser Gln Val Gln Leu Gln Gln Ser
        275                 280                 285

Gly Ala Glu Leu Ala Arg Pro Gly Ala Ser Val Lys Met Ser Cys Lys
    290                 295                 300

Thr Ser Gly Tyr Thr Phe Thr Arg Tyr Thr Met His Trp Val Lys Gln
305                 310                 315                 320

Arg Pro Gly Gln Gly Leu Glu Trp Ile Gly Tyr Ile Asn Pro Ser Arg
                325                 330                 335

Gly Tyr Thr Asn Tyr Asn Gln Lys Phe Lys Asp Lys Ala Thr Leu Thr
                340                 345                 350

Thr Asp Lys Ser Ser Ser Thr Ala Tyr Met Gln Leu Ser Ser Leu Thr
            355                 360                 365

Ser Glu Asp Ser Ala Val Tyr Tyr Cys Ala Arg Tyr Tyr Asp Asp His
        370                 375                 380

Tyr Ser Leu Asp Tyr Trp Gly Gln Gly Thr Thr Leu Thr Val Ser Ser
385                 390                 395                 400

Gly Gly Gly Gly Ser Gly Gly Gly Ser Gly Gly Gly Gly Ser Gly
                405                 410                 415

Gly Gly Gly Ser Gln Ile Val Leu Thr Gln Ser Pro Ala Ile Met Ser
            420                 425                 430

Ala Ser Pro Gly Glu Lys Val Thr Met Thr Cys Arg Ala Ser Ser Ser
                435                 440                 445

Val Ser Tyr Met Asn Trp Tyr Gln Gln Lys Ser Gly Thr Ser Pro Lys
    450                 455                 460

Arg Trp Ile Tyr Asp Thr Ser Lys Val Ala Ser Gly Val Pro Tyr Arg
465                 470                 475                 480

Phe Ser Gly Ser Gly Ser Gly Thr Ser Tyr Ser Leu Thr Ile Ser Ser
                485                 490                 495

Met Glu Ala Glu Asp Ala Ala Thr Tyr Tyr Cys Gln Gln Trp Ser Ser
            500                 505                 510

Asn Pro Leu Thr Phe Gly Ala Gly Thr Lys Leu Glu Leu Lys Gly Gly
                515                 520                 525

Ser His His His His His His
    530                 535

<210> SEQ ID NO 84
<211> LENGTH: 535
<212> TYPE: PRT
<213> ORGANISM: artificial
<220> FEATURE:
<223> OTHER INFORMATION: artificial Antibody

<400> SEQUENCE: 84

Met Gly Trp Ser Cys Ile Ile Leu Phe Leu Val Ala Thr Ala Thr Gly
1               5                   10                  15

Val His Ser Asp Ile Val Met Thr Gln Ser Pro Ser Ser Leu Thr Val
                20                  25                  30

Thr Ala Gly Glu Lys Val Thr Met Ser Cys Lys Ser Ser Gln Ser Leu
            35                  40                  45

Leu Asn Ser Gly Asn Gln Lys Asn Tyr Leu Thr Trp Tyr Gln Gln Lys
        50                  55                  60

Pro Gly Gln Pro Pro Lys Leu Leu Ile Tyr Trp Ala Ser Thr Arg Glu
65                  70                  75                  80

```
Ser Gly Val Pro Asp Arg Phe Thr Gly Ser Gly Ser Gly Thr Asp Phe
            85                  90                  95

Thr Leu Thr Ile Ser Ser Val Gln Ala Glu Asp Leu Ala Val Tyr Tyr
        100                 105                 110

Cys Gln Asn Asp Tyr Ser Tyr Pro Phe Thr Phe Gly Ser Gly Thr Lys
        115                 120                 125

Leu Glu Ile Lys Gly Gly Gly Ser Gly Gly Gly Ser Gly Gly
        130                 135                 140

Gly Gly Ser Gly Gly Gly Ser Gly Gly Gly Ser Gln Val Gln
145                 150                 155                 160

Leu Gln Gln Pro Gly Ala Glu Leu Val Arg Pro Gly Ala Ser Val Lys
            165                 170                 175

Leu Ser Cys Lys Ala Ser Gly Tyr Thr Phe Thr Ser Tyr Trp Ile Asn
            180                 185                 190

Trp Val Lys Gln Arg Pro Gly Gln Gly Leu Glu Trp Ile Gly Asn Ile
        195                 200                 205

Tyr Pro Ser Asp Ser Tyr Thr Asn Tyr Asn Gln Lys Phe Lys Asp Lys
        210                 215                 220

Ala Thr Leu Thr Val Asp Lys Ser Ser Ser Thr Ala Tyr Met Gln Leu
225                 230                 235                 240

Ser Ser Pro Thr Ser Glu Asp Ser Ala Val Tyr Tyr Cys Thr Arg Ser
            245                 250                 255

Trp Arg Gly Asn Ser Phe Asp Tyr Trp Gly Gln Gly Thr Thr Leu Thr
            260                 265                 270

Val Ser Ser Gly Gly Gly Gly Ser Gln Val Gln Leu Gln Gln Ser
        275                 280                 285

Gly Ala Glu Leu Ala Arg Pro Gly Ala Ser Val Lys Met Ser Cys Lys
        290                 295                 300

Thr Ser Gly Tyr Thr Phe Thr Arg Tyr Thr Met His Trp Val Lys Gln
305                 310                 315                 320

Arg Pro Gly Gln Gly Leu Glu Trp Ile Gly Tyr Ile Asn Pro Ser Arg
            325                 330                 335

Gly Tyr Thr Asn Tyr Asn Gln Lys Phe Lys Asp Lys Ala Thr Leu Thr
            340                 345                 350

Thr Asp Lys Ser Ser Ser Thr Ala Tyr Met Gln Leu Ser Ser Leu Thr
            355                 360                 365

Ser Glu Asp Ser Ala Val Tyr Tyr Cys Ala Arg Tyr Tyr Asp Asp His
        370                 375                 380

Tyr Ser Leu Asp Tyr Trp Gly Gln Gly Thr Thr Leu Thr Val Ser Ser
385                 390                 395                 400

Gly Gly Gly Gly Ser Gly Gly Gly Ser Gly Gly Gly Ser Gly
                405                 410                 415

Gly Gly Gly Ser Gln Ile Val Leu Thr Gln Ser Pro Ala Ile Met Ser
            420                 425                 430

Ala Ser Pro Gly Glu Lys Val Thr Met Thr Cys Arg Ala Ser Ser Ser
            435                 440                 445

Val Ser Tyr Met Asn Trp Tyr Gln Gln Lys Ser Gly Thr Ser Pro Lys
        450                 455                 460

Arg Trp Ile Tyr Asp Thr Ser Lys Val Ala Ser Gly Val Pro Tyr Arg
465                 470                 475                 480

Phe Ser Gly Ser Gly Ser Gly Thr Ser Tyr Ser Leu Thr Ile Ser Ser
            485                 490                 495

Met Glu Ala Glu Asp Ala Ala Thr Tyr Tyr Cys Gln Gln Trp Ser Ser
```

```
                500                 505                 510
Asn Pro Leu Thr Phe Gly Ala Gly Thr Lys Leu Glu Leu Lys Gly Gly
            515                 520                 525

Ser His His His His His
    530                 535

<210> SEQ ID NO 85
<211> LENGTH: 535
<212> TYPE: PRT
<213> ORGANISM: artificial
<220> FEATURE:
<223> OTHER INFORMATION: artificial Antibody

<400> SEQUENCE: 85

Met Gly Trp Ser Cys Ile Ile Leu Phe Leu Val Ala Thr Ala Thr Gly
1               5                   10                  15

Val His Ser Asp Ile Val Met Thr Gln Ser Pro Ser Ser Leu Thr Val
            20                  25                  30

Thr Ala Gly Glu Lys Val Thr Met Ser Cys Lys Ser Ser Gln Ser Leu
        35                  40                  45

Leu Asn Ser Gly Asn Gln Lys Asn Tyr Leu Thr Trp Tyr Gln Gln Lys
    50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ser Ser Val Gln Ala Glu Asp Leu Ala Val Tyr Tyr
            100                 105                 110

Cys Gln Asn Asp Tyr Ser Tyr Pro Phe Thr Phe Gly Cys Gly Thr Lys
        115                 120                 125

Leu Glu Ile Lys Gly Gly Gly Gly Ser Gly Gly Gly Gly Ser Gly Gly
    130                 135                 140

Gly Gly Ser Gly Gly Gly Gly Ser Gly Gly Gly Gly Ser Gln Val Gln
145                 150                 155                 160

Leu Gln Gln Pro Gly Ala Glu Leu Val Arg Pro Gly Ala Ser Val Lys
                165                 170                 175

Leu Ser Cys Lys Ala Ser Gly Tyr Thr Phe Thr Ser Tyr Trp Ile Asn
            180                 185                 190

Trp Val Lys Gln Arg Pro Gly Gln Cys Leu Glu Trp Ile Gly Asn Ile
        195                 200                 205

Tyr Pro Ser Asp Ser Tyr Thr Asn Tyr Asn Gln Lys Phe Lys Asp Lys
    210                 215                 220

Ala Thr Leu Thr Val Asp Lys Ser Ser Ser Thr Ala Tyr Met Gln Leu
225                 230                 235                 240

Ser Ser Pro Thr Ser Glu Asp Ser Ala Val Tyr Tyr Cys Thr Arg Ser
                245                 250                 255

Trp Arg Gly Asn Ser Phe Asp Tyr Trp Gly Gln Gly Thr Thr Leu Thr
            260                 265                 270

Val Ser Ser Ser Gly Gly Gly Ser Gln Val Gln Leu Gln Gln Ser
        275                 280                 285

Gly Ala Glu Leu Ala Arg Pro Gly Ala Ser Val Lys Met Ser Cys Lys
    290                 295                 300

Thr Ser Gly Tyr Thr Phe Thr Arg Tyr Thr Met His Trp Val Lys Gln
305                 310                 315                 320

Arg Pro Gly Gln Gly Leu Glu Trp Ile Gly Tyr Ile Asn Pro Ser Arg
```

```
                      325                 330                 335
Gly Tyr Thr Asn Tyr Asn Gln Lys Phe Lys Asp Lys Ala Thr Leu Thr
                340                 345                 350

Thr Asp Lys Ser Ser Ser Thr Ala Tyr Met Gln Leu Ser Ser Leu Thr
            355                 360                 365

Ser Glu Asp Ser Ala Val Tyr Tyr Cys Ala Arg Tyr Tyr Asp Asp His
        370                 375                 380

Tyr Ser Leu Asp Tyr Trp Gly Gln Gly Thr Thr Leu Thr Val Ser Ser
385                 390                 395                 400

Gly Gly Gly Gly Ser Gly Gly Gly Ser Gly Gly Gly Gly Ser Gly
                405                 410                 415

Gly Gly Gly Ser Gln Ile Val Leu Thr Gln Ser Pro Ala Ile Met Ser
                420                 425                 430

Ala Ser Pro Gly Glu Lys Val Thr Met Thr Cys Arg Ala Ser Ser Ser
            435                 440                 445

Val Ser Tyr Met Asn Trp Tyr Gln Gln Lys Ser Gly Thr Ser Pro Lys
        450                 455                 460

Arg Trp Ile Tyr Asp Thr Ser Lys Val Ala Ser Gly Val Pro Tyr Arg
465                 470                 475                 480

Phe Ser Gly Ser Gly Ser Gly Thr Ser Tyr Ser Leu Thr Ile Ser Ser
                485                 490                 495

Met Glu Ala Glu Asp Ala Ala Thr Tyr Tyr Cys Gln Gln Trp Ser Ser
                500                 505                 510

Asn Pro Leu Thr Phe Gly Ala Gly Thr Lys Leu Glu Leu Lys Gly Gly
            515                 520                 525

Ser His His His His His His
        530                 535

<210> SEQ ID NO 86
<211> LENGTH: 535
<212> TYPE: PRT
<213> ORGANISM: artificial
<220> FEATURE:
<223> OTHER INFORMATION: artificial Antibody

<400> SEQUENCE: 86

Met Gly Trp Ser Cys Ile Ile Leu Phe Leu Val Ala Thr Ala Thr Gly
1               5                   10                  15

Val His Ser Asp Ile Val Met Thr Gln Ser Pro Ser Ser Leu Thr Val
                20                  25                  30

Thr Ala Gly Glu Lys Val Thr Met Ser Cys Lys Ser Ser Gln Ser Leu
            35                  40                  45

Leu Asn Ser Gly Asn Gln Lys Asn Tyr Leu Thr Trp Tyr Gln Gln Lys
        50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ser Ser Val Gln Ala Glu Asp Leu Ala Val Tyr Tyr
            100                 105                 110

Cys Gln Asn Asp Tyr Ser Tyr Pro Leu Thr Phe Gly Ala Gly Thr Lys
        115                 120                 125

Leu Glu Leu Lys Gly Gly Gly Gly Ser Gly Gly Gly Gly Ser Gly Gly
130                 135                 140

Gly Gly Ser Gly Gly Gly Gly Ser Gly Gly Gly Gly Ser Gln Ile Gln
```

```
            145                 150                 155                 160
Leu Val Gln Ser Gly Pro Glu Leu Lys Lys Pro Gly Glu Thr Val Lys
                165                 170                 175
Ile Ser Cys Lys Ala Ser Gly Tyr Thr Phe Thr Asn Tyr Gly Met Asn
                180                 185                 190
Trp Val Lys Gln Ala Pro Gly Lys Gly Leu Lys Trp Met Gly Trp Ile
                195                 200                 205
Asn Thr Asn Thr Gly Glu Pro Thr Tyr Ala Glu Glu Phe Lys Gly Arg
            210                 215                 220
Phe Ala Phe Ser Leu Glu Thr Ser Ala Ser Thr Ala Tyr Leu Gln Ile
225                 230                 235                 240
Asn Asn Leu Lys Asn Glu Asp Thr Ala Thr Tyr Phe Cys Ala Arg Leu
                245                 250                 255
Gly Phe Gly Asn Ala Met Asp Tyr Trp Gly Gln Gly Thr Ser Val Thr
                260                 265                 270
Val Ser Ser Gly Gly Gly Gly Ser Gln Val Gln Leu Gln Gln Ser
                275                 280                 285
Gly Ala Glu Leu Ala Arg Pro Gly Ala Ser Val Lys Met Ser Cys Lys
            290                 295                 300
Thr Ser Gly Tyr Thr Phe Thr Arg Tyr Thr Met His Trp Val Lys Gln
305                 310                 315                 320
Arg Pro Gly Gln Cys Leu Glu Trp Ile Gly Tyr Ile Asn Pro Ser Arg
                325                 330                 335
Gly Tyr Thr Asn Tyr Asn Gln Lys Phe Lys Asp Lys Ala Thr Leu Thr
                340                 345                 350
Thr Asp Lys Ser Ser Ser Thr Ala Tyr Met Gln Leu Ser Ser Leu Thr
            355                 360                 365
Ser Glu Asp Ser Ala Val Tyr Tyr Cys Ala Arg Tyr Tyr Asp Asp His
            370                 375                 380
Tyr Ser Leu Asp Tyr Trp Gly Gln Gly Thr Thr Leu Thr Val Ser Ser
385                 390                 395                 400
Gly Gly Gly Gly Ser Gly Gly Gly Ser Gly Gly Gly Ser Gly
                405                 410                 415
Gly Gly Gly Ser Gln Ile Val Leu Thr Gln Ser Pro Ala Ile Met Ser
            420                 425                 430
Ala Ser Pro Gly Glu Lys Val Thr Met Thr Cys Arg Ala Ser Ser Ser
            435                 440                 445
Val Ser Tyr Met Asn Trp Tyr Gln Gln Lys Ser Gly Thr Ser Pro Lys
            450                 455                 460
Arg Trp Ile Tyr Asp Thr Ser Lys Val Ala Ser Gly Val Pro Tyr Arg
465                 470                 475                 480
Phe Ser Gly Ser Gly Ser Gly Thr Ser Tyr Ser Leu Thr Ile Ser Ser
                485                 490                 495
Met Glu Ala Glu Asp Ala Ala Thr Tyr Tyr Cys Gln Gln Trp Ser Ser
                500                 505                 510
Asn Pro Leu Thr Phe Gly Cys Gly Thr Lys Leu Glu Leu Lys Gly Gly
                515                 520                 525
Ser His His His His His His
            530                 535

<210> SEQ ID NO 87
<211> LENGTH: 535
<212> TYPE: PRT
<213> ORGANISM: artificial
```

<220> FEATURE:
<223> OTHER INFORMATION: artificial Antibody

<400> SEQUENCE: 87

Met Gly Trp Ser Cys Ile Ile Leu Phe Leu Val Ala Thr Ala Thr Gly
1               5                   10                  15

Val His Ser Asp Ile Val Met Thr Gln Ser Pro Ser Ser Leu Thr Val
            20                  25                  30

Thr Ala Gly Glu Lys Val Thr Met Ser Cys Lys Ser Ser Gln Ser Leu
        35                  40                  45

Leu Asn Ser Gly Asn Gln Lys Asn Tyr Leu Thr Trp Tyr Gln Gln Lys
    50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ser Ser Val Gln Ala Glu Asp Leu Ala Val Tyr Tyr
            100                 105                 110

Cys Gln Asn Asp Tyr Ser Tyr Pro Leu Thr Phe Gly Cys Gly Thr Lys
        115                 120                 125

Leu Glu Leu Lys Gly Gly Gly Gly Ser Gly Gly Gly Gly Ser Gly Gly
130                 135                 140

Gly Gly Ser Gly Gly Gly Ser Gly Gly Gly Ser Gln Ile Gln
145                 150                 155                 160

Leu Val Gln Ser Gly Pro Glu Leu Lys Lys Pro Gly Glu Thr Val Lys
            165                 170                 175

Ile Ser Cys Lys Ala Ser Gly Tyr Thr Phe Thr Asn Tyr Gly Met Asn
        180                 185                 190

Trp Val Lys Gln Ala Pro Gly Lys Cys Leu Lys Trp Met Gly Trp Ile
    195                 200                 205

Asn Thr Asn Thr Gly Glu Pro Thr Tyr Ala Glu Glu Phe Lys Gly Arg
210                 215                 220

Phe Ala Phe Ser Leu Glu Thr Ser Ala Ser Thr Ala Tyr Leu Gln Ile
225                 230                 235                 240

Asn Asn Leu Lys Asn Glu Asp Thr Ala Thr Tyr Phe Cys Ala Arg Leu
            245                 250                 255

Gly Phe Gly Asn Ala Met Asp Tyr Trp Gly Gln Gly Thr Ser Val Thr
        260                 265                 270

Val Ser Ser Ser Gly Gly Gly Ser Gln Val Gln Leu Gln Gln Ser
    275                 280                 285

Gly Ala Glu Leu Ala Arg Pro Gly Ala Ser Val Lys Met Ser Cys Lys
290                 295                 300

Thr Ser Gly Tyr Thr Phe Thr Arg Tyr Thr Met His Trp Val Lys Gln
305                 310                 315                 320

Arg Pro Gly Gln Cys Leu Glu Trp Ile Gly Tyr Ile Asn Pro Ser Arg
            325                 330                 335

Gly Tyr Thr Asn Tyr Asn Gln Lys Phe Lys Asp Lys Ala Thr Leu Thr
        340                 345                 350

Thr Asp Lys Ser Ser Ser Thr Ala Tyr Met Gln Leu Ser Ser Leu Thr
    355                 360                 365

Ser Glu Asp Ser Ala Val Tyr Tyr Cys Ala Arg Tyr Tyr Asp Asp His
370                 375                 380

Tyr Ser Leu Asp Tyr Trp Gly Gln Gly Thr Thr Leu Thr Val Ser Ser
385                 390                 395                 400

```
Gly Gly Gly Gly Ser Gly Gly Gly Ser Gly Gly Gly Ser Gly
            405             410             415
Gly Gly Gly Ser Gln Ile Val Leu Thr Gln Ser Pro Ala Ile Met Ser
            420             425             430
Ala Ser Pro Gly Glu Lys Val Thr Met Thr Cys Arg Ala Ser Ser Ser
            435             440             445
Val Ser Tyr Met Asn Trp Tyr Gln Gln Lys Ser Gly Thr Ser Pro Lys
            450             455             460
Arg Trp Ile Tyr Asp Thr Ser Lys Val Ala Ser Gly Val Pro Tyr Arg
465             470             475             480
Phe Ser Gly Ser Gly Ser Gly Thr Ser Tyr Ser Leu Thr Ile Ser Ser
            485             490             495
Met Glu Ala Glu Asp Ala Ala Thr Tyr Tyr Cys Gln Gln Trp Ser Ser
            500             505             510
Asn Pro Leu Thr Phe Gly Cys Gly Thr Lys Leu Glu Leu Lys Gly Gly
            515             520             525
Ser His His His His His
            530             535

<210> SEQ ID NO 88
<211> LENGTH: 535
<212> TYPE: PRT
<213> ORGANISM: artificial
<220> FEATURE:
<223> OTHER INFORMATION: artificial Antibody

<400> SEQUENCE: 88

Met Gly Trp Ser Cys Ile Ile Leu Phe Leu Val Ala Thr Ala Thr Gly
1               5               10              15
Val His Ser Asp Ile Val Met Thr Gln Ser Pro Ser Ser Leu Thr Val
            20              25              30
Thr Ala Gly Glu Lys Val Thr Met Ser Cys Lys Ser Ser Gln Ser Leu
            35              40              45
Leu Asn Ser Gly Asn Gln Lys Asn Tyr Leu Thr Trp Tyr Gln Gln Lys
        50              55              60
Pro Gly Gln Pro Pro Lys Leu Leu Ile Tyr Trp Ala Ser Thr Arg Glu
65              70              75              80
Ser Gly Val Pro Asp Arg Phe Thr Gly Ser Gly Ser Gly Thr Asp Phe
            85              90              95
Thr Leu Thr Ile Ser Ser Val Gln Ala Glu Asp Leu Ala Val Tyr Tyr
            100             105             110
Cys Gln Asn Asp Tyr Ser Tyr Pro Phe Thr Phe Gly Ser Gly Thr Lys
            115             120             125
Leu Glu Ile Lys Gly Gly Gly Gly Ser Gly Gly Gly Gly Ser Gly Gly
        130             135             140
Gly Gly Ser Gly Gly Gly Gly Ser Gly Gly Gly Gly Ser Gln Val Gln
145             150             155             160
Leu Gln Gln Pro Gly Ala Glu Leu Val Arg Pro Gly Ala Ser Val Lys
            165             170             175
Leu Ser Cys Lys Ala Ser Gly Tyr Thr Phe Thr Ser Tyr Trp Ile Asn
            180             185             190
Trp Val Lys Gln Arg Pro Gly Gln Gly Leu Glu Trp Ile Gly Asn Ile
            195             200             205
Tyr Pro Ser Asp Ser Tyr Thr Asn Tyr Asn Gln Lys Phe Lys Asp Lys
        210             215             220
```

```
Ala Thr Leu Thr Val Asp Lys Ser Ser Thr Ala Tyr Met Gln Leu
225                 230                 235                 240

Ser Ser Pro Thr Ser Glu Asp Ser Ala Val Tyr Tyr Cys Thr Arg Ser
            245                 250                 255

Trp Arg Gly Asn Ser Phe Asp Tyr Trp Gly Gln Gly Thr Thr Leu Thr
            260                 265                 270

Val Ser Ser Gly Gly Gly Gly Ser Gln Val Gln Leu Gln Gln Ser
            275                 280                 285

Gly Ala Glu Leu Ala Arg Pro Gly Ala Ser Val Lys Met Ser Cys Lys
    290                 295                 300

Thr Ser Gly Tyr Thr Phe Thr Arg Tyr Thr Met His Trp Val Lys Gln
305                 310                 315                 320

Arg Pro Gly Gln Cys Leu Glu Trp Ile Gly Tyr Ile Asn Pro Ser Arg
                325                 330                 335

Gly Tyr Thr Asn Tyr Asn Gln Lys Phe Lys Asp Lys Ala Thr Leu Thr
            340                 345                 350

Thr Asp Lys Ser Ser Ser Thr Ala Tyr Met Gln Leu Ser Ser Leu Thr
        355                 360                 365

Ser Glu Asp Ser Ala Val Tyr Tyr Cys Ala Arg Tyr Tyr Asp Asp His
370                 375                 380

Tyr Ser Leu Asp Tyr Trp Gly Gln Gly Thr Thr Leu Thr Val Ser Ser
385                 390                 395                 400

Gly Gly Gly Gly Ser Gly Gly Gly Ser Gly Gly Gly Ser Gly
                405                 410                 415

Gly Gly Gly Ser Gln Ile Val Leu Thr Gln Ser Pro Ala Ile Met Ser
            420                 425                 430

Ala Ser Pro Gly Glu Lys Val Thr Met Thr Cys Arg Ala Ser Ser Ser
        435                 440                 445

Val Ser Tyr Met Asn Trp Tyr Gln Gln Lys Ser Gly Thr Ser Pro Lys
450                 455                 460

Arg Trp Ile Tyr Asp Thr Ser Lys Val Ala Ser Gly Val Pro Tyr Arg
465                 470                 475                 480

Phe Ser Gly Ser Gly Ser Gly Thr Ser Tyr Ser Leu Thr Ile Ser Ser
                485                 490                 495

Met Glu Ala Glu Asp Ala Ala Thr Tyr Tyr Cys Gln Gln Trp Ser Ser
            500                 505                 510

Asn Pro Leu Thr Phe Gly Cys Gly Thr Lys Leu Glu Leu Lys Gly Gly
            515                 520                 525

Ser His His His His His His
    530                 535

<210> SEQ ID NO 89
<211> LENGTH: 535
<212> TYPE: PRT
<213> ORGANISM: artificial
<220> FEATURE:
<223> OTHER INFORMATION: artificial Antibody

<400> SEQUENCE: 89

Met Gly Trp Ser Cys Ile Ile Leu Phe Leu Val Ala Thr Ala Thr Gly
1               5                   10                  15

Val His Ser Asp Ile Val Met Thr Gln Ser Pro Ser Ser Leu Thr Val
            20                  25                  30

Thr Ala Gly Glu Lys Val Thr Met Ser Cys Lys Ser Ser Gln Ser Leu
        35                  40                  45
```

Leu Asn Ser Gly Asn Gln Lys Asn Tyr Leu Thr Trp Tyr Gln Gln Lys
    50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ser Ser Val Gln Ala Glu Asp Leu Ala Val Tyr Tyr
            100                 105                 110

Cys Gln Asn Asp Tyr Ser Tyr Pro Phe Thr Phe Gly Cys Gly Thr Lys
        115                 120                 125

Leu Glu Ile Lys Gly Gly Gly Gly Ser Gly Gly Gly Gly Ser Gly Gly
    130                 135                 140

Gly Gly Ser Gly Gly Gly Ser Gly Gly Gly Ser Gln Val Gln
145                 150                 155                 160

Leu Gln Gln Pro Gly Ala Glu Leu Val Arg Pro Gly Ala Ser Val Lys
                165                 170                 175

Leu Ser Cys Lys Ala Ser Gly Tyr Thr Phe Thr Ser Tyr Trp Ile Asn
            180                 185                 190

Trp Val Lys Gln Arg Pro Gly Gln Cys Leu Glu Trp Ile Gly Asn Ile
        195                 200                 205

Tyr Pro Ser Asp Ser Tyr Thr Asn Tyr Asn Gln Lys Phe Lys Asp Lys
    210                 215                 220

Ala Thr Leu Thr Val Asp Lys Ser Ser Ser Thr Ala Tyr Met Gln Leu
225                 230                 235                 240

Ser Ser Pro Thr Ser Glu Asp Ser Ala Val Tyr Tyr Cys Thr Arg Ser
                245                 250                 255

Trp Arg Gly Asn Ser Phe Asp Tyr Trp Gly Gln Gly Thr Thr Leu Thr
            260                 265                 270

Val Ser Ser Ser Gly Gly Gly Ser Gln Val Gln Leu Gln Gln Ser
        275                 280                 285

Gly Ala Glu Leu Ala Arg Pro Gly Ala Ser Val Lys Met Ser Cys Lys
290                 295                 300

Thr Ser Gly Tyr Thr Phe Thr Arg Tyr Thr Met His Trp Val Lys Gln
305                 310                 315                 320

Arg Pro Gly Gln Cys Leu Glu Trp Ile Gly Tyr Ile Asn Pro Ser Arg
                325                 330                 335

Gly Tyr Thr Asn Tyr Asn Gln Lys Phe Lys Asp Lys Ala Thr Leu Thr
            340                 345                 350

Thr Asp Lys Ser Ser Ser Thr Ala Tyr Met Gln Leu Ser Ser Leu Thr
        355                 360                 365

Ser Glu Asp Ser Ala Val Tyr Tyr Cys Ala Arg Tyr Tyr Asp Asp His
    370                 375                 380

Tyr Ser Leu Asp Tyr Trp Gly Gln Gly Thr Thr Leu Thr Val Ser Ser
385                 390                 395                 400

Gly Gly Gly Gly Ser Gly Gly Gly Gly Ser Gly Gly Gly Ser Gly
                405                 410                 415

Gly Gly Gly Ser Gln Ile Val Leu Thr Gln Ser Pro Ala Ile Met Ser
            420                 425                 430

Ala Ser Pro Gly Glu Lys Val Thr Met Thr Cys Arg Ala Ser Ser Ser
        435                 440                 445

Val Ser Tyr Met Asn Trp Tyr Gln Gln Lys Ser Gly Thr Ser Pro Lys
    450                 455                 460

Arg Trp Ile Tyr Asp Thr Ser Lys Val Ala Ser Gly Val Pro Tyr Arg
465                 470                 475                 480

Phe Ser Gly Ser Gly Ser Gly Thr Ser Tyr Ser Leu Thr Ile Ser Ser
                485                 490                 495

Met Glu Ala Glu Asp Ala Ala Thr Tyr Tyr Cys Gln Gln Trp Ser Ser
                500                 505                 510

Asn Pro Leu Thr Phe Gly Cys Gly Thr Lys Leu Glu Leu Lys Gly Gly
            515                 520                 525

Ser His His His His His His
    530                 535

<210> SEQ ID NO 90
<211> LENGTH: 540
<212> TYPE: PRT
<213> ORGANISM: artificial
<220> FEATURE:
<223> OTHER INFORMATION: artificial Antibody

<400> SEQUENCE: 90

Met Gly Trp Ser Cys Ile Ile Leu Phe Leu Val Ala Thr Ala Thr Gly
1               5                   10                  15

Val His Ser Asp Ile Val Met Thr Gln Ser Pro Ser Ser Leu Thr Val
                20                  25                  30

Thr Ala Gly Glu Lys Val Thr Met Ser Cys Lys Ser Ser Gln Ser Leu
            35                  40                  45

Leu Asn Ser Gly Asn Gln Lys Asn Tyr Leu Thr Trp Tyr Gln Gln Lys
        50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ser Ser Val Gln Ala Glu Asp Leu Ala Val Tyr Tyr
            100                 105                 110

Cys Gln Asn Asp Tyr Ser Tyr Pro Leu Thr Phe Gly Ala Gly Thr Lys
        115                 120                 125

Leu Glu Leu Lys Gly Gly Gly Gly Ser Gly Gly Gly Gly Ser Gly Gly
    130                 135                 140

Gly Gly Ser Gly Gly Gly Gly Ser Gly Gly Gly Gly Ser Gln Ile Gln
145                 150                 155                 160

Leu Val Gln Ser Gly Pro Glu Leu Lys Lys Pro Gly Glu Thr Val Lys
                165                 170                 175

Ile Ser Cys Lys Ala Ser Gly Tyr Thr Phe Thr Asn Tyr Gly Met Asn
            180                 185                 190

Trp Val Lys Gln Ala Pro Gly Lys Gly Leu Lys Trp Met Gly Trp Ile
        195                 200                 205

Asn Thr Asn Thr Gly Glu Pro Thr Tyr Ala Glu Glu Phe Lys Gly Arg
    210                 215                 220

Phe Ala Phe Ser Leu Glu Thr Ser Ala Ser Thr Ala Tyr Leu Gln Ile
225                 230                 235                 240

Asn Asn Leu Lys Asn Glu Asp Thr Ala Thr Tyr Phe Cys Ala Arg Leu
                245                 250                 255

Gly Phe Gly Asn Ala Met Asp Tyr Trp Gly Gln Gly Thr Ser Val Thr
            260                 265                 270

Val Ser Ser Ser Gly Gly Gly Ser Gln Ile Val Leu Thr Gln Ser
        275                 280                 285

Pro Ala Ile Met Ser Ala Ser Pro Gly Glu Lys Val Thr Met Thr Cys
            290                 295                 300

Arg Ala Ser Ser Val Ser Tyr Met Asn Trp Tyr Gln Gln Lys Ser
305                 310                 315                 320

Gly Thr Ser Pro Lys Arg Trp Ile Tyr Asp Thr Ser Lys Val Ala Ser
                325                 330                 335

Gly Val Pro Tyr Arg Phe Ser Gly Ser Gly Ser Gly Thr Ser Tyr Ser
                340                 345                 350

Leu Thr Ile Ser Ser Met Glu Ala Glu Asp Ala Ala Thr Tyr Tyr Cys
            355                 360                 365

Gln Gln Trp Ser Ser Asn Pro Leu Thr Phe Gly Cys Gly Thr Lys Leu
        370                 375                 380

Glu Leu Lys Gly Gly Gly Gly Ser Gly Gly Gly Gly Ser Gly Gly Gly
385                 390                 395                 400

Gly Ser Gly Gly Gly Ser Gly Gly Gly Gly Ser Gln Val Gln Leu
                405                 410                 415

Gln Gln Ser Gly Ala Glu Leu Ala Arg Pro Gly Ala Ser Val Lys Met
        420                 425                 430

Ser Cys Lys Thr Ser Gly Tyr Thr Phe Thr Arg Tyr Thr Met His Trp
        435                 440                 445

Val Lys Gln Arg Pro Gly Gln Cys Leu Glu Trp Ile Gly Tyr Ile Asn
450                 455                 460

Pro Ser Arg Gly Tyr Thr Asn Tyr Asn Gln Lys Phe Lys Asp Lys Ala
465                 470                 475                 480

Thr Leu Thr Thr Asp Lys Ser Ser Thr Ala Tyr Met Gln Leu Ser
                485                 490                 495

Ser Leu Thr Ser Glu Asp Ser Ala Val Tyr Tyr Cys Ala Arg Tyr Tyr
            500                 505                 510

Asp Asp His Tyr Ser Leu Asp Tyr Trp Gly Gln Gly Thr Thr Leu Thr
        515                 520                 525

Val Ser Ser Gly Gly Ser His His His His His
            530                 535                 540

<210> SEQ ID NO 91
<211> LENGTH: 540
<212> TYPE: PRT
<213> ORGANISM: artificial
<220> FEATURE:
<223> OTHER INFORMATION: artificial Antibody

<400> SEQUENCE: 91

Met Gly Trp Ser Cys Ile Ile Leu Phe Leu Val Ala Thr Ala Thr Gly
1               5                   10                  15

Val His Ser Asp Ile Val Met Thr Gln Ser Pro Ser Ser Leu Thr Val
                20                  25                  30

Thr Ala Gly Glu Lys Val Thr Met Ser Cys Lys Ser Ser Gln Ser Leu
            35                  40                  45

Leu Asn Ser Gly Asn Gln Lys Asn Tyr Leu Thr Trp Tyr Gln Gln Lys
        50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ser Ser Val Gln Ala Glu Asp Leu Ala Val Tyr Tyr
                100                 105                 110

```
Cys Gln Asn Asp Tyr Ser Tyr Pro Leu Thr Phe Gly Cys Gly Thr Lys
            115                 120                 125
Leu Glu Leu Lys Gly Gly Gly Ser Gly Gly Gly Ser Gly Gly
130                 135                 140
Gly Gly Ser Gly Gly Gly Ser Gly Gly Gly Ser Gln Ile Gln
145                 150                 155                 160
Leu Val Gln Ser Gly Pro Glu Leu Lys Lys Pro Gly Glu Thr Val Lys
                165                 170                 175
Ile Ser Cys Lys Ala Ser Gly Tyr Thr Phe Thr Asn Tyr Gly Met Asn
            180                 185                 190
Trp Val Lys Gln Ala Pro Gly Lys Cys Leu Lys Trp Met Gly Trp Ile
        195                 200                 205
Asn Thr Asn Thr Gly Glu Pro Thr Tyr Ala Glu Glu Phe Lys Gly Arg
210                 215                 220
Phe Ala Phe Ser Leu Glu Thr Ser Ala Ser Thr Ala Tyr Leu Gln Ile
225                 230                 235                 240
Asn Asn Leu Lys Asn Glu Asp Thr Ala Thr Tyr Phe Cys Ala Arg Leu
                245                 250                 255
Gly Phe Gly Asn Ala Met Asp Tyr Trp Gly Gln Gly Thr Ser Val Thr
            260                 265                 270
Val Ser Ser Ser Gly Gly Gly Ser Gln Ile Val Leu Thr Gln Ser
    275                 280                 285
Pro Ala Ile Met Ser Ala Ser Pro Gly Glu Lys Val Thr Met Thr Cys
        290                 295                 300
Arg Ala Ser Ser Ser Val Ser Tyr Met Asn Trp Tyr Gln Gln Lys Ser
305                 310                 315                 320
Gly Thr Ser Pro Lys Arg Trp Ile Tyr Asp Thr Ser Lys Val Ala Ser
                325                 330                 335
Gly Val Pro Tyr Arg Phe Ser Gly Ser Gly Ser Gly Thr Ser Tyr Ser
            340                 345                 350
Leu Thr Ile Ser Ser Met Glu Ala Glu Asp Ala Ala Thr Tyr Tyr Cys
        355                 360                 365
Gln Gln Trp Ser Ser Asn Pro Leu Thr Phe Gly Cys Gly Thr Lys Leu
370                 375                 380
Glu Leu Lys Gly Gly Gly Ser Gly Gly Gly Ser Gly Gly
385                 390                 395                 400
Gly Ser Gly Gly Gly Ser Gly Gly Gly Ser Gln Val Gln Leu
                405                 410                 415
Gln Gln Ser Gly Ala Glu Leu Ala Arg Pro Gly Ala Ser Val Lys Met
            420                 425                 430
Ser Cys Lys Thr Ser Gly Tyr Thr Phe Thr Arg Tyr Thr Met His Trp
        435                 440                 445
Val Lys Gln Arg Pro Gly Gln Cys Leu Glu Trp Ile Gly Tyr Ile Asn
450                 455                 460
Pro Ser Arg Gly Tyr Thr Asn Tyr Asn Gln Lys Phe Lys Asp Lys Ala
465                 470                 475                 480
Thr Leu Thr Thr Asp Lys Ser Ser Ser Thr Ala Tyr Met Gln Leu Ser
                485                 490                 495
Ser Leu Thr Ser Glu Asp Ser Ala Val Tyr Tyr Cys Ala Arg Tyr Tyr
            500                 505                 510
Asp Asp His Tyr Ser Leu Asp Tyr Trp Gly Gln Gly Thr Thr Leu Thr
        515                 520                 525
Val Ser Ser Gly Gly Ser His His His His His His
```

<210> SEQ ID NO 92
<211> LENGTH: 540
<212> TYPE: PRT
<213> ORGANISM: artificial
<220> FEATURE:
<223> OTHER INFORMATION: artificial Antibody

<400> SEQUENCE: 92

Met Gly Trp Ser Cys Ile Ile Leu Phe Leu Val Ala Thr Ala Thr Gly
1               5                   10                  15

Val His Ser Asp Ile Val Met Thr Gln Ser Pro Ser Ser Leu Thr Val
            20                  25                  30

Thr Ala Gly Glu Lys Val Thr Met Ser Cys Lys Ser Ser Gln Ser Leu
        35                  40                  45

Leu Asn Ser Gly Asn Gln Lys Asn Tyr Leu Thr Trp Tyr Gln Gln Lys
    50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ser Ser Val Gln Ala Glu Asp Leu Ala Val Tyr Tyr
            100                 105                 110

Cys Gln Asn Asp Tyr Ser Tyr Pro Phe Thr Phe Gly Ser Gly Thr Lys
        115                 120                 125

Leu Glu Ile Lys Gly Gly Gly Gly Ser Gly Gly Gly Gly Ser Gly Gly
    130                 135                 140

Gly Gly Ser Gly Gly Gly Gly Ser Gly Gly Gly Gly Ser Gln Val Gln
145                 150                 155                 160

Leu Gln Gln Pro Gly Ala Glu Leu Val Arg Pro Gly Ala Ser Val Lys
                165                 170                 175

Leu Ser Cys Lys Ala Ser Gly Tyr Thr Phe Thr Ser Tyr Trp Ile Asn
            180                 185                 190

Trp Val Lys Gln Arg Pro Gly Gln Gly Leu Glu Trp Ile Gly Asn Ile
        195                 200                 205

Tyr Pro Ser Asp Ser Tyr Thr Asn Tyr Asn Gln Lys Phe Lys Asp Lys
    210                 215                 220

Ala Thr Leu Thr Val Asp Lys Ser Ser Ser Thr Ala Tyr Met Gln Leu
225                 230                 235                 240

Ser Ser Pro Thr Ser Glu Asp Ser Ala Val Tyr Tyr Cys Thr Arg Ser
                245                 250                 255

Trp Arg Gly Asn Ser Phe Asp Tyr Trp Gly Gln Gly Thr Thr Leu Thr
            260                 265                 270

Val Ser Ser Ser Gly Gly Gly Ser Gln Ile Val Leu Thr Gln Ser
        275                 280                 285

Pro Ala Ile Met Ser Ala Ser Pro Gly Glu Lys Val Thr Met Thr Cys
    290                 295                 300

Arg Ala Ser Ser Val Ser Tyr Met Asn Trp Tyr Gln Gln Lys Ser
305                 310                 315                 320

Gly Thr Ser Pro Lys Arg Trp Ile Tyr Asp Thr Ser Lys Val Ala Ser
                325                 330                 335

Gly Val Pro Tyr Arg Phe Ser Gly Ser Gly Ser Gly Thr Ser Tyr Ser
            340                 345                 350

Leu Thr Ile Ser Ser Met Glu Ala Glu Asp Ala Ala Thr Tyr Tyr Cys

```
                355                 360                 365
Gln Gln Trp Ser Ser Asn Pro Leu Thr Phe Gly Cys Gly Thr Lys Leu
    370                 375                 380

Glu Leu Lys Gly Gly Gly Ser Gly Gly Gly Ser Gly Gly Gly
385                 390                 395                 400

Gly Ser Gly Gly Gly Ser Gly Gly Gly Ser Gln Val Gln Leu
                405                 410                 415

Gln Gln Ser Gly Ala Glu Leu Ala Arg Pro Gly Ala Ser Val Lys Met
        420                 425                 430

Ser Cys Lys Thr Ser Gly Tyr Thr Phe Thr Arg Tyr Thr Met His Trp
            435                 440                 445

Val Lys Gln Arg Pro Gly Gln Cys Leu Glu Trp Ile Gly Tyr Ile Asn
    450                 455                 460

Pro Ser Arg Gly Tyr Thr Asn Tyr Asn Gln Lys Phe Lys Asp Lys Ala
465                 470                 475                 480

Thr Leu Thr Thr Asp Lys Ser Ser Thr Ala Tyr Met Gln Leu Ser
                485                 490                 495

Ser Leu Thr Ser Glu Asp Ser Ala Val Tyr Tyr Cys Ala Arg Tyr Tyr
            500                 505                 510

Asp Asp His Tyr Ser Leu Asp Tyr Trp Gly Gln Gly Thr Thr Leu Thr
        515                 520                 525

Val Ser Ser Gly Gly Ser His His His His His
    530                 535                 540

<210> SEQ ID NO 93
<211> LENGTH: 540
<212> TYPE: PRT
<213> ORGANISM: artificial
<220> FEATURE:
<223> OTHER INFORMATION: artificial Antibody

<400> SEQUENCE: 93

Met Gly Trp Ser Cys Ile Ile Leu Phe Leu Val Ala Thr Ala Thr Gly
1               5                   10                  15

Val His Ser Asp Ile Val Met Thr Gln Ser Pro Ser Ser Leu Thr Val
                20                  25                  30

Thr Ala Gly Glu Lys Val Thr Met Ser Cys Lys Ser Ser Gln Ser Leu
            35                  40                  45

Leu Asn Ser Gly Asn Gln Lys Asn Tyr Leu Thr Trp Tyr Gln Gln Lys
        50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ser Ser Val Gln Ala Glu Asp Leu Ala Val Tyr Tyr
            100                 105                 110

Cys Gln Asn Asp Tyr Ser Tyr Pro Phe Thr Phe Gly Cys Gly Thr Lys
        115                 120                 125

Leu Glu Ile Lys Gly Gly Gly Gly Ser Gly Gly Gly Gly Ser Gly Gly
    130                 135                 140

Gly Gly Ser Gly Gly Gly Gly Ser Gly Gly Gly Ser Gln Val Gln
145                 150                 155                 160

Leu Gln Gln Pro Gly Ala Glu Leu Val Arg Pro Gly Ala Ser Val Lys
                165                 170                 175

Leu Ser Cys Lys Ala Ser Gly Tyr Thr Phe Thr Ser Tyr Trp Ile Asn
```

```
                180                 185                 190
Trp Val Lys Gln Arg Pro Gly Gln Cys Leu Glu Trp Ile Gly Asn Ile
        195                 200                 205

Tyr Pro Ser Asp Ser Tyr Thr Asn Tyr Asn Gln Lys Phe Lys Asp Lys
    210                 215                 220

Ala Thr Leu Thr Val Asp Lys Ser Ser Ser Thr Ala Tyr Met Gln Leu
225                 230                 235                 240

Ser Ser Pro Thr Ser Glu Asp Ser Ala Val Tyr Tyr Cys Thr Arg Ser
                245                 250                 255

Trp Arg Gly Asn Ser Phe Asp Tyr Trp Gly Gln Gly Thr Thr Leu Thr
            260                 265                 270

Val Ser Ser Gly Gly Gly Ser Gln Ile Val Leu Thr Gln Ser
        275                 280                 285

Pro Ala Ile Met Ser Ala Ser Pro Gly Glu Lys Val Thr Met Thr Cys
        290                 295                 300

Arg Ala Ser Ser Ser Val Ser Tyr Met Asn Trp Tyr Gln Gln Lys Ser
305                 310                 315                 320

Gly Thr Ser Pro Lys Arg Trp Ile Tyr Asp Thr Ser Lys Val Ala Ser
                325                 330                 335

Gly Val Pro Tyr Arg Phe Ser Gly Ser Gly Ser Gly Thr Ser Tyr Ser
            340                 345                 350

Leu Thr Ile Ser Ser Met Glu Ala Glu Asp Ala Ala Thr Tyr Tyr Cys
        355                 360                 365

Gln Gln Trp Ser Ser Asn Pro Leu Thr Phe Gly Cys Gly Thr Lys Leu
    370                 375                 380

Glu Leu Lys Gly Gly Gly Gly Ser Gly Gly Gly Gly Ser Gly Gly Gly
385                 390                 395                 400

Gly Ser Gly Gly Gly Gly Ser Gly Gly Gly Gly Ser Gln Val Gln Leu
                405                 410                 415

Gln Gln Ser Gly Ala Glu Leu Ala Arg Pro Gly Ala Ser Val Lys Met
            420                 425                 430

Ser Cys Lys Thr Ser Gly Tyr Thr Phe Thr Arg Tyr Thr Met His Trp
        435                 440                 445

Val Lys Gln Arg Pro Gly Gln Cys Leu Glu Trp Ile Gly Tyr Ile Asn
    450                 455                 460

Pro Ser Arg Gly Tyr Thr Asn Tyr Asn Gln Lys Phe Lys Asp Lys Ala
465                 470                 475                 480

Thr Leu Thr Thr Asp Lys Ser Ser Ser Thr Ala Tyr Met Gln Leu Ser
                485                 490                 495

Ser Leu Thr Ser Glu Asp Ser Ala Val Tyr Tyr Cys Ala Arg Tyr Tyr
            500                 505                 510

Asp Asp His Tyr Ser Leu Asp Tyr Trp Gly Gln Gly Thr Thr Leu Thr
        515                 520                 525

Val Ser Ser Gly Gly Ser His His His His His
530                 535                 540

<210> SEQ ID NO 94
<211> LENGTH: 119
<212> TYPE: PRT
<213> ORGANISM: Mus musculus

<400> SEQUENCE: 94

Asp Ile Lys Leu Gln Gln Ser Gly Ala Glu Leu Ala Arg Pro Gly Ala
1               5                   10                  15
```

```
Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
            50                  55                  60

Lys Asp Lys Ala Thr Leu Thr Thr Asp Lys Ser Ser Ser Thr Ala Tyr
 65                  70                  75                  80

Met Gln Leu Ser Ser Leu Thr Ser Glu Asp Ser Ala Val Tyr Tyr Cys
            85                  90                  95

Ala Arg Tyr Tyr Asp Asp His Tyr Ser Leu Asp Tyr Trp Gly Gln Gly
            100                 105                 110

Thr Thr Leu Thr Val Ser Ser
            115
```

<210> SEQ ID NO 95
<211> LENGTH: 116
<212> TYPE: PRT
<213> ORGANISM: Mus musculus

<400> SEQUENCE: 95

```
Leu Gln Gln Ser Gly Ala Glu Leu Ala Arg Pro Gly Ala Ser Val Lys
 1               5                   10                  15

Met Ser Cys Lys Thr Ser Gly Tyr Thr Phe Thr Arg Tyr Thr Met His
            20                  25                  30

Trp Val Lys Gln Arg Pro Gly Gln Gly Leu Glu Trp Ile Gly Tyr Ile
            35                  40                  45

Asn Pro Ser Arg Gly Tyr Thr Asn Tyr Asn Gln Lys Phe Lys Asp Lys
            50                  55                  60

Ala Thr Leu Thr Thr Asp Lys Ser Ser Ser Thr Ala Tyr Met Gln Leu
 65                  70                  75                  80

Ser Ser Leu Thr Ser Glu Asp Ser Ala Val Tyr Tyr Cys Ala Arg Tyr
            85                  90                  95

Tyr Asp Asp His Tyr Ser Leu Asp Tyr Trp Gly Gln Gly Thr Thr Leu
            100                 105                 110

Thr Val Ser Ser
            115
```

<210> SEQ ID NO 96
<211> LENGTH: 103
<212> TYPE: PRT
<213> ORGANISM: Mus musculus

<400> SEQUENCE: 96

```
Leu Thr Gln Ser Pro Ala Ile Met Ser Ala Ser Pro Gly Glu Lys Val
 1               5                   10                  15

Thr Met Thr Cys Arg Ala Ser Ser Ser Val Ser Tyr Met Asn Trp Tyr
            20                  25                  30

Gln Gln Lys Ser Gly Thr Ser Pro Lys Arg Trp Ile Tyr Asp Thr Ser
            35                  40                  45

Lys Val Ala Ser Gly Val Pro Tyr Arg Phe Ser Gly Ser Gly Ser Gly
            50                  55                  60

Thr Ser Tyr Ser Leu Thr Ile Ser Ser Met Glu Ala Glu Asp Ala Ala
 65                  70                  75                  80

Thr Tyr Tyr Cys Gln Gln Trp Ser Ser Asn Pro Leu Thr Phe Gly Ala
            85                  90                  95
```

```
Gly Thr Lys Leu Glu Leu Lys
        100

<210> SEQ ID NO 97
<211> LENGTH: 107
<212> TYPE: PRT
<213> ORGANISM: Mus musculus

<400> SEQUENCE: 97

Asp Ile Val Leu Thr Gln Ser Pro Ser Ile Met Ser Val Ser Pro Gly
1               5                   10                  15

Glu Lys Val Thr Ile Thr Cys Ser Ala Ser Ser Ser Val Ser Tyr Met
            20                  25                  30

His Trp Phe Gln Gln Lys Pro Gly Thr Ser Pro Lys Leu Leu Ile Tyr
        35                  40                  45

Ser Thr Ser Asn Leu Ala Ser Gly Val Pro Ala Arg Phe Ser Gly Arg
    50                  55                  60

Gly Ser Gly Thr Ser Tyr Ser Leu Thr Ile Ser Arg Val Ala Ala Glu
65                  70                  75                  80

Asp Ala Ala Thr Tyr Tyr Cys Gln Gln Arg Ser Asn Tyr Pro Pro Trp
                85                  90                  95

Thr Phe Gly Gly Gly Thr Lys Leu Glu Ile Lys
            100                 105

<210> SEQ ID NO 98
<211> LENGTH: 106
<212> TYPE: PRT
<213> ORGANISM: Mus musculus

<400> SEQUENCE: 98

Ile Val Leu Thr Gln Ser Pro Ser Ile Met Ser Val Ser Pro Gly Glu
1               5                   10                  15

Lys Val Thr Ile Thr Cys Ser Ala Ser Ser Ser Val Ser Tyr Met His
            20                  25                  30

Trp Phe Gln Gln Lys Pro Gly Thr Ser Pro Lys Leu Leu Ile Tyr Ser
        35                  40                  45

Thr Ser Asn Leu Ala Ser Gly Val Pro Ala Arg Phe Ser Gly Arg Gly
    50                  55                  60

Ser Gly Thr Ser Tyr Ser Leu Thr Ile Ser Arg Val Ala Ala Glu Asp
65                  70                  75                  80

Ala Ala Thr Tyr Tyr Cys Gln Gln Arg Ser Asn Tyr Pro Pro Trp Thr
                85                  90                  95

Phe Gly Gly Gly Thr Lys Leu Glu Ile Lys
            100                 105

<210> SEQ ID NO 99
<211> LENGTH: 106
<212> TYPE: PRT
<213> ORGANISM: Mus musculus

<400> SEQUENCE: 99

Ile Val Leu Thr Gln Ser Pro Ser Ile Met Ser Val Ser Pro Gly Glu
1               5                   10                  15

Lys Val Thr Ile Thr Cys Ser Ala Ser Ser Ser Val Ser Tyr Met His
            20                  25                  30

Trp Phe Gln Gln Lys Pro Gly Thr Ser Pro Lys Leu Trp Ile Tyr Ser
        35                  40                  45

Thr Ser Asn Leu Ala Ser Gly Val Pro Ala Arg Phe Ser Gly Arg Gly
```

```
                50                  55                  60
Ser Gly Thr Ser Tyr Ser Leu Thr Ile Ser Arg Val Ala Ala Glu Asp
 65                  70                  75                  80

Ala Ala Thr Tyr Tyr Cys Gln Gln Arg Ser Asn Tyr Pro Pro Trp Thr
                 85                  90                  95

Phe Gly Gly Gly Thr Lys Leu Glu Ile Lys
                100                 105
```

<210> SEQ ID NO 100
<211> LENGTH: 106
<212> TYPE: PRT
<213> ORGANISM: Mus musculus

<400> SEQUENCE: 100

```
Ile Val Leu Thr Gln Ser Pro Ser Ile Met Ser Val Ser Pro Gly Glu
 1               5                  10                  15

Lys Val Thr Ile Thr Cys Ser Ala Ser Ser Val Ser Tyr Met His
                 20                  25                  30

Trp Phe Gln Gln Lys Pro Gly Thr Ser Pro Lys Leu Ser Ile Tyr Ser
                 35                  40                  45

Thr Ser Asn Leu Ala Ser Gly Val Pro Ala Arg Phe Ser Gly Arg Gly
             50                  55                  60

Ser Gly Thr Ser Tyr Ser Leu Thr Ile Ser Arg Val Ala Ala Glu Asp
 65                  70                  75                  80

Ala Ala Thr Tyr Tyr Cys Gln Gln Arg Ser Asn Tyr Pro Pro Trp Thr
                 85                  90                  95

Phe Gly Gly Gly Thr Lys Leu Glu Ile Lys
                100                 105
```

<210> SEQ ID NO 101
<211> LENGTH: 513
<212> TYPE: PRT
<213> ORGANISM: artificial
<220> FEATURE:
<223> OTHER INFORMATION: bispecific molecule 107

<400> SEQUENCE: 101

```
Met Gly Trp Ser Cys Ile Ile Leu Phe Leu Val Ala Thr Ala Thr Gly
 1               5                  10                  15

Val His Ser Asp Ile Lys Leu Gln Gln Ser Gly Ala Glu Leu Ala Arg
                 20                  25                  30

Pro Gly Ala Ser Val Lys Met Ser Cys Lys Thr Ser Gly Tyr Thr Phe
                 35                  40                  45

Thr Arg Tyr Thr Met His Trp Val Lys Gln Arg Pro Gly Gln Gly Leu
 50                  55                  60

Glu Trp Ile Gly Tyr Ile Asn Pro Ser Arg Gly Tyr Thr Asn Tyr Asn
 65                  70                  75                  80

Gln Lys Phe Lys Asp Lys Ala Thr Leu Thr Thr Asp Lys Ser Ser Ser
                 85                  90                  95

Thr Ala Tyr Met Gln Leu Ser Ser Leu Thr Ser Glu Asp Ser Ala Val
                100                 105                 110

Tyr Tyr Cys Ala Arg Tyr Tyr Asp Asp His Tyr Ser Leu Asp Tyr Trp
                115                 120                 125

Gly Gln Gly Thr Thr Leu Thr Val Ser Ser Val Glu Gly Gly Ser Gly
            130                 135                 140

Gly Ser Gly Gly Ser Gly Gly Ser Gly Gly Val Asp Asp Ile Gln Leu
145                 150                 155                 160
```

Thr Gln Ser Pro Ala Ile Met Ser Ala Ser Pro Gly Glu Lys Val Thr
            165                 170                 175
Met Thr Cys Arg Ala Ser Ser Val Ser Tyr Met Asn Trp Tyr Gln
        180                 185                 190
Gln Lys Ser Gly Thr Ser Pro Lys Arg Trp Ile Tyr Asp Thr Ser Lys
        195                 200                 205
Val Ala Ser Gly Val Pro Tyr Arg Phe Ser Gly Ser Gly Ser Gly Thr
210                 215                 220
Ser Tyr Ser Leu Thr Ile Ser Ser Met Glu Ala Glu Asp Ala Ala Thr
225                 230                 235                 240
Tyr Tyr Cys Gln Gln Trp Ser Ser Asn Pro Leu Thr Phe Gly Ala Gly
            245                 250                 255
Thr Lys Leu Glu Leu Lys Ser Gly Gly Gly Gly Ser Glu Val Gln Leu
            260                 265                 270
Gln Gln Ser Gly Pro Glu Leu Val Lys Pro Gly Ala Ser Met Lys Ile
        275                 280                 285
Ser Cys Lys Ala Ser Gly Tyr Ser Phe Thr Gly Tyr Thr Met Asn Trp
        290                 295                 300
Val Lys Gln Ser His Gly Lys Asn Leu Glu Trp Ile Gly Leu Ile Asn
305                 310                 315                 320
Pro Tyr Asn Gly Gly Thr Ile Tyr Asn Gln Lys Phe Lys Gly Lys Ala
                325                 330                 335
Thr Leu Thr Val Asp Lys Ser Ser Thr Ala Tyr Met Glu Leu Leu
            340                 345                 350
Ser Leu Thr Ser Glu Asp Ser Ala Val Tyr Tyr Cys Ala Arg Asp Tyr
            355                 360                 365
Gly Phe Val Leu Asp Tyr Trp Gly Gln Gly Thr Thr Leu Thr Val Ser
        370                 375                 380
Ser Gly Gly Gly Gly Ser Gly Gly Gly Ser Gly Gly Gly Gly Ser
385                 390                 395                 400
Asp Ile Val Leu Thr Gln Ser Pro Ser Ile Met Ser Val Ser Pro Gly
                405                 410                 415
Glu Lys Val Thr Ile Thr Cys Ser Ala Ser Ser Ser Val Ser Tyr Met
            420                 425                 430
His Trp Phe Gln Gln Lys Pro Gly Thr Ser Pro Lys Leu Cys Ile Tyr
        435                 440                 445
Ser Thr Ser Asn Leu Ala Ser Gly Val Pro Ala Arg Phe Ser Gly Arg
        450                 455                 460
Gly Ser Gly Thr Ser Tyr Ser Leu Thr Ile Ser Arg Val Ala Ala Glu
465                 470                 475                 480
Asp Ala Ala Thr Tyr Tyr Cys Gln Gln Arg Ser Asn Tyr Pro Pro Trp
                485                 490                 495
Thr Phe Gly Gly Gly Thr Lys Leu Glu Ile Lys His His His His
            500                 505                 510
His

<210> SEQ ID NO 102
<211> LENGTH: 513
<212> TYPE: PRT
<213> ORGANISM: artificial
<220> FEATURE:
<223> OTHER INFORMATION: bispecific molecule 123

<400> SEQUENCE: 102

```
Met Gly Trp Ser Cys Ile Ile Leu Phe Leu Val Ala Thr Ala Thr Gly
1               5                   10                  15

Val His Ser Asp Ile Lys Leu Gln Gln Ser Gly Ala Glu Leu Ala Arg
            20                  25                  30

Pro Gly Ala Ser Val Lys Met Ser Cys Lys Thr Ser Gly Tyr Thr Phe
            35                  40                  45

Thr Arg Tyr Thr Met His Trp Val Lys Gln Arg Pro Gly Gln Gly Leu
        50                  55                  60

Glu Trp Ile Gly Tyr Ile Asn Pro Ser Arg Gly Tyr Thr Asn Tyr Asn
65                  70                  75                  80

Gln Lys Phe Lys Asp Lys Ala Thr Leu Thr Thr Asp Lys Ser Ser Ser
                85                  90                  95

Thr Ala Tyr Met Gln Leu Ser Ser Leu Thr Ser Glu Asp Ser Ala Val
                100                 105                 110

Tyr Tyr Cys Ala Arg Tyr Tyr Asp Asp His Tyr Ser Leu Asp Tyr Trp
            115                 120                 125

Gly Gln Gly Thr Thr Leu Thr Val Ser Ser Val Glu Gly Gly Ser Gly
        130                 135                 140

Gly Ser Gly Gly Ser Gly Gly Ser Gly Gly Val Asp Asp Ile Gln Leu
145                 150                 155                 160

Thr Gln Ser Pro Ala Ile Met Ser Ala Ser Pro Gly Glu Lys Val Thr
                165                 170                 175

Met Thr Cys Arg Ala Ser Ser Ser Val Ser Tyr Met Asn Trp Tyr Gln
                180                 185                 190

Gln Lys Ser Gly Thr Ser Pro Lys Arg Trp Ile Tyr Asp Thr Ser Lys
            195                 200                 205

Val Ala Ser Gly Val Pro Tyr Arg Phe Ser Gly Ser Gly Ser Gly Thr
        210                 215                 220

Ser Tyr Ser Leu Thr Ile Ser Ser Met Glu Ala Glu Asp Ala Ala Thr
225                 230                 235                 240

Tyr Tyr Cys Gln Gln Trp Ser Ser Asn Pro Leu Thr Phe Gly Ala Gly
                245                 250                 255

Thr Lys Leu Glu Leu Lys Ser Gly Gly Gly Gly Ser Glu Val Gln Leu
                260                 265                 270

Gln Gln Ser Gly Pro Glu Leu Val Lys Pro Gly Ala Ser Met Lys Ile
            275                 280                 285

Ser Cys Lys Ala Ser Gly Tyr Ser Phe Thr Gly Tyr Thr Met Asn Trp
        290                 295                 300

Val Lys Gln Ser His Gly Lys Asn Leu Glu Trp Ile Gly Leu Ile Asn
305                 310                 315                 320

Pro Tyr Asn Gly Gly Thr Ile Tyr Asn Gln Lys Phe Lys Gly Lys Ala
                325                 330                 335

Thr Leu Thr Val Asp Lys Ser Ser Ser Thr Ala Tyr Met Glu Leu Leu
                340                 345                 350

Ser Leu Thr Ser Glu Asp Ser Ala Val Tyr Tyr Cys Ala Arg Asp Tyr
            355                 360                 365

Gly Phe Val Leu Asp Tyr Trp Gly Gln Gly Thr Thr Leu Thr Val Ser
        370                 375                 380

Ser Gly Gly Gly Gly Ser Gly Gly Gly Gly Ser Gly Gly Gly Gly Ser
385                 390                 395                 400

Asp Ile Val Leu Thr Gln Ser Pro Ser Ile Met Ser Val Ser Pro Gly
                405                 410                 415

Glu Lys Val Thr Ile Thr Cys Ser Ala Ser Ser Ser Val Ser Tyr Met
```

```
              420                 425                 430
His Trp Phe Gln Gln Lys Pro Gly Thr Ser Pro Lys Leu Leu Ile Tyr
            435                 440                 445

Ser Thr Ser Asn Leu Ala Ser Gly Val Pro Ala Arg Phe Ser Gly Arg
        450                 455                 460

Gly Ser Gly Thr Ser Tyr Ser Leu Thr Ile Ser Arg Val Ala Ala Glu
465                 470                 475                 480

Asp Ala Ala Thr Tyr Tyr Cys Gln Gln Arg Ser Asn Tyr Pro Pro Trp
                485                 490                 495

Thr Phe Gly Gly Gly Thr Lys Leu Glu Ile Lys His His His His His
            500                 505                 510

His

<210> SEQ ID NO 103
<211> LENGTH: 520
<212> TYPE: PRT
<213> ORGANISM: artificial
<220> FEATURE:
<223> OTHER INFORMATION: bispecific molecule 124

<400> SEQUENCE: 103

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Thr Phe
        35                  40                  45

Thr Ser Tyr Trp Ile Asn Trp Val Lys Gln Arg Pro Gly Gln Gly Leu
    50                  55                  60

Glu Trp Ile Gly Asn Ile Tyr Pro Ser Asp Ser Tyr Thr Asn Tyr Asn
65                  70                  75                  80

Gln Lys Phe Lys Asp Lys Ala Thr Leu Thr Val Asp Lys Ser Ser Ser
                85                  90                  95

Thr Ala Tyr Met Gln Leu Ser Ser Pro Thr Ser Glu Asp Ser Ala Val
            100                 105                 110

Tyr Tyr Cys Thr Arg Ser Trp Arg Gly Asn Ser Phe Asp Tyr Trp Gly
        115                 120                 125

Gln Gly Thr Thr Leu Thr Val Ser Ser Gly Gly Gly Gly Ser Gly Gly
    130                 135                 140

Gly Gly Ser Gly Gly Gly Gly Ser Asp Ile Val Met Thr Gln Ser Pro
145                 150                 155                 160

Ser Ser Leu Thr Val Thr Ala Gly Glu Lys Val Thr Met Ser Cys Lys
                165                 170                 175

Ser Ser Gln Ser Leu Leu Asn Ser Gly Asn Gln Lys Asn Tyr Leu Thr
            180                 185                 190

Trp Tyr Gln Gln Lys Pro Gly Gln Pro Pro Lys Leu Leu Ile Tyr Trp
        195                 200                 205

Ala Ser Thr Arg Glu Ser Gly Val Pro Asp Arg Phe Thr Gly Ser Gly
    210                 215                 220

Ser Gly Thr Asp Phe Thr Leu Thr Ile Ser Ser Val Gln Ala Glu Asp
225                 230                 235                 240

Leu Ala Val Tyr Tyr Cys Gln Asn Asp Tyr Ser Tyr Pro Phe Thr Phe
                245                 250                 255

Gly Ser Gly Thr Lys Leu Glu Ile Lys Ser Gly Gly Gly Gly Ser Asp
            260                 265                 270
```

```
Ile Lys Leu Gln Gln Ser Gly Ala Glu Leu Ala Arg Pro Gly Ala Ser
        275                 280                 285

Val Lys Met Ser Cys Lys Thr Ser Gly Tyr Thr Phe Thr Arg Tyr Thr
    290                 295                 300

Met His Trp Val Lys Gln Arg Pro Gly Gln Gly Leu Glu Trp Ile Gly
305                 310                 315                 320

Tyr Ile Asn Pro Ser Arg Gly Tyr Thr Asn Tyr Asn Gln Lys Phe Lys
                325                 330                 335

Asp Lys Ala Thr Leu Thr Thr Asp Lys Ser Ser Ser Thr Ala Tyr Met
            340                 345                 350

Gln Leu Ser Ser Leu Thr Ser Glu Asp Ser Ala Val Tyr Tyr Cys Ala
        355                 360                 365

Arg Tyr Tyr Asp Asp His Tyr Ser Leu Asp Tyr Trp Gly Gln Gly Thr
    370                 375                 380

Thr Leu Thr Val Ser Ser Val Glu Gly Gly Ser Gly Gly Ser Gly Gly
385                 390                 395                 400

Ser Gly Gly Ser Gly Gly Val Asp Asp Ile Gln Leu Thr Gln Ser Pro
                405                 410                 415

Ala Ile Met Ser Ala Ser Pro Gly Glu Lys Val Thr Met Thr Cys Arg
            420                 425                 430

Ala Ser Ser Ser Val Ser Tyr Met Asn Trp Tyr Gln Gln Lys Ser Gly
        435                 440                 445

Thr Ser Pro Lys Arg Trp Ile Tyr Asp Thr Ser Lys Val Ala Ser Gly
    450                 455                 460

Val Pro Tyr Arg Phe Ser Gly Ser Gly Ser Gly Thr Ser Tyr Ser Leu
465                 470                 475                 480

Thr Ile Ser Ser Met Glu Ala Glu Asp Ala Ala Thr Tyr Tyr Cys Gln
                485                 490                 495

Gln Trp Ser Ser Asn Pro Leu Thr Phe Gly Ala Gly Thr Lys Leu Glu
            500                 505                 510

Leu Lys His His His His His His
        515                 520

<210> SEQ ID NO 104
<211> LENGTH: 20
<212> TYPE: PRT
<213> ORGANISM: Artificial Sequence
<220> FEATURE:
<223> OTHER INFORMATION: Linker

<400> SEQUENCE: 104

Gly Gly Gly Gly Ser Gly Gly Gly Ser Gly Gly Gly Ser Gly
1               5                   10                  15

Gly Gly Gly Ser
        20

<210> SEQ ID NO 105
<211> LENGTH: 25
<212> TYPE: PRT
<213> ORGANISM: Artificial Sequence
<220> FEATURE:
<223> OTHER INFORMATION: Linker

<400> SEQUENCE: 105

Gly Gly Gly Gly Ser Gly Gly Gly Gly Ser Gly Gly Gly Ser Gly
1               5                   10                  15

Gly Gly Gly Ser Gly Gly Gly Gly Ser
```

```
                20              25

<210> SEQ ID NO 106
<211> LENGTH: 18
<212> TYPE: PRT
<213> ORGANISM: Artificial Sequence
<220> FEATURE:
<223> OTHER INFORMATION: Linker

<400> SEQUENCE: 106

Gly Gly Gly Gly Ser Gly Gly Ser Gly Gly Ser Gly Gly Ser Gly Gly
1               5                   10                  15

Gly Ser

<210> SEQ ID NO 107
<211> LENGTH: 6
<212> TYPE: PRT
<213> ORGANISM: Artificial Sequence
<220> FEATURE:
<223> OTHER INFORMATION: His Tag

<400> SEQUENCE: 107

His His His His His His
1               5

<210> SEQ ID NO 108
<211> LENGTH: 9
<212> TYPE: PRT
<213> ORGANISM: Artificial Sequence
<220> FEATURE:
<223> OTHER INFORMATION: His Tag

<400> SEQUENCE: 108

Gly Gly Ser His His His His His His
1               5
```